US011660392B2

(12) United States Patent
Kamen et al.

(10) Patent No.: US 11,660,392 B2
(45) Date of Patent: May 30, 2023

(54) DEVICES, METHODS AND SYSTEMS FOR WIRELESS CONTROL OF MEDICAL DEVICES

(71) Applicant: DEKA Products Limited Partnership, Manchester, NH (US)

(72) Inventors: Dean Kamen, Bedford, NH (US); Gregory R. Lanier, Jr., Merrimack, NH (US); Gregg W. Rivinius, Bedford, NH (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 442 days.

(21) Appl. No.: 16/266,613

(22) Filed: Feb. 4, 2019

(65) Prior Publication Data

US 2019/0167902 A1 Jun. 6, 2019

Related U.S. Application Data

(63) Continuation of application No. 14/173,359, filed on Feb. 5, 2014, now Pat. No. 10,195,343, and a (Continued)

(51) Int. Cl.
*A61M 5/172* (2006.01)
*A61B 5/145* (2006.01)
(Continued)

(52) U.S. Cl.
CPC ........ *A61M 5/1723* (2013.01); *A61B 5/14532* (2013.01); *A61B 5/742* (2013.01);
(Continued)

(58) Field of Classification Search
CPC ........ A61M 5/1723; A61M 2205/3553; A61M 2205/3561; A61M 2205/3569;
(Continued)

(56) References Cited

U.S. PATENT DOCUMENTS 3,951,147 A 4/1976 Tucker et al.
4,265,241 A 5/1981 Portner et al.
(Continued)

FOREIGN PATENT DOCUMENTS

EP 420620 4/1991
EP 763368 3/1997
(Continued)

OTHER PUBLICATIONS

European Search Report, dated Jul. 21, 2011, received in European patent application No. 11154417.7, 7 pgs.
(Continued)

*Primary Examiner* — Quynh-Nhu H. Vu
(74) *Attorney, Agent, or Firm* — McCormick, Paulding & Huber PLLC

(57) ABSTRACT

A medical device system. The system includes a first medical device, a first remote interface, and a second remote interface in communication with the first remote interface and the first medical device, wherein the first medical device sends a command to the first medical device through the second remote interface, and wherein when the second remote interface receives the command, the command must be confirmed by the second remote interface before the command is send by the second remote interface to the first medical device.

12 Claims, 136 Drawing Sheets

Related U.S. Application Data continuation-in-part of application No. 14/236,381, filed as application No. PCT/US2012/071280 on Dec. 21, 2012, now Pat. No. 10,238,794, which is a continuation-in-part of application No. 13/322,896, filed on Dec. 21, 2011, now Pat. No. 9,662,438, said application No. 14/173,359 is a continuation-in-part of application No. 13/322,896, which is a continuation-in-part of application No. 13/021,000, filed on Feb. 4, 2011, now Pat. No. 9,750,896.

(60) Provisional application No. 61/842,687, filed on Jul. 3, 2013, provisional application No. 61/760,988, filed on Feb. 5, 2013, provisional application No. 61/301,957, filed on Feb. 5, 2010.

(51) Int. Cl.
*A61B 5/00* (2006.01)
*A61M 5/142* (2006.01)
*G16H 10/65* (2018.01)
*A61M 5/168* (2006.01)
*A61M 5/44* (2006.01)
*A61M 5/14* (2006.01)

(52) U.S. Cl.
CPC .... *A61M 5/14244* (2013.01); *A61M 5/14248* (2013.01); *G16H 10/65* (2018.01); *A61M 5/16831* (2013.01); *A61M 5/16886* (2013.01); *A61M 5/44* (2013.01); *A61M 2005/1402* (2013.01); *A61M 2005/14264* (2013.01); *A61M 2005/1726* (2013.01); *A61M 2205/332* (2013.01); *A61M 2205/3358* (2013.01); *A61M 2205/3368* (2013.01); *A61M 2205/3372* (2013.01); *A61M 2205/3553* (2013.01); *A61M 2205/3561* (2013.01); *A61M 2205/3569* (2013.01); *A61M 2205/3592* (2013.01); *A61M 2205/364* (2013.01); *A61M 2205/3606* (2013.01); *A61M 2205/368* (2013.01); *A61M 2205/3653* (2013.01); *A61M 2205/3673* (2013.01); *A61M 2205/3686* (2013.01); *A61M 2205/3693* (2013.01); *A61M 2205/502* (2013.01); *A61M 2205/505* (2013.01); *A61M 2205/52* (2013.01); *A61M 2205/70* (2013.01); *A61M 2205/7536* (2013.01); *A61M 2209/045* (2013.01); *A61M 2230/201* (2013.01)

(58) Field of Classification Search
CPC .......... A61M 2205/3592; G16H 10/65; G16H 10/60; G16H 20/10; G16H 20/17; G16H 20/00; G16H 15/00; G16H 40/67; G16H 70/20

See application file for complete search history.

(56) References Cited

U.S. PATENT DOCUMENTS

| | | |
|---|---|---|
| 4,486,190 A | 12/1984 | Reinicke |
| 4,525,165 A | 6/1985 | Fischell |
| 4,604,090 A | 8/1986 | Reinicke |
| 4,699,615 A | 10/1987 | Fischell |
| 4,976,162 A | 12/1990 | Kamen |
| 5,349,852 A | 9/1994 | Kamen et al. |
| 5,533,381 A | 7/1996 | Seale |
| 5,641,892 A | 6/1997 | Larkins |
| 5,871,478 A | 2/1999 | Berrigan |
| 6,124,699 A | 9/2000 | Suzuki et al. |
| 6,191,552 B1 | 2/2001 | Kates et al. |
| 6,344,727 B1 | 2/2002 | Desai et al. |
| 6,442,432 B2 | 8/2002 | Lee |
| 6,497,655 B1 | 12/2002 | Linberg et al. |
| 6,540,672 B1 | 4/2003 | Simonsen et al. |
| 6,589,169 B1* | 7/2003 | Surwit .................. G16H 20/10 128/920 |
| 6,597,946 B2* | 7/2003 | Avrahami ................ A61N 1/30 604/20 |
| 7,127,300 B2 | 10/2006 | Mazar et al. |
| 7,742,821 B1 | 6/2010 | Vamos et al. |
| 8,588,687 B2 | 11/2013 | Ramey et al. |
| 8,712,327 B2 | 4/2014 | Abratowski et al. |
| 9,662,438 B2 | 5/2017 | Kamen et al. |
| 9,750,896 B2 | 9/2017 | Kamen et al. |
| 10,195,343 B2 | 2/2019 | Kamen et al. |
| 10,238,794 B2 | 3/2019 | Kamen et al. |
| 2003/0048096 A1 | 3/2003 | Liu et al. |
| 2005/0069425 A1 | 3/2005 | Gray et al. |
| 2005/0182366 A1 | 8/2005 | Vogt et al. |
| 2005/0189921 A1 | 9/2005 | Bayne et al. |
| 2006/0237001 A1 | 10/2006 | Stangl |
| 2006/0267549 A1 | 11/2006 | Kung |
| 2007/0106218 A1 | 5/2007 | Yodfat et al. |
| 2007/0179549 A1 | 8/2007 | Russie |
| 2007/0219480 A1 | 9/2007 | Kamen et al. |
| 2007/0233206 A1 | 10/2007 | Frikart et al. |
| 2007/0265533 A1 | 11/2007 | Tran |
| 2008/0122402 A1 | 5/2008 | Hoffman et al. |
| 2008/0125064 A1 | 5/2008 | Das et al. |
| 2008/0140162 A1 | 6/2008 | Goetz et al. |
| 2008/0174265 A1 | 7/2008 | Toya |
| 2008/0249590 A1 | 10/2008 | Simms |
| 2009/0005729 A1 | 1/2009 | Hendrixson et al. |
| 2009/0171269 A1 | 7/2009 | Jennewine et al. |
| 2009/0177769 A1 | 7/2009 | Roberts |
| 2009/0254037 A1 | 10/2009 | Bryant, Jr. et al. |
| 2009/0299277 A1 | 12/2009 | Kamen et al. |
| 2009/0299289 A1 | 12/2009 | Kamen et al. |
| 2010/0010330 A1 | 1/2010 | Rankers et al. |
| 2010/0063445 A1 | 3/2010 | Sternberg et al. |
| 2010/0067197 A1 | 3/2010 | Guccione et al. |
| 2010/0130933 A1 | 5/2010 | Holland et al. |
| 2010/0211011 A1 | 8/2010 | Haar |
| 2011/0009813 A1 | 1/2011 | Rankers |
| 2011/0009814 A1 | 1/2011 | Tsoukalis |
| 2011/0009824 A1 | 1/2011 | Yodfat et al. |
| 2011/0010257 A1 | 1/2011 | Hill et al. |
| 2011/0082377 A1 | 4/2011 | Mahajan et al. |
| 2011/0105955 A1 | 5/2011 | Yudovsky et al. |
| 2011/0106050 A1 | 5/2011 | Yodfat et al. |
| 2011/0118578 A1* | 5/2011 | Timmerman ........ A61B 5/4839 604/890.1 |
| 2011/0118699 A1 | 5/2011 | Yodfat et al. |
| 2011/0124996 A1 | 5/2011 | Reinke et al. |
| 2011/0144616 A1 | 6/2011 | Michaud et al. |
| 2011/0163719 A1 | 7/2011 | Law |
| 2011/0168496 A1 | 7/2011 | Bunter |
| 2011/0178462 A1* | 7/2011 | Moberg ................ H04L 63/061 604/151 |
| 2011/0190694 A1 | 8/2011 | Lanier, Jr. et al. |
| 2011/0266999 A1 | 11/2011 | Yodfat et al. |
| 2012/0010562 A1 | 1/2012 | Hill et al. |
| 2012/0109047 A1 | 5/2012 | Yodfat et al. |
| 2012/0198353 A1 | 8/2012 | Lee et al. |
| 2012/0226259 A1 | 9/2012 | Yodfat et al. |
| 2012/0238851 A1 | 9/2012 | Kamen et al. |
| 2014/0222450 A1* | 8/2014 | Gray ...................... G16H 40/20 705/2 |
| 2015/0061890 A1* | 3/2015 | Rees ...................... G16H 80/00 340/870.01 |
| 2016/0210416 A1* | 7/2016 | Whitehurst ............ G16H 40/63 |

FOREIGN PATENT DOCUMENTS

| | | |
|---|---|---|
| WO | WO 199640330 | 12/1996 |
| WO | 01/52990 A1 | 7/2001 |
| WO | WO 2004006981 | 1/2004 |
| WO | WO 2004022136 | 3/2004 |

(56) References Cited

OTHER PUBLICATIONS

International Partial Search Report, dated Oct. 18, 2011, received in International patent application No. PCT/US201 1/030553 6 pgs.
European Search Report, dated Nov. 8, 2011, received in European patent application No. 11154414.4, 11 pgs.
International Search Report & Written Opinion, dated Dec. 23, 2011, received in International patent application No. PCT/US201 1/030553 12 pgs.
International Preliminary Report on Patentability & Written Opinion, dated Jul. 12, 2012, received in International patent application No. PCT/US2010/062443 13 pgs.
International Preliminary Report on Patentability & Written Opinion, dated Jul. 12, 2012, received in International patent application No. PCT/US2010/062426 9 pgs.
International Search Report & Written Opinion, dated Dec. 21, 2012, received in International patent application No. PCT/US2012/71280 13 pgs.
International Search Report & Written Opinion, dated Mar. 7, 2013, received in International patent application No. PCT/US2012/71280 13 pgs.
European Search Report dated Jul. 21, 2011, in connection with corresponding EP Application No. 11154418.5; 2 pages.
International Search Report dated Mar. 7, 2013, in connection with corresponding International Application No. PCT/US2012/71280; 2 pages.

\* cited by examiner

Each HW interface has its own Driver instance
Driver Interaction Data Flow Diagram

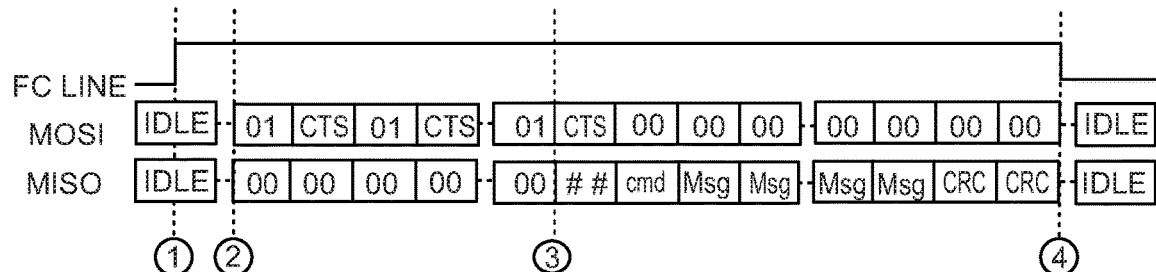

····· Indicates a time lapse

① Slave raises FlowControl line indicating a packet is pending
② Master begins sending 1 byte Clear To Send commands
③ Slave responds with the # of bytes being sent, Msg appended command & the Msg
④ The transaction is complete and the Slave lowers the FlowControl line

FIG. 8Q

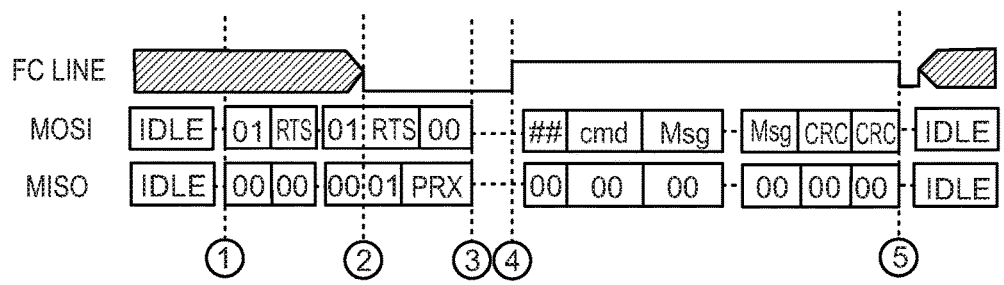

··· Indicates a time

① Master begins sending single byte RTS commands (state of Flow Control line is ignored
② Slave sends a Prepare for RX command indicating it is setting up dma to receive
③ Master stops clocking bytes and waits for the Flow Control Signal
④ Slave asserts the Flow Control line indicating the RX dma is ready to receive
⑤ The transaction is complete.

FIG. 8R

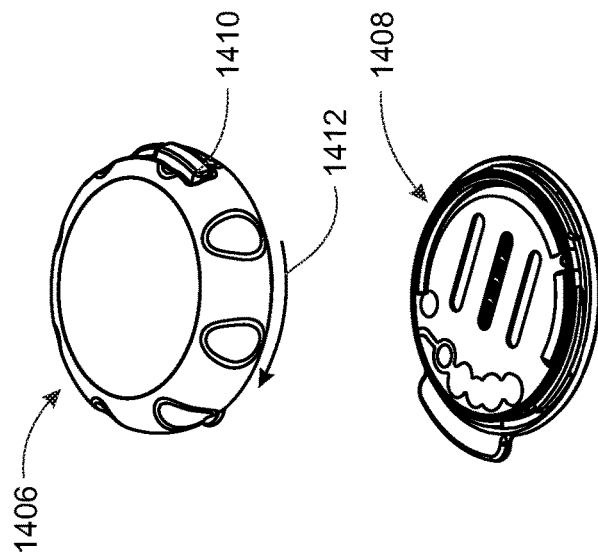
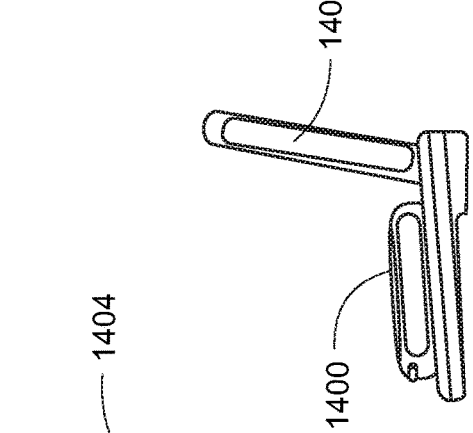
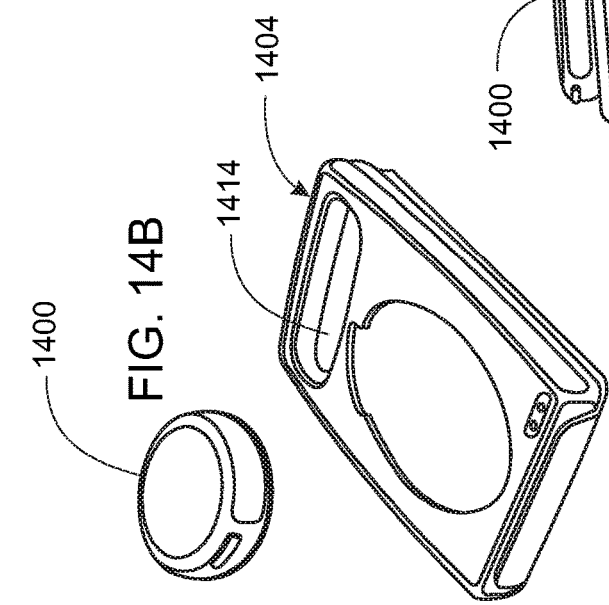
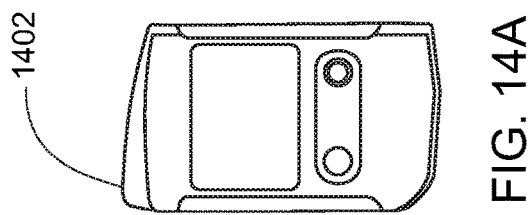
FIG. 14E
FIG. 14D
FIG. 14B
FIG. 14C
FIG. 14A

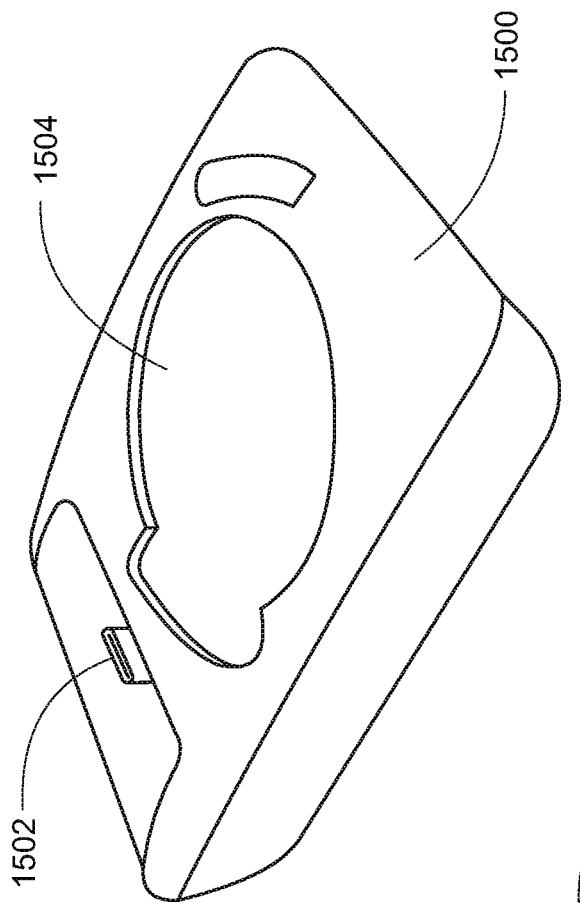
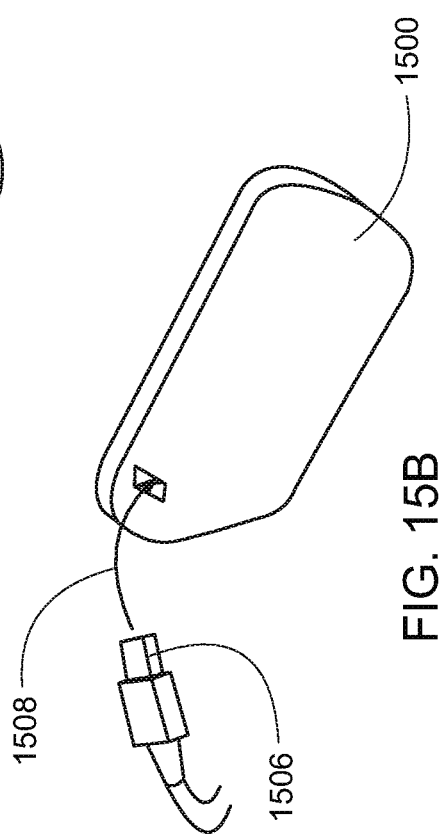
FIG. 15A
FIG. 15B

WiFi 4:04 PM

Measure Glucose

Blood Glucose Test Result

Result 123 mg/dL

After Lunch ▽

Add/Edit

Notes:
-Headache
-Feeling low

Redo | Home | Bolus

FIG. 24B

WiFi 4:07 PM

Edit Note went for a walk.

Add Tag

☑ Light exercise
☐ Moderate exercise
☐ Basketball game
☐ Sick

Ok | Cancel

Program Bolus — 6:06 PM

Enter Carbohydrate Amount

0 grams

| 1 | 2 | 3 |
| 4 | 5 | 6 |
| 7 | 8 | 9 |
| Clear | 0 | Delete |

Back — Library — OK

Program Bolus — 4:19 PM

Review bolus settings.
Insulin on Board: 0.01

Normal
3.51 Units

Extended
0 hrs 00 min
0.00 Units

Total Amount
3.51 Units

Slide to Start >>>>

Confirm — Back — Cancel — Use Slider

Program Bolus — 4:31 PM

Enter Bolus Amount
Insulation On Board: 3.47

1.56 Units

| 1 | 2 | 3 |
| 4 | 5 | 6 |
| 7 | 8 | 9 |
| Clear | 0 | Delete |

Back ▽ | ✕ Cancel | Next △

FIG. 26G

Program Bolus — 4:12 PM

Review Recommendation

Meal Bolus 1.40 Units
Carbs 21 g

Program Bolus — 2600

Modify Bolus Amount

3.51 Units

20% — 2602

OK | Cancel

Stop Basal

Are you sure you want to stop delivering basal insulin?

Yes, Stop | No, Continue

FIG. 27E

Cancel

Do you wish to cancel?

Yes, Cancel | No, Continue

FIG. 27C

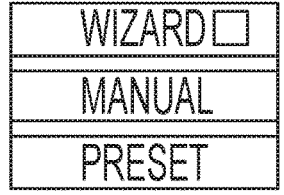
FIG. 43H
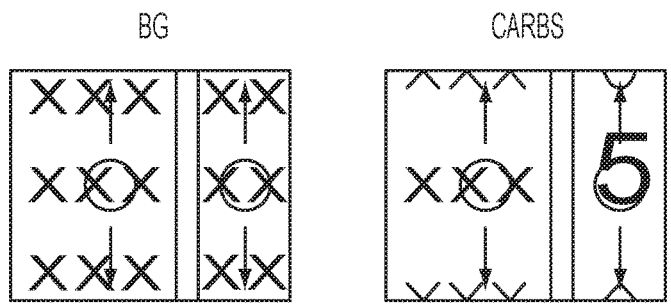
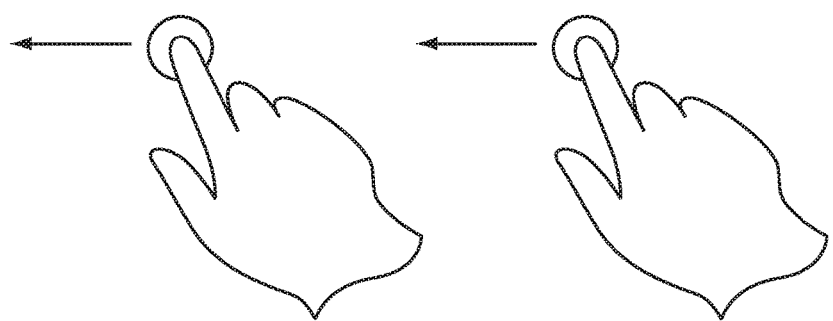
FIG. 43I FIG. 43J

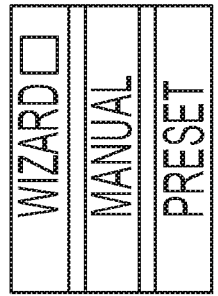
FIG. 43K
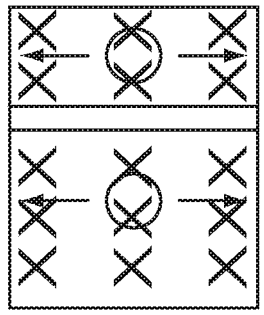
FIG. 43L
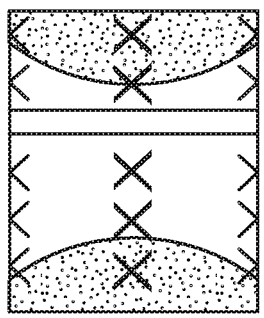
FIG. 43M
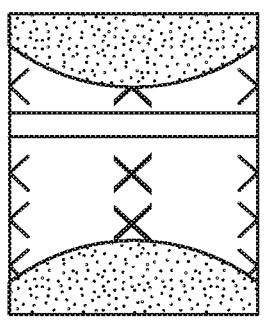
FIG. 43N
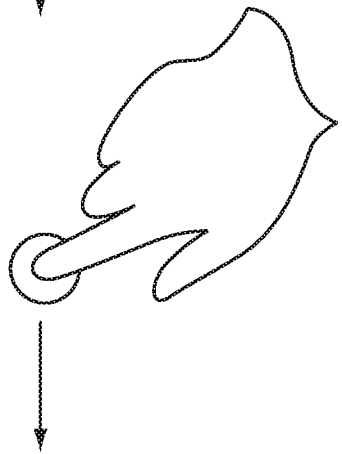
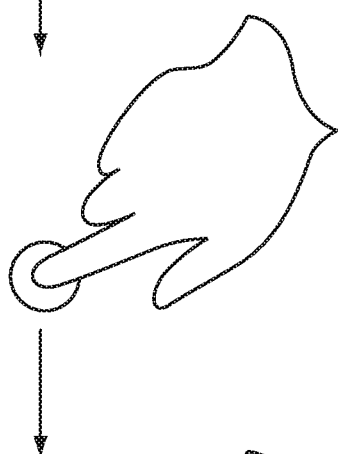
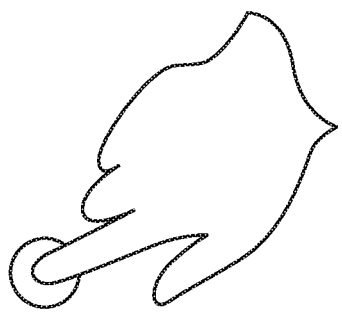

DEVICES, METHODS AND SYSTEMS FOR WIRELESS CONTROL OF MEDICAL DEVICES

CROSS REFERENCE TO RELATED APPLICATIONS

The present application is a Continuation of U.S. patent application Ser. No. 14/173,359, filed Feb. 5, 2014 and entitled Devices, Methods and Systems for Wireless Control of Medical Devices, now U.S. Pat. No. 10,195,343, issued Feb. 5, 2019, which is a Non-Provisional application which claims the benefit of U.S. Provisional Patent Application Ser. No. 61/760,988, filed Feb. 5, 2013 and entitled Devices, Methods and Systems for Wireless Control or Medical Devices; and U.S. Provisional Patent Application Ser. No. 61/842,687, filed Jul. 3, 2013 and entitled Devices, Methods and Systems for Wireless Control or Medical Devices, each of which is hereby incorporated herein by reference in their entireties.

U.S. patent application Ser. No. 14/173,359, is also a Continuation-in-Part Application of U.S. patent application Ser. No. 14/236,381, filed Jan. 31, 2014 and entitled Devices, Methods and Systems for Wireless Control of Medical Devices which is a '371 Application of International Application Serial No. PCT/US12/71280, filed Dec. 21, 2012 and entitled Devices, Methods and Systems for Wireless Control of Medical Devices, now International Publication No. WO 2013/096789, published Jun. 27, 2013, which is an International Application claiming priority to U.S. patent application Ser. No. 13/332,896, filed Dec. 21, 2011 and entitled Devices, Methods and Systems for Wireless Control of Medical Devices, now U.S. Publication No. US-2012-0238851-A1, published Sep. 20, 2012, each of which is hereby incorporated herein by reference in their entireties.

U.S. patent application Ser. No. 14/173,359, is also a Continuation-in-Part Application of U.S. patent application Ser. No. 13/332,896, filed Dec. 21, 2011 and entitled Devices, Methods and Systems for Wireless Control of Medical Devices, now U.S. Publication No. US-2012-0238851-A1, published Sep. 20, 2012, which is a Continuation-in-Part Application of U.S. patent application Ser. No. 13/021,000, filed Feb. 4, 2011 and entitled Infusion Pump Apparatus, Method and System, now U.S. Publication No. US-2011-0319813-A1, published Dec. 29, 2011, which claims priority to U.S. Provisional Application Ser. No. 61/301,957, filed Feb. 5, 2010 and entitled Infusion Pump Apparatus, Method and System, each of which is hereby incorporated herein by reference in their entireties.

TECHNICAL FIELD

The present disclosure relates to medical devices and more particularly, to a system for controlling at least one medical device.

BACKGROUND INFORMATION

Many potentially valuable medicines or compounds, including biologicals, are not orally active due to poor absorption, hepatic metabolism or other pharmacokinetic factors. Additionally, some therapeutic compounds, although they can be orally absorbed, are sometimes required to be administered so often it is difficult for a patient to maintain the desired schedule. In these cases, parenteral delivery is often employed or could be employed.

Effective parenteral routes of drug delivery, as well as other fluids and compounds, such as subcutaneous injection, intramuscular injection, and intravenous (IV) administration include puncture of the skin with a needle or stylet. Insulin is an example of a therapeutic fluid that is self-injected by millions of diabetic patients. Users of parenterally delivered drugs may benefit from a wearable device that would automatically deliver needed drugs/compounds over a period of time.

To this end, there have been efforts to design portable and wearable devices for the controlled release of therapeutics. Such devices are known to have a reservoir such as a cartridge, syringe, or bag, and to be electronically controlled. These devices suffer from a number of drawbacks including the malfunction rate. Reducing the size, weight and cost of these devices is also an ongoing challenge. Additionally, these devices often apply to the skin and pose the challenge of frequent re-location for application.

Managing multiple medical devices simultaneously for a single user presents challenges. One includes the hardware, for many medical devices include a designated interface and with respect to medical devices that are wirelessly controlled, multiple "controllers" or "hand helds" present logistical challenges. Firstly, the variety of interfaces may be difficult to transfer attention from one to another and to master. Secondly, recharging multiple devices may present a challenge and thirdly, carrying the multiple controllers, together with the medical devices, presents challenges.

SUMMARY

In accordance with one aspect of the present invention, a medical device system is disclosed. The system includes a first medical device, a first remote interface, and a second remote interface in communication with the first remote interface and the first medical device, wherein the first medical device sends a command to the first medical device through the second remote interface, and wherein when the second remote interface receives the command, the command must be confirmed by the second remote interface before the command is send by the second remote interface to the first medical device.

Some embodiments of this aspect of the invention may include one or more of the following. Wherein the first medical device is an infusion pump. Wherein the first remote interface is a medical device data system. Wherein the second remote interface is not a medical device data system. Wherein the system further comprising a blood glucose meter in communication with the second remote interface. Wherein the system further comprising a continuous glucose monitor transmitter in communication with the second remote interface. Wherein the first remote interface receives a command related to the communication of safety critical information to the first medical device, displays a message that the communication of the safety critical information to the first medical device requires confirmation using the second remote interface, sends the communication to the second remote interface, and once confirmation received by the second remote interface, the second remote interface communicates the command to the first medical device. Wherein the first remote interface receives an input of information related to the delivery by the infusion pump of a bolus volume of infusible fluid, displays a message that the delivery of the bolus volume requires confirmation using the second remote interface, and once confirmation received by the second remote interface, the second remote interface communicates the information required for the delivery of the bolus volume of infusible fluid to the infusion pump.

In accordance with one aspect of the present invention, a medical device system is disclosed. The medical device system includes a first medical device, a first remote interface comprising a medical device data system, and a second remote interface in communication with the first remote interface and the first medical device, wherein the first medical device sends a safety critical command to the first medical device through the second remote interface, and wherein when the second remote interface receives the safety critical command, the command must be confirmed by the second remote interface before the safety critical command is send by the second remote interface to the first medical device.

Some embodiments of this aspect of the invention may include one or more of the following. Wherein the first medical device is an infusion pump. Wherein the first remote interface is a medical device data system. Wherein the second remote interface is not a medical device data system. Wherein the system further comprising a blood glucose meter in communication with the second remote interface. Wherein the system further comprising a continuous glucose monitor transmitter in communication with the second remote interface. Wherein the first remote interface receives an input of information related to the delivery by the infusion pump of a bolus volume of infusible fluid, displays a message that the delivery of the bolus volume requires confirmation using the second remote interface; and once confirmation received by the second remote interface, the second remote interface communicates the information required for the delivery of the bolus volume of infusible fluid to the infusion pump.

In accordance with one aspect of the present invention, a method of communication for a medical system is disclosed. The method includes a first remote interface receiving a command related to the communication of safety critical information to a first medical device, the first remote interface displaying a message that the communication of the safety critical information to the first medical device requires confirmation using the second remote interface, the first remote interface sending the communication to the second remote interface, the second remote interface receiving confirmation, and the second remote interface communicating the command to the first medical device.

Some embodiments of this aspect of the invention may include one or more of the following. Wherein the first medical device is an infusion pump. Wherein the command is related to the delivery of a bolus of infusible fluid. Wherein the command is related to stopping the delivery of a basal rate of infusible fluid. Wherein the first remote interface is a medical device data system.

In accordance with one aspect of the present invention, a medical device system is disclosed. The medical device system includes a first medical device and a second medical device. The system also includes a remote interface including a touch screen. The remote interface is in wireless communication with the first medical device and the second medical device. The remote interface is configured to provide a user interface to the first medical device and the second medical device. The remote interface is configured to receive user input through a touch screen. Also, a charging device is included. The charging device is configured to receive at least the first medical device and the remote interface and the charging device is configured to recharge a first medical device battery and the charging device is configured to recharge an interface battery in the remote interface. The charging device is connected to a personal computer wherein the personal computer provides information to the remote interface.

Some embodiments of this aspect of the invention may include one or more of the following. Wherein the first medical device is an infusion pump; wherein the first medical device further includes at least one disposable portion and at least two reusable portions, each of the two reusable portions configured to connect to the at least one disposable portion; wherein the charging device is configured to receive at least one of the at least two reusable portions of the first medical device; wherein the second medical device is a continuous glucose monitor system comprising at least one transmitter wherein the at least one transmitter in wireless communication with the remote interface; wherein the system further includes a third medical device in wireless communication with the remote interface; wherein the remote interface configured to provide a user interface to the third medical device; wherein the third medical device is at least one blood glucose meter; wherein the system further includes wherein the wireless communication is radio frequency communication; wherein the first medical device and the remote interface are paired using near field communication; and/or wherein the remote interface further comprising at least one camera.

In accordance with one aspect of the present invention, a medical device system is disclosed. The medical device system includes a first medical device and a second medical device, in wireless communication with the first medical device. The system also includes a remote interface including a touch screen. The remote interface is in wireless communication with the first medical device and the remote interface is configured to provide a user interface to the first medical device and the second medical device. The remote interface is configured to receive user input through a touch screen. The system also includes a charging device configured to receive the first medical device and the remote interface. The charging device configured to recharge a first medical device battery, and the charging device is configured to recharge an interface battery in the remote interface. The charging device is connected to a personal computer wherein the personal computer provides information to the remote interface.

Some embodiments of this aspect of the invention may include one or more of the following. Where the first medical device is an infusion pump; wherein the first medical device further includes at least one disposable portion and at least two reusable portions, each of the two reusable portions configured to connect to the at least one disposable portion; wherein the charging device configured to receive at least one of the at least two reusable portions of the first medical device; wherein the second medical device including a continuous glucose monitor system including at least one transmitter wherein the at least one transmitter in wireless communication with the first medical device; wherein the second medical device including a blood glucose meter in wireless communication with the first medical device; wherein the first medical device and the remote interface are paired using near field communication; wherein the first medical device and the second medical device are paired using near field communication.

In accordance with one aspect of the present invention, an infusion pump system is disclosed. The infusion pump system includes at least one disposable portion of an infusion pump, at least two reusable portions of an infusion pump, each of the two reusable portions of an infusion pump configured to connect to the at least one disposable portion.

The system also includes a remote interface including a touch screen, the remote interface in wireless communication with at least one of the at least two reusable portions, the remote interface configured to provide user instructions to the at least one of the at least two reusable portions, wherein the remote interface configured to receive user input through a touch screen. The system also includes a charging device configured to receive at least one of the at least two reusable portions and the remote interface. The charging device is configured to recharge a pump battery of the at least one of the at least two reusable portions, and the charging device is configured to recharge an interface battery in the remote interface. The charging device is connected to a personal computer wherein the personal computer provides information to the remote interface.

Some embodiments of this aspect of the invention may include one or more of the following. Wherein the system further includes a continuous glucose monitor system including at least one transmitter wherein the at least one transmitter in wireless communication with the remote interface; wherein the system further includes at least one blood glucose meter wherein the blood glucose meter in wireless communication with the remote interface; wherein the at least one reusable portion and the remote interface are paired using near field communication; wherein the remote interface further including at least one accelerometer; wherein the remote interface further includes at least one camera.

In accordance with one aspect of the present invention, an infusion pump system is disclosed. The infusion pump system includes an infusion pump, and a remote interface device in wireless communication with the infusion pump including instructions for controlling the infusion pump wherein the instructions may be synchronized with a secure web portal.

Some embodiments of this aspect of the invention may include one or more of the following. Wherein the system further includes a continuous glucose monitor system including a transmitter wherein the transmitter in wireless communication with the remote interface device. Wherein the system further includes a blood glucose meter wherein the blood glucose meter in wireless communication with the remote interface device. Wherein the wireless communication is radio frequency ("RF") communication. Wherein the infusion pump and the remote interface device are paired using near field communication. Wherein the system further includes at least one accelerometer.

In accordance with one aspect of the present invention, a medical device system is disclosed. The medical device system includes a first medical device and a second medical device in wireless communication with the first medical device, the second medical device including instructions for controlling the first medical device wherein the instructions may be synchronized with a secure web portal.

Some embodiments of this aspect of the invention may include one or more of the following. Wherein the first medical device is an infusion pump and the second medical device is a remote interface device. Wherein the infusion pump and the remote interface device are paired using near field communication. Wherein the first medical device is a continuous glucose monitor sensor and the second medical device is a remote interface device. Wherein the infusion pump and the remote interface device are paired using near field communication. Wherein the first medical device is a blood glucose meter and the second medical device is a remote interface device. Wherein the infusion pump and the remote interface device are paired using near field communication.

In accordance with one aspect of the present invention, a method for communication between two medical devices is disclosed. The method includes a first medical device sending a radio signal together with an acoustic signal to a second medical device, calculating the distance between the first medical device and the second medical device using the acoustic signal, determining whether the calculated distance exceeds a predetermined threshold, and if the calculated distance exceeds a predetermined threshold, notifying the user.

Some embodiments of this aspect of the invention may include one or more of the following. Wherein the first medical device is a remote interface and the second medical device is an infusion pump. Wherein the first medical device is a remote interface and the second medical device is a continuous glucose monitor sensor/transmitter. Wherein the first medical device is a remote interface and the second medical device is a blood glucose meter.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIGS. 14A-14E are illustrations of one embodiment of the system;

FIGS. 15A-15B are illustrations of one embodiment of a charging station in one embodiment of the system;

FIGS. 20A-30 are embodiments of various screen shots of a remote interface according to one embodiment of the system;

FIGS. 44A-58T are embodiments of various screen shots of a remote interface according to one embodiment of the system.

DETAILED DESCRIPTION OF THE EXEMPLARY EMBODIMENTS

Definitions

Figure 1B:
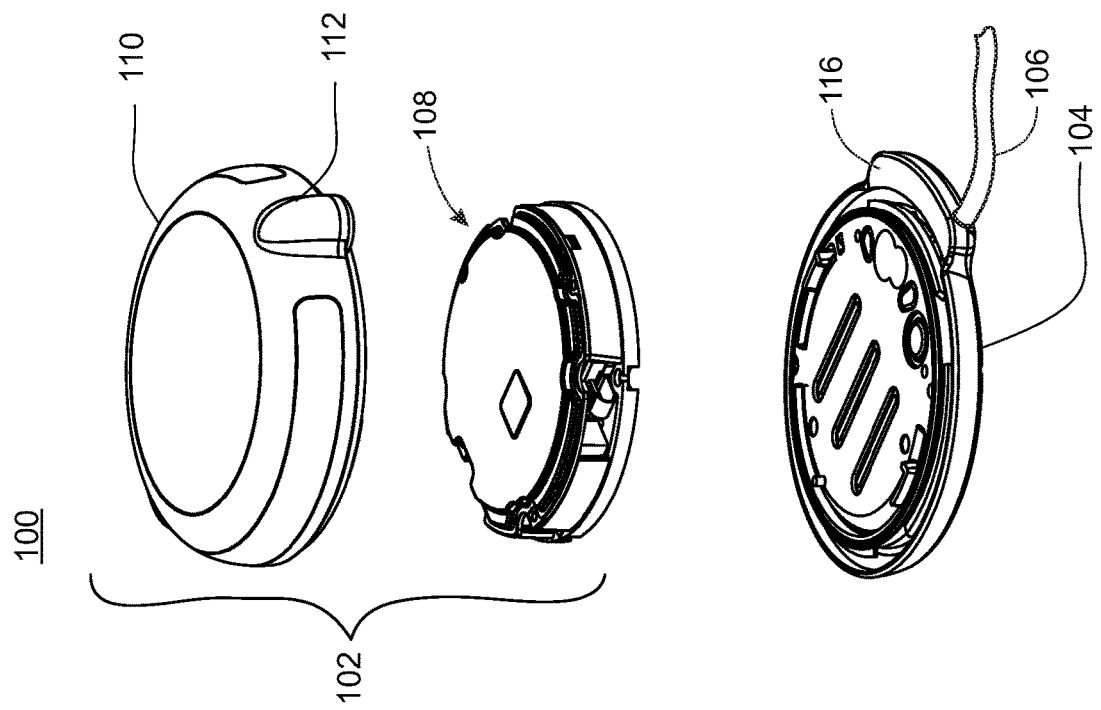
FIG. 1B is an exploded view of an embodiment of an infusion pump.

As used in this description and the accompanying claims, the following terms shall have the meanings indicated, unless the context otherwise requires:

A "remote interface" shall mean a device for wireless communication with a device which may include, but is not limited to, a medical device.

A "device" shall mean any medical device, which includes, but is not limited to, a medical device, which includes, but is not limited to, an infusion pump and/or a microinfusion pump, a drug delivery pump and/or apparatus, a sensor, a measuring device and/or meter, a blood pressure monitor, ECG monitor, pill dispenser, pulse oximetry monitor, a CO2 capometer, an intravenous bag, a drop-flow meter, a temperature monitor, a peritoneal dialysis machine, including, but not limited to, a home peritoneal dialysis machine, a hemodialysis machine, including, but not limited to, a home hemodialysis machine, and any other medical device or device configured to deliver, treat and/or determine medical care.

An "input" of a device includes any mechanism by which a user and/or other operator/caregiver of the device and/or remote interface may control a function of the device and/or remote interface. User inputs may include mechanical arrangements (e.g., switches, pushbuttons, jogwheel(s)), electrical arrangements (e.g., a slider, touch screen), wireless interfaces for communication with a remote interface (e.g., radio frequency ("RF"), infrared ("IR"), BLUETOOTH), acoustic interfaces (e.g., with speech recognition), computer network interfaces (e.g., USB port), light/light wave image including, but not limited to, camera input and/or images captured using a camera), sound wave and/or other types of interfaces.

A "button" in the context of an input such as the so-called "bolus button" discussed below may be any type of user input capable of performing a desired function, and is not limited to a pushbutton, a slider, switch, touch screen and/or a jog wheel.

An "alarm" includes any mechanism by which an alert may be generated to a user and/or third party/operator/caregiver. Alarms may include audible alarms (e.g., a speaker, a buzzer, a speech generator), visual alarms (e.g., an LED, an LCD screen, an image), tactile alarms (e.g., a vibrating element), wireless signals (e.g., a wireless transmission to a remote interface or caretaker), and/or other mechanism. Alarms may be generated using multiple mechanisms simultaneously, concurrently, or in a sequence, including redundant mechanisms (e.g., two different audio alarms) or complementary mechanisms (e.g., an audio alarm, a tactile alarm, and a wireless alarm) and/or mechanisms of increasing volume and/or intensity (e.g. escalating alarm sequence).

"Fluid" shall mean a substance, e.g., a liquid, capable of flowing through a flow line or fluid line.

A "user" includes a person or animal receiving treatment from or connected to the device whether as part of a medical treatment or otherwise and/or a caregiver or third party involved in programming the device or otherwise interacting with the device to convey treatment and or collect information from the device, which may include, but is not limited to, a physician and/or medical provider and/or companion and/or parent and/or guardian.

"Cannula" shall mean a disposable device capable of infusing fluid to a user. A cannula as used herein may refer to a traditional cannula/flexible tube or to a needle.

"Disposable" refers to a part, device, portion or other that is intended to be used for a fixed duration of time, then discarded and replaced.

"Reusable" refers to a portion that is intended to have an open-ended duration of use.

"Acoustic volume measurement" shall mean quantitative measurement of a relevant volume using acoustical techniques such as those described in U.S. Pat. Nos. 5,349,852 and 5,641,892, and in U.S. patent application Ser. No. 11/704,899, filed Feb. 9, 2007 and entitled Fluid Delivery Systems and Methods, now U.S. Publication No. US-2007-0228071-A1 published Oct. 4, 2007, and U.S. patent application Ser. No. 12/347,985, filed Dec. 31, 2008, and entitled Infusion Pump Assembly, now U.S. Publication No. US-2009-0299277 published Dec. 3, 2009, which are each hereby incorporated herein by reference in their entireties, as well as other techniques.

An exemplary use of various embodiments of the devices, methods and systems described here is for the delivery of insulin to people living with diabetes, but other uses include delivery of any fluid, sensing of any condition and/or state and/or providing medical treatment and/or medical care. Fluids may include, but are not limited to, analgesics to those in pain, chemotherapy to cancer patients and enzymes to patients with metabolic disorders. Various therapeutic fluids may include, but are not limited to, small molecules, natural products, peptide, proteins, nucleic acids, carbohydrates, nanoparticulate suspensions, and associated pharmaceutically acceptable carrier molecules. Therapeutically active molecules may be modified to improve stability in the device (e.g., by pegylation of peptides or proteins). Although illustrative embodiments herein describe drug-delivery applications, embodiments may be used for other applications including liquid dispensing of reagents for high throughput analytical measurements such as lab-on-chip applications and capillary chromatography. For purposes of description below, terms "therapeutic", "insulin" or "fluid" are used interchangeably, however, in other embodiments, any fluid, as described above, may be used. Thus, the devices, systems, methods and description thereof included herein are not limited to use with therapeutics.

Some embodiments of the device are adapted for use by people living with diabetes and/or their caregivers. Thus, in these embodiments, the devices, methods and systems work to deliver insulin which supplements or replaces the action of the person living with diabetes' (referred to as the user) pancreatic islet beta cells. Embodiments adapted for insulin delivery seek to replace the action of the pancreatic islet beta cells by providing both a basal level of fluid delivery as well as bolus levels of fluid delivery. Basal levels, bolus levels and timing may be set by the user by using a remote interface user interface or directly by using a user interface on the device. Additionally, basal and/or bolus levels may be triggered or adjusted in response to the output of one or more glucose meters and/or glucose monitors (i.e., devices) which, in the exemplary embodiments, may be integral to, or in wireless communication with, the remote interface. In other embodiments, the remote interface may include one or more analyte monitoring devices which may include, but is not limited to, a blood glucose meter/device which receives blood samples and/or receives a device that is configured to receive a blood sample, e.g., a blood glucose strip. In some embodiments, a bolus may be triggered by a user using a designated button or other input means located on a device, i.e., on an infusion pump, and/or on a remote interface. In still other embodiments, the bolus or basal may be programmed or administered through a user interface located either on the device (e.g., on the infusion pump and/or on the remote interface).

With respect to the names given to screens and types of screens herein, as well as proper names given to various features, throughout various embodiments, these terms may vary and are for descriptive purposes. The description is not limited by these names.

The devices, systems and methods described herein may be used to control an infusion pump. For purposes of this description, the various embodiments of the user interface and the infusion pump may be described with reference to an insulin pump, or a pump which infuses insulin. However, it should be understood that the user interface may be on an infusion pump and/or on a remote interface and the medical device to which the remote interface communicates with may be any medical device, i.e., is not limited to an infusion pump. Additionally, where the description pertains to an infusion pump "screen", this "screen" may also appear on a remote interface, or may appear on a remote interface in lieu of on an infusion pump.

Infusion pumps contemplated by this description include a pump which may pump any fluid, including, but not limited to, a therapeutic fluid, which includes, but is not limited to, insulin. Thus, where this description describes an embodiment as pertaining to insulin, this is meant merely for descriptive purpose only, as the device is not intended to be limited to insulin. Other fluids are also contemplated. In some embodiments, the methods, systems and devices described herein may be used in conjunction with other fluid delivery devices, e.g., pens and/or syringes, which are known in the art.

The system for controlling a device described herein may be used for any one or more device, and in some embodiments, the device may include an infusion pump and/or an infusion pump system which may deliver fluid and/or may be configured to deliver fluid to a user through a cannula. For descriptive purposes only, an infusion pump system, which may include at least one insulin pump, is described herein. However, the system is not limited to use with one or more infusion pumps and/or an insulin pump systems, rather, may be used with any device and/or with any one or more devices.

Figure 1A:
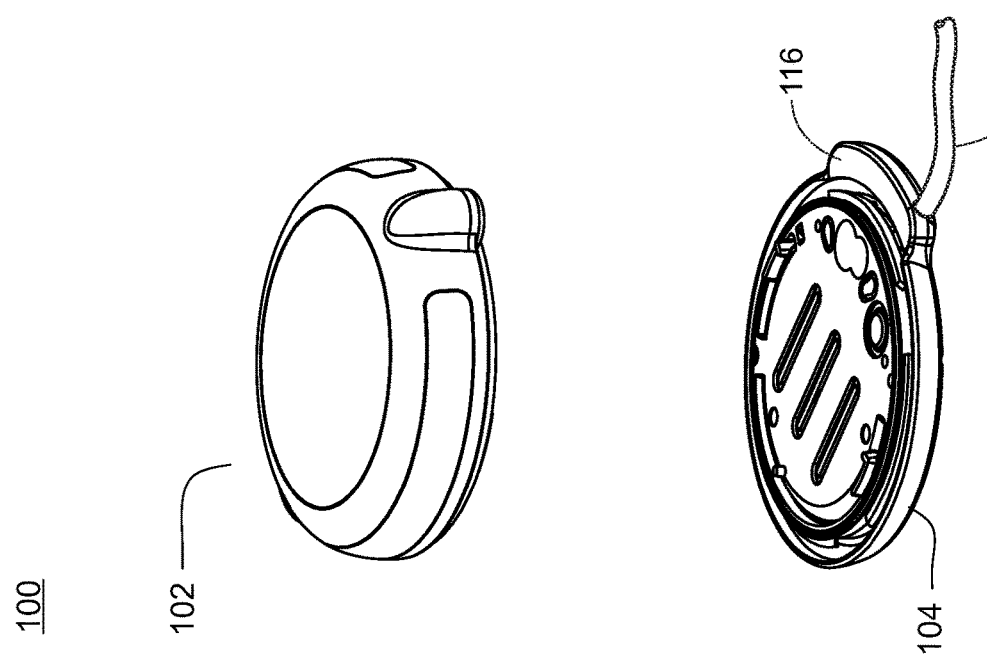
FIG. 1A is an exploded view of an embodiment of an infusion pump.

Referring now to FIGS. 1A and 1B, one embodiment of a device 100 is shown. The device 100, in the illustrative embodiment, is an infusion pump, which may be any infusion pump, however, in some embodiments, may be one of the embodiments of the infusion pumps shown and described in U.S. Publication No. US-2007-0228071, published Oct. 4, 2007 (E70) or U.S. Publication No. US-2009-0299277-A1 published Dec. 3, 2009. However, and as discussed above, in various other embodiments, the device may be any medical device and in some embodiments, one or more devices are included in a system.

The device 100 includes a reusable portion 102 and a disposable portion 104. In various embodiments, disposable portion 104 includes a reservoir and a fluid line, i.e., the "wetted" components of an infusion pump. In some embodiments, the disposable portion 104 includes a tab 116.

Figure 3:
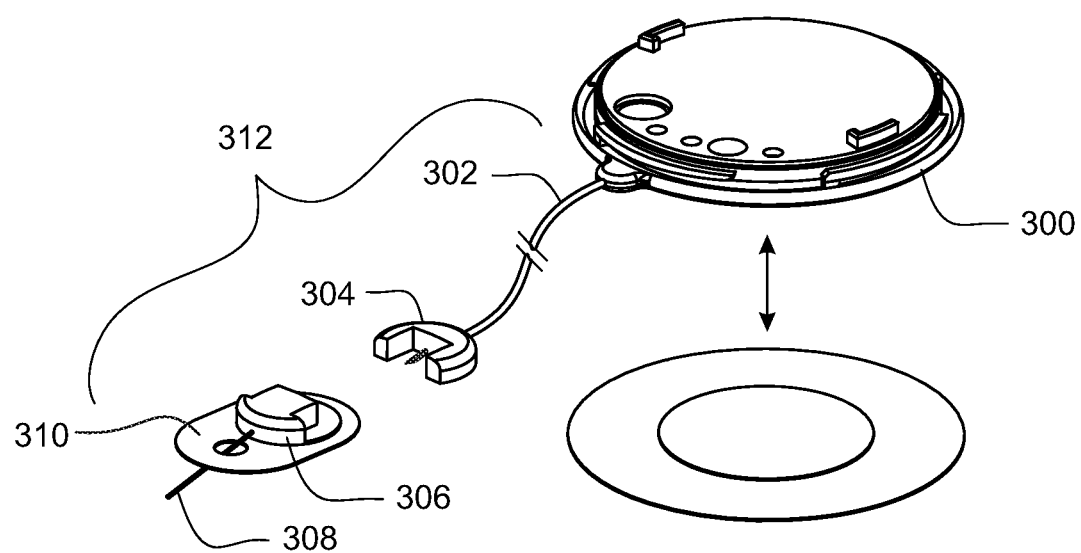
FIG. 3 is a perspective view of one embodiment of the infusion pump disposable portion showing an external infusion set.

The reusable portion 102 includes mechanical and electrical components 108 configured to cause fluid in the reservoir to be pumped from the reservoir to the tubing 106 which may be connected to a cannula (not shown, shown in FIG. 3 as 308). In some embodiments, the reusable portion 102 may include a locking ring assembly 110 and a position nub 808 that may facilitate rotation of the locking ring assembly 110. The reusable portion 102 may be releasably engaged to the disposable portion 104 which may be effectuated by, for example, but not limited to, a screw-on, twist-lock, or compression fit configuration, or other configuration. In some embodiments, the reusable portion 104 may be properly positioned relative to the disposable portion 102, and locking ring assembly 110 may be rotated to releasable engage the reusable portion 104 to the disposable portion 102.

Figure 4A:
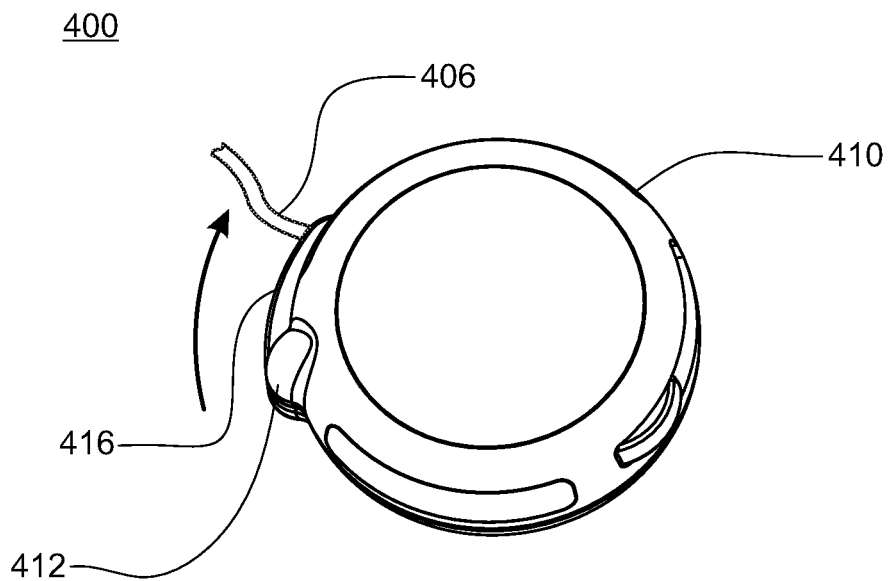
FIGS. 4A and 4B depict an embodiment of an infusion pump.
Figure 4B:
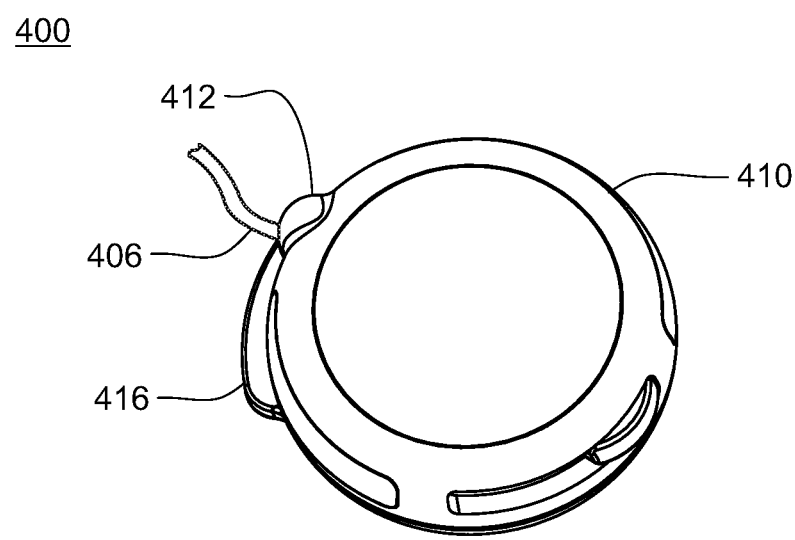

Additionally, the position of nub 112, e.g., relative to tab 116 of disposable housing assembly 104, may provide verification that the reusable portion 102 is fully engaged with the disposable portion 104. For example, as shown in FIG. 4A, when the reusable portion 402 is properly aligned with the disposable portion 104, the nub 412 may be aligned in a first position, relative to the tab 416. Upon achieving a fully engaged condition, by rotation of the locking ring assembly 410 (direction of rotation shown by arrow in FIG. 4A), the nub 412 may be aligned in a second position relative to the tab 416, as shown in FIG. 4B.

Figure 2:
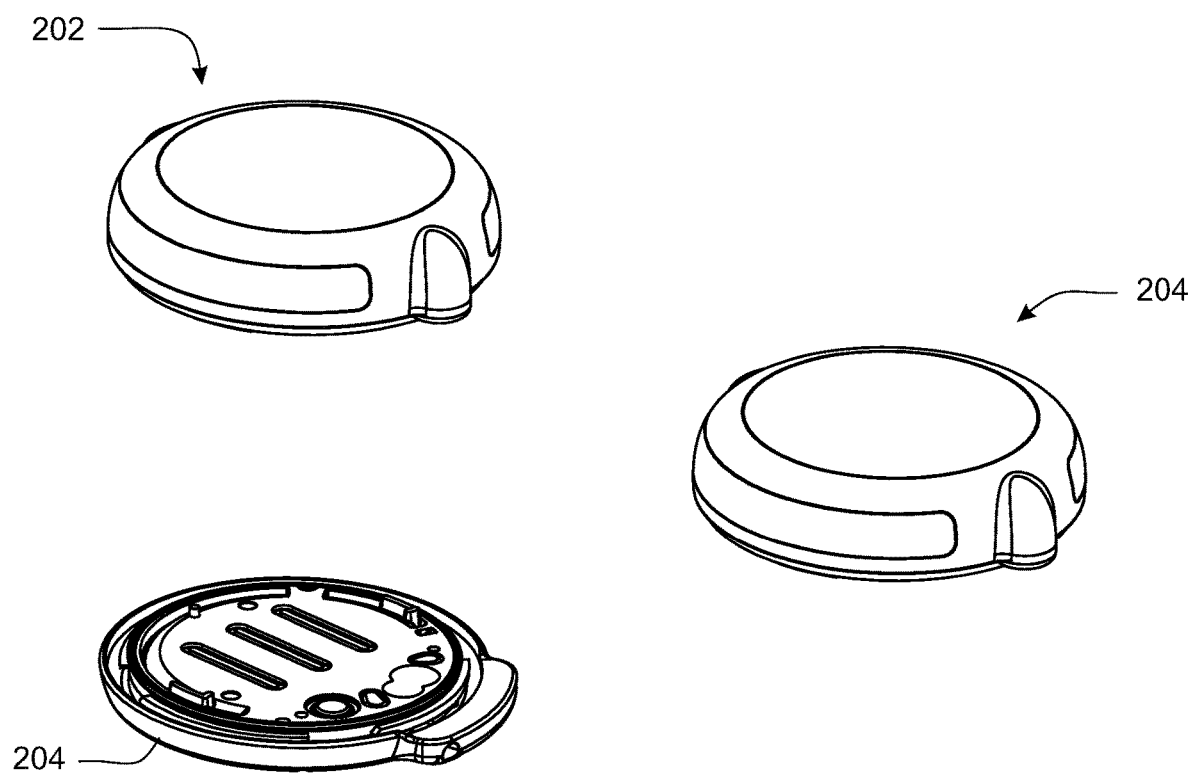
FIG. 2 is an exploded view of an embodiment of an infusion pump and a second reusable portion.

Referring now also to FIG. 2, in some embodiments of the system, the system may include one or more devices, and in some embodiments, the system may include two devices 200, 202. In some embodiments of the system, the system may include two reusable portions 200, 202 and at least one disposable portion 204. The reusable portions 200, 202 and the disposable portion 204 may be, in some embodiments, the embodiments of the device 100 described above. In some embodiments of the system, the system may include two reusable portions 200, 202 that may each include rechargeable power device, e.g., a rechargeable battery. Therefore, in some embodiments, while one reusable portion 200 is connected to a disposable portion 204 and in use by a user, the other reusable portion 202 may be recharged. Thus, in some embodiments, the system may include a backup device that may be recharged or serviced while the other device is in use.

Referring also to FIG. 3, in some embodiments, the disposable portion 300 includes a tubing 302 which may include a male connector 304 connected to the tubing 302. The male connector 304, in some embodiments, is configured to be connected to a female connector 306. The completed connection of the male connector 304 to the female connector 306 provides a fluid pathway from the tubing 302 to the cannula 308 and therefore from the reservoir to the cannula. The cannula 308 may be held in place on a user by a cannula adhesive pad 310. The tubing 302, male connector 304, female connector 306, cannula 308 and cannula adhesive pad 310 may collectively be referred to as an infusion set 312. In some embodiments, the reusable portion 300 may be held onto a user by a patch 314 which may, in some embodiments, may be a disposable adhesive patch (connected to the lower surface of the disposable portion 300 and the adhesive may be exposed and then attached to a user) or a hook and loop fastener patch, for example. In embodiments where the disposable patch is a loop and hook fastener patch (e.g. such as hook and loop fastener systems offered by VELCRO USA Inc. of Manchester, N.H.) the lower surface of the disposable portion 300 may include a complementary hook or loop surface.

Referring now also to FIGS. 5A-5F, in some embodiments, the reusable portion 500 may include an input switch assembly that may be configured to receive user commands (e.g., for bolus delivery, pairing with a remote interface, or the like). The input switch assembly, in some embodiments, may include a button 824 that may be disposed in an opening 526 of the body 520. As shown, e.g., in FIG. 5B, the locking ring assembly 506 may include a radial slot 528 that may be configured to allow the locking ring assembly 506 to be rotated relative to body 520 while still providing facile access to the button 524.

Still referring to FIGS. 5A-5F, electrical control assembly 516 may include printed circuit board 530 as well as battery 532, which in some embodiments may be a rechargeable battery. The printed circuit board 530 may include the various control electronics for monitoring and controlling the amount of infusible fluid that has been and/or is being pumped. For example, the electrical control assembly 516 may measure the amount of infusible fluid that has just been dispensed, and determine, based upon the dosage required by the user, whether enough infusible fluid has been dispensed. If not enough infusible fluid has been dispensed, the electrical control assembly 516 may determine that more infusible fluid should be pumped. The electrical control assembly 516 may provide the appropriate signal to the mechanical control assembly 512 so that any additional necessary dosage may be pumped or the electrical control assembly 516 may provide the appropriate signal to the mechanical control assembly 512 so that the additional dosage may be dispensed with the next dosage. Alternatively, if too much infusible fluid has been dispensed, the electrical control assembly 516 may provide the appropriate signal to the mechanical control assembly 512 so that less infusible fluid may be dispensed in the next dosage. The electrical control assembly 516 may include one or more microprocessors. In an exemplary embodiment, the electrical control assembly 516 may include three microprocessors. One processor (e.g., which may include, but is not limited to a CC2510 microcontroller/radio frequency ("RF") transceiver, available from Chipcon AS, of Oslo, Norway) may be dedicated to radio communication, e.g., for communicating with a remote interface. Two additional microprocessors (example of which may include, but is not limited to an MSP430 microremote interface, available from Texas Instruments Inc. of Dallas, Tex.) may be dedicated to issuing and carrying out commands (e.g., to dispense a dosage of infusible fluid, process feedback signals from a volume measurement device, and the like).

Figure 5A:
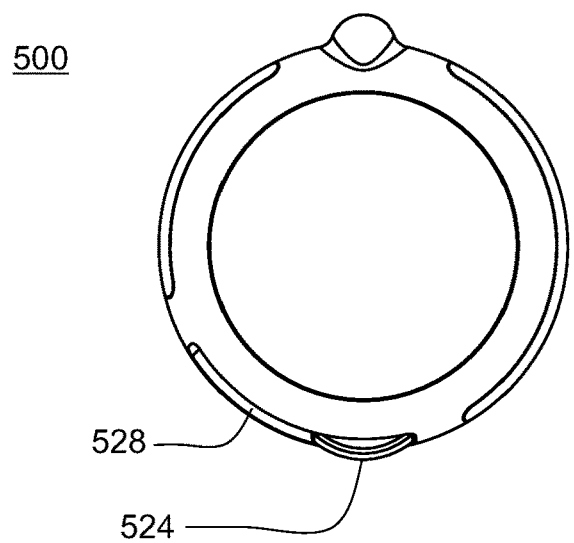
FIGS. 5A-5C depict an embodiment of an infusion pump.
Figure 5B:
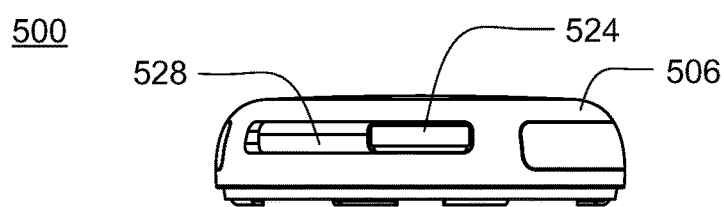
Figure 5C:
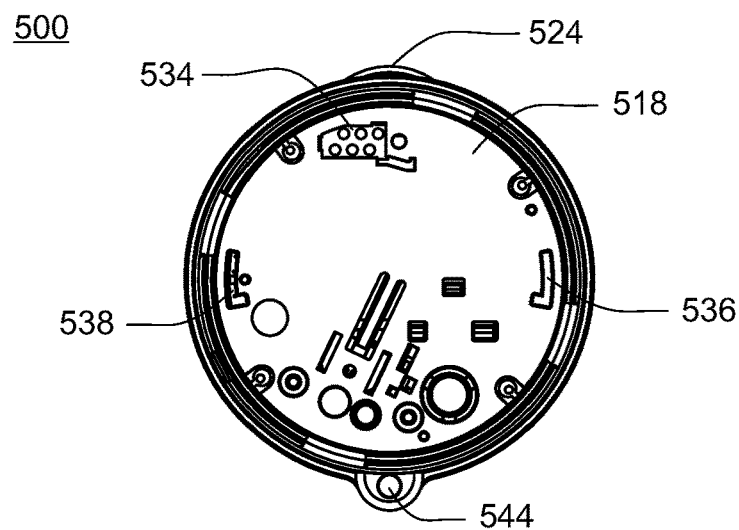
Figure 5D:
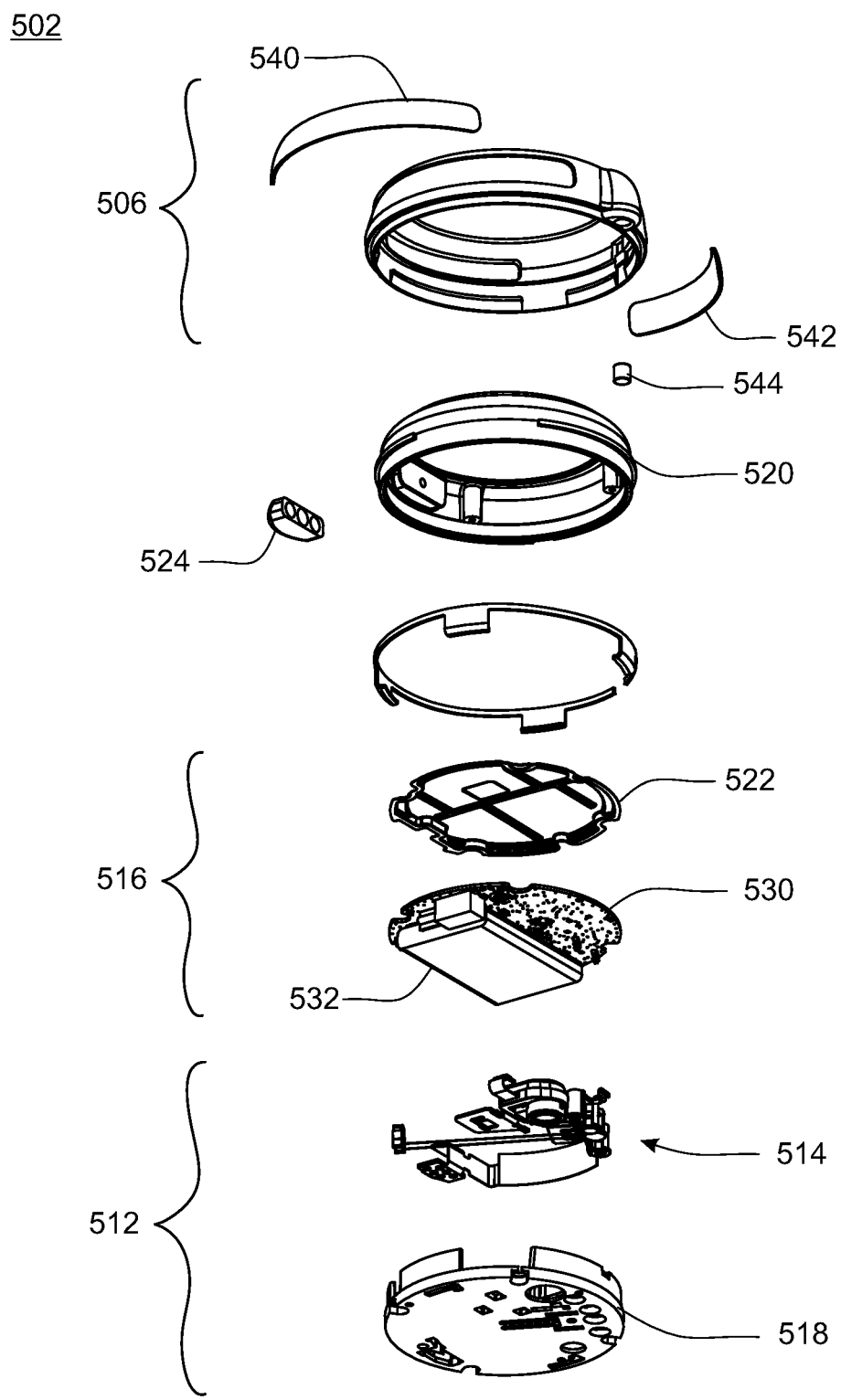
FIG. 5D is an exploded view of an embodiment of a reusable portion.
Figure 5E:
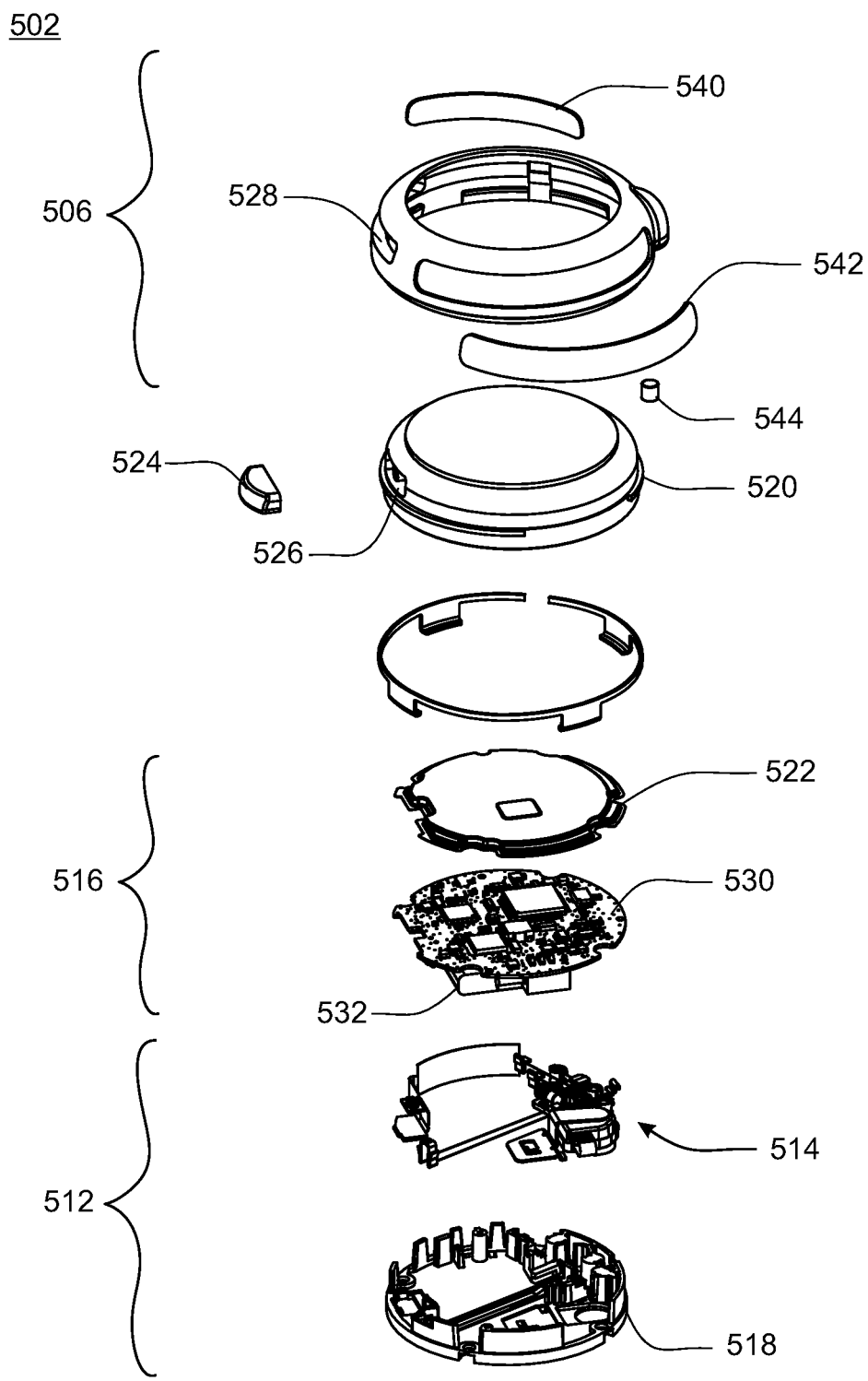
FIG. 5E is an exploded view of an embodiment of a reusable portion.
Figure 5F:
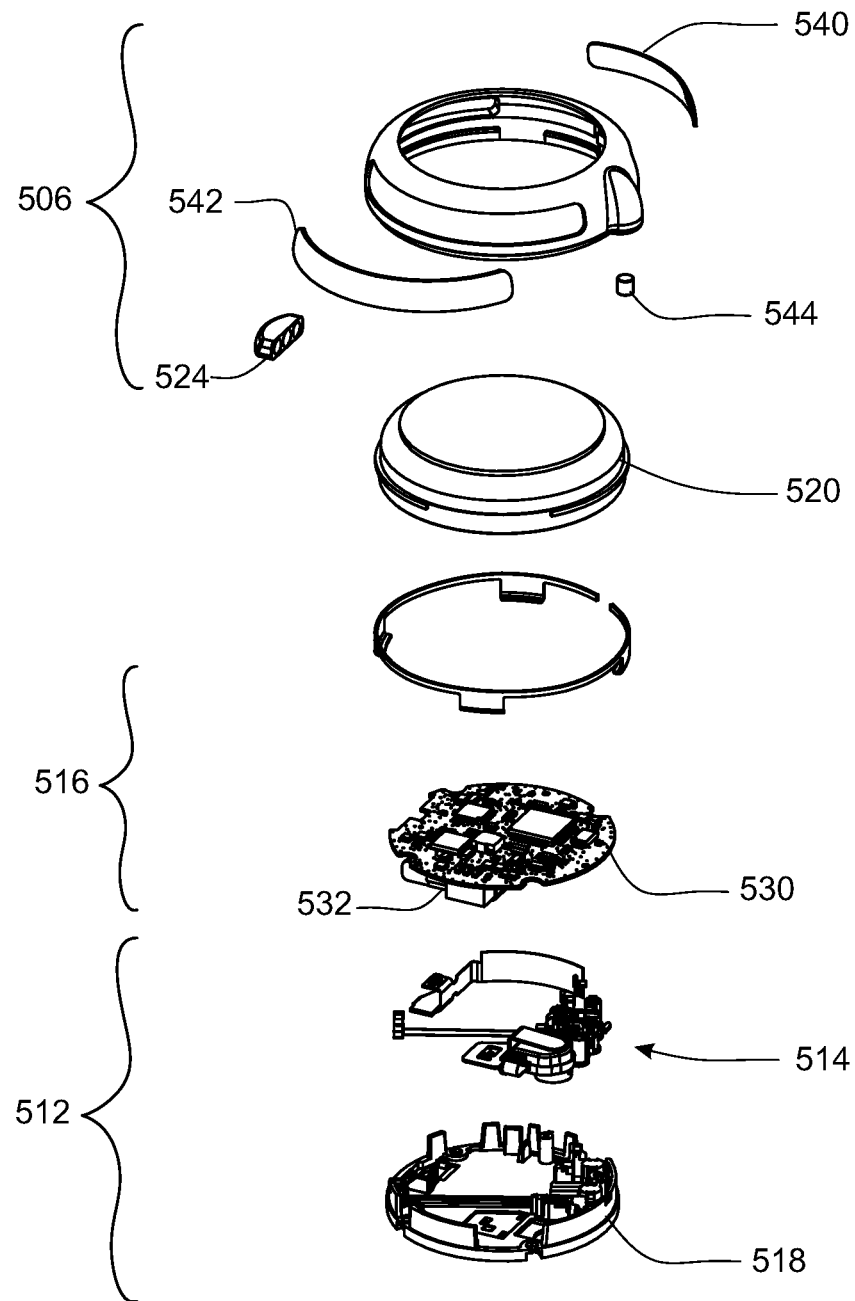
FIG. 5F is an exploded view of an embodiment of a reusable portion.

As shown in FIG. 5C, base plate 518 may provide access to the electrical contacts 534, e.g., which may be electrically coupled to the electrical control assembly 516 for rechargeable battery 532. The base plate 518 may include one or more features (e.g., openings 536, 538) which may be configured to facilitate proper alignment with the disposable housing assembly 504 by way of cooperating features (e.g., tabs) of the disposable housing assembly 504. Additionally, base plate 518 may include various features for mounting a valve assembly 514 and the electrical control assembly 516, as well as providing access to the disposable portion 504 by valve assembly 514 (shown in FIGS. 5D-5F).

The locking ring assembly 506 may include grip inserts 540, 542, e.g., which may include an elastomeric or textured material that may facilitate gripping and twisting the locking ring assembly 506, e.g., for engaging/disengaging the reusable portion 500 and the disposable portion 504. Additionally, the locking ring assembly 506 may include one or more sensing components, which in some embodiments may be a magnet 544, but in other embodiments may be an electrical contact or other sensing component. In various embodiments, the sensing component may interact with one or more components of the reusable portion 500 (e.g., a Hall Effect sensor), e.g., to provide an indication of the nature of a mating component (e.g., which in some embodiments may include, but is not limited to, one or more of the disposable portion 504, a charging station, or a filling station) and/or of whether the reusable portion 500 is properly engaged with the mating component. In some embodiments, a Hall Effect sensor (not shown) may be located on the pump printed circuit board 530. The Hall Effect sensor may detect when the locking ring assembly 506 has been rotated to a closed position. Thus, in some embodiments, the Hall Effect sensor together with the magnet 544 may provide a system for determining whether the locking ring assembly 506 has been rotated to a closed position.

The sensing component (magnet) 544 together with the reusable portion components, i.e., in the some embodiments, the Hall Effect sensor, may work to provide for a determination of whether the reusable portion 500 is properly attached to the intended component or device. In some embodiments, the locking ring assembly 506 may not turn without being attached to a component, which may include, but is not limited to, a disposable portion 504, a dust cover (not shown) or a battery charger (not shown). Thus, the sensing component 544 together with the reusable portion 500 may function to provide many advantageous safety features to the infusion pump system. These features may include, but are not limited to, one or more of the following. Where the system does not detect being attached to a disposable portion 504, a dust cover or a charger, the system may notify, alert or alarm the user as the reusable portion 500, e.g., the valves and pumping components, may be vulnerable to contamination or destruction which may compromise the integrity of the reusable assembly. Thus, the system may provide for an integrity alarm to alert the user of potential reusable integrity threats. Also, where the system senses the reusable assembly is attached to a dust cover, the system may power off or reduce power to conserve power. This may provide for more efficient use of power where the reusable portion is not connecting to a component in which it needs to interact.

Figure 5G:
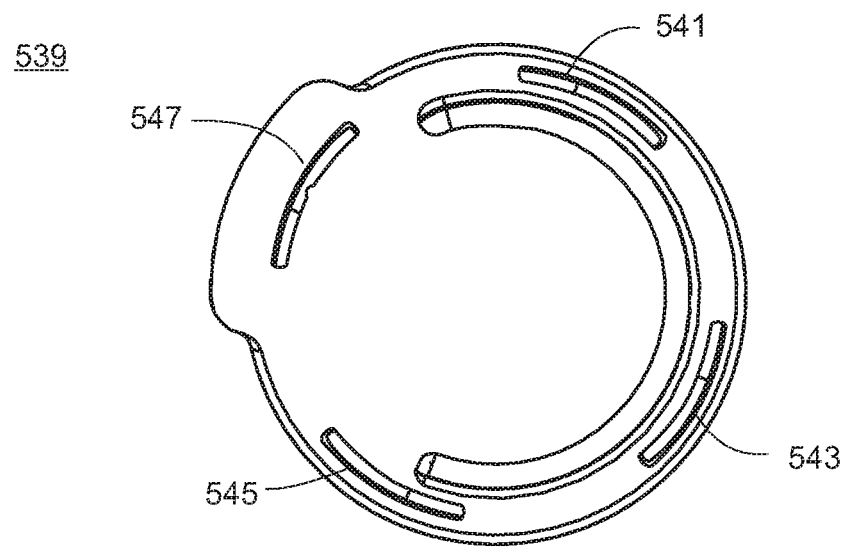
FIGS. 5G-5I are views of an embodiment of a disposable portion.
Figure 5H:
Figure 5I:
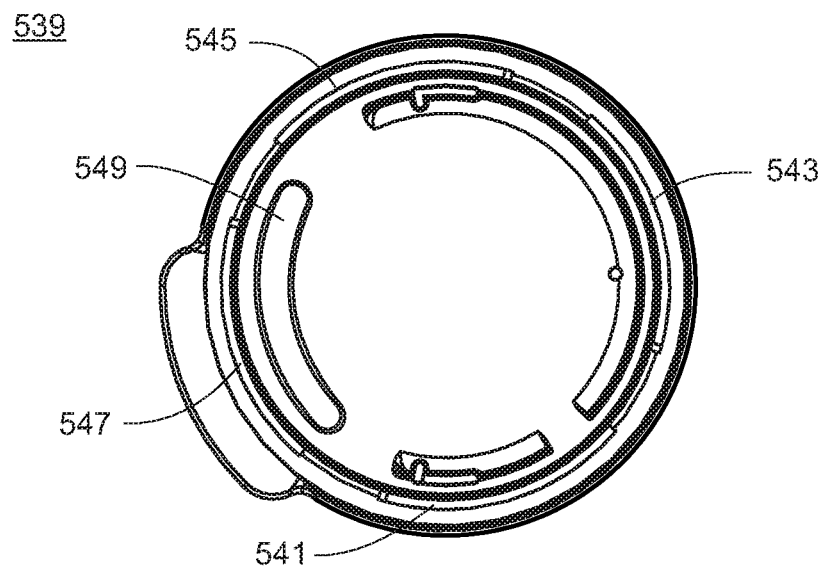

The reusable portion 500 may attach to a number of different components, including but not limited to, a disposable housing assembly, a dust cover or a battery charger/battery charging station. In each case, the Hall Effect sensor may detect that the locking ring assembly 506 is in the closed position, and therefore, that reusable portion 500 is releasably engaged to a disposable portion 504, a dust cover, or a battery charger/battery charging station (or, another component in various embodiments). The infusion pump system may determine the component to which it is attached by using an AVS system, such as one described in the above referenced patent publications and patents, or by an electronic contact. Referring now also to FIGS. 5G-5I, one embodiment of a dust cover (e.g., dust cover 539) is shown. In the exemplary embodiment, dust cover 539 may include features 541, 543, 545, 547 such that the locking ring assembly 506 of the reusable portion 500 may releasably engage the dust cover 539. In addition, the dust cover 539 may further include a recess region 5849 for accommodating the valving and pumping features of reusable portion 500. For example, with respect to the dust cover, the AVS system may determine that a dust cover, and not a disposable portion, is connected to the reusable portion. The AVS system may distinguish using a look-up table or other comparative data and comparing the measurement data with characteristic dust cover or empty disposable portion data. With respect to the battery charger, the battery charger, in some embodiments, may include electric contacts. When the reusable portion is attached to the battery charger, the infusion pump assembly electronic system may sense that the contacts have been made, and will thus indicate that the reusable portion is attached to a battery charger.

Various embodiments of the infusion pump may include, or be similar to, a reservoir assembly configured to contain infusible fluid. In some embodiments, reservoir assembly may be a reservoir assembly similar to that described in U.S. Pat. No. 7,498,563, issued Mar. 3, 2009 and entitled Optical Displacement Sensor for Infusion Devices, which is herein incorporated by reference in its entirety; and/or as described in U.S. Pat. No. 7,306,578, issued Dec. 11, 2007 and entitled Loading Mechanism for Infusion Pump; PCT Application Serial No. PCT/US2009/060158, filed Oct. 9, 2009 and entitled Infusion Pump Assembly, now Publication No. WO 2010/042814, published Apr. 15, 2010; and/or U.S. patent application Ser. No. 12/249,882, filed Oct. 10, 2008 and entitled Infusion Pump Assembly, now U.S. Publication No. US-2010-0094222, published Apr. 15, 2010; and/or U.S. patent application Ser. No. 13/076,067, filed Mar. 30, 2011 and entitled Infusion Pump Methods, Systems and Apparatus, now U.S. Publication No. US-2011-0230837, published Sep. 22, 2011; and/or U.S. patent application Ser. No. 13/121,822, filed Mar. 30, 2011 and entitled Infusion Pump Assembly, now U.S. Publication No. US-2011-0208123, published Aug. 25, 2011; all of which are hereby incorporated herein by reference in their entireties.

In some embodiments, the various embodiments of the infusion pump may include or be similar to one or more described in U.S. Pat. No. 7,306,578, issued Dec. 11, 2007 and entitled Loading Mechanism for Infusion Pump; U.S. patent application Ser. No. 12/249,882, filed Oct. 10, 2008 and entitled Infusion Pump Assembly, now U.S. Publication No. US-2010-0094222, published Apr. 15, 2010; and U.S. patent application Ser. No. 12/249,891, filed Oct. 10, 2008 and entitled Infusion Pump Assembly, now U.S. Publication No. US-2009-0099523 published Apr. 16, 2009, all of which are hereby incorporated herein by reference in their entireties.

In some embodiments, the device, which may be in some embodiments, an infusion pump such as one described above, includes hardware for wireless radio frequency ("RF") communication with a remote interface. However, in various embodiments, the device may be any device and is not limited to an infusion pump. In some exemplary embodiments of the system, the device may include a display assembly, which may include, but is not limited to, one or more of the following: at least one screen or other display including a visual indication to a user; however, in other embodiments, such as those shown in FIGS. 1A-5F, the device may not include a display assembly. In these embodiments, a display assembly may be included on a remote interface. In some embodiments of the system, even if the device includes a display, the system may include a remote interface that also includes a display. Some embodiments of a remote interface are shown in FIGS. 6, 7, 7A and 8.

Referring to the infusion pump system shown in FIGS. 1A-5I, but also to other devices that may be used with the system, the device may include processing logic (not shown), which may be referred to as one or more processors, that execute one or more processes that may be required for the device to operate. Processing logic may include one or more microprocessors (not shown), one or more input/output remote interfaces (not shown), and cache memory devices (not shown). One or more data buses and/or memory buses may be used to interconnect processing logic with one or more subsystems.

Where the system requires an interaction between the user and the device, the interaction may be accomplished using an input either on the remote interface or on the device, for example, in some embodiments, where the device is an infusion pump, the input on the device may be the switch assembly on the infusion pump.

Processing logic, in some embodiments, is used to receive inputs from a user. The user may use one or more input devices or assemblies, including but not limited to, one or more of the following: button/switch assembly, slider assemblies, including, but not limited to, capacitive sliders (which may include, for example, including but not limited to any slider described in U.S. patent application Ser. No. 11/999,268, filed Dec. 4, 2007 and entitled Medical Device Including a Slider Assembly, now U.S. Publication No. US-2008-0177900, published Jul. 24, 2008, which is hereby incorporated herein by reference in its entirety, jog wheel, audio input, tactile input and/or touch screen. In some embodiments, the device may additionally receive inputs from internal systems. These internal systems may include, for example, in embodiments where the device is an infusion pump, these may include, but are not limited to, one or more of the following: occlusion detection processes, confirmation processes, and volume measurement technology, e.g., acoustic volume sensing ("AVS"). Using these inputs, the device, which, in some embodiments may be an infusion pump, may produce outputs, for example including, but not limited to, infusion fluid delivery to the user; and/or these inputs may produce outputs that may include, but are not limited to, one or more of the following: comments, alerts, alarms or warnings to the user. The inputs are thus either directly from the user to the device, directly from the device systems to the processing logic, or from another device or remote interface, to the device. The user interaction experience thus includes, but is not limited to, one or more of the following: interaction with a display (either on the device itself or a remote interface or both), which includes but is not limited to, reading/seeing text and/or graphics on a display, direct interaction with a display, for example, through a touch screen, interaction with one or more buttons, sliders, jog wheels or other inputs, interaction with one or more glucose strip readers, and sensing either through touch sensation or audio, one or more vibration motors, and/or an audio system. Thus, the term "user interface" is used to encompass all of the systems, methods and devices in which a user uses to interact with the device to control and/or receive information from the device.

Figure 6:
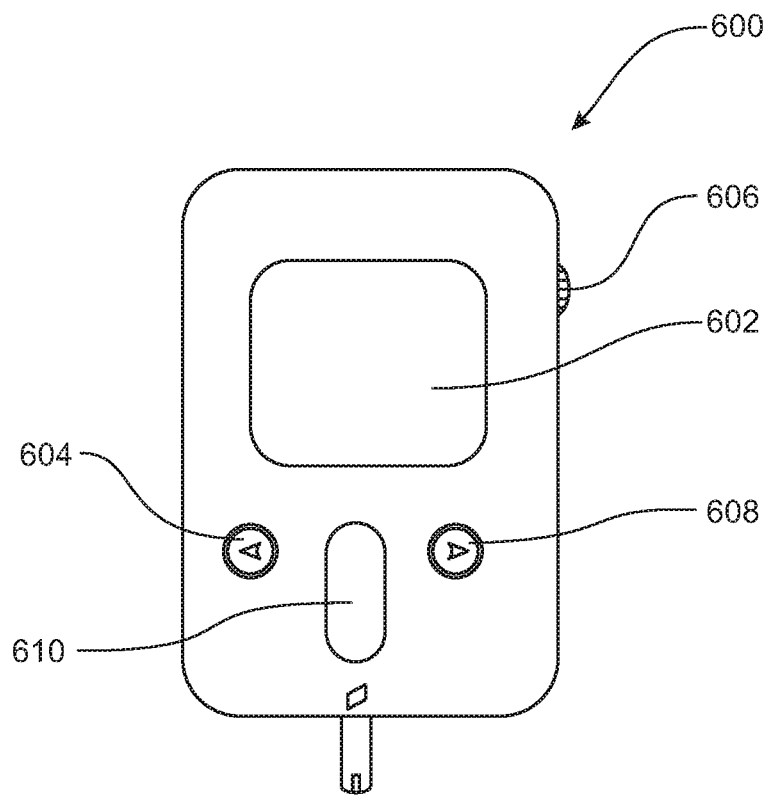
FIG. 6 is a view of an embodiment of a remote interface.
Figure 7A:
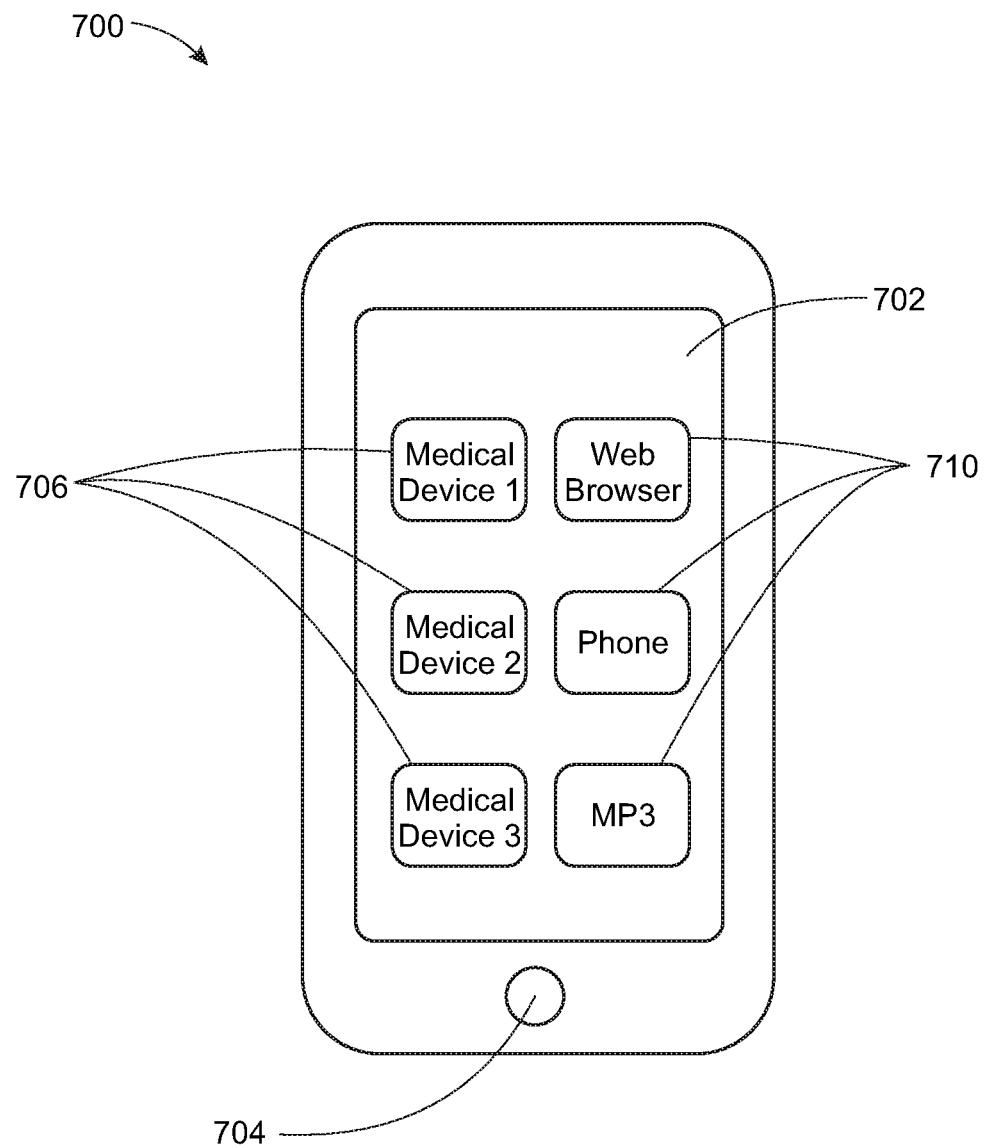
FIGS. 7A and 7B are views of an embodiment of a remote interface.
Figure 7B:
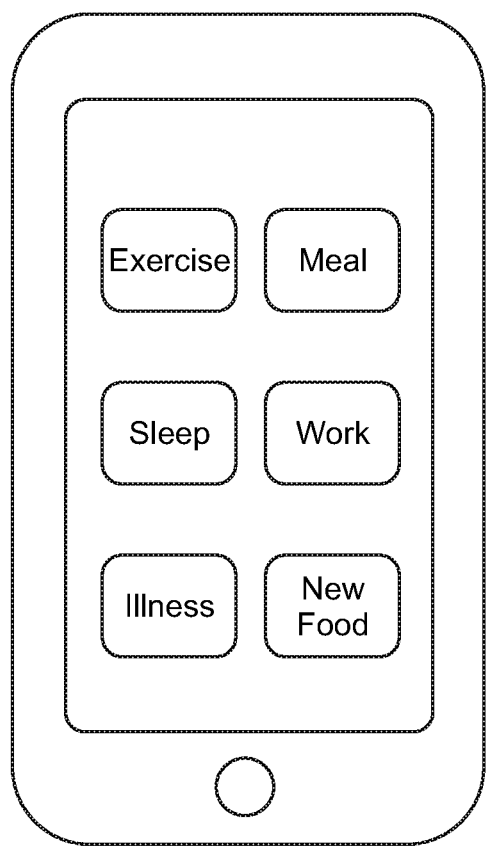

Referring now to FIGS. 6 and 7A-7B, in some embodiments of the infusion pump system, the infusion pump may be remotely controlled using a remote interface 600, 700. Two embodiments of the remote interface are shown, however, in various other embodiments, the remote interface may be any type of device that is capable of interaction with a device, including by way of wireless and/or remote communication. The remote interface 600, 700 may include all, or a portion of, the functionality of the device, which, in some embodiments, may include an infusion pump similar to one shown and described herein with respect to FIGS. 1A-5I. As discussed above, for purposes of description, the device may be described as an infusion pump, however, this disclosure is not limited to an infusion pump. Also, the systems, methods and apparatus described herein may be used with any device.

In some embodiments of the above-described infusion pump, the infusion pump may be configured using a remote interface 600, 700. In these embodiments, the infusion pump may include telemetry circuitry (not shown) that allows for communication (e.g., wired or wireless) between the infusion pump and the remote interface 600, 700, thus allowing the remote interface 600, 700 to remotely control the infusion pump. The remote interface 600, 700 (which may also include telemetry circuitry (not shown) and may be capable of communicating with infusion pump) may include a display assembly 602, 702 and at least one input assembly, which may include one or more of the following: an input control device (such as jog wheel 606, slider assembly 610, or another conventional mode for input into a device), and/or switch assemblies 604, 608, 704. Thus, although the remote interface 600 as shown in FIG. 6 includes a jog wheel 606 and slider assembly 610, some embodiments may include only one of either the jog wheel 606 or the slider assembly 610, or another conventional mode for input into a device. In embodiments having a jog wheel 606, the jog wheel 606 may include a wheel, ring, knob, or the like, that may be coupled to a rotary encoder, or other rotary transducer, for providing a control signal based upon, at least in part, movement of the wheel, ring, knob, or the like.

In some embodiments, the remote interface may include a touch screen and in such embodiments, as depicted in FIGS. 7A and 7B, the touch screen may include one or more icons 706, 710 indicating functions of the remote interface 700. In some embodiments, one or more the icons 706, 710 may relate to launching applications configured to communicate with a device. As shown in FIG. 7A, in some embodiments, one or more icons 706 may indicate one or more devices, which, in some embodiments, may be medical devices (e.g., medical device 1, medical device 2, medical device 3) applications. However, in various embodiments, less than or more than three icons 706 may be included on the remote interface 700. Also, as shown in FIG. 7A, in some embodiments, the remote interface 700 may include icons 710 relating to launching applications related to another functionality of the remote interface 700 (in addition to communicating with at least one device). In some embodiments, these may include, but are not limited to, launching a web browser, launching a cell phone or mobile phone functionality and/or launching an MP3 or other "audio" player functionality. In some embodiments, it may be desirable for the user to "launch" the various functions and/or applications of the remote interface 700. In some embodiments, the non-device related functionalities may be dormant and/or may "sleep" until and unless launched. This may be desirable for many reasons, including, but not limited to, extending the battery life and/or preventing distraction and/or slowing performance with respect to use of the remote interface 700 to communicate with one or more devices. In some embodiments, once a device is paired with the remote interface 700 (as described in more detail below), the application may be automatically launched. In some embodiments, the icons 706 with respect to the devices on the remote interface 700 may indicate that the "application" is "minimized" in the display 702, but the application is active. Thus, in some embodiments, launching of the applications related to the devices using the icons 706 may not be necessary and may be automatic once the remote interface 700 is paired with the device. Referring to FIG. 7B, in some embodiments, the remote interface 700 may include various buttons on the display assembly that are links to add notes and or tags to a logbook. Thus, in some embodiments, when the user taps one of the buttons, a note may open and the user may add a note to the logbook. In some embodiments, tapping the icon may automatically register that event in the logbook.

The various embodiments of the remote interface may include the ability to pre-program basal rates, bolus alarms, delivery limitations, user profiles, etc., and allow the user to view history, logbook, etc and to establish user preferences. In some embodiments, the remote interface may also include a glucose strip reader. However, in various embodiments, where the remote interface does not communicate with an infusion pump, but rather, other devices, the abilities of the remote interface may vary.

During use, in some embodiments, the remote interface 600, 700 may communicate with the infusion pump assembly using a wireless communication channel established between remote interface 600, 700 and the infusion pump. Accordingly, the user may use the remote interface 600,700 to program/configure the infusion pump. In some embodiments, some or all of the communication between remote interface 600, 700 and the infusion pump may be encrypted to provide an enhanced level of security.

In various embodiments of the user interface, the user interface may require user confirmation and/or user input. In some embodiments, the user interface is centered on ensuring the user knows the effect of various interactions with the device. Many examples will be presented throughout this description of the device communicating the result of the user's actions to the user. These features ensure the user understands their actions and therefore, imparts greater safety onto the user. One such example is where a user presses the back button on a screen after a value has been changed; the user interface displays a "Cancel Changes?" confirmation screen. If the user selects "Yes", in various embodiments the user interface discards any pending changes, closes the confirmation screen and goes back to the previous screen (i.e., the screen previous to the screen where the user pressed the Back button). When the action selection is "No", on the "Cancel Changes?" confirmation screen, the user presses the enter button or other depending on the embodiment, and the user interface closes the confirmation screen and returns to the screen with pending changes. This feature prevents the outcome where the user assumes the changes have been implemented, but in fact, they have not been. Thus, this feature prevents that circumstance and ensures the user understands that the changes have not been implemented. This is just one of many examples of the user interface requiring user confirmation and/or input.

Figure 8:
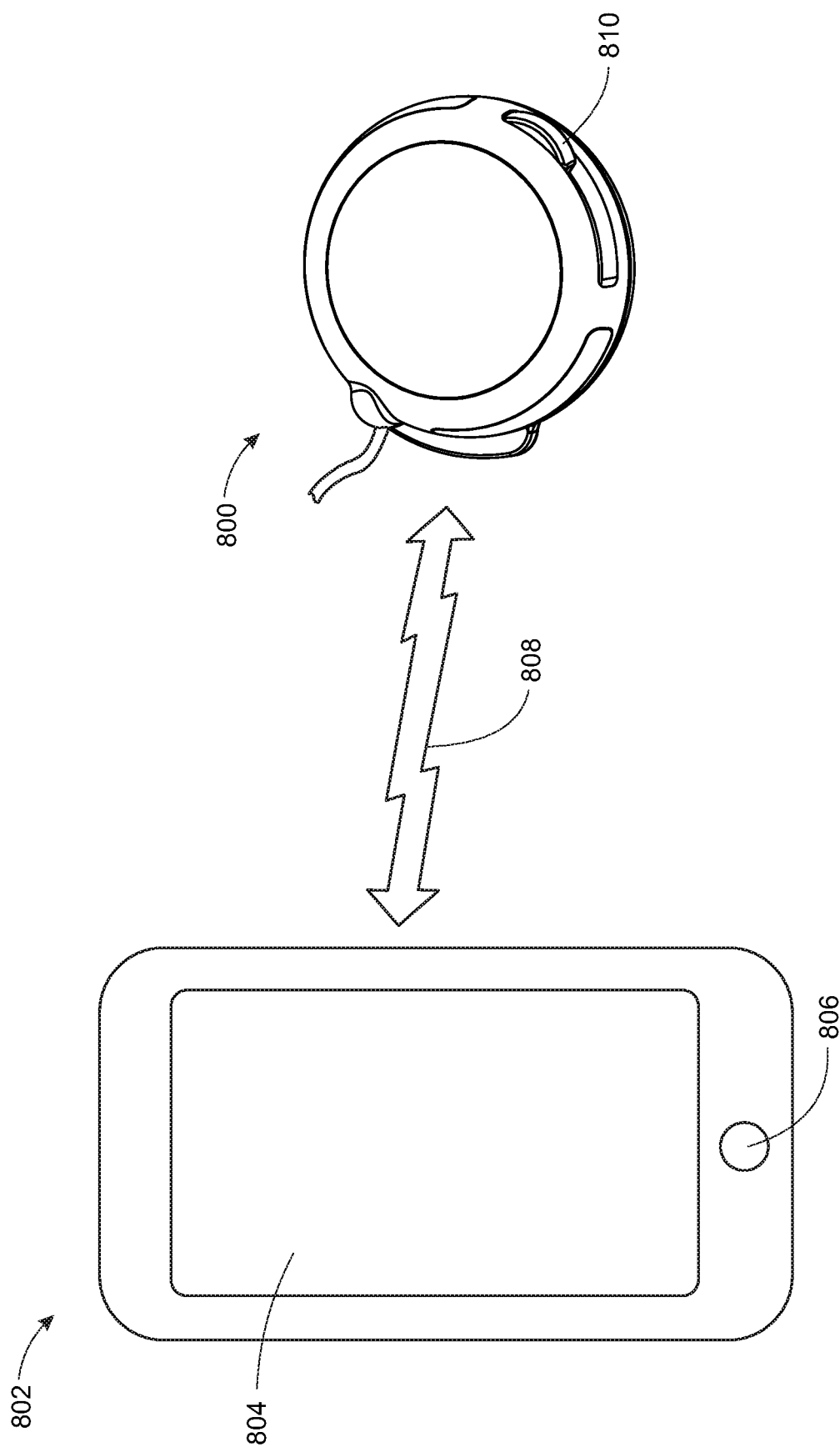
FIG. 8 is a view of an embodiment of the system.

Additionally and referring also to FIG. 8, in some embodiments of the device, the device 800 may be configured by a remote interface 802. In some embodiments, the device 800 may include telemetry circuitry (not shown) that allows for communication (e.g., wired or wireless) between the device 800 and at least one remote interface 802, thus allowing the remote interface 802 to remotely communicate with the device 800. The remote interface 802 (which may also include telemetry circuitry (not shown) and may be capable of communicating with the device 800 may include, in various embodiments, a display assembly 804 and at least one input assembly 806. The input assembly 806 may include at least one switch assembly in some embodiments and in some embodiments may include, but are not limited to, any of one or more of the input assemblies described above. Thus, in some embodiments, the input assembly may include a jog wheel, a plurality of switch assemblies, a capacitive slider or the like.

The remote interface 802 may include the ability to command the device and/or to receive information from the device. In some embodiments, the remote interface 802 may include the ability to view history, receive and view alarms, program limitations, for example, delivery limitations, and/or establish user preferences. In some embodiments, the remote interface 802 may allow the user to view the status of the device which may include the power status, delivery status, values read, alarm status, progress of the device, and/or any other data that may be communicated from the device to the remote interface 802. In some embodiments, the remote interface 802 may include a glucose strip reader and/or a temperature indication device and or other medical functionalities that may be desired to treat and/or to diagnose and/or to provide a medical service to the user.

In some embodiments, the remote interface 802 may provide instructions to the device 800 by way of a wireless communication channel 808 established between the remote interface 802 and the device 800. Accordingly, the user may use remote interface 802 to program/configure the device 800. Some or all of the communication between remote interface 802 and the device may be encrypted to provide an enhanced level of security.

Figure 8B:
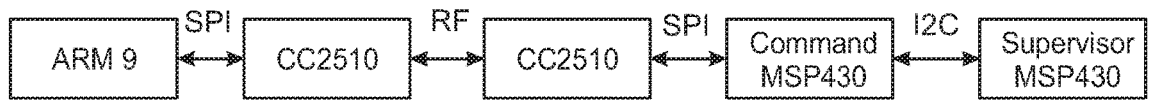
FIGS. 8B-8R depicts various views of high level schematics and flow charts of an embodiment of the system.

Communication between the remote interface 802 and the device 800 may be accomplished utilizing a standardized communication protocol. Further, communication between the various components included the device 800 may be accomplished using the same protocol. One example of such a communication protocol is the Packet Communication Gateway Protocol (PCGP) developed by DEKA Research & Development of Manchester, N.H. As discussed above, the device 800, which, in some embodiments may be an infusion pump, may include an electrical control assembly 516 that may include one or more electrical components. For example, electrical control assembly 516 may include a plurality of data processors (e.g. a supervisor processor and a command processor) and a radio processor for allowing the device 800 to communicate with the remote interface 802. Further, the remote interface 802 may include one or more electrical components, examples of which may include but are not limited to a command processor and a radio processor for allowing the remote interface 802 to communicate with the device 800. A high-level diagrammatic view of one example of such a system is shown in FIG. 8B.

Each of these electrical components may be manufactured from a different component provider and, therefore, may utilize native (i.e. unique) communication commands. Accordingly, through the use of a standardized communication protocol, efficient communication between such disparate components may be accomplished.

Figure 8C:
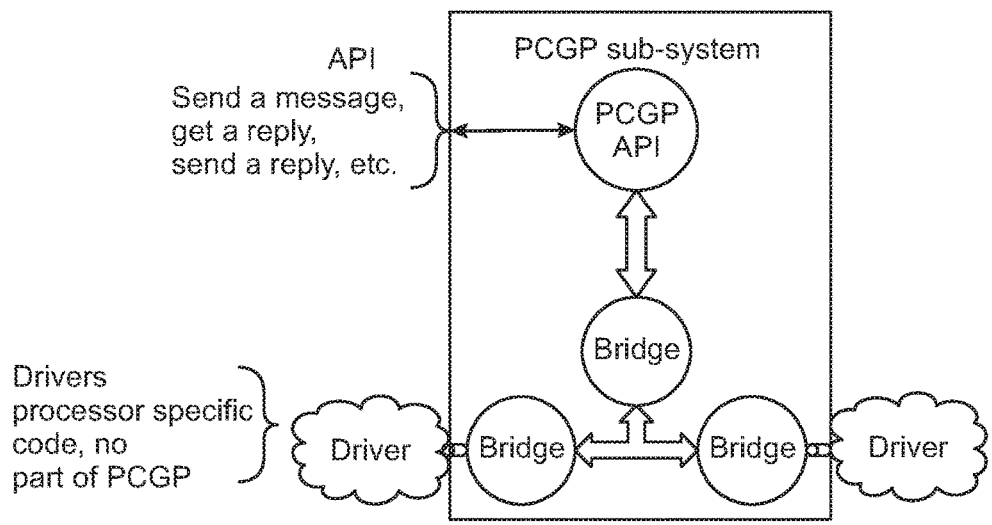

PCGP may be a flexible extendable software module that may be used on the processors within the device 800 and the remote interface 802 to build and route packets. PCGP may abstract the various interfaces and may provide a unified application programming interface (API) to the various applications being executed on each processor. PCGP may also provide an adaptable interface to the various drivers. For illustrative purposes only, PCGP may have the conceptual structure illustrated in FIG. 8C for any given processor.

PCGP may ensure data integrity by utilizing cyclic redundancy checks (CRCs). PCGP may also provide guaranteed delivery status. As a non limiting example, all new messages should have a reply. If such a reply is not sent back in time, the message may time out and PCGP may generate a negative acknowledge reply message for the application (i.e., a NACK). Accordingly, the message-reply protocol may let the application know whether the application should retry sending a message.

In some embodiments, PCGP may also limit the number of messages in-flight from a given node, and may be coupled with a flow-control mechanism at the driver level to provide a deterministic approach to message delivery and may let individual nodes have different quantities of buffers without dropping packets. As a node runs out of buffers, drivers may provide back pressure to other nodes and prevent sending of new messages.

PCGP may use a shared buffer pool strategy to minimize data copies, and may avoid mutual exclusions, which may have a small affect on the API used to send/receive messages to the application, and a larger affect on the drivers. PCGP may use a "Bridge" base class that provides routing and buffer ownership. The main PCGP class may be sub-classed from the bridge base class. In some embodiments, drivers may be derived from a bridge class, or talk to or own a derived bridge class.

Figure 8D:
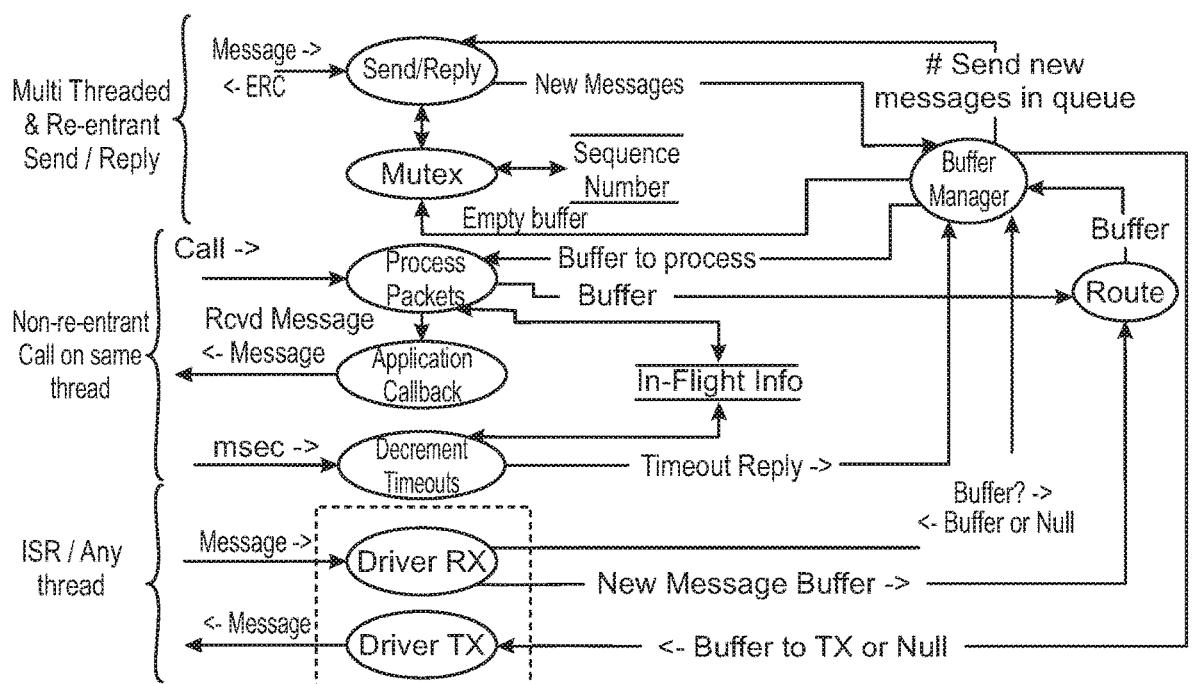

In some embodiments, PCGP may be designed to work in an embedded environment with or without an operating system by using a semaphore to protect shared data such that some calls can be re-entrant and run on a multiple threads. One non-limiting illustrative example of such an implementation is shown in FIG. 8D. PCGP may operate the same way in both environments, but there may be versions of the call for specific processor types (e.g., the ARM 9/OS version). So while the functionality may be the same, in some embodiments, there may be an operating system abstraction layer with slightly different calls tailored for e.g., the ARM 9 Nucleus OS environment.

Figure 8E:
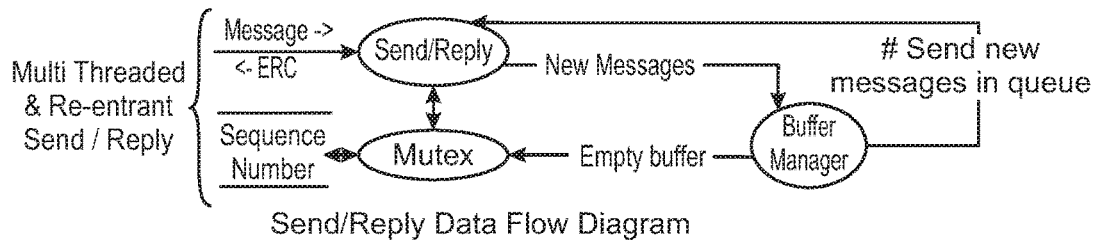

Referring also to FIG. 8E, PCGP may:
allow multiple Send/Reply calls to occur';
have multiple drivers running asynchronously for RX and TX on different interfaces; and/or
provide packet ordering for send/receive, and deterministic timeout on message send.

In some embodiments, each software object may ask the buffer manager for the next buffer to use, and may then give that buffer to another object. Buffers may pass from one exclusive owner to another autonomicly, and queues may occur automatically by ordering buffers by sequence number. In some embodiments, when a buffer is no longer in use, the buffer may be recycled (e.g., object attempts to give the buffer to itself, or frees it for the buffer manager to re-allocate later). Accordingly, in some embodiments, data generally does not need to be copied, and routing simply writes over the buffer ownership byte.

Such an implementation of PCGP may provide various benefits, examples of which may include, but are not limited to:
dropping a message due to lack of buffers may be impossible, as once a message is put into a buffer, the message may live there until it is transferred or received by the application;
data may not need to be copied, as offsets are used to access driver, PCGP and payload sections of a buffer;
drivers may exchange ownership of message data by writing over one byte (i.e., the buffer ownership byte);
there may be no need for multiple exclusions except for re-entrant calls, as a mutual exclusion may be needed only when a single buffer owner could simultaneously want to use a buffer or get a new sequence number;
there may be fewer rules for application writers to follow to implement a reliable system;
drivers may use ISR/push/pull and polled data models, as there are a set of calls provided to push/pull data out of the buffer management system from the drivers;
drivers may not do much work beyond TX and RX, as drivers may not copy, CRC or check anything but the destination byte and CRC and other checks may be done off of the ISR hot path later;
as the buffer manager may order access by sequence number, queue ordering may automatically occur; and
a small code/variable foot print may be utilized; hot path code may be small and overhead may be low.

Figure 8F:
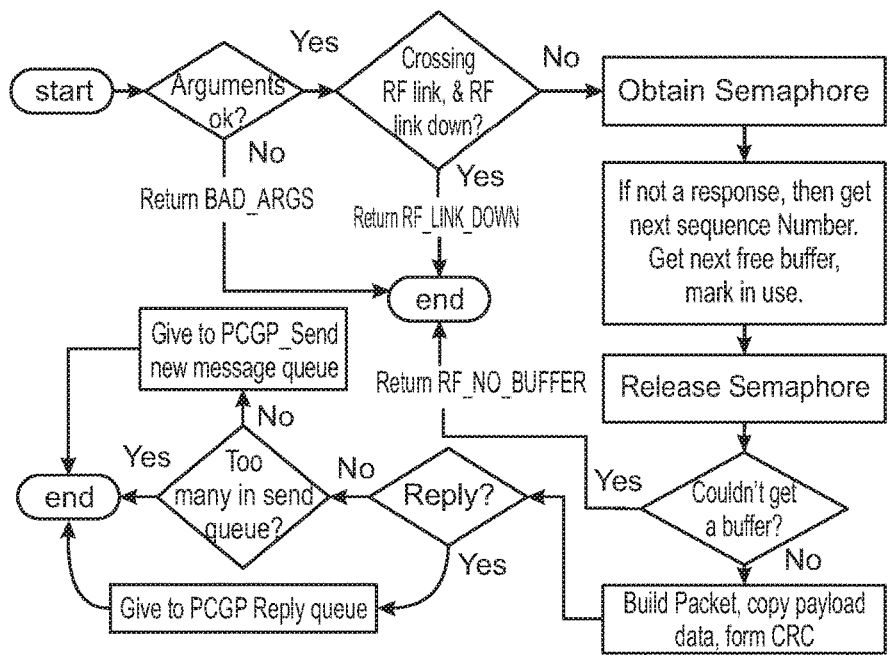

As shown in FIG. 8F, when a message needs to be sent, the PCGP may build the packet quickly and may insert it into the buffer management system. Once in the buffer management system, a call to "packetProcessor" may apply protocol rules and may give the messages to the drivers/application.

To send a new message or send a reply, PCGP may perform one or more of the following:
check the call arguments to e.g., make sure the packet length is legal, destination is ok, etc.;
avoid trying to send a message across a link that is down unless the down link is the radio node, which may allow PCGP to be used by the radio processors to establish a link, pair, etc. and, in some embodiments, may notify the application when PCGP is trying to talk across a link that is not functional (instead of timing out);
obtain a sequence number for a new message or utilize an existing sequence number for an existing message;
build the packet, copy the payload data and write in the CRC, wherein (from this point forward) the packet integrity may be protected by the CRC; and/or
either give the message to the buffer manager as a reply or as a new message, and check to see if putting this buffer into the buffer manager would exceed the maximum number of en-queued send messages.

Figure 8G:
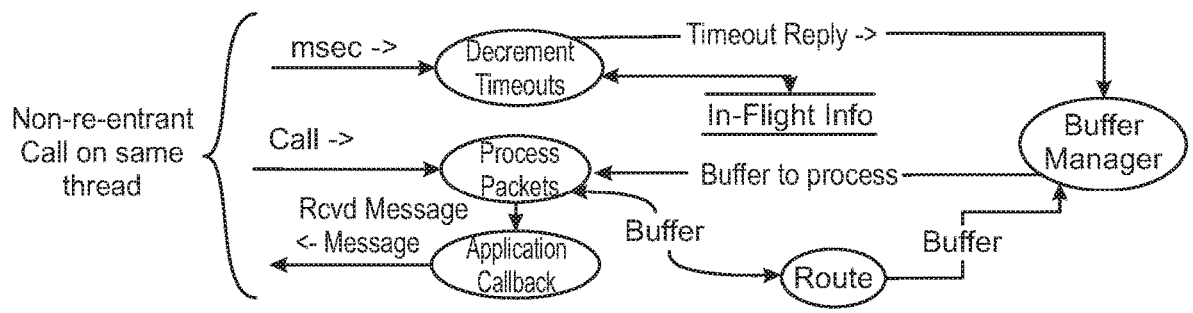
Figure 8H:
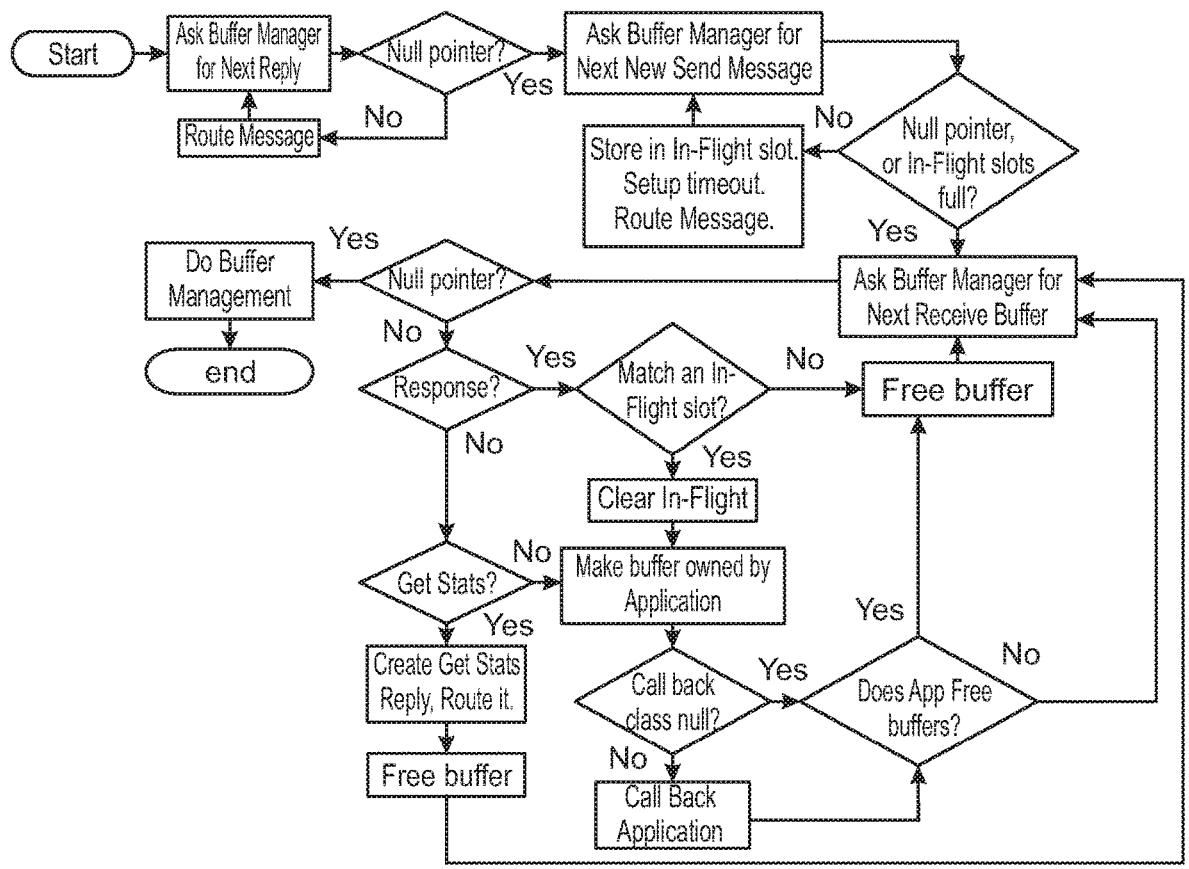

Referring also to FIGS. 8G-8H, in some embodiments, PCGP may work by doing all of the main work on one thread to avoid mutual exclusions, and to avoid doing considerable work on the send/reply or driver calls. The "packetProcessor" call may have to apply protocol rules to replies, new sent messages, and received messages. Reply messages may simply get routed, but new messages and received messages may have rules for routing the messages. In each case, the software may loop while a message of the right type is available to apply protocol rules until it cannot process the packets.

Sending a new message may, in some embodiments, conform to one or more of the following rules:
only two messages may be allowed "in-flight" on the network; and/or
enough data about an in-flight message may be stored to match the response and handle timeout.

Receiving a message may conform to the following rules:
responses that match may clear out the "in-flight" information slot so a new packet may be sent;
responses that do not match may be dropped;
new messages may be for the protocol (e.g., getting/clearing network statistics for this node);
to receive a message, the buffer may be given up to the application and may use a call back; and/or
the buffer may be freed or left owned by the application.

Accordingly, in some embodiments, PCGP may be configured such that:
the call back function may copy the payload data out or may use it completely before returning;
the call back function owns the buffer and may reference the buffer and the buffer's payload by the payload address, wherein the message may be processed later;
applications may poll the PCGP system for received messages; and/or
applications may use the call back to set an event and then poll for received messages.

The communication system may have a limited number of buffers. When PCGP runs out of buffers, drivers may stop receiving new packets and the application may be told that the application cannot send new packets. To avoid this and maintain optimal performance, the application may try to perform one or more procedures, examples of which may include but are not limited to:

a) The application may keep PCGP up to date with radio status. Specifically, in some embodiments, if the link goes down and PCGP does not know, PCGP may accept and queue new messages to send (or not timeout messages optimally), which may jam the send queue and delay the application from using the link optimally;

b) The application may call "decrement timeouts" regularly. Optimally, in some embodiments, the application may call "decrement timeouts" every 20-100 milliseconds unless the processor is asleep. In general, a message moves fast (milliseconds) slow (seconds) or not at all. Timeouts, in some embodiments, are an attempt to remove "in-flight" messages that should be dropped to free up buffers and bandwidth. Doing this less often may delay when a new message gets sent, or when the application can queue a new message;

c) The application may ask PCGP if it has work to do that is pending before going to sleep. Thus, in some embodiments, if PCGP has nothing to do, driver activity may wake up the system and thus PCGP, and then PCGP will not need a call to "packetProcessor" or "decrement timeouts" until new packets enter the system. In some embodiments, failure to do this may cause messages that could have been sent/forwarded/received successfully to be dropped due to a timeout condition;

d) The application may not hold onto received messages indefinitely: The message system relies on prompt replies. If the application is sharing PCGP buffers, then holding onto a message means holding onto a PCGP buffer. In some embodiments, the receiving node does not know if the sending node has timeout configured for slow or fast radio. This means that when a node receives a message it should assume the network's fast timeout speed; and/or e) The application may call the "packetProcessor" often. In some embodiments, the call may cause new messages queued by the application to get sent and may handle receipt of new messages. The call may also cause buffers to re-allocate and calling it infrequently may delay message traffic.

Figure 8I:
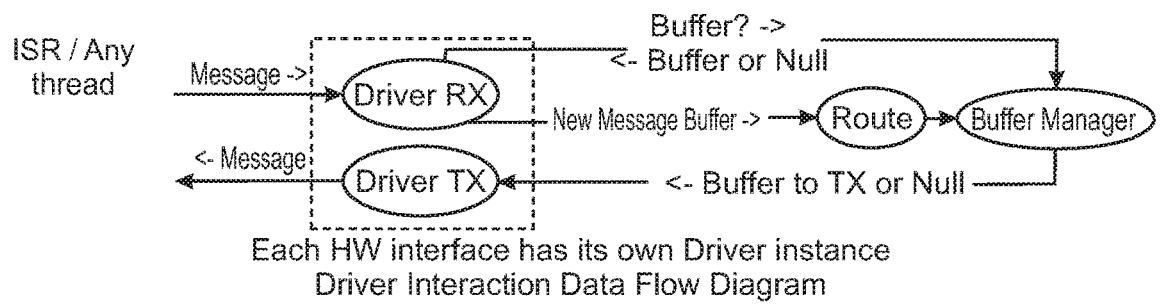

As shown in FIG. 8I, in some embodiments, at some point the RX driver may be asked to receive a message from the other side of the interface. To ensure a message does not get dropped, in some embodiments, the RX driver may ask the buffer manager if there is an available buffer for storing a new message. The driver may then ask for a buffer pointer and may start filling the buffer with received data. When a complete message is received, the RX driver may call a function to route the packet. The route function may examine the destination byte in the packet header and may, in some embodiments, perform one or more of the following: change the owner to either the other driver, and/or the application, and/or may detect that the packet is bad and may drop the packet by freeing the buffer.

PCGP RX overhead may include asking for the next available buffer and calling the route function. A non-limiting example of code that performs such a function is as follows:

```
@ Receive request
uint8 i=0, *p;
if (Bridge::canReceiveFlowControl( ) )
{
    p = Bridge::nextBufferRX( );
    while (not done) { p[i] = the next byte; }
    Bridge::route(p);
}
```

A driver may perform a TX by asking the buffer manager for the pointer to the next buffer to send. The TX driver may then ask the other side of the interface if it can accept a packet. If the other side denies the packet, the TX driver may do nothing to the buffer, as its status has not changed. Otherwise, the driver may send the packet and may recycle/free the buffer. A non-limiting example of code that performs such a function is as follows:

```
uint8 *p = Bridge::nextBufferTX( );
if (p != (uint8 *)0)
{
    send the buffer p;
    Bridge::recycle(p);
}
```

To avoid forwarding packets that are past the maximum message system timeout time, in some embodiments, asking for the nextBuffer may call the BufferManager:first(uint8 owner) function that may scan for buffers to free. Accordingly, full TX buffers where a timeout is unlikely, may be freed on the thread that owns the buffer. In some embodiments, a bridge that is doing TX (i.e., while looking for the next TX buffer) may free all of the TX buffers that are expired before receiving the next TX buffer for processing.

Figure 8J:
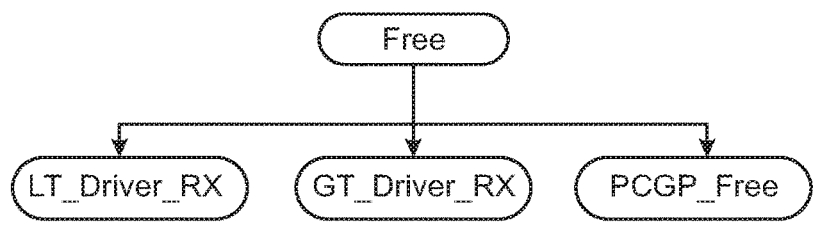
Figure 8K:
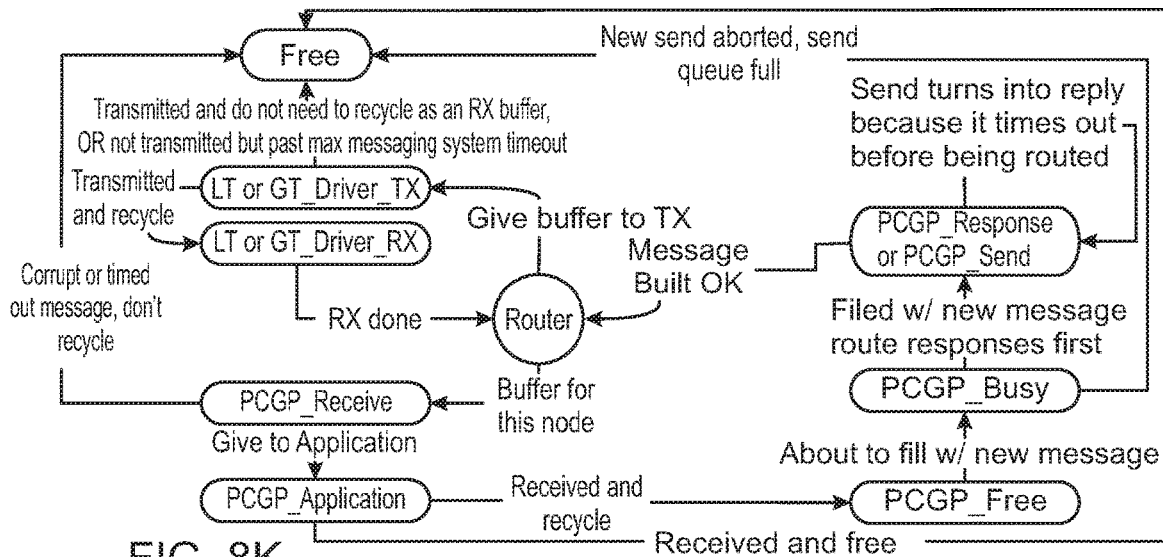
Figure 8L:

As shown in FIG. 8J-8L, in some embodiments, during the buffer allocation process, buffers marked free may be transferred to the drivers to receive new packets, or to PCGP to receive new payloads for TX. Allocation from "free" may be done by the "packetProcessor" function. The number of sends and receives between "packetProcessor" calls may dictate how many LT_Driver_RX, GT_Driver_RX and PCGP_Free buffers need to be allocated. LT_Driver may represent drivers that handle addresses that are less than the node address. GT_Driver may represent drivers that handle addresses that are greater than the node address.

When a driver receives a packet, the driver may put the data into an RX buffer that gets handed to the router. The router may then reassign the buffer to PCGP_Receive or to the other driver's TX (not shown). If the buffer contains obviously invalid data, the buffer may transition to free.

After a router marks a buffer for TX, the driver may discover the buffer is TX and may send the message. After sending the message, the buffer may immediately become an RX buffer if the driver was low in RX buffers, or the buffer may be freed for re-allocation.

During the "packetProcessor" call, PCGP may process all buffers that the router marked as PCGP_Receive. At this point, data may be acted upon, so the CRC and other data items may be checked. If the data is corrupted, a statistic may be incremented and the buffer may be freed. Otherwise, the buffer may be marked as owned by the application. Buffers marked as owned by the application may be either recycled for the use of PCGP or freed for reallocation by the buffer manager.

In some embodiments, when the application wants to send a new message, it may be done in a re-entrant friendly/mutual exclusion manner. If the buffer may be allocated, PCGP may mark the buffer as busy. Once marked busy, no other thread calling the send or reply functions may grab this buffer, as it is owned by this function call's invocation. The remainder of the process of error checking and building the message may be done outside the isolated race condition mutual exclusion guarded code. The buffer may either transition to free or may become a valid filled CRC-checked buffer and passed to the router. In some embodiments, these buffers may not be routed immediately and may be queued so that messages may be sent later (assuming that protocol rules allow). Reply messages may be marked differently than new send messages because reply messages may be routed with a higher priority than regular send messages and reply messages may have no rules limiting how many/when they can be sent.

In some embodiments, the PCGP works with flow control, and flow control may negotiate the transfer of messages from one node to another node so that a buffer is never dropped because the other side of an interface lacks a buffer (which may cause back pressure on the sending node).

Flow control may be part of the shared buffer format. In some embodiments, the first two bytes may be reserved for the driver so that the driver never needs to shift the packet bytes. Two bytes may be used so that one byte is the DMA length−1, and the second byte is to control the flow of messages. These same two bytes may be synchronizing bytes if a PCGP message is transmitted over RS232. Various other configurations and sizes may be used in various embodiments.

In some embodiments, when a packet is "in-flight", the packet may be in the process of being sent by a driver on the way to its destination, being processed by the destination, or being sent back as a response.

Typical delays are as follows:

| Interface/Delay cause | Delay (seconds) | Notes |
| --- | --- | --- |
| SPI | <3 | Roughly 400 kbps |
| I2C | <1 | |
| Waking a CC2510 | <6? | Clock calibration, min. sleep time. |
| Flow control | <0.2 | |
| RF link | 20 to 2000 | |
| Interference/separation | Minutes, never | |

Accordingly, in some embodiments, messages tend to complete the round trip either quickly (e.g., <50 ms); slowly (e.g., one or more seconds); or not at all.

In various embodiments, PCGP may use two different times (set at initialization) for all timeouts, one for when the RF link is in fast heartbeat mode, and another for when the RF link is in slow mode, however, in other embodiments, the PCGP may use more or less than two different times. In some embodiments, if a message is in-flight and the link status changes from fast to slow, the timeout may be adjusted and the difference between fast and slow may be added to the time-to-live counter for the packet. No additional transitions back and forth may affect the time-to-live time for the message.

In some embodiments, there is a second timeout that may be twice as long as the slow timeout that is used to monitor buffer allocation inside PCGP. Accordingly, if a message is "stuck" inside a driver and has not been sent due to e.g., flow control or hardware damage, the buffer may be freed by the buffer manager, resulting in the buffer being dropped. For a "new" message, this may mean that the packet already timed out and the application was already given a reply saying the message wasn't delivered, resulting in the buffer being freed. Since the driver polls the buffer manager for buffers that need to be sent, the buffer is freed up so that a message that could be sent is handed to the driver the next time that it unblocks. For a reply message, the reply may simply get dropped and the sending node may time out.

In some embodiments, the PCGP messaging system may pass messages that contain header information and payload. However, in various embodiments, the PCGP messaging system may pass messages that contain different information. Outside of PCGP, the header may be a set of data items in a call signature. In some embodiments, however, internal to PCGP, there may be a consistent, driver friendly byte layout. In some embodiments, drivers may insert bytes either into the PCGP packet or before the PCGP packet such:

DE, CA: Synch bytes for use with RS232, nominal value of 0xDE, 0xCA or 0x5A, 0xA5.

LD: Driver DMA length byte, equals amount driver is pushing in this DMA transfer, which is the total size, not including the size byte or synch bytes.

Cmd: Driver command and control byte used for flow control.

LP: PCGP packet length, always the total header+payload size in bytes+CRC size. LD=LP+1.

Dst: Destination address.

Src: Source address

Cmd: Command byte

Scd: Sub command byte

AT: Application Tag is defined by the application and has no significance to PCGP. It allows the application to attach more information to a message e.g., the thread from which the message originated.

SeqNum: thirty-two bit sequence number is incremented by PCGP for a new message sent, guarantees the number will not wrap, acts as a token, endianess isn't relevant.

CRC16: A sixteen bit CRC of the PCGP header and payload.

An example of a message with no payload, cmd=1, subcmd=2 is as follows:

0xDE, 0xCA, 0xC, 0x5, 0x14, 1, 2, 0, 0, 0, 0, 0x1, crchigh, crclow.

0x0D, cmd, 0xC, 0x5, 0x14, 1, 2, 0, 0, 0, 0, 0x1, crchigh, crclow.

There may be several advantages to this methodology, examples of which may include but are not limited to:

In various embodiments, most of the hardware DMA engines may use the first byte to define how many additional bytes to move, so in this methodology, drivers and PCGP may share buffers.

A byte may be provided right after the DMA length to pass flow control information between drivers.

Driver length and "Cmd" byte may be outside the CRC region so they may be altered by the driver, may be owned by the driver transport mechanism, and the driver may guard for invalid lengths.

There may be a separate PGCP packet length byte that is CRC protected. Accordingly, the application may trust that payload length is correct.

The endianness of the sequence number may not be relevant, as it is just a byte pattern that may be matched that happens to also be a thirty-two bit integer.

The sequence number may be four bytes aligned to the edge of the shared buffer pool length.

There may be optional RS232 synchronizing bytes so that users may move cables around while debugging a message stream and both sides of the interface may resynchronize.

The application, driver and PCGP may share buffers and may release them by pointer.

Figure 8M:
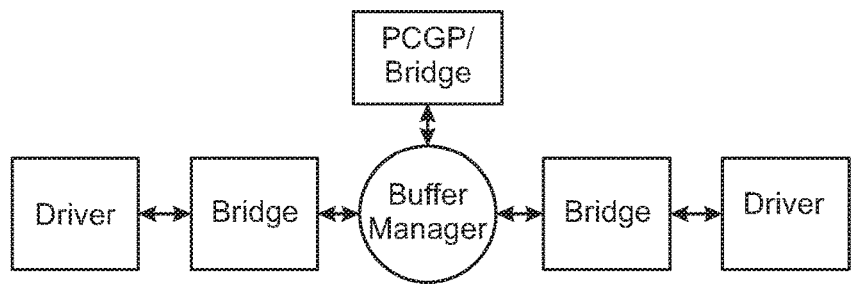
Figure 8N:
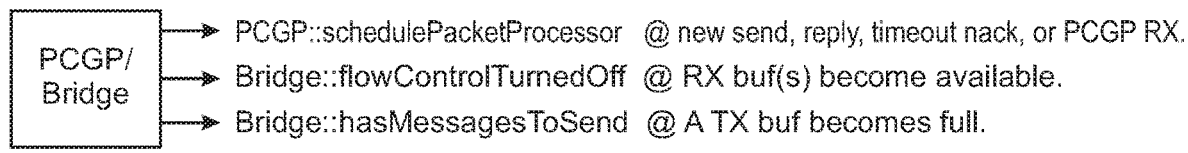

Although, in some embodiments, PCGP may not be an event driven software design, but it may be used in event driven architectures by how the sub-classes are written. Data may be exchanged between the classes conceptually (as shown in FIG. 8M-8N).

In some embodiments, some event model in the driver may wake the driver, may receive a message and may pass the message through the bridge into the buffer manager that routes the message to new owner of the new message (through a bridge to either a driver or PCGP).

The following summarizes some exemplary events:

| Event: | Possible use: | Where this occurs: |
|---|---|---|
| When a new send or reply is queued, or decTimeouts generates a timeout reply. | Decide to run packetProcessor. | Inside PCGP::sendInternal |
| When a messages is received for PCGP. | Decide to run packetProcessor. | BufferManager::give |
| When a driver has something new to send. | Wake driver for TX. | BufferManager::give |
| When a Driver RX buffer becomes available. | Turn off flow control. | BufferManager::give |

The following illustrative example shows how the PCGP event model may work with Nucleus to wakeup the PCGP task after every message send, reply, or decTimeout that generated a NACK:

```
class PcgpOS : public Pcgp
{
  virtual void schedulePacketProcessor(void)
  {
    OS_EventGrp_Set(g_RCVEvGrps[EVG_RF_TASK].pEvgHandle,
      RfRadioTxEvent, OS_EV_OR_NO_CLEAR);
  }
}
```

The following is a pseudo code driver that is event based, illustrating how driver events work. The Driver subclasses Bridge and overrides hasMessagesToSend and flowControl-TurnedOff to schedule the TX and RX functions to run if they are not already running.

```
class SPI_Driver : public Bridge
{
  virtual void hasMessagesToSend( )
  {
    Trigger_ISR(TX_ISR, this);
  }
  virtual void flowControlTurnedOff( )
  {
    Trigger_ISR(RX_ISR, this);
  }
  static void TX_RetryTimer( )
  {
    Trigger_ISR(TX_ISR, this);
  }
  static void TX_ISR(Bridge *b)
  {
    DisableISRs( );
    do
    {
      uint8 *p = b->nextBufferTX( );
      if (p == null) break;
      if (b->_bufferManager->bufferTimedOut(p)==false)
      {
        if (OtherSideSPI_FlowControl( ) == false)
        {
          Trigger TX_RetryTimer in 20 msec.
          break;
        }
        send(p);
      }
      free(p);
    } while (true) ;
    EnableISRs( );
  }
  static void RX_ISR(Bridge *b)
  {
    DisableISRs( );
```

-continued

```
    do
    {
      uint8* p = b->nextBufferRX( );
      if (p == null) break;
      uint i;
      while (not done receiving)
        p[i++] = getChar( );
      b->route (p);
    } while (true) ;
    EnableISRs( );
  }
}
```

One or more, but not limited to, the following statistics may be supported by PCGP:

Number of packets sent;

Number of packets received;

CRC errors;

Timeouts; and

Buffer unavailable (ran out of buffers)

In various embodiments, PCGP may be designed to run in multiple processing environments. Most parameters may be run time configured because it facilitates testing, and any run time fine tuning for performance. Other parameters may be compile time e.g., anything that alters memory allocation must be done statically at compile time and still other parameters may be used in various embodiments.

The following may be compile time configuration #defines that may vary where PCGP is implemented:

driver bytes: may be two bytes reserved in the common buffer scheme for the driver, but, in some embodiments, this may be a compile time option to accommodate other drivers such as RF protocol.

RX driver buffers: may be tuned to how many buffers desired for that processor/traffic flow, etc.

PCGP RX buffers: may be tuned to how many buffers desired for that processor/traffic flow, etc.

Total # of buffers: may be tuned to how many buffers desired for that processor.

In some embodiments, the CRC may be used to ensure data integrity. In some embodiments, if a CRC is invalid, it may not be delivered to the application and the CRC error may be tracked. The message may eventually timeout and may be retried by the originator.

Likewise, if the messaging system informs the application that a message was delivered when it was not, this may not be desirable for the system. The Stop Bolus Command is an example of such a command. This may be mitigated by the Request/Action sequence of messages which may be required by the application to change therapy. In some embodiments, the remote interface 802 may receive a matching command from the device 800 application to consider the message delivered.

Figure 8O:
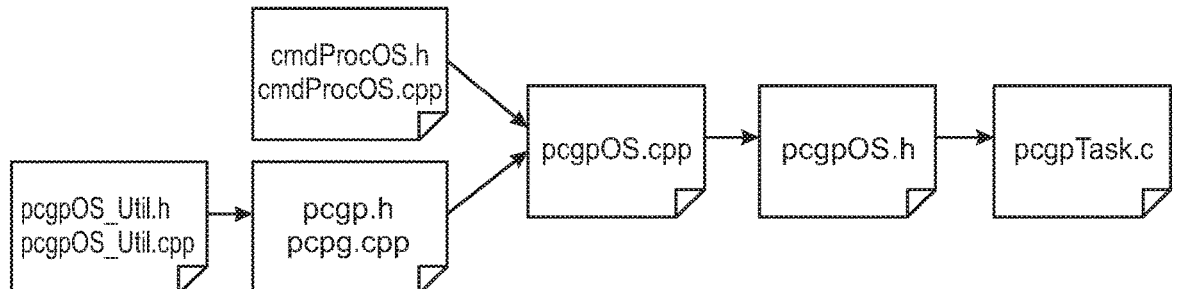

In some embodiments, a reference way of interfacing PCGP into the Nucleus OS system on the ARM 9 (as shown in FIG. 8O) may be used.

Figure 8P:
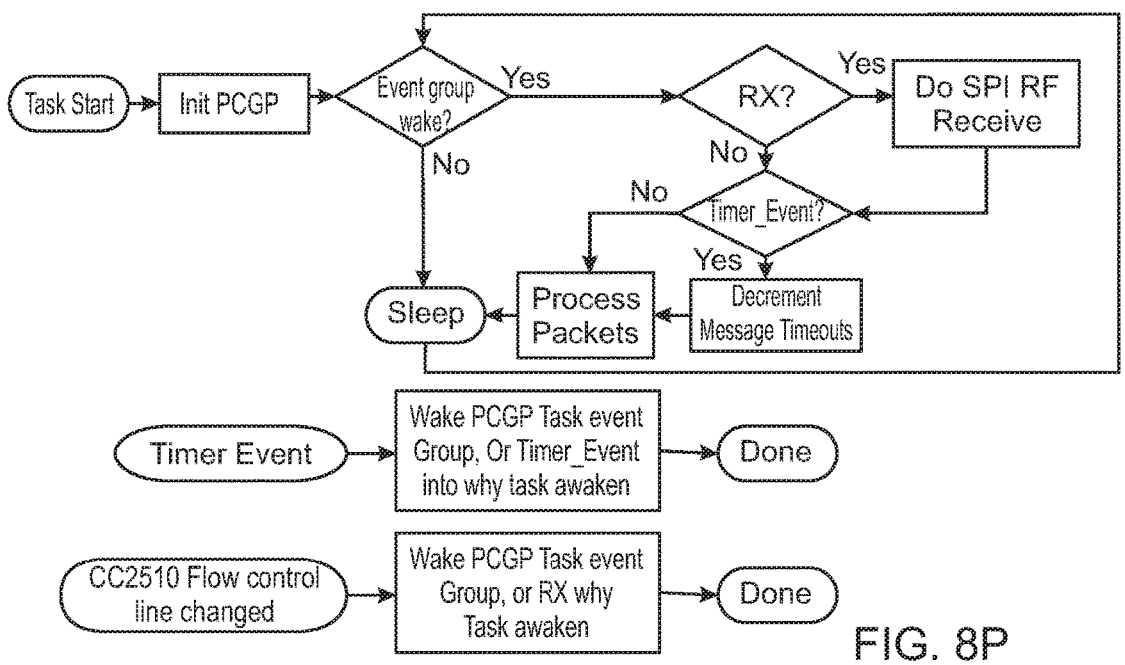

As shown in FIG. 8P, the pcgpOS.cpp file may instantiate a PCGP node instance (Pcgp, a Bridge, etc.) and may provide through pcgpOS.h a 'C' linkable set of function calls that provide a 'C' language interface to the C++ code. This may simplify the 'C' code as the objects acted upon are implicit.

The following general rules may be applied in some embodiments:
PCGP may run on all nodes: any driver may support a generic driver interface.
Race conditions may not be permitted.
May support half duplex on the SPI port between slave processor and master processor.
Data transfer may not be attempted; as it either succeeds or returns fail/false.
May require low overhead (time, processing, bandwidth wasted).
May support CC2510 operating at DMA (fast) SPI clock rates.

In some embodiments, SPI flow control may prevent data from being sent if the receiving side does not currently have an empty buffer to place the packet. In some embodiments, this may be accomplished by asking for permission to send and waiting for a response indicating that you have been cleared to do so. In some embodiments, another method may be used to indicate to the other side that there are currently no free buffers and the transfer should be attempted at a later time.

In some embodiments, all transmission may begin with a length byte that indicates the number of bytes to be sent, not including the length byte itself. Following, the length may be a single byte indicating the command being sent.

In some embodiments, the actual transmission of a packet may be the length of the packet plus one for the command byte, followed by the command byte for a message appended and finally the packet itself. However, in other embodiments, the transmission of the packet may vary.

In addition to the command bytes that will be sent, an additional hardware line called the FlowControl line may be added to the traditional four SPI signals. This line may be used to allow the protocol to run as quickly as possible without a need for preset delays. It also allows the slave processor to tell the master processor that it has a packet waiting to be sent, thus eliminating the need for the master processor to poll the slave processor for status.

The following exemplary command values may be used in some embodiments:
Commands to be Sent by the Master Processor:

| Command | Value | Description |
| --- | --- | --- |
| M_RTS | 0xC1 | Master is requesting to send a packet |
| M_MSG_APPENDED | 0xC2 | Master is sending a packet |
| M_CTS | 0xC3 | Master is tell slave it is Cleared to Send |
| M_ERROR | 0xC4 | An Error condition has been encountered |

Commands to be Sent by the Slave Processor:

| Command | Value | Description |
| --- | --- | --- |
| S_PREPARING_FOR_RX | 0xA1 | Slave is prepare the dma to receive a packet |
| S_RX_BUFF_FULL | 0xA2 | Slave is currently out of RX buffers, retry later |
| S_MSG_APPENDED | 0xA3 | Slave is sending a packet |
| S_ERROR | 0xA4 | An Error condition has been encountered |

As illustrated in FIG. 8Q, when the slave processor has a packet to send to the master processor, the slave processor may notify the master processor (for example, by asserting the FlowControl line) that it has a pending packet that is waiting to be sent. Doing so may result in an IRQ on the master processor at which time the master processor may decide when to go retrieve the message from the slave processor. Retrieving the packet may be delayed at the discretion of the master processor, and the master processor may even decide to attempt to send a packet to the slave processor before retrieving from the slave processor.

In some embodiments, the master processor may begin the retrieval by sending the slave processor M_CTS commands; in some embodiments, this may be repeated until the slave processor responds by sending the S_MSG_APPENDED command along with the packet itself. The FlowControl line may be cleared after the packet has been sent. If a M_CTS command is received by the slave processor when one is not expected, the M_CTS command may be ignored.

As illustrated in FIG. 8R, in some embodiments, when the master processor has a packet to send to the slave processor, the master processor may initiate the transfer by sending a M_RTS command. Upon receiving the M_RTS command, if the slave processor currently has a send packet pending, in some embodiments, the slave processor will lower the FlowControl line so that it may be re-used as a Cleared To Send signal. The slave processor may then tell the master processor that it is in the process of preparing the SPI DMA to receive the packet, during which time the master processor may stop clocking bytes onto the bus and may allow the slave processor to finish preparing for the receive.

In some embodiments, the slave processor may then indicate it is ready to receive the full packet by raising the FlowControl line (which is now used as the CTS signal). Upon receiving the CTS signal, the master processor may proceed to send the M_MSG_APPENDED command along with the packet itself.

After the completion of the transfer, the slave processor may lower the FlowControl line. If a packet was pending at the start of the transfer, or a send occurred on the slave processor when the packet was being received, the slave processor may reassert the FlowControl line now indicating that it has a pending packet.

Referring again to FIG. 8, device 800 may include switch assembly 810 coupled to electrical control assembly 510 (FIG. 5D) that may allow a user (not shown) to perform at least one, and in some embodiments, a plurality of tasks. One illustrative example of such a task, in embodiments where the device 800 is an infusion pump or other drug delivery device, is the administration of a bolus dose of the infusible fluid (e.g., insulin) without the use of a display assembly. The remote interface 802 may allow the user to enable/disable/configure the device 800 to administer the bolus dose of insulin.

The display assembly 804 may be configured, at least in part, to enable the user to manipulate menu-based information rendered the on display assembly 804. An example may be that display assembly 804 is a touch screen. In some embodiments, the touch screen/display assembly 804 may be configured so that the rate at which e.g. the highlighted portion of a menu scrolls "upward" or "downward" varies depending upon the displacement of the finger of the user with respect to a point of origin. Therefore, in some embodiments, for example, if the user wishes to quickly scroll "upward", the user may position their finger near the top of display assembly 804. Likewise, if the user wishes to quickly scroll "downward", the user may position their finger near the bottom of the display assembly 804. Additionally, if the user wishes to slowly scroll "upward", the user may position their finger slightly "upward" with respect to a point of origin. Further, if the user wishes to slowly scroll "downward", the user may position their finger slightly "downward" with respect to a point of origin. Once the appropriate menu item is highlighted, the user may select the highlighted menu item either by touching the screen a predetermined number of times in either the vicinity of the highlighted menu item, for example, and/or by using the one or more switch assemblies 806 that may be included on the remote interface 802 in some embodiments.

As discussed above, in one embodiment of the above-described infusion pump device, the device 800 may be used to communicate with the remote interface 802. When such a remote interface 802 is utilized, the device 800 and the remote interface 802 may routinely contact each other to ensure that the two devices are still in communication with each other. For example, the device 800 may "ping" the remote interface 802 to ensure that the remote interface 802 is present and active. Further, the remote interface 802 may "ping" the device 800 to ensure that the device 800 is still present and active. In the event that one of the device 800 and the remote interface 802 fails to establish communication with one other, the one (i.e., either the device 800 or the remote interface 802) that is unable to establish communication may sound a "separation" alarm. For example, assume that the remote interface 802 is left in the car of the user, while the device 800 is in the pocket of the user. Accordingly and after a defined period of time, the device 800 may begin sounding the "separation" alarm, indicating that communication with the remote interface 802 cannot be established. In some embodiments, the user may acknowledge and or silence the "separation" alarm by using switch assembly 810.

In various embodiments, the user may define and administer a delivery of fluid using the switch assembly 810 of the device 800 while the remote interface 802 is not in communication the device 800, the device 800 may store information concerning the administered bolus insulin dose within a log file (not shown) stored within the device 800. This log file (not shown) may be stored within nonvolatile memory (not shown) included within the device 800. Upon communication being reestablished between the device 800 and the remote interface 802, the device 800 may provide the information concerning the administered bolus insulin dose stored within the log file (not shown) of the device 800 to the remote interface 802.

Further, in some embodiments, where the user anticipates separating the remote interface 802 from the device 800, the user may configure the device 800 and the remote interface 802 to be in "separation" mode, thus eliminating the occurrence of the above-described "separation" alarms. However, in some embodiments, the remote interface 802 and the device e800 may continue to "ping" each other so that when they come back into communication with each other, the device 800 and the remote interface 802 may automatically exit "separation" mode.

Further, in some embodiments, if the user anticipates traveling in an airplane, the user, using the remote interface 802 may configure the device 800 and the remote interface 802 to be in "airplane" mode, in which each of the device 800 and the remote interface 802 suspend any and all data transmissions. While in "airplane" mode, the device 800 and the remote interface 802 may, or may not, continue to receive data.

In some embodiments, the switch assembly 810 may be used to perform additional functions, which may include, but are not limited to, one or more of the following: checking the battery life of the reusable portion 502; pairing reusable portion 502 with the remote interface 802; and/or aborting the administration of a bolus does of infusible fluid.

Figure 9A:
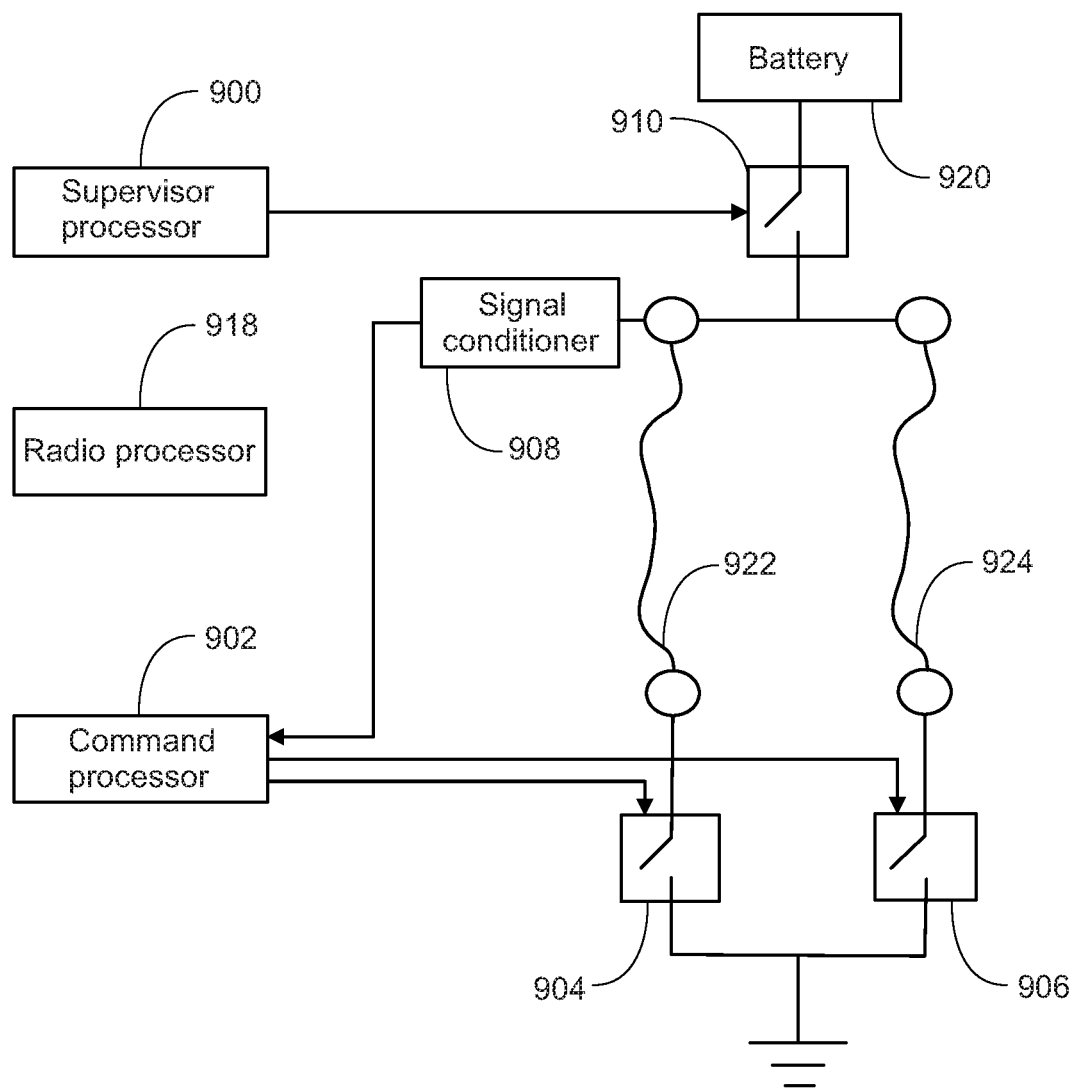
FIG. 9A diagrammatically depicts an embodiment of a multi-processor control configuration that may be included within one embodiment of the device.

Referring also to FIG. 9A and as discussed above, in some embodiments, to, for example, enhance the safety of the device 800, electrical control assembly 516 may include two separate and distinct microprocessors, namely supervisor processor 900 and command processor 902. Specifically, command processor 902 may perform the functions such as, but not limited to, generating pump drive signals and may control relay/switch assemblies that control the functionality of, for example, shape memory actuators. The command processor 902 may receive feedback from a signal conditioner 908 concerning the condition (e.g., voltage level) of the voltage signal applied to pump actuators 922, 924, which in some embodiments, may be shape memory actuators. The command processor 900 may control relay/switch assembly 910 independently of relay/switch assemblies 904, 906. Accordingly, when, for example, an infusion event is desired, both of supervisor processor 900 and command processor 902 must agree that the infusion event is proper (which may include whether the infusion event does not exceed any set limitations of the system, when inherent or user selected/pre programmed, and/or is intentional) and must both actuate their respective relays/switches. In the event that either of the supervisor processor 900 and the command processor 902 fail to actuate their respective relays/switches, the infusion event will not occur. Accordingly through the use of the supervisor processor 900 and command processor 902 and the cooperation and concurrence that must occur, the safety of the device 800 is enhanced.

In some embodiments, the supervisor processor 900 may prevent the command processor 902 from delivering when it is not proper and/or may alarm if the command processor 902 does not deliver when it should be delivering. The supervisor processor 900 may deactivate the relay/switch assembly, for example, if the command processor 902 actuates the wrong switch, or if the command processor tries to apply power for too long.

The supervisor processor 900 may redundantly perform calculations for how much fluid should be delivered (i.e., double checking the calculations of the command processor 902). In some embodiments, the command processor 902 may determine the delivery schedule, and the supervisor processor 900 may redundantly check/confirm those calculations.

The supervisor processor 900 may redundantly hold the profiles (for example, delivery profiles and/or user preferences that are preprogrammed/pre-entered into the device) in RAM, so that the command processor 902 may be doing the correct calculations, but if it has bad RAM, would cause the command to come up with the wrong result. Thus, the supervisor processor 900 uses its local copy of the profile/user preference, e.g., a basal profile, etc., to double check/confirm.

The supervisor processor 900 may double check one or more calculations performed by the device, for example, AVS measurements, by reviewing the AVS calculations and applied safety checks. In some embodiments of the device, for example, each time AVS measurement is taken, the supervisor processor 900 double checks.

Figure 9B:
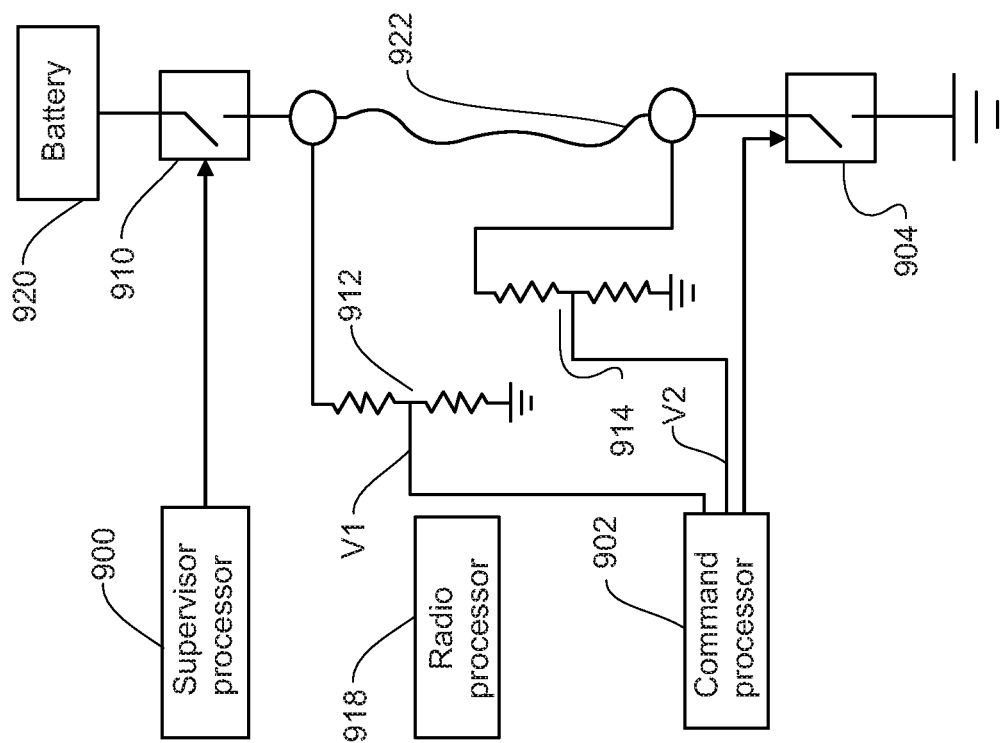
FIG. 9B diagrammatically depicts an embodiment of a multi-processor control configuration that may be included within one embodiment of the device in some embodiments.

Referring also to FIG. 9B, one or more of supervisor processor 900 and command processor 902 may perform diagnostics on various portions of the infusion pump/device 800. For example, voltage dividers 912, 914 may be configured to monitor the voltages (V1 & V2 respectively) sensed at distal ends of e.g., shape memory actuator 922. The value of voltages V1 & V2 in combination with the knowledge of the signals applied to relay/switch assemblies 904, 910 may allow for diagnostics to be performed on various components of the circuit shown in FIG. 9B (in a manner similar to that shown in illustrative diagnostic table 916).

As discussed above and as illustrated in FIGS. 9A-9B, to enhance the safety of the device 800, electrical control assembly 910 may include a plurality of microprocessors (e.g., supervisor processor 900 and command processor 902), each of which may be required to interact and concur in order to effectuate action, for example, where the device 800 effectuates the delivery of a drug, the action may be the delivery of a dose of the e.g., infusible fluid. In the event that the microprocessors 900, 902 fail to interact/concur, the delivery of the dose of infusible fluid/action may fail and one or more alarms may be triggered, thus enhancing the safety and reliability of the device 800.

A master alarm may be utilized that tracks the error, for example, volume error, which may refer to the volume of fluid delivered being less than or more than requested, over time. Accordingly, if the sum of the errors becomes too large, the master alarm may be initiated, indicating that something may be wrong with the system. Accordingly, the master alarm may be indicative of a total volume comparison being performed and a discrepancy being noticed. A typical value of the discrepancy required to initiate the master alarm in embodiments including the infusion pump described above may be 1.00 milliliters. The master alarm may monitor the sum in a leaky fashion (i.e., inaccuracies have a time horizon).

Figure 10A:
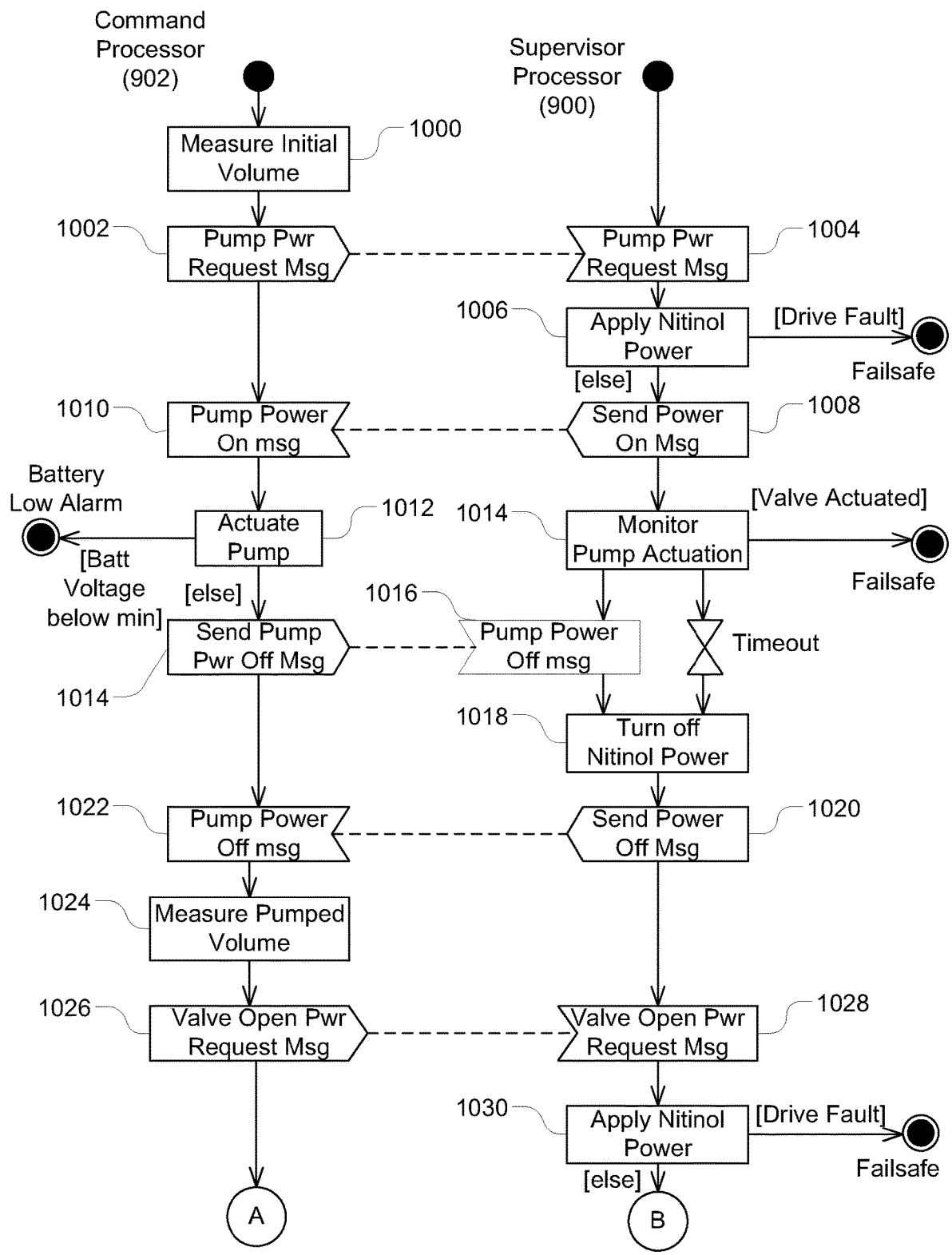
FIGS. 10A and 10B diagrammatically depict one embodiment of multi-processor functionality.
Figure 10B:
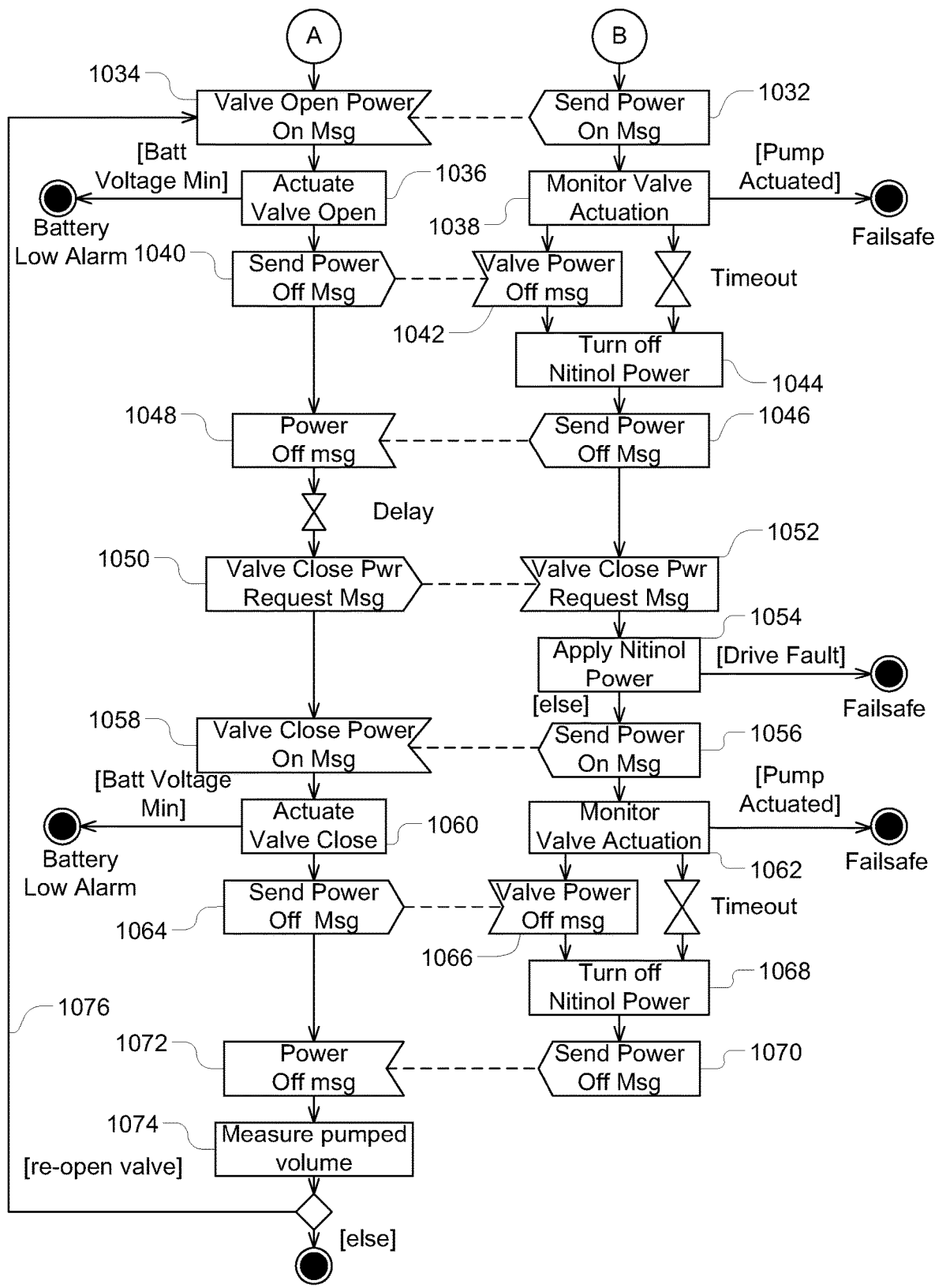

Referring also to FIGS. 10A-10B, there is shown one such illustrative example of such interaction amongst multiple microprocessors, in this example, the interaction is during the delivery of a dose of the infusible fluid by the infusion pump. Specifically, the command processor 902 may first determine 900 the initial volume of infusible fluid within a volume sensor chamber. The command processor 902 may then provide 1002 a "pump power request" message to the supervisor processor 900. Upon receiving 1004 the "pump power request" message, the supervisor processor 900 may e.g., energize 1006 relay/switch 910 (thus energizing the shape memory actuator 922) and may send 1008 a "pump power on" message to the command processor 902. Upon receiving 1010 the "pump power on" message, the command processor 902 may actuate 1012 e.g., the pump assembly (by energizing relay/switch 904 and which energizes the valve assembly 514), during which time the supervisor processor 900 may monitor 1014 the actuation of e.g., the pump assembly.

Once actuation of the pump assembly is complete, the command processor 902 may provide 1014 a "pump power off" message to the supervisor processor 900. Upon receiving 1016 the "pump power off" message, the supervisor processor 900 may de-energize 1018 relay/switch 910 and provide 1020 a "pump power off" message to the command processor 902. Upon receiving 1022 the "pump power off" message, the command processor 902 may measure 1024 the quantity of infusible fluid pumped by the pump assembly (which may, in some embodiments, include the valve assembly 514). This may be accomplished by measuring the current quantity of fluid within a volume sensor chamber and comparing it with the quantity determined above (in step 1000). Once determined 1024, the command processor 902 may provide 1026 a "valve open power request" message to the supervisor processor 900. Upon receiving 1028 the "valve open power request" message, the supervisor processor 900 may energize 1030 relay/switch 910 (thus energizing shape memory actuator 924) and may send 1032 a "valve open power on" message to the command processor 902. Upon receiving 1034 the "valve open power on" message, the command processor 902 may actuate 1036 e.g., measurement valve assembly (by energizing relay/switch 906), during which time the supervisor processor 900 may monitor 1038 the actuation of e.g., a measurement valve assembly.

Once actuation of a measurement valve assembly is complete, the command processor 902 may provide 1040 a "valve power off" message to the supervisor processor 900. Upon receiving 1042 the "valve power off" message, the supervisor processor 900 may de-energize 1044 relay/switch 910 and provide 1046 a "valve power off" message to the command processor 902.

Upon receiving 1048 the "valve power off" message, the command processor 902 may provide 1050 a "valve close power request" message to the supervisor processor 900. Upon receiving 1052 the "valve close power request" message, the supervisor processor 900 may energize 1054 relay/switch 910 (thus energizing a shape memory actuator) and may send 1056 a "power on" message to command processor 902. Upon receiving 1058 the "power on" message, the command processor 902 may actuate 1060 an energizing relay/switch (not shown) that is configured to energize the shape memory actuator, during which time the supervisor processor 900 may monitor 1062 the actuation of e.g., the shape memory actuator.

In various embodiments, the shape memory actuator may be anchored on a first end using an electrical contact. The other end of the shape memory actuator may be connected to bracket assembly. When the shape memory actuator is activated, the shape memory actuator may pull the bracket assembly forward and release the valve assembly. As such, the measurement valve assembly may be activated by way of the shape memory actuator. Once the measurement valve assembly has been activated, the bracket assembly may automatically latch the measurement valve assembly into the activated position. Actuating the shape memory actuator may pull the bracket assembly forward and release the measurement valve assembly. Assuming the shape memory actuator is no longer activated, the measurement valve assembly may move to a de-activated state once the bracket assembly has released the measurement valve assembly. Accordingly, by actuating the shape memory actuator, the measurement valve assembly may be deactivated.

Once actuation of the shape memory actuator is complete, the command processor 902 may provide 1064 a "power off" message to supervisor processor 900. Upon receiving 1066 the "power off" message, the supervisor processor 900 may de-energize 1068 relay/switch 910 and may provide 1070 a "power off" message to the command processor 902. Upon receiving 1072 the "power off" message, the command processor 902 may determine the quantity of infusible fluid within the volume sensor chamber, thus allowing command processor 902 to compare this measured quantity to the quantity determined above (in step 1024) to determine 1074 the quantity of infusible fluid delivered to the user.

In the event that the quantity of infusible fluid delivered 1074 to the user is less than the quantity of infusible fluid specified for the basal/bolus infusion event, the above-described procedure may be repeated (by way of loop 1076).

Figure 11:
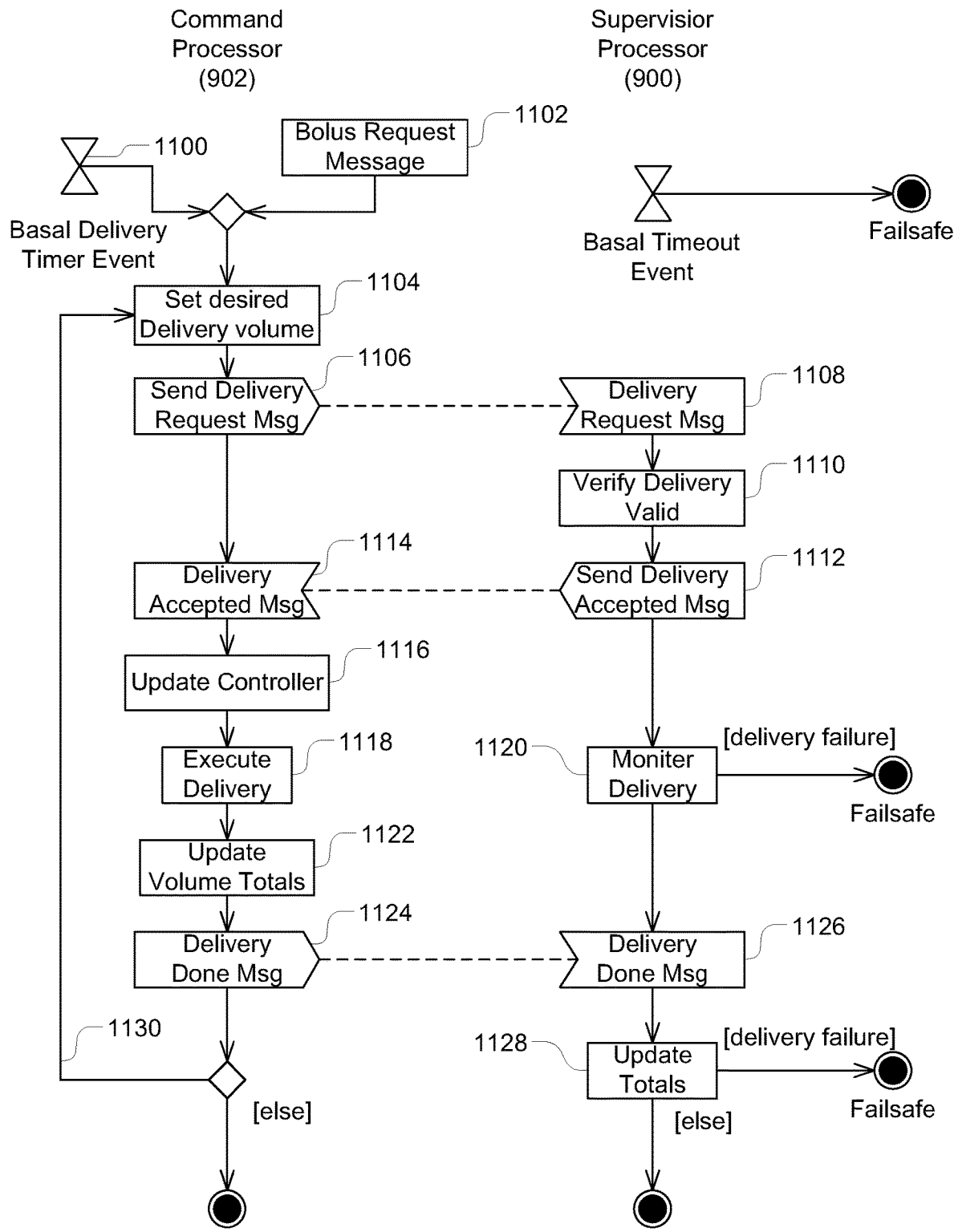
FIG. 11 diagrammatically depicts one embodiment of multi-processor functionality.

Referring also to FIG. 11, there is shown another illustrative example of the interaction amongst processors 900, 902, this time during the scheduling of a dose of infusible fluid. The command processor 902 may monitor 1100, 1102 for the receipt of a basal scheduling message or a bolus request message (respectively). Upon receipt 1100, 1102 of either of these messages, the command processor 902 may set 1104 the desired delivery volume and may provide 1106 a "delivery request" message to the supervisor processor 900. Upon receiving 1108 the "delivery request" message, supervisor processor 900 may verify 1110 the volume defined 1104 by command processor 902. Once verified 1110, the supervisor processor 900 may provide 1112 a "delivery accepted" message to the command processor 902. Upon receipt 1114 of the "delivery accepted" message, the command processor 902 may update 1116 the remote interface (e.g., the remote interface discussed above and illustrated in FIGS. 6-8) and execute 1118 delivery of the basal/bolus dose of infusible fluid. The command processor 902 may monitor and update 1122 the total quantity of infusible fluid delivered to the user (as discussed above and illustrated in FIGS. 10A-10B). Once the appropriate quantity of infusible fluid is delivered to the user, the command processor 902 may provide 1124 a "delivery done" message to the supervisor processor 900. Upon receipt 1126 of the "delivery done" message, the supervisor processor 900 may update 1128 the total quantity of infusible fluid delivered to the user. In the event that the total quantity of infusible fluid delivered 1118 to the user is less than the quantity defined above (in step 1104), the infusion process discussed above may be repeated (by way of loop 1130).

Figure 12:
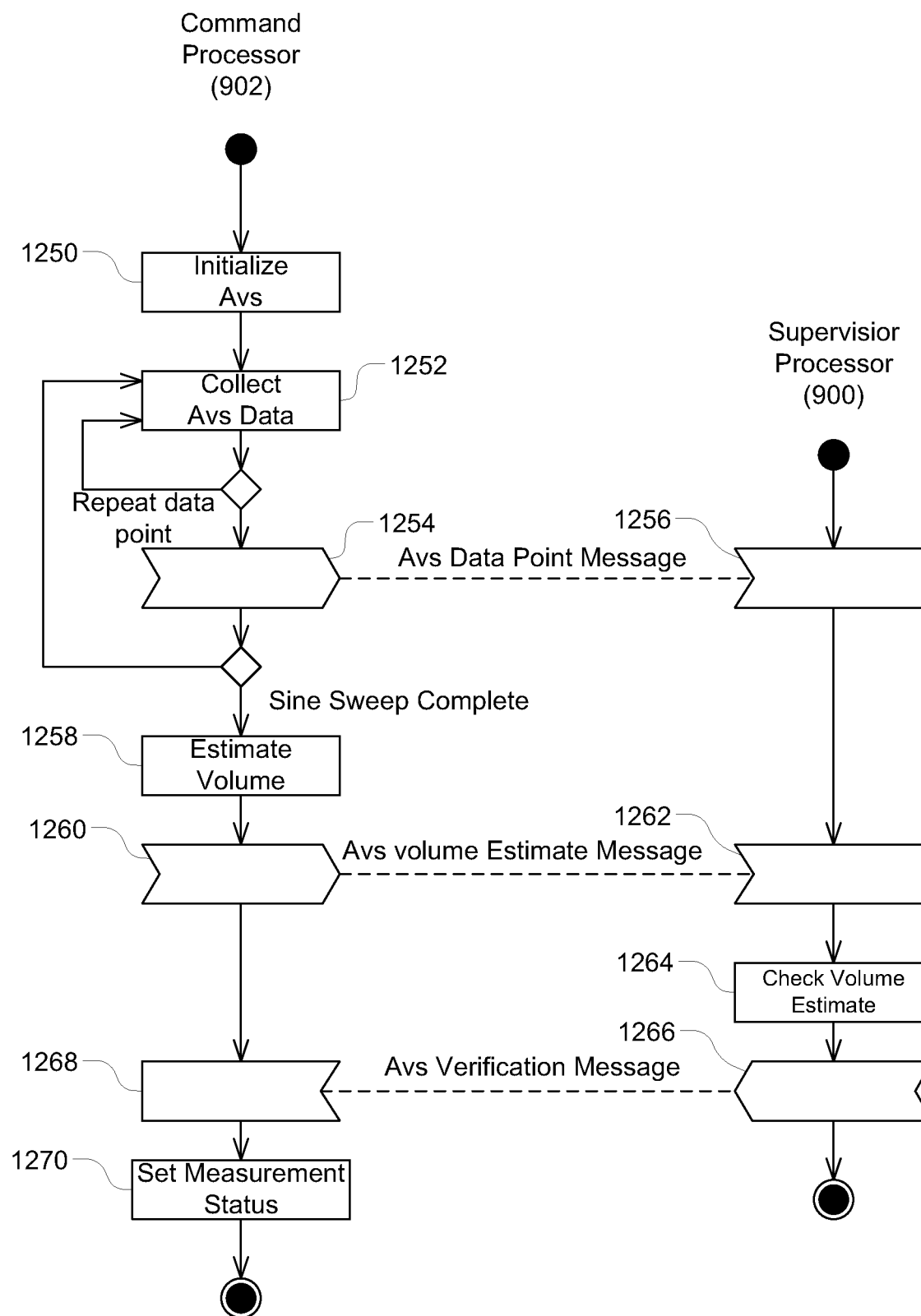
FIG. 12 diagrammatically depicts one embodiment of multi-processor functionality.
Figure 12A:
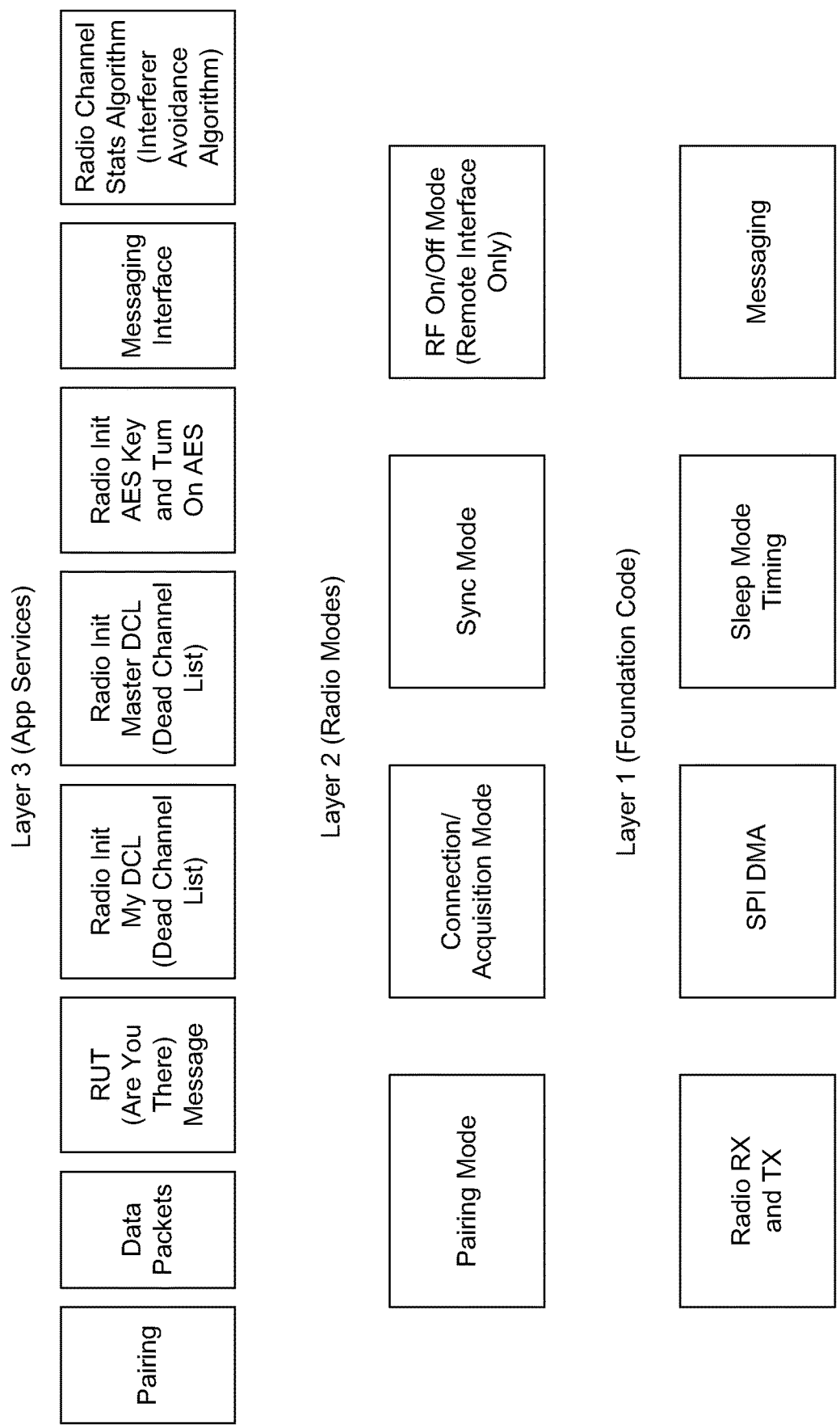
FIGS. 12A-12E graphically depict various software layers according to one embodiment.

Referring also to FIG. 12, there is shown an example of the manner in which the supervisor processor 900 and the command processor 902 may interact while effectuating a volume measurements by way of the volume sensor assembly (as described above).

Specifically, the command processor 902 may initialize 1250 volume sensor assembly and begin collecting 1252 data from the volume sensor assembly, the process of which may be repeated for each frequency utilized in the sine sweep, for example, as described in U.S. Publication No. US-2009-0299277-A1 published Dec. 3, 2009. Each time that data is collected for a particular sweep frequency, a data point message may be provided 1254 from the command processor 902, which may be received 1256 by the supervisor processor 900.

Once data collection 1252 is completed for the entire sine sweep, the command processor 902 may estimate 1258 the volume of infusible fluid delivered by infusion the device 800. The command processor 902 may provide 1260 a volume estimate message to the supervisor processor 900. Upon receiving 1262 this volume estimate message, the supervisor processor 900 may check (i.e., confirm) 1264 the volume estimate message. Once checked (i.e., confirmed), the supervisor processor 900 may provide 1266 a verification message to the command processor 902. Once received 1268 from the supervisor processor 900, the command processor 902 may set the measurement status for the dose of infusible fluid delivered by the volume sensor assembly.

As discussed above (and referring temporarily to FIGS. 1A-5I), the various embodiments and components of the infusion pump system may be configured using a the remote interface 802 (see FIGS. 6-8). When configurable by way of the remote interface 802, the infusion pump 800 may include telemetry circuitry (not shown) that allows for communication (e.g., wired or wireless) between the infusion pump and e.g., the remote interface 802, thus allowing the remote interface 802 to remotely communicate with the infusion pump 800. Various embodiments of the remote interface 802 (which may also include telemetry circuitry (not shown) and may be capable of communicating with the infusion pump 800) may include a display assembly (602, 702, 804) and at least one input assembly 608, 604, 610, 606, 704, 702, 804 806), however, in various embodiments, the display assembly may also serve as an input assembly.

When used herein, the term remote interface refers to any embodiment of the remote interface. However, although the embodiment shown in FIG. 8 is used for illustrative purposes below, the description is not limited to that embodiment of the remote interface shown in FIG. 8.

In some embodiments, the remote interface 802 may include two processors, one processor (e.g., which may include, but is not limited to a CC2510 microremote interface/RF transceiver, available from Chipcon AS, of Oslo, Norway) may be dedicated to radio communication, e.g., for communicating with the device 800. The second processor included within the remote interface 802 (which may include but are not limited to an ARM920T and an ARM922T manufactured by ARM Holdings PLC of the United Kingdom) may be a command processor and may perform data processing tasks associated with e.g., configuring the device 800. However, in various other embodiments, as described below, the remote interface 802 may include various processors and/or communications protocols and/or various antennas for communication.

Further and as discussed above, one embodiment of electrical control assembly 516 may include three microprocessors. One processor (e.g., which may include, but is not limited to a CC2510 microremote interface/RF transceiver, available from Chipcon AS, of Oslo, Norway) may be dedicated to radio communication, e.g., for communicating with the remote interface 802. Two additional microprocessors (e.g., supervisor processor 1800 and command processor 1802) may effectuate the delivery of the infusible fluid (as discussed above). Examples of supervisor processor 1800 and command processor 1802 may include, but is not limited to an MSP430 microremote interface, available from Texas Instruments Inc. of Dallas, Tex.

The OS may be a non-preemptive scheduling system, in that all tasks may run to completion before the next task is allowed to run regardless of priority. Additionally, context switches may not be performed. When a task completes executing, the highest priority task that is currently scheduled to run may then be executed. If no tasks are scheduled to execute, the OS may place the processor (e.g., the supervisor processor 900 and/or the command processor 902) into a low power sleep mode and may wake when the next task is scheduled. The OS may only be used to manage main loop code and may leave interrupt-based functionality unaffected.

In some embodiments, the OS may be written to take advantage of the C++ language. Inheritance as well as virtual functions may be key elements of the design, allowing for easy creation, scheduling and managing of tasks.

At the base of the OS infrastructure may be the ability to keep track of system time and controlling the ability to place the processor in Low Power Mode (LPM; also known as sleep mode). This functionality along with the control and configuration of all system clocks may be encapsulated by the SysClocks class.

The SysClocks class may contain the functionality to place the processor (e.g., the supervisor processor 900 and/or the command processor 902) into LPM to reduce energy consumption. While in LPM, the slow real time clock may continue to run while the fast system clock that runs the CPU core and most peripherals may be disabled.

In some embodiments, placing the processor into LPM may always be done by the provided SysClocks function. This function may contain all required power down and power up sequences resulting in consistency whenever entering or exiting LPM. Waking from LPM may be initiated by any interrupts based on the slow clock.

The OS may keep track of three aspects of time: seconds, milliseconds and the time of day. Concerning seconds, SysClocks may count seconds starting when the processor comes out of reset. The second counter may be based on the slow system clocks and, therefore, may increment regardless of whether the processor is in LPM or at full power. As a result, it is the boundary at which the processor may wake from sleep to execute previously scheduled tasks. If a task is scheduled to run immediately from an interrupt service routine (ISR), the ISR may wake the processor from LPM on exit and the task may be executed immediately. Concerning milliseconds, in addition to counting the seconds since power on, SysClocks may also count milliseconds while the processor is in full power mode. Since the fast clock is stopped during LPM, the millisecond counter may not increment. Accordingly, whenever a task is scheduled to execute based on milliseconds, the processor may not enter LPM. Concerning time of day, the time of day may be represented within SysClocks as seconds since a particular point time (e.g., seconds since 1 Jan. 2008 and/or in some embodiments, POSIX standard time, 1 Jan. 1971).

The SysClocks class may provide useful functionality to be used throughout the Command and Supervisor project code base. The code delays may be necessary to allow hardware to settle or actions to be completed. SysClocks may provide two forms of delays, a delay based on seconds or a delay based on milliseconds. When a delay is used, the processor may simply wait until the desired time has passed before continue with its current code path. Only ISRs may be executed during this time. SysClocks may provide all of the required functionality to set or retrieve the current time of day.

The word "task" may be associated with more complex scheduling systems; therefore within the OS, task may be represented by and referred to as Managed Functions. The ManagedFunc class may be an abstract base class that provides all the necessary control members and functionality to manage and schedule the desired functionality.

The ManagedFunc base class may have five control members, two scheduling manipulation member functions, and one pure virtual execute function that may contain the managed functionality. All of the ManagedFunc control members may be hidden from the derived class and may only be directly set by the derived class during creation, thus simplifying the use and enhancing the safety of the infusion pump 800.

In some embodiments, the Function ID may be set at the time of creation and may never be changed. All Function IDs may be defined within a single .h file, and the base ManagedFunc constructor may strongly enforce that the same ID may not be used for more than one managed function. The ID may also define the priority of a function (with respect to other functions) based upon the function ID assigned, wherein higher priority functions are assigned lower function IDs. The highest priority task that is currently scheduled to execute may execute before lower priority tasks.

All other control members may be used to represent the function's current scheduled state, when it should be executed, and if (upon execution) the function should be rescheduled to execute in a previously set amount of time. Manipulation of these controls and states may be allowed but only through the public member functions (thus enforcing safety controls on all settings).

To control the scheduling of a managed function, the set start and set repeat functions may be used. Each of these member functions may be a simple interface allowing the ability to configure or disable repeat settings as well as control whether a managed function is inactive, scheduled by seconds, milliseconds, or time of day.

Through inheritance, creating a Managed Function may be done by creating a derived class and defining the pure virtual 'execute' function containing the code that needs to be under scheduling control. The ManagedFunc base class constructor may be based upon the unique ID of a function, but may also be used to set default control values to be used at start up.

For example to create a function that runs e.g., thirty seconds after start up and every e.g., 15 seconds thereafter, the desired code is placed into the virtual execute function and the function ID, scheduled by second state, thirty second start time, and repeat setting of fifteen seconds is provided to the constructor.

The following is an illustrative code example concerning the creation of a managed function. In this particular example, a "heartbeat" function is created that is scheduled to execute for the first time one second after startup of the device 800 and execute every ten seconds thereafter:

```
#include "ManagedFunc.h"
// The SendGoodFunc is a "heartbeat" status message
class SendGoodFunc : public ManagedFunc
{
public:
    // Initialize the managed func to run 2 seconds after start up
    // and repeat every second.
    SendGoodFunc( ) :
        ManagedFunc(IPC_SEND_GOOD, SCHEDULED_SEC, 1, true, 10) { };
    ~SendGoodFunc( ) { };
protected:
    void execute(void);
};
void SendGoodFunc::execute(void)
{
    // << code to send the heartbeat >>
}
SendGoodFunc g_sendGoodFunc;
// to manipulate the heartbeat timing simply call:
//      g_sendGoodFunc.setFuncStart(...) or g_sendGoodFunc.setRepeat(
... )
```

The actual execution of the Managed Functions may be controlled and performed by the SleepManager class. The SleepManager may contain the actual prioritized list of managed functions. This prioritized list of functions may automatically be populated by the managed function creation process and may ensure that each function is created properly and has a unique ID.

The main role of the SleepManager class may be to have its 'manage' function called repeatedly from the processors main loop and/or from a endless while loop. Upon each call of manage, the SleepManager may execute all functions that are scheduled to run until the SleepManager has exhausted all scheduled functions; at which time the SleepManager may place the processor in LPM. Once the processor wakes from LPM, the manage function may be reentered until the processor is again ready to enter LPM (this process may be repeated until stopped, e.g., by a user or by the system).

If the processor has to be kept in full power mode for an extended period of time (e.g., while an analog-to-digital conversion is being sampled), the SleepManager may provide functionality to disable entering LPM. While LPM is disabled, the manage function may continuously search for a scheduled task.

The SleepManager may also provide an interface to manipulate the scheduling and repeat settings of any managed function through the use of the unique ID of the function, which may allow any section of code to perform any required scheduling without having direct access to or unnecessary knowledge of the desired ManagedFunc object.

Radio circuitry included within the device 800 and the remote interface 802 may effectuate wireless communication between the remote interface 802 and device 800. In some embodiments, a 2.4 GHz radio communications chip (e.g., a Texas Instruments CC2510 radio transceiver) with an internal 8051 microremote interface may be used for radio communications.

The radio link may balance the following three objectives: link availability; latency; and energy.

Concerning link availability, the remote interface 802 may provide the primary means for commanding the device 800 and may provide detailed feedback to the user by way of the graphical user interface (GUI) (display assembly 804) of the remote interface 802. Concerning latency, the communications system may be designed to provide for low latency to deliver data from the remote interface 802 to the device 800 (and vice versa). Concerning energy, both the remote interface 802 and the device 800 may have a maximum energy expenditure for radio communications.

The radio link may support half-duplex communications. In some embodiments, the remote interface 802 may be the master of the radio link, initiating all communications. In these embodiments, the device 800 may only respond to communications and may not initiate communications. The use of such a radio communication system may provide various benefits, such as: increased security: a simplified design (e.g., for airplane use); and coordinated control of the radio link. In other embodiments, the device 800 may instigate an action, but communication may be instigated by the remote interface 802.

Referring also to FIG. 12, there is shown one illustrative example of the various software layers of the radio communication system discussed above.

In some embodiments, the radio processors included within the remote interface 802 and the device 800 may transfer messaging packets between an SPI port and a 2.4 GHz radio link (and vice versa). In some embodiments, the radio may always be the SPI slave. On the device 800, the radio processor (PRP) 918 (See FIGS. 9A-9B) may, in some embodiments, service two additional nodes (the number of additional nodes may vary in various embodiments) over the SPI port that are upstream (namely the command processor 900 and the supervisor processor 902). In some embodiments, on the remote interface 802, the radio processor 918 (CRP) may service at least one additional node over the SPI port that may be either upstream or downstream, for example, in some embodiments, the above-described remote control processor (UI) and a Continuous Glucose Monitor (CGM) and/or a Blood Glucose Monitor (BGM)

A messaging system may allow for communication of messages between various nodes in the network. The UI processor of the remote interface 802 and e.g., the supervisor processor 900 may use the messaging system to configure and initiate some of the mode switching on the two system radios. It may be also used by the radios to convey radio and link status information to other nodes in the network.

In some embodiments, when the radio of the remote interface 802 wishes to gather channel statistics from the device 800 or update the master channel list of the radio of the device 800, the radio of the remote interface 802 may use system messages. Synchronization for putting the new updated list into effect may use flags in the heartbeat messages to remove timing uncertainty.

The radio communication system may be written in C++ to be compatible with the messaging software. In some embodiments, a four byte radio serial number may be used to address each radio node. A hash table may be used to provide a one-to-one translation between the device "readable" serial number string and the radio serial number. The hash table may provide a more randomized e.g., 8-bit logical address so that devices or remote interfaces with similar readable serial numbers are more likely to have unique logical addresses. In some embodiments, radio serial numbers may not have to be unique between device 800 and remote interfaces 802 due to the unique roles each has in the radio protocol.

The radio serial number of the remote interface 802 and the radio serial number of the device 800 may be included in all radio packets, in some embodiments, except for the RF Pairing Request message that may only include the radio serial number of the remote interface 802, thus ensuring that only occur with the remote control assembly/infusion pump assembly to which it is paired. The CC2510 may support a one byte logical node address and it may be advantageous to use one byte of the radio serial number as the logical node address to provide a level of filtering for incoming packets.

The Quiet_Radio signal may be used by the UI processor of the remote interface 802 to prevent noise interference on the board of the remote interface 802 by other systems on the board. When Quiet_Radio is asserted, the radio application of the remote interface 802 may send a message to the radio of the device 800 asserting Radio Quiet Mode for a predetermined period of time. In some embodiments, the Quiet_Radio feature may not be required based on noise interference levels measured on the PC board of the remote interface 802. During this period of time, the radio of the remote interface 802 may stay in Sleep Mode 2 for up to a maximum of 100 ms. The radio of the remote interface 802 may come out of Sleep Mode 2 when the Quiet_Radio signal is de-asserted or the maximum time period has expired. The UI processor of the remote interface 802 may assert Quiet_Radio at least one radio communication's interval before the event needs to be asserted. The radio of the remote interface 802 may inform the radio of the device 800 such that communications will be shutdown during this quiet period. The periodic radio link protocol may have status bits/bytes that accommodate the Quiet_Radio feature unless Quiet_Radio is not required.

The radio software may integrate with the messaging system and radio bootloader on the same processor, and may be verified using a throughput test. The radio software may integrate with the messaging system, SPI Driver using DMA, and radio bootloader, all on the same processor (e.g., the TI CC2510).

In some embodiments, the radio of the remote interface 802 may be configured to consume no more than 32 mAh in three days (assuming one hundred minutes of fast heartbeat mode communications per day). In some embodiments, the radio of the device 800 may be configured to consume no more than 25 mAh in three days (assuming one hundred minutes of fast heartbeat mode communications per day). However, these configurations may vary throughout the embodiments and in some embodiments, may be more or less than the stated examples.

The maximum time to reacquire communications may be ≤6.1 seconds including connection request mode and acquisition mode, however, in various other embodiments, the maximum time may be lower or higher. In some embodiments, the radio of the remote interface 802 may use the fast heartbeat mode or slow heartbeat mode setting to its advantage in order to conserve power and minimize latency to the user. The difference between the device 800 and the remote interface 802 entering acquisition mode may be that the device 800 needs to enter acquisition mode often enough to ensure communications may be restored within the maximum latency period. However, the remote interface 802 may change how often to enter acquisition mode with the device 800 when in slow heartbeat mode and heartbeats are lost. In some embodiments, the radio of the remote interface 802 may have knowledge of the user GUI interaction, but the device 800 may not.

The radio of the remote interface 802 may set the heartbeat period for both radios. In some embodiments, the period may be selectable in order to optimize power and link latency depending on activity. The desired heartbeat period may be communicated in each heartbeat from the radio of the remote interface 802 to the radio of the device 800. This may not exclusively establish the heartbeat rate of the device 800 due to other conditions that determine what mode to be in. When in fast heartbeat mode, the radio of the remote interface 802 may set the heartbeat period to 20 ms if data packets are available to send or receive, thus providing low link latency communications when data is actively being exchanged.

When in fast heartbeat mode, the radio of the remote interface 802 may set the heartbeat period to 60 ms four heartbeats after a data packet was last exchanged in either direction on the radio. Keeping the radio heartbeat period short after a data packet has been sent or received may assure that any data response packet may be also serviced using a low link latency. When in slow heartbeat mode, the heartbeat rate may be 2.00 seconds or 6.00 second, depending upon online or offline status respectively. However, in various embodiments, these values may vary.

The device 800 may use the heartbeat rate set by the radio of the remote interface 802. The radio of the remote interface 802 may, in some embodiments, support one or more, but not limited to, the following mode requests by way of the messaging system:
 Pairing Mode
 Connection Mode
 Acquisition Mode (includes the desired paired infusion pump assembly 100, 100', 400, 500 radio serial number)
 Sync Mode—Fast Heartbeat
 Sync Mode—Slow Heartbeat
 RF Off Mode The radio of infusion pump assembly 100, 100', 400, 500 may support the following mode requests via the messaging system:
 Pairing Mode
 Acquisition Mode
 RF Off Mode In some embodiments, the radio may use a system message to obtain the local radio serial number. On the remote interface 802, the radio may get the serial number from the UI processor of the remote interface 802. The radio may use a system message to store the paired radio serial number.

The remote interface 802 and the radio of the device 800 may issue a status message using the messaging system to the UI processor of the remote interface 802 and the command processor 902 in some embodiments whenever one or more, but not limited to, the following status changes:
 Online Fast: Successful connection
 Online Fast: Change from Acquisition Mode to Fast Heartbeat Mode
 Online Slow: Successful request change from Fast Heartbeat to Slow Heartbeat
 Offline: Automatic change to Search Sync mode due to lack of heartbeat exchanges.
 Online Fast: Successful request change from Slow Heartbeat to Fast Heartbeat
 Offline: Bandwidth falls below 10% in Sync Mode
 Online: Bandwidth rises above 10% in Search Sync mode
 Offline: Successful request change to RF Off Mode In some embodiments, the radio configuration message may be used to configure the number of radio retries. This message may be sent over the messaging system. In some embodiments, the UI processor of the remote interface 802 will send this command to both the radio of the remote interface 802 and the radio the device 800 to configure these radio settings.

In some embodiments, there may be two parameters in the radio configuration message: namely the number of RF retries (e.g., the value may be from 0 to 10); and the radio offline parameters (e.g., the value may be from 1 to 100 in percent of bandwidth). However, in various other embodiments, there may be more than or less than two parameters.

The radio application on both the remote interface 802 and the device 800 may have an API that allows the messaging system to configure the number of RF retries and radio offline parameters.

In some embodiments, one or more of, but not limited to, the following parameters may be recommended for the radio hardware configuration:
 Base Radio Specifications
 MSK
 250 kbps over air baud rate
 Up to 84 channels
 Channel spacing 1000 kHz
 Filter bandwidth 812 kHz
 No Manchester encoding
 Data whitening
 4 byte preamble
 4 byte sync (word)
 CRC appended to packet
 LQI (Link Quality Indicator) appended to packet
 Automatic CRC filtering enabled In some embodiments, Forward Error Correction (FEC) may or may not be utilized. Although Forward Error Correction (FEC) may be used to increase the effective signal dynamic range by approximately 3 dB, FEC requires fixed packet sizes and doubles the number of over the air bits for the same fixed size message, so this may not be desirable in some embodiments.

In some embodiments, the radio may function within 1.83 meters distance under nominal operating conditions (except in pairing mode). In some embodiments, the radio may function within 7.32 meters distance under nominal operating conditions. In some embodiments, the transmit power level may be 0 dBm (except in pairing mode) and the transmit power level in pairing mode may be −22 dBm. Since the desired radio node address of the device 800 may be not known by the remote interface 802 in pairing mode, in some embodiments, both the device 800 and the remote interface 802 may use a lower transmit power to reduce the likelihood of inadvertently pairing with another infusion pump assembly. However, in various other embodiment, either the device 800 or the remote interface 802 may us a lower transmit power.

In some embodiments, AES Encryption may be used for all packets but may not be required, for example, in embodiments using the Texas Instruments CC2510 radio transceiver as this transceiver includes this functionality. In the embodiments where AES encryption is used, fixed keys may be utilized, as fixed keys may be desirable for many reasons, including that they provide a quick way to enable encryption without passing keys. However, in some embodiments, key exchange may be provided in the device 800. In some embodiments, the fixed keys may be contained in one separate header source file with no other variables but the fixed keys data, thus allowing for easier management of read access of the file.

Figure 12B:
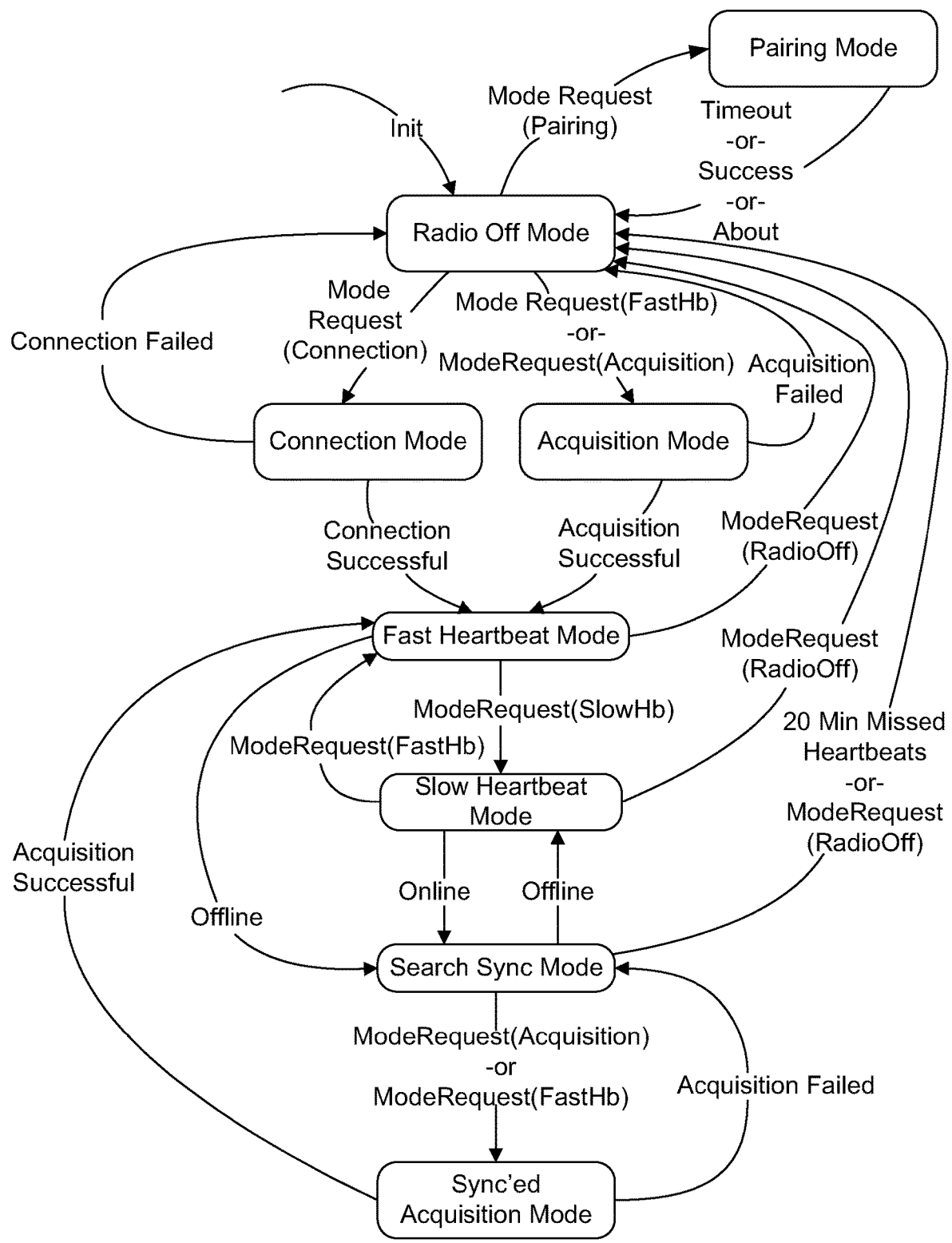
Figure 12C:
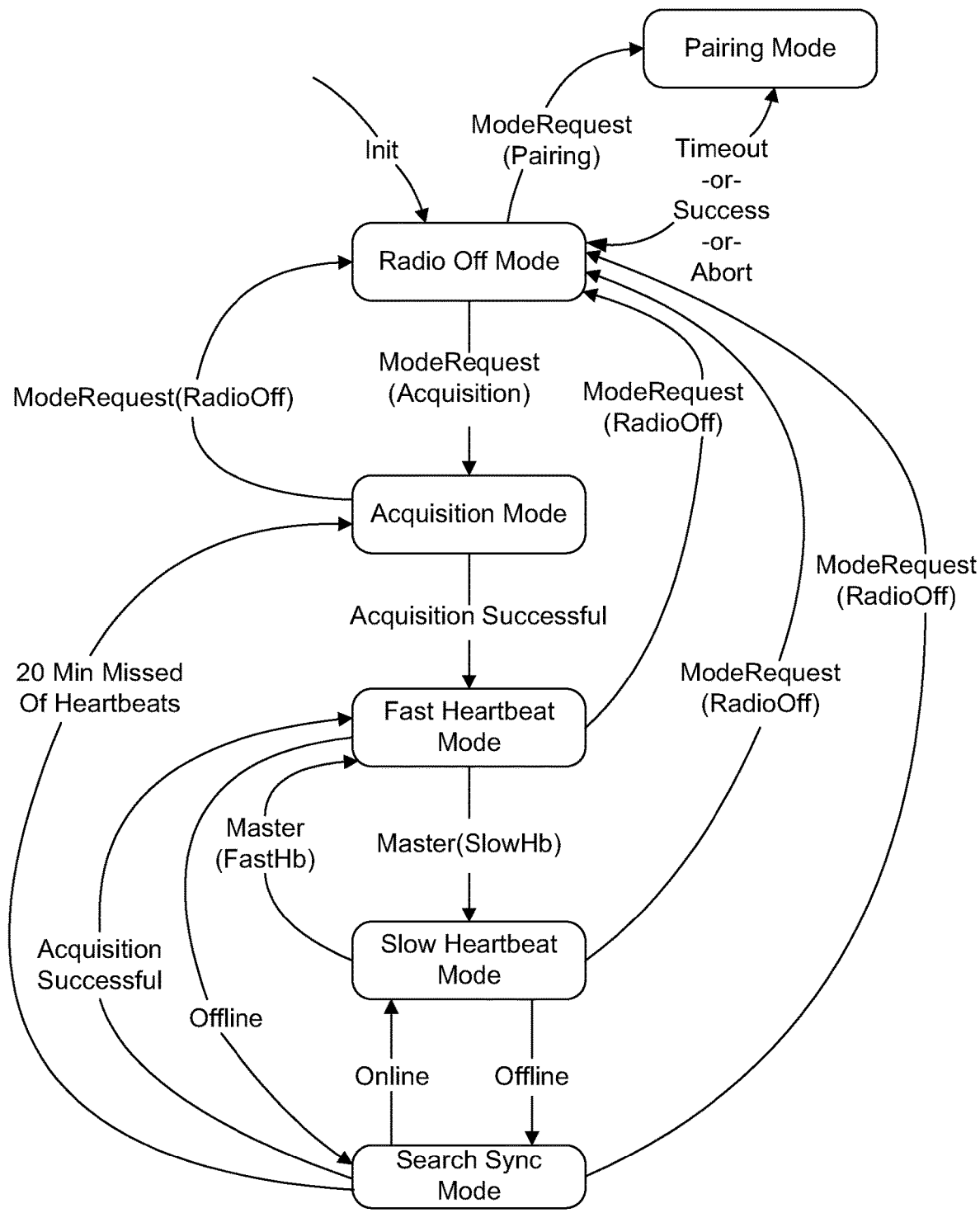

In some embodiments, the radio software may support one or more, but not limited to, of the following eight modes:
  Pairing Mode
  RF Off Mode
  Connection Mode
  Acquisition Mode
  Fast Heartbeat Mode
  Slow Heartbeat Mode
  Search Sync Mode
  Sync'ed Acquisition Mode
  all of which are graphically depicted in FIGS. 12B-12C.

Pairing may be the process of exchanging radio serial numbers between the remote interface 802 and the device 800. The remote interface 802 may be "paired" with the device 800 when the device 800 knows its serial number. The device 800 may be "paired" with the remote interface 802 when the remote interface 802 knows its serial number.

Figure 12D:
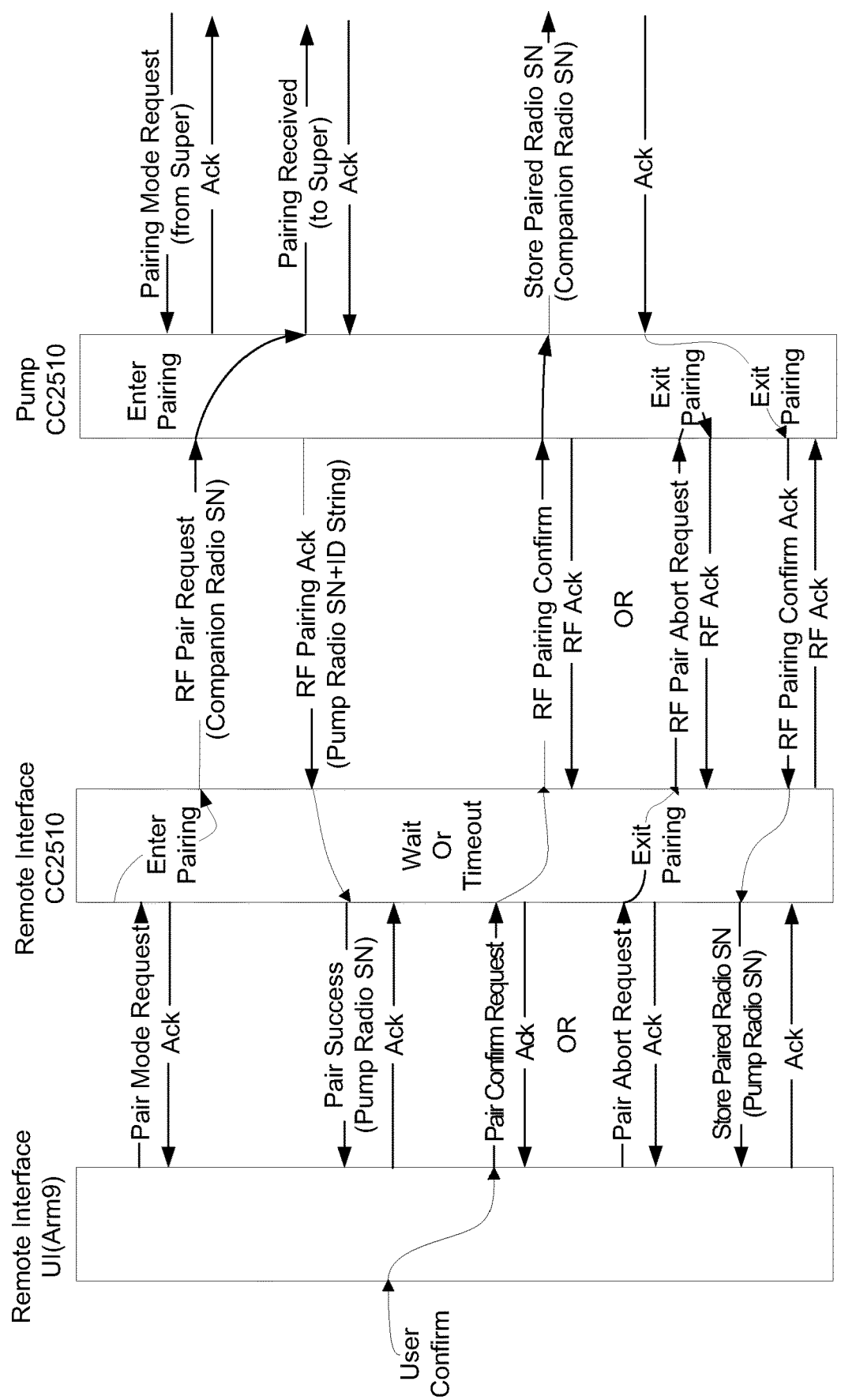

In some embodiments, pairing mode (one embodiment of which is graphically depicted in FIG. 12D) may require that four messages to be exchanged over the RF link (however, various embodiments may require more, less or no messages be exchanged over the RF link):
  RF Pairing Request (broadcast from the remote interface 802 to any device 800)
  RF Pairing Acknowledge (from the device to the remote interface 802)
  RF Pairing Confirm Request (from the remote interface 802 to the device 800)
  RF Pairing Confirm Acknowledge (from the device 800 to the remote interface 802)

Additionally, the remote interface 802 may cancel the pairing process at any time using the RF pairing abort message (from the remote interface 802 to the device 800. In some embodiments, pairing mode may not support messaging system data transfers.

In some embodiments, the radio of the device 800 may enter pairing mode upon receiving a pairing mode request message. In some embodiments, it may be the responsibility of the supervisor processor 900 on the device 800 to request the radio to enter pairing mode if there is no disposable portion attached to the device 800 and the user has pressed the switch assembly 810 of the device 800 for a predetermined amount of time, e.g., six seconds (which may vary throughout the embodiments) to indicate to the system that pairing mode is requested. The radio of the device 800 may set the appropriate transmit power level for pairing mode. In some embodiment, the device 800 may only be paired with one the remote interface 802 at a time.

In some embodiment, a Near Field Communication ("NFC") protocol may be used to identify the device 800 and remote interface 802 to be paired. For example, using NFC, the user may touch the disposable portion to the remote interface 802, while the devices are in pairing mode, and this may trigger the pairing protocol, i.e., the device 800 and remote interface 802 to be paired are identified. In some embodiments, a camera, located on the remote interface 802, may be used to capture the image of a 2 D barcodes on the device 800 and identify the device 800 using this image and/or image identification. In some embodiments, the device 800 may include a RFID transmitter which may be used in the NPC protocol for recognition).

In some embodiments, upon receiving the first valid RF pairing request message while in pairing mode, the radio of device 800 may use the serial number of the remote interface 802 for the duration of pairing mode and respond with an RF pairing acknowledge message containing the radio serial number of the device 800.

In some embodiments, the radio of the device 800 may timeout of pairing mode automatically after a predetermined amount of time, for example, 2.0±0.2 seconds, if no RF pairing request is received. In some embodiments, this time may be less than or more than 2.0±0.2 seconds. In some embodiments, the radio of the device 800 may issue a pairing request received message after transmitting the RF pairing acknowledge. This message to the supervisor processor 900 will allow feedback to the user during the pairing confirm process. The radio of the device 800 may automatically timeout of pairing mode in, for example, 1.0±0.1 minutes after sending an RF pairing acknowledge unless an RF pairing confirm request is received. In some embodiments, this time may be less than or more than 1.0±0.1 seconds. In some embodiments, the radio of the device 800 may issue a store paired radio serial number message if an RF pairing confirm request message is received after receiving a RF pairing request message. This action may store the radio serial number of the remote interface 802 in the non-volatile memory of the device 800 and may overwrite the existing pairing data for the device 800.

The radio of the device 800 may transmit an RF pairing confirm acknowledge and exit pairing mode after the acknowledgment from the store paired radio serial number message is received. In some embodiments, this may be the default exit of pairing mode on the device 800 and may result in the device 800 powering down until connection mode or paring mode entered by the user.

In some embodiments, if the radio of the device 800 exits pairing mode upon successfully receiving a pairing confirm request message, then the radio of the device 800 may revert to the newly paired remote interface 802 and may send a pairing completion success message to the command processor 902. In some embodiments, the radio of the device 800 may exit pairing mode upon receiving an RF pairing abort message. The radio of the device 800 may exit pairing mode upon receiving a pairing abort request message addressed to it. In some embodiments, this may allow the command processor 902 or the supervisor processor 900 to abort the pairing process locally on the device 800.

In some embodiments, the radio of the remote interface 802 may enter pairing mode upon receiving a pairing mode request message. In some embodiments, it may be the responsibility of the UI processor of the remote interface 802 to request that the radio enter pairing mode under the appropriate conditions. The radio of the remote interface 802 may set the appropriate transmit power level for pairing mode. In some embodiments, the radio of the remote interface 802 may transmit RF pairing requests until an RF pairing acknowledge is received or pairing is aborted.

In some embodiments, the radio of the remote interface 802 may automatically abort pairing mode if the RF pairing acknowledge message is not received within a predetermined time, for example, 30.0±1.0 seconds after entering pairing mode. However, in various embodiments, the predetermined time may be greater than or less than 30.0±1.0 seconds. In some embodiments, upon receiving the first valid RF pairing acknowledge message while in pairing mode, the radio of the remote interface 802 may send a pairing success message to the UI processor of the remote interface 802 that includes the serial number of the device 800 and may use that serial number for the duration of pairing mode. This message may provide a means for the UI processor of the remote interface 802 to have the user confirm the serial number of the desired device 800. In some embodiments, if the radio of the remote interface 802 receives multiple responses (concerning a single pairing request) the device 800, the first valid one may be used.

In some embodiments, the radio of the remote interface 802 may only accept an RF pairing confirm acknowledge messages after an RF pairing acknowledge is received while in pairing mode. The radio of the remote interface 802 may transmit the RF pairing confirm message upon receiving a pair confirm request message from the UI processor of the remote interface 802.

In some embodiments, the radio of the remote interface 802 may check that the device 800 confirms the pairing before adding the device 800 to the pairing list. In some embodiments, the radio of the remote interface 802 may issue a store paired radio serial number message if an RF pairing complete message is received. This action may allow the UI processor of the remote interface 802 to store the new serial number of the device 800 and provide user feedback of a successful pairing. It may be the responsibility of the UI processor of the remote interface 802 to manage the list of paired infusion pump assemblies. Thus, in some embodiments of the system, the system may include more than one device, and each of the more than one device may be paired with the remote interface 802. However, in some embodiments, it may be desirable that one device of the paired devices, be in use with the remote interface 802 at any given time. Thus, in these embodiments, once the initial pairing process is complete and the remote interface 802 includes the device on its list of paired devices, the user indicates to the remote interface 802 the device in which communication is desired for that duration (predetermined amount of time) for use.

In some embodiments, the radio of the remote interface 802 may send an RF pairing abort message and exit pairing mode upon receiving a pairing abort request message. This may allow the UI processor of the remote interface 802 to abort the pairing process on both the remote interface 802 and the acknowledged device 800.

Figure 12E:
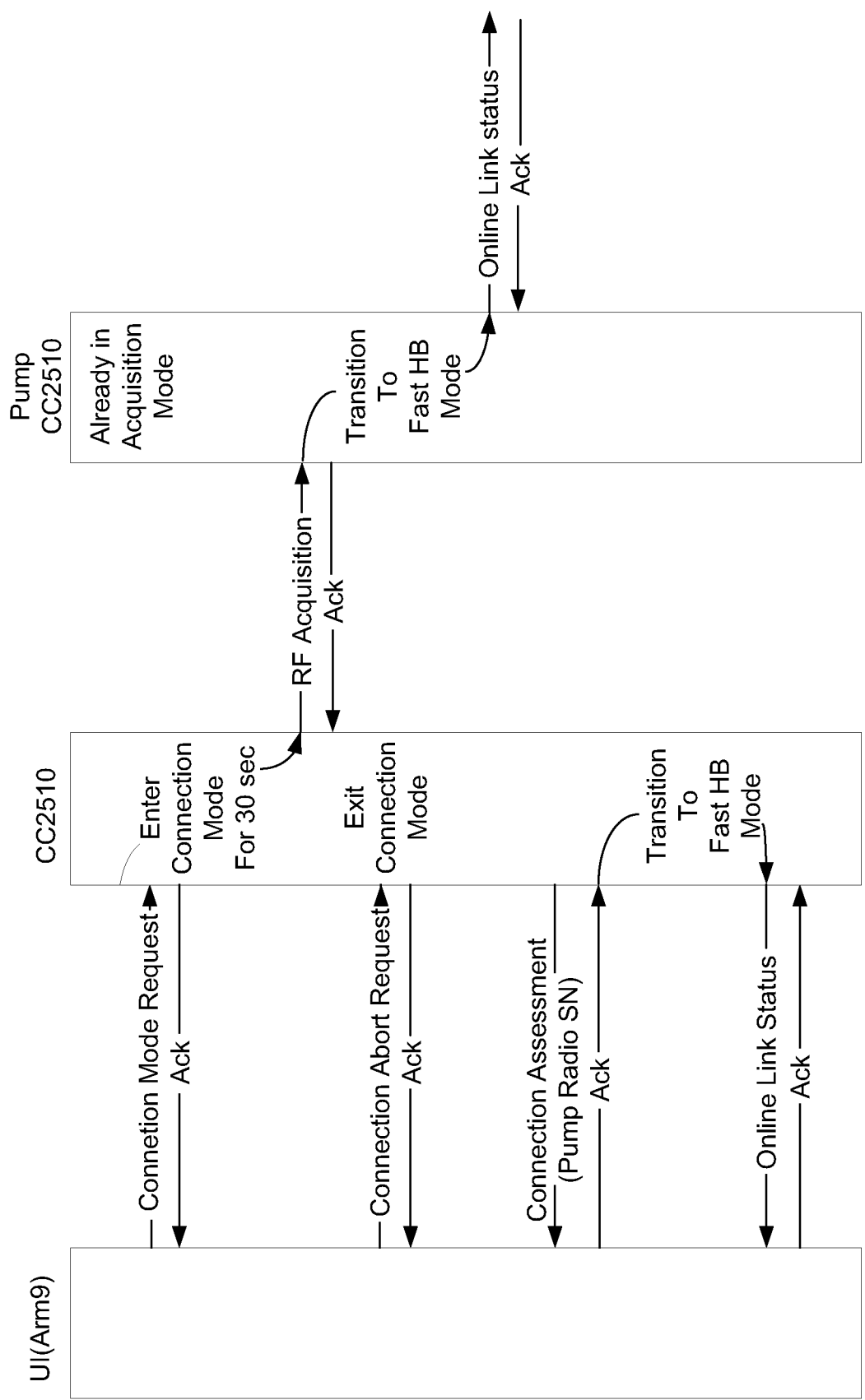

In connection request mode, the radio of the remote interface 802 may attempt to acquire each device 800 in its paired device list and retrieve its "connection ready" status. The "connection" process, one embodiment of which is graphically depicted in FIG. 12E, in some embodiments may allow the remote interface 802 to quickly identify one of its paired devices that may be ready to be used. The radio of the remote interface 802 may be capable of performing the connection request mode with a plurality of devices, for example, in some embodiments, up to six paired reusable portions of infusion pumps. The connection request mode may be only supported on the remote interface 802 and may be a special form of acquisition mode. In connection request mode, the remote interface 802 may connect with the first device to respond. However, each message may be directed to a specific device serial number.

In some embodiments, the radio of the remote interface 802 may obtain the latest paired device's serial number list upon entering connection mode. The radio of the remote interface 802 may enter connection mode upon receiving a connection mode request message. It may be the responsibility of the UI processor of the remote interface 802 to request that the radio enter connection mode when it desires communications with a paired device. The radio of the remote interface 802 may issue a connection assessment message to the UI processor of the remote interface 802 containing the radio serial number of the first device, if any, that is "connection ready". The radio of the remote interface 802 may generate the connection assessment message within a predetermined amount of time, for example, thirty seconds, of entering connection request mode. However, the predetermined amount of time may be less than or more than thirty seconds in various embodiments. In some embodiments, the radio of the remote interface 802 may exit connection request mode upon receipt of the connection assessment acknowledgement and transition to fast heartbeat mode. The radio of the remote interface 802 may exit connection request mode upon receipt of a connection request abort message from the UI processor of the remote interface 802.

On the remote interface 802, acquisition mode may be used to find a particular paired device. In some embodiments, the radio of the remote interface 802 may send RF RUT (aRe yoU There) packets to the desired paired device. If the device receives the RF RUT message, it may respond to the radio of the remote interface 802. In some embodiments, multiple channels may be used in the acquisition mode algorithm to improve the opportunity for the radio of the remote interface 802 to find the paired device.

The radio of the remote interface 802 may enter acquisition mode upon receiving an acquisition mode request or fast heartbeat mode request message while in RF Off Mode. The radio of the remote interface 802 may enter sync'ed acquisition mode upon receiving an acquisition mode request or fast heartbeat mode request message while in search sync mode. It may be the responsibility of the UI processor of the remote interface 802 to request that the radio enter acquisition mode when the RF link is off-line and the remote interface 802 desires communications with a device.

In some embodiments, particularly in those embodiments where the device is an infusion pump, the radio of the remote interface 802 may only communicate with one paired infusion pump 800 (except in pairing and connection modes). In some embodiments, when communications are lost, the UI processor of the remote interface 802 may use acquisition mode (at some periodic rate limited by the power budget) to attempt to restore communications.

In some embodiments, the device 800 may enter acquisition mode under one or more of the following condition, although in various other embodiments, additional conditions may trigger acquisition mode:

When in Radio Off Mode and Acquisition Mode may be requested.

When Search Sync Mode times out due to lack of heartbeats.

Upon entering acquisition mode, the radio of the device 800 may obtain the serial number of the last stored paired the remote interface 802. The radio of the device 800 may only communicate with the remote interface 802 to which it has been "paired" (except while in the "pairing request" mode). The radio of the device 800 may transition from acquisition mode to fast heartbeat mode upon successfully acquiring synchronization with the remote interface 802. The acquisition mode of the device 800 may be capable of acquiring synchronization within 6.1 seconds, which, in some embodiments, may indicate that the device 800 may always be listening at least every ~6 seconds when in acquisition mode. However, in various embodiments, the listening may be at shorter or increased durations.

In some embodiments, data packets may be sent between, for example, a paired device 800 and the remote interface 802 when the device 800 and the remote interface 802 are in sync mode and online. The two devices may sync via a heartbeat packet before data packets are exchanged. Each radio may send data packets at known time intervals after the heartbeat exchange. The device 800 may adjust its timing to anticipate reception of a packet. In some embodiments, the radio may support one data packet in each direction on each heartbeat. The radio may provide a negative response to a fast heartbeat mode request if the radio is offline. The radio of the remote interface 802 may change to fast heartbeat mode if a system request for fast heartbeat mode is received while in slow heartbeat mode and the radio is online.

Upon transitioning to fast heartbeat mode from acquisition mode, the radio of the remote interface 802 may send the master channel list message. The master channel list may be built by the radio of the remote interface 802 and sent to the radio of the device 800 to allow a selection of frequency hopping channels based on historical performance. When in fast heartbeat mode or slow heartbeat mode, periodic heartbeat messages may be exchanged between the radio of the remote interface 802 and the radio of the device 800. The periodicity of these messages may be at the heartbeat rate. The heartbeat messages may allow data packet transfers to take place and may also exchange status information. In some embodiments, the two radios may exchange the following status information, however, in other embodiments, additional information or less information may be exchanged: Quiet Mode, data availability, buffer availability, heartbeat rate, and prior channel performance. In some embodiments, it may be a goal to keep the packet size of the heartbeat messages small in order to conserve power. In these embodiments, the radio may provide for a maximum data packet size of eighty-two bytes when in Sync Mode. The messaging system may be designed to support packet payload sizes up to, for example, sixty-four bytes. The maximum size may be selected as an optimal trade-off between minimum messages types and non-fragmented messages. In some embodiments, the eighty-two bytes may be the maximum packet size of the messaging system including packet overhead, however, in various embodiments, this maximum packet size may be larger or smaller.

In some embodiments, the messaging system has an API that may allow the radio protocol to send an incoming radio packet to it. The messaging system may also have an API that allows the radio protocol to get a packet for transmission over the radio network. The messaging system may be responsible for packet routing between the radio protocol and the SPI port. Data packets may be given to the messaging system for processing. The messaging system may have an API that allows the radio protocol to obtain a count of the number of data packets waiting to be sent over the radio network. The radio protocol may query the messaging system on each heartbeat to determine if data packets are available to send over the radio network. It may be desirable for the software to check the availability of a message just before the heartbeat is sent to minimize round trip message latency.

The radio protocol may be capable of buffering one incoming radio data packet and passing the packet to the messaging system. In some embodiments, the radio protocol may send the data packet to the messaging system upon receipt of the data packet. The message system may be responsible for routing radio data packets to the proper destination node. The radio protocol may be capable of buffering one packet from the messaging system.

The radio protocol may be responsible for acknowledging receipt of valid data packets over the RF link via an RF ACK reply packet to the sending radio. The RF ACK packet may contain the source and destination radio serial numbers, RF ACK command identification, and sequence number of the data packet being acknowledged.

In some embodiments, the radio transmitting a radio data packet may retransmit that radio data packet on the next heartbeat with the same sequence number if an RF ACK is not received and the retry count is within the maximum RF retries allowed. If interference corrupts a transmission on a particular frequency, in some embodiments, an RF retry allows the same packet to be retransmitted at the next opportunity at a different frequency. The sequence number provides a means of uniquely identifying the packet over a short time window. The number of radio packet retries may be configurable using the radio configuration command. Allowing more retries may increase the probability of a packet being exchanged but introduces more latency for a round trip messages. The default number of radio retries at power up may be ten (i.e., the maximum transmission attempts before dropping the message). However, this maximum number may vary in various embodiments.

In some embodiments, a one byte (modulo 256) radio sequence number may be included in all radio data packets over the RF link. Since the radio may be responsible for retrying data packet transmission if not acknowledged, the sequence number may provide a way for the two radios to know if a data packet is a duplicate. The transmitted sequence number may be incremented for each new radio data packet and may be allowed to rollover. When a data packet is successfully received with the same sequence number as the previous successfully received data packet (and in the same direction), the data packet may be ACK'd and the received data packet discarded. This may remove duplicate packets generated by the RF protocol before they are introduced into the network. Note that it may be possible that multiple data packets in a row may need to be dropped with the same sequence number under extreme situations.

In some embodiments, if a heartbeat is missed, the radio of the remote interface 802 and the radio of the device 800 may attempt to send and listen respectively for subsequent heartbeats. The radio of the remote interface 802 and the radio of the device 800 may automatically change from fast heartbeat mode or slow heartbeat mode to search sync mode if heartbeats are missed for two seconds. This may minimize power consumption when the link is lost by allowing the radios to continue to use their synchronization information, as two seconds allows sufficient time to hop through all channels.

In some embodiments, the radio may be considered online while in the following modes:
Fast Heartbeat mode
Slow Heartbeat mode For, in some embodiments, these may be the only conditions where the messaging system traffic may be exchanged. All other conditions may be considered offline.

The radio may initialize to radio off mode at the start of code execution from reset. When code first executes on the radio processor, the initial state may be the radio off mode to allow other processors to perform self-tests before requesting the radio to be active. This requirement does not intend to define the mode when waking from sleep mode. The radio may cease RF communications when set to radio off mode. On the remote interface 802, this mode may be intended for use on an airplane, or in airplane mode, to suppress RF emissions. Since the device 800 only responds to transmissions from the remote interface 802 (which will have ceased transmitting in airplane mode), radio off mode may only be used on the device 800 when charging.

In some embodiments, the command processor 902 may be informed of airplane mode and that, therefore, the RF was intentionally turned off on the remote interface 802 so that it does not generate walk-away alerts. However, this may be completely hidden from the radio of the device 800.

In some embodiments, the radio of the remote interface 802 and the radio of the device 800 may periodically attempt to exchange heartbeats in order to reestablish data bandwidth while in search sync mode. The radio of the remote interface 802 may transition to radio off mode after a predetermined period of time, for example, twenty minutes, of search sync mode with no heartbeats successfully exchanged.

In some embodiments, the radio of the device may transition to acquisition mode after a predetermined amount of time, for example, twenty minutes, of search sync mode with no heartbeats successfully exchanged. In some embodiments, listening during pre-agreed time slots may be the most efficient use of power for the device 800 to re-establish the RF link. After a loss of communications, the crystal tolerance and temperature drift may make it necessary to expand the receive window of the device 800 over time. Staying in search sync mode for extended periods (e.g., 5-20 minutes) after communications loss may cause the instantaneous power consumed to exceed the average power budgeted for the radio of the device 800. The radio of the remote interface 802 may not be forced to expand its window, so staying in search sync mode may be very power efficient. Acquisition mode may consume more power for the remote interface 802. In some embodiments, twenty minutes may be used as a compromise to balance power consumption on both the radio of the remote interface 802 and the radio of the device 800, however, this time may vary with the embodiment.

The radio of the remote interface 802 and the radio of the device 800 may transition to slow heartbeat mode if they successfully exchange a predetermine percentage of a group of heartbeats, for example, three of the last five heartbeats. Then, at a predetermined interval, for example, approximately every six seconds, a burst of five (or more, or less, or less, depending on the embodiment) heartbeats may be attempted. If a predetermined percentage of these, for example, three of these are successful, the bandwidth may be assumed to be sufficient to transition to slow heartbeat mode. The radio of the device 800 may be acquirable while in search sync mode with a latency of, for example, 6.1 seconds, however, this latency may vary with embodiments. In this embodiments, this may imply that the device 800 may always be listening at least every ~6 seconds when in search sync mode.

Radio protocol performance statistics may be desired to promote troubleshooting of the radio and to assess radio performance. In some embodiments, the following radio performance statistics may be maintained by the radio protocol in a data structure, however, these are merely one embodiment and these may vary throughout the embodiments. Some embodiments may not use statistics or may use more, less or different statistics:

| NAME | SIZE | DESCRIPTION |
|---|---|---|
| TX Heartbeat Count | 32 Bits | Total transmitted heartbeats |
| RX Heartbeat Count | 32 bits | Total valid received heartbeats |
| CRC Errors | 16 bits | Total packets received over the RF link which were dropped due to bad CRC. This may be a subset of RX Packets Nacked. |
| First Retry Count | 32 bits | Total number of packets which were successfully acknowledged after 1 retry |
| Second Retry Count | 32 bits | Total number of packets which were successfully acknowledged after 2 retries |
| Third Retry Count | 32 bits | Total number of packets which were successfully acknowledged after 3 retries |
| Fourth Retry Count | 32 bits | Total number of packets which were successfully acknowledged after 4 retries |
| Fifth Retry Count | 16 bits | Total number of packets which were successfully acknowledged after 5 retries |
| Sixth Retry Count | 16 bits | Total number of packets which were successfully acknowledged after 6 retries |
| Seventh Retry Count | 16 bits | Total number of packets which were successfully acknowledged after 7 retries |
| Eighth Retry Count | 16 bits | Total number of packets which were successfully acknowledged after 8 retries |

-continued

| NAME | SIZE | DESCRIPTION |
| --- | --- | --- |
| Ninth Retry Count | 16 bits | Total number of packets which were successfully acknowledged after 9 retries |
| Tenth Retry Count | 16 bits | Total number of packets which were successfully acknowledged after 10 retries |
| Dropped Retry Count | 16 bits | Total number of packets which were dropped after maximum retries attempts |
| Duplicate Packet Count | 16 bits | Total number of received packets dropped due to duplicate packet |
| 1 to 5 Missed Fast Mode Hops | 16 bits | Count of 1 to 5 consecutive missed hops in Fast mode (i.e. not received) |
| 6 to 16 Missed Fast Mode Hops | 16 bits | Count of 6 to 16 consecutive missed hops in Fast mode. |
| 17 to 33 Missed Fast Mode Hops | 16 bits | Count of 17 to 33 consecutive missed hops in Fast mode |
| 34+ Missed Fast Mode Hops | 16 bits | Count of 34 or more consecutive missed hops in Fast mode |
| 1 to 2 Missed Slow Mode Hops | 16 bits | Count of 1 to 2 consecutive missed hops in Slow mode (i.e. not received) |
| 3 to 5 Missed Slow Mode Hops | 16 bits | Count of 3 to 5 consecutive missed hops in Slow mode |
| 5 to 7 Missed Slow Mode Hops | 16 bits | Count of 5 to 7 consecutive missed hops in Slow mode |
| 8+ Missed Slow Mode Hops | 16 bits | Count of 8 or more consecutive missed hops in Slow mode |
| Destination Radio Serial Number Mismatch | 16 bits | Count of received packets in which the destination made it past the hardware filtering but does not match this radio's serial number. This may be not an error but indicates that the radio may be waking up and receiving (but not processing) packets intended for other radios |
| Total Walkaway Time (minutes) | 16 bits | |
| Total Walkaway Events | 16 bits | Together with total walkaway time provides an average walkaway time |
| Number of Pairing Attempts | 16 bits | |
| Total Time in Acquisition Mode (Device 800 Only) | 16 bits | |
| Total Acquisition Mode Attempts (the Remote Interface 802 Only) | 16 bits | Successful Acquisition Count 16 bits Count of transitions from Connect or Acquisition Mode to Fast Heartbeat Mode |
| Requested Slow Heartbeat Mode Transitions | 16 bits | |
| Automatic Slow Heartbeat Mode Transitions | 16 bits | |
| Radio offline messages sent | 16 bits | |
| Radio online messages sent | 16 bits | |

In some embodiments, a #define DEBUG option (compiler option) may be used to gather one or more of the following additional radio performance statistics per each channel (16 bit numbers), however, in various other embodiments, additional information may also be gathered:

Number of missed hops
CCA good count
CCA bad count
Average RSSI (accumulated for good RX packets only)
Dropped from Frequency Hop List count
Acquisition Mode count (found pair on this channel)

In some embodiments, the debug option may be used to gather engineering only statistics. If processor performance, power, and memory allow, it may be desirable to keep this information at runtime. The radio statistics may be made available to the messaging system.

In some embodiments, link quality may be intended to be used/viewable on the remote interface 802 to provide a bar indicator, similar to a cell phone, of the radio link quality. Link quality may be made available to both the remote interface 802 and the device 800. In some embodiments, the link quality status may consist of a one byte indicator of the quality of the radio link.

In some embodiments, the radio may change frequency for each heartbeat. An adaptive pseudo random frequency hopping algorithm may be used for sync mode and heartbeat attempts in search sync mode. In some embodiments, it may be a goal to use, for example, sixty-four channels for frequency hopping. However, in other embodiments using frequency hopping, more than or less than sixty-four channels may be used. In some embodiments, an algorithm may be developed to adaptively generate a channel list on the remote interface 802 for frequency hopping. The radio of the remote interface 802 may build, maintain, and distribute the master channel list. In some embodiments, prior channel statistics and historical performance information may be obtained from the radio of the device 800 by the radio of the remote interface 802 using the messaging system as needed to meet performance requirements. By building the channel list from the perspective of both the device 800 and the remote interface 802, the radio interference environment of both units may be considered. The radios may adaptively select hopping channels to meet the round trip message latency, while operating in a desirable RF environment.

Figure 13:
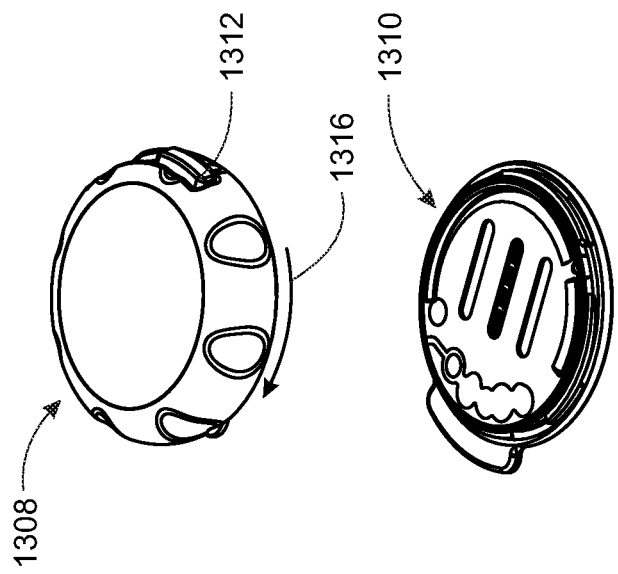
FIG. 13 is an illustration of one embodiment of the system.
Figure 13:
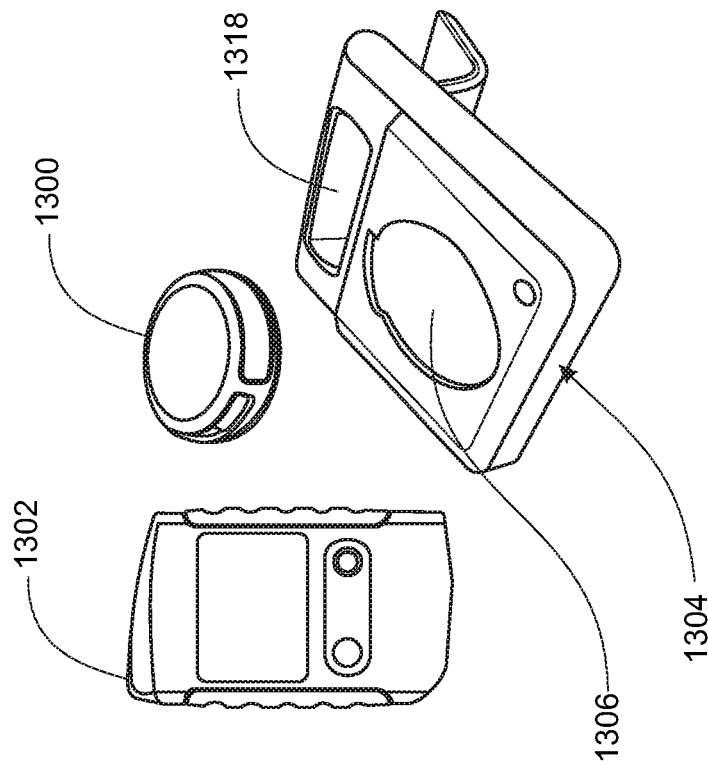

Referring now also to FIG. 13, in some embodiments, the system may include at least two reusable portions 1300, 1308 of an infusion pump and at least one disposable portion 1310 of the infusion pump. In some embodiments, the reusable portions 1300, 1308 include a rechargeable battery 532. In some embodiments, the two disposable portions may be paired to the same remote interface(s) which may include the embodiment shown in FIG. 13 as 1302 and/or any one or more shown in FIGS. 6-8 as 600, 700, 802. In some embodiments, a user may connect a reusable portion 1308 to a disposable portion 1310 by, as described above, rotating in the direction of the arrow 1316 the reusable portion 1308 while lined up with the disposable portion 1310 to connect the reusable portion 1308 with the disposable portion 1310. The second reusable portion 1300 may be docked onto the recharge station 1304 by connecting to the recharge station 1304 through electric contacts (not shown) in recharge area 1306. While the user is sleeping or otherwise remaining in a single area for an extended period of time, for example, three hours, the remote interface 1302 may be recharged by docking the remote interface 1302 onto the recharge station 1304 by connecting to the recharge station 1304 through electric contacts (not shown) in slot 1318. In some embodiments, the electric contract may be a USB plug which may be configured to couple with the remote interface 1302 when the remote interface 1302 is disposed in the slot 1318. The USB plug may allow for data transfer to/from the remote interface 1302 as well as charging of the remote interface 1302. In some embodiments, a user may use one reusable portion 1308 whilst recharging the second reusable portion 1300.

Referring now to FIGS. 14A-14E, another embodiment of the infusion pump system is shown. The system may include a remote interface 1402, one reusable portion 1400, a second reusable portion 1406, at least one disposable portion 1408 and a charging station 1404 to charge the remote interface 1402 and/or to charge one or the two disposable portions 1400, 1406. In some embodiments, the charging station may be any charging station shown in, or similar to any charging station shown and/or described in one or more of the following: U.S. Publication No. US-2007-0228071 published Oct. 4, 2007 and U.S. Publication No. US-2009-0299277 published Dec. 3, 2009 and U.S. patent application Ser. No. 12/981,283, filed Dec. 29, 2010, and entitled Infusion Pump Assembly, which are hereby incorporated herein by reference in their entireties. As discussed above with respect to FIG. 13, the charging station may include a USB plug which may be configured to couple with the remote interface 1402 when the remote interface 1402 is disposed in the slot 1414. The USB plug may allow for data transfer to/from the remote interface 1402 as well as charging of the remote interface 1402.

Referring now to FIGS. 15A-15B, another embodiment of the charging station 1500 is shown. As shown, in some embodiments, the charging station 1500 may include a charging area for a reusable portion 1504 and a charging area for the remote interface which may include a USB plug 1502. In some embodiments, the charging station 1500 may include a USB port 1508, and in some embodiments, may include a mini-USB port, allowing for the charging station 1500 to receive power, in some embodiments, for charging the reusable portion and/or the remote interface through a USB 1506. Additionally and/or alternatively the USB port 1508 may be configured for data transfer to/from a remote interface and/or a reusable portion and/or by connection to a computer or other device and/or other computer-type apparatus. In embodiments including a USB port, whilst the remote interface is being charged, the system may call to a personal computer and/or web portal to check for updated software and if there is updated software available, may download software updates. These updates may then be transferred to the reusable upon pairing.

Referring now also to FIGS. 16A-16F, as discussed above, reusable portion 1602 may include battery 1632, e.g., which may include a rechargeable battery. The battery charger 1600 may be configured to recharge battery 1632. Battery charger 1600 may include housing 1602 having top plate 1604. Top plate 1604 may include one or more electrical contacts 1606, generally, configured to be electrically coupled to electrical contacts 1634 of reusable housing assembly 1602. Electrical contacts 1606 may include, but are not limited to, electrical contact pads, spring biased electrical contact members, or the like. Additionally, top plate 1604 may include alignment tabs 1608, 1610, which may be configured to mate with openings 1636, 1638 in base plate 1618 of reusable housing assembly 1602 (e.g., as shown in FIG. 5C). The cooperation of alignment tabs 1608, 1610 and openings 1636, 1638 may ensure that reusable housing assembly 1602 is aligned with battery charger 1600 such that electrical contacts 1606 of battery charger 1600 may electrically couple with electrical contacts 1634 of reusable housing assembly 1602.

Figure 16A:
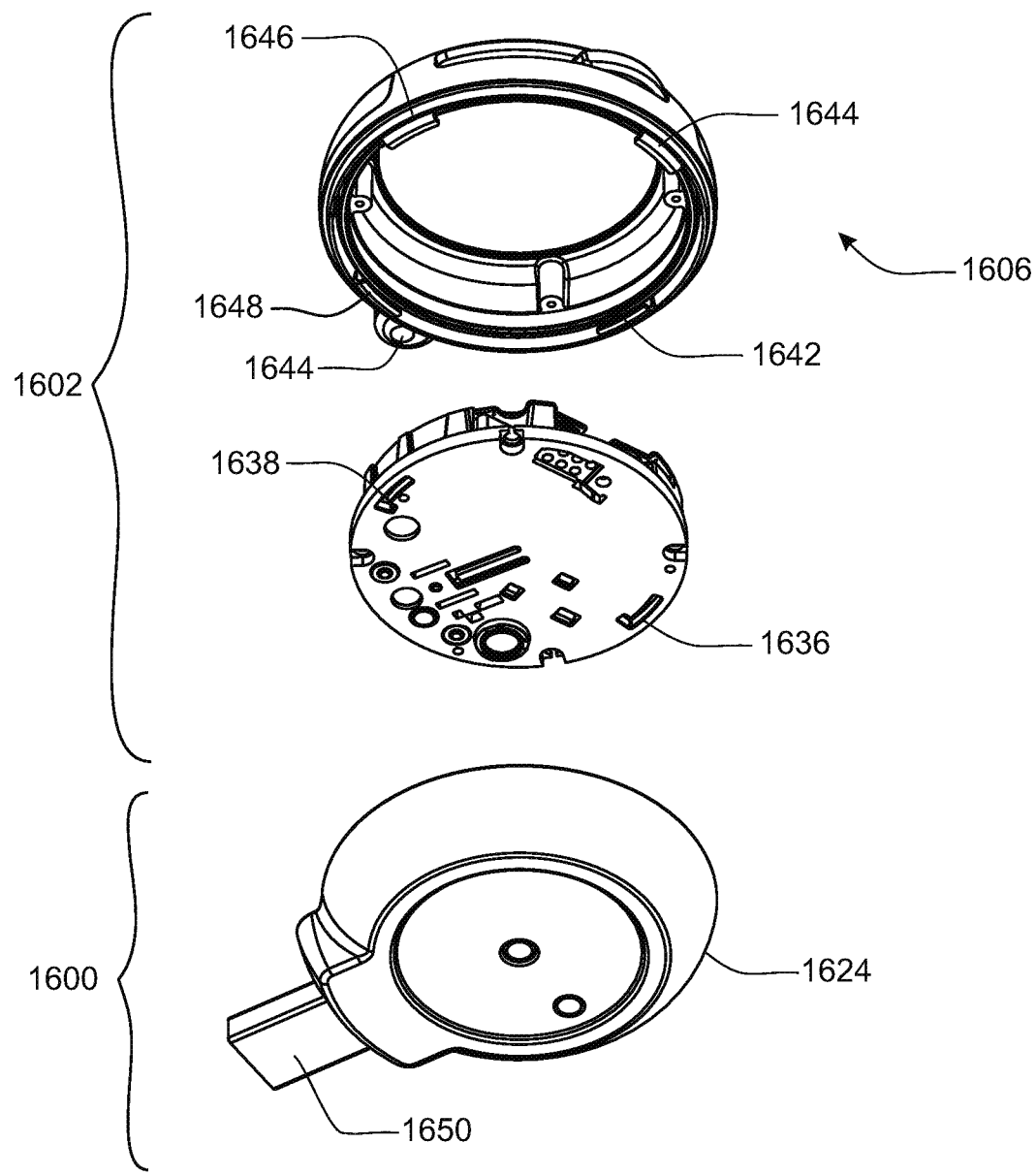
FIGS. 16A-16F depict various views of an embodiment of a battery charger/charging station according to one embodiment of the system.
Figure 16B:
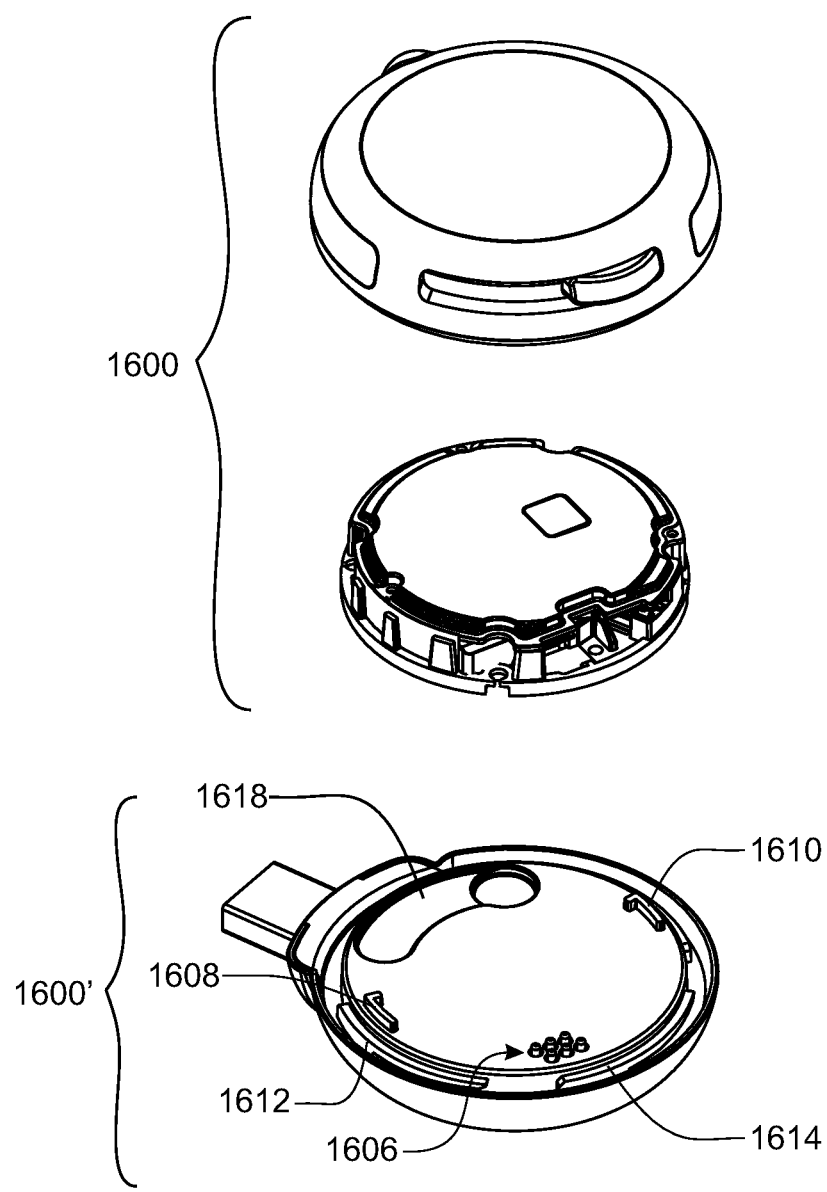
Figure 16C:
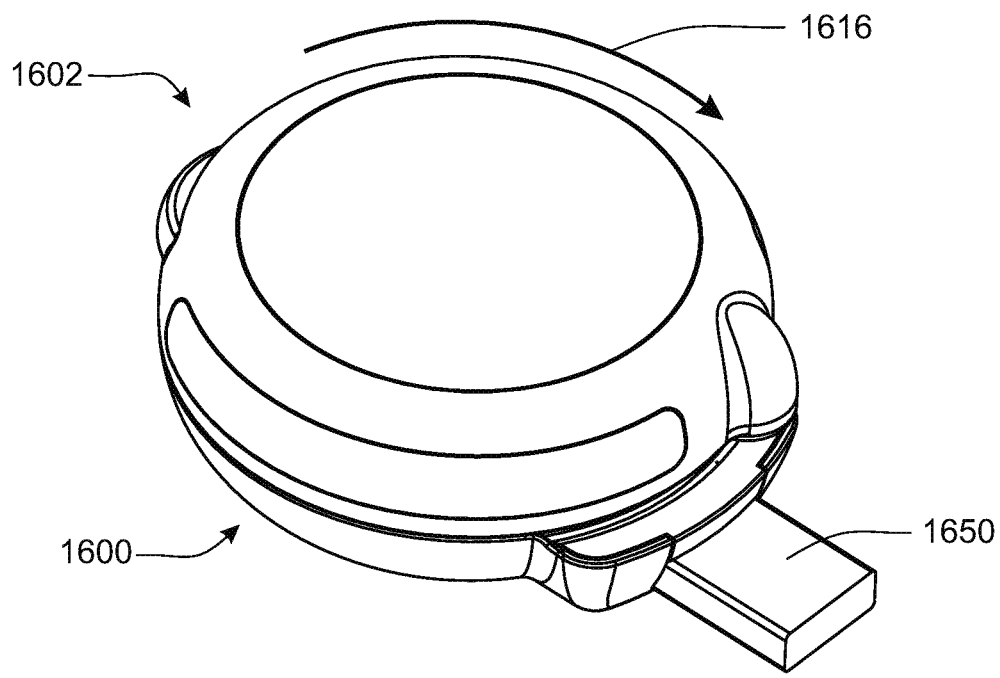
Figure 16D:
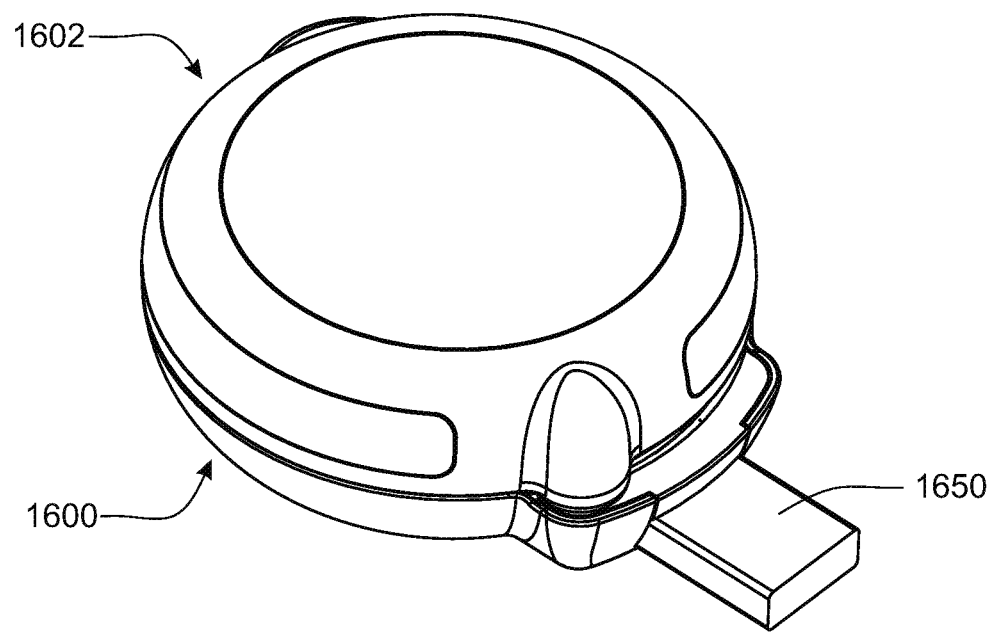

The battery charger 1600 may be configured to releasably engage the reusable portion 1602. For example, in a similar manner as disposable the disposable portion, the battery charger 1600 may include one or more locking tabs (e.g., locking tabs 1612, 1614). The locking tabs (e.g., locking tabs 1612, 1614) may be engaged by tabs 1642, 1644, 1646, 1648 of locking ring assembly 1606. As such, the reusable portion 1602 may be aligned with the battery charger 1600 (by way of the alignment tabs 1608, 1610) with the locking ring 1606 in a first, unlocked position, as shown in FIG. 16C. The locking ring 1606 may be rotated relative to the battery charger 1600 in the direction of the arrow 1616 to releasably engage the tabs 1642, 1644, 1646, 1648 of the locking ring 1606 with the locking tabs (e.g., locking tabs 1612, 1614) of the battery charger 1600, as shown in FIG. 16D.

Figure 16E:
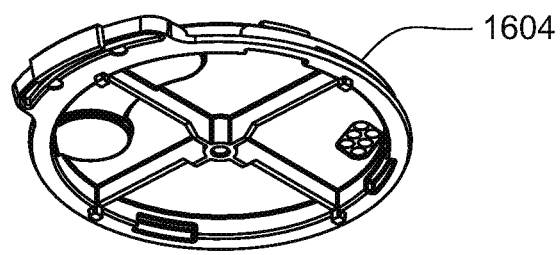
Figure 16E:
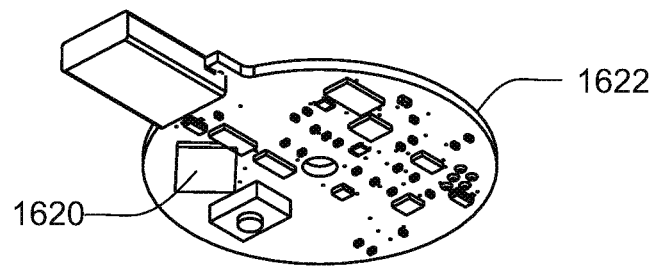
Figure 16E:
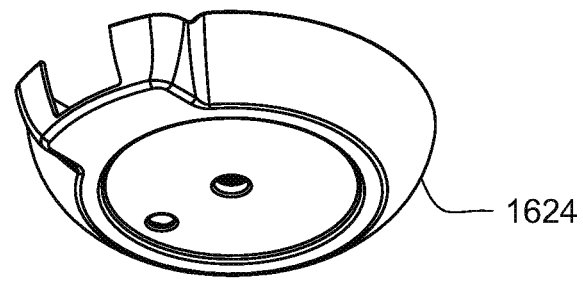
Figure 16E:
Figure 16F:
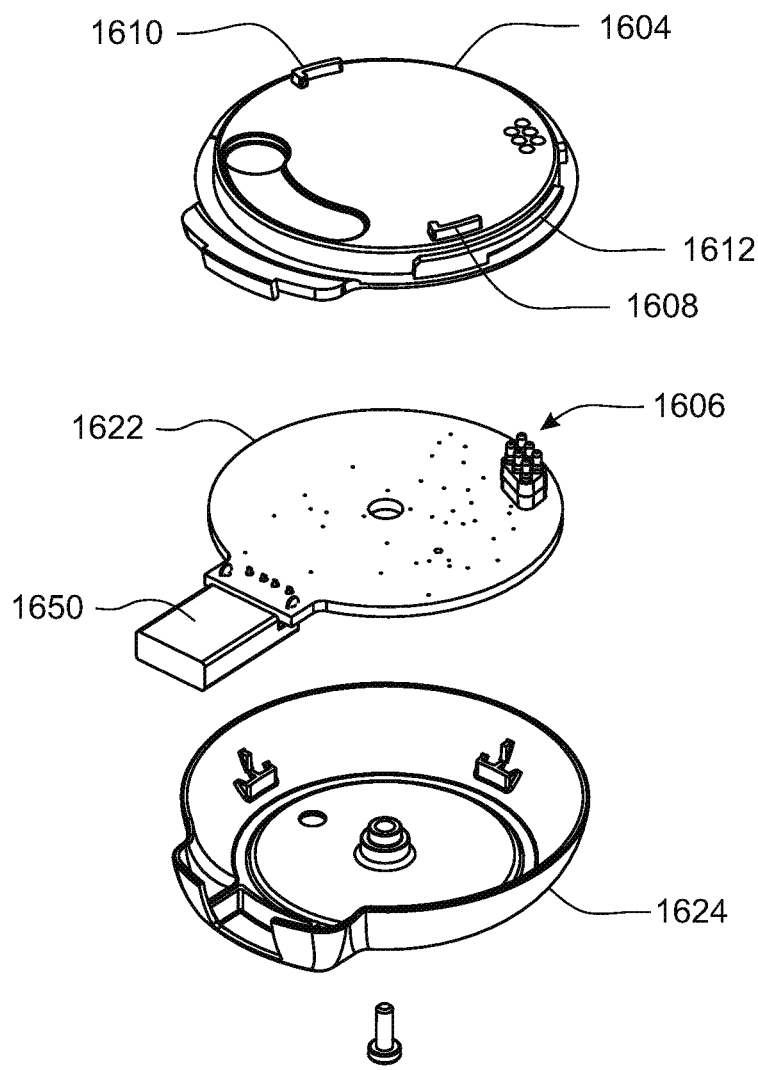

In some embodiments, battery charger 1600 may include a recessed region 1618, e.g., which may, in some embodiments, provide clearance to accommodate the reusable portion's 1602 pumping and valving components. Referring also to FIGS. 16E-16F, the battery charger 1600 may provide electrical current to the electrical contacts 1606 (and thereby to the reusable portion 1602 by way of the electrical contacts 1634) for the recharging battery 1632 of the reusable portion 1602. In some embodiments, when a signal indicative of a fully engaged reusable portion is not provided, current may not be provided to the electrical contacts 1606. According to such an embodiment, the risk associated with an electrical short circuit (e.g., resulting from foreign objects contacting the electrical contacts 1606) and damage to the reusable portion 1602 (e.g., resulting from improper initial alignment between the electrical contacts 1606 and the electrical contacts 1634) may be reduced. Additionally, in some embodiments, the battery charger 1600 may not unnecessarily draw current when the battery charger is not charging the reusable portion 1602. Still referring to FIGS. 16E-16F, the battery charger 1600 may include a lower housing portion 1624 and top plate 1604. The printed circuit board 1622 (e.g., which may include electrical contacts 1606) may be disposed within a cavity included between the top plate 1604 and the lower housing portion 1624.

Still referring to FIGS. 16A-16F, in some embodiments, the battery charger 1600 may include a USB plug 1650 which may be configured to couple with a wall charger and/or a computer and/or a personal computer and/or with a remote interface. The USB plug 1650 may allow for data transfer to/from the computer/remote interface 1402 as well as providing power to the charging of the reusable portion 1602 using the battery charger 1600.

Figure 17:
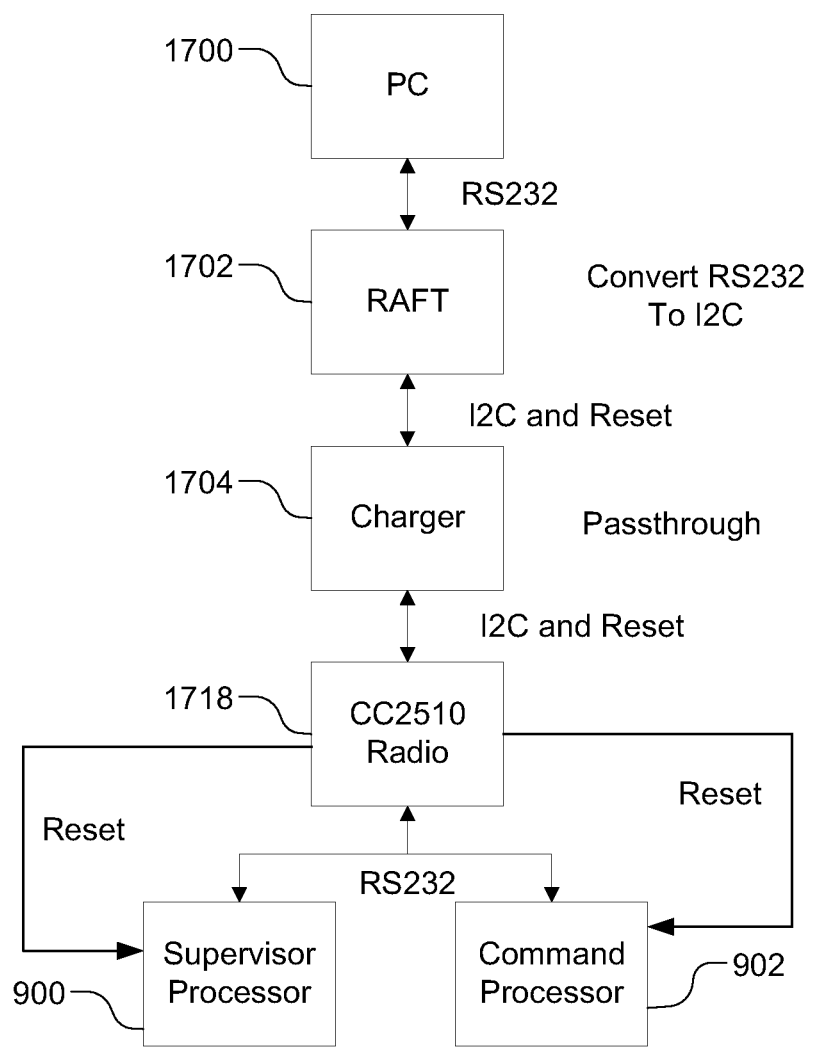
FIG. 17 diagrammatically depicts one embodiment of an inter-connection of the various elements of the system.

Referring also to FIG. 17, there is shown one illustrative example of the manner in which the various parts of the infusion pump system are connected/communicate with one another. For example, battery charger 1704 may be coupled to computing device 1700 (which, in some embodiments, may be a personal computer or any device that may be used in a similar fashion as a personal computer, for example, but not limited to, a tablet) by way of bus translator 1702, which converts, for example, and in some embodiments, RS232 formatted data to e.g., I2C formatted data. Bus translator 1702 may execute a pass-through program that effectuates the above-described translation. Battery charger 1704 may be coupled to the radio processor 1718 by way of electrical contacts 1606 (described above). Radio processor 1718 may then be coupled to supervisor processor 900 and command processor 902 via e.g., an RS232 bus. The Radio processor 1718 may, in some embodiments, execute an update program that allows radio processor 1718 to control/orchestrate the updating of the flash memories accessible by supervisor processor 900 and command processor 902. Accordingly, through the use of the above-described coupling, software updates obtained by computing device 1700 may be uploaded to flash memory (not shown) accessible by supervisor processor 900 and command processor 902. The above-described software updates may, in some embodiments, be command line program that may be automatically invoked by a script process.

Figure 18:
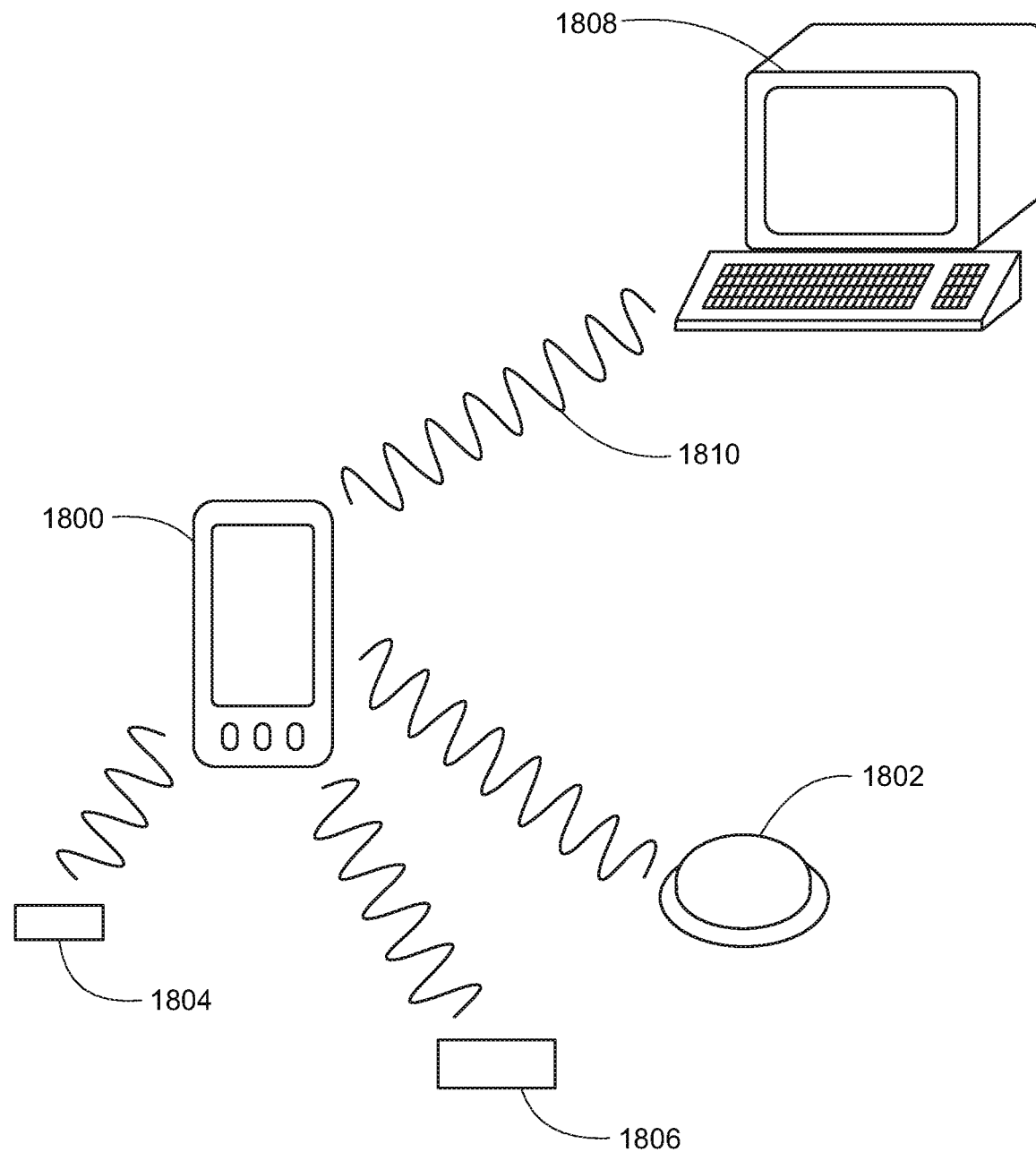
FIG. 18 is an illustration of one embodiment of the system.
Figure 19:
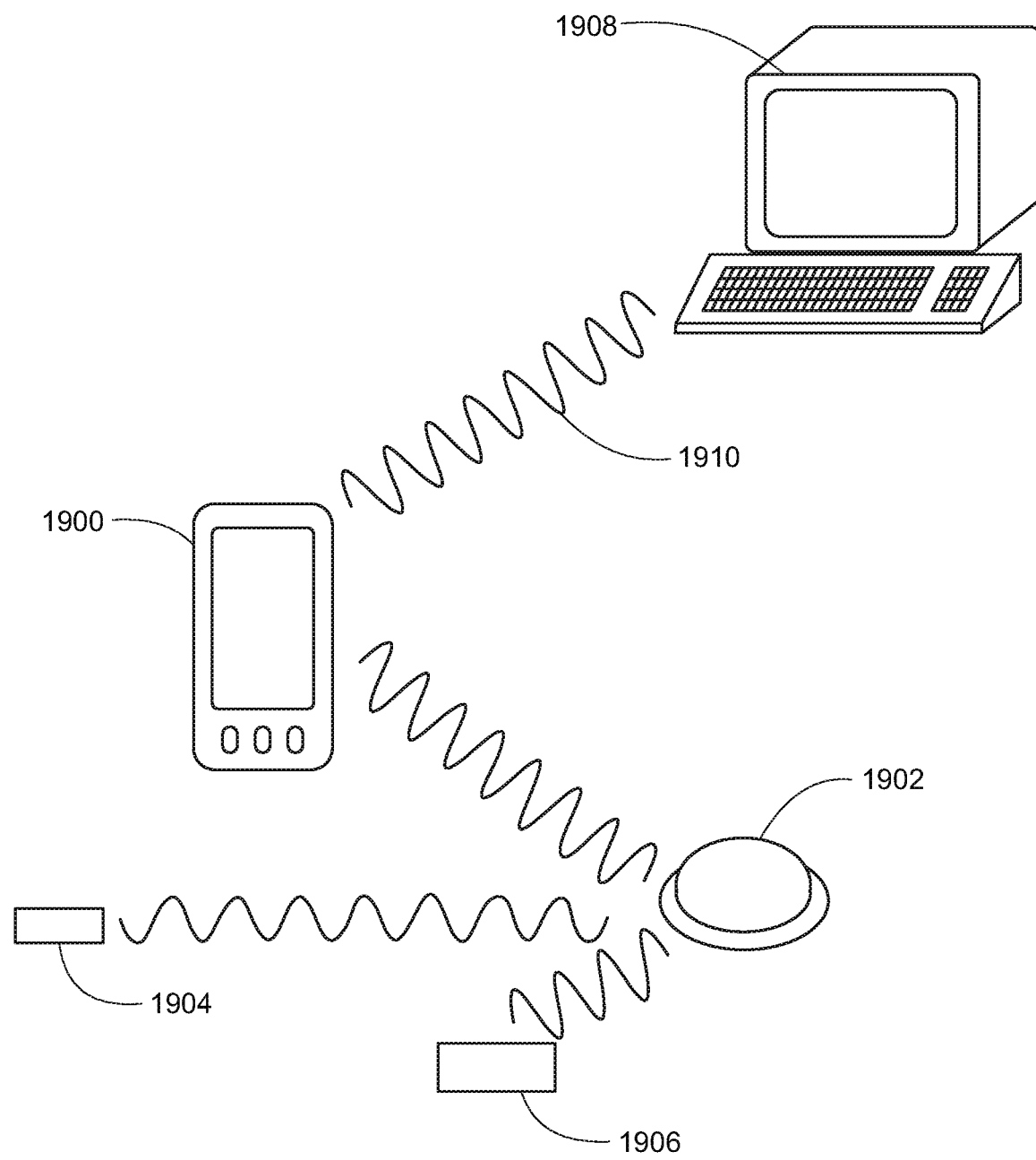
FIG. 19 is an illustration of one embodiment of the system.

Referring now to FIG. 18 and FIG. 19, two embodiments of communication between device(s), the remote interface and a personal computer (which, in some embodiments has access to one or more web portals and/or one or more secure web portals) are shown. In FIG. 18, a remote interface 1800 is in communication with an infusion pump 1802 and two other devices, which, in some embodiments, may include a blood glucose meter 1806 and a continuous glucose monitor sensor/transmitter 1804. In some embodiments, the communication is wireless communication and may be using RF communication, for example, RF communication protocols as described above and/or may use BLUETOOTH/BLUETOOTH Low Energy or other non-proprietary protocols. In some embodiments, the remote interface 1800 is in wireless communication with a personal computer 1808, however, in some embodiments, the remote interface 1800 may be connected to the personal computer 1808 by way of a USB connection and/or other wired connection. In some embodiments, the remote interface 1800 and personal computer 1808 may be in communication by way of a web/internet connection 1810 and or by way of the remote interface 1800 uploading information to the internet and the personal computer 1808 downloading the information from the internet. In some embodiments, the remote interface 1800 and personal computer 1808 may be in communication by way of a wired and/or infrared ("IR") connection 1810 i.e., by way of the remote interface 1800 uploading information to the personal computer 1808.

In FIG. 19, a remote interface 1900 is in communication with an infusion pump 1902. The infusion pump 1902 is in communication with two other devices, which, in some embodiments may include a blood glucose meter 1906 and/or a continuous glucose monitor sensor/transmitter 1904, and in some embodiments, may be two continuous glucose monitor sensors. In some embodiments, the communication is wireless communication and may be using RF communication, for example, RF communication protocols as described above and/or may use BLUETOOTH or other non-proprietary protocols, including but not limited to, low energy BLUETOOTH/BLUETOOTH Low Energy. In some embodiments, the infusion pump 1902, which is in wireless communication with the remote interface 1900, may communicate the information received from the two devices 1904, 1906, to the remote interface 1900. The remote interface 1900 therefore serves as the visual UI as the remote interface 1900, in some embodiments, includes display. In some embodiments, the remote interface 1900 is in wireless communication with a personal computer 1908 (which in some embodiments, has access to at least one web portal and/or secure web portal), however, in some embodiments, the remote interface 1900 may be connected to the personal computer 1908 by way of a USB connection and/or other wired connection. In some embodiments, the remote interface 1900 and personal computer 1908 may be in communication by way of a web/internet connection 1910 and or by way of the remote interface 1900 uploading information to the internet and the personal computer 1908 downloading the information from the internet.

With respect to both FIGS. 18 and 19, although shown are three devices in communication, either directly or indirectly, with a remote interface, the system is not limited to three devices, and in some embodiments, may include more than three devices. Additionally, in some embodiments, the system may include one device in communication with the remote interface 1900. Also, although one personal computer is illustrated in FIGS. 18 and 19, in other embodiments, one or more personal computer may be used to receive information from a remote interface. Additionally, as discussed above with respect to the battery charger and charging station, in some embodiments, the infusion pump and/or the remote interface may be connected to a charging station and may upload and/or download and/or communicated with the personal computer by way of a USB connection.

Figure 35A:
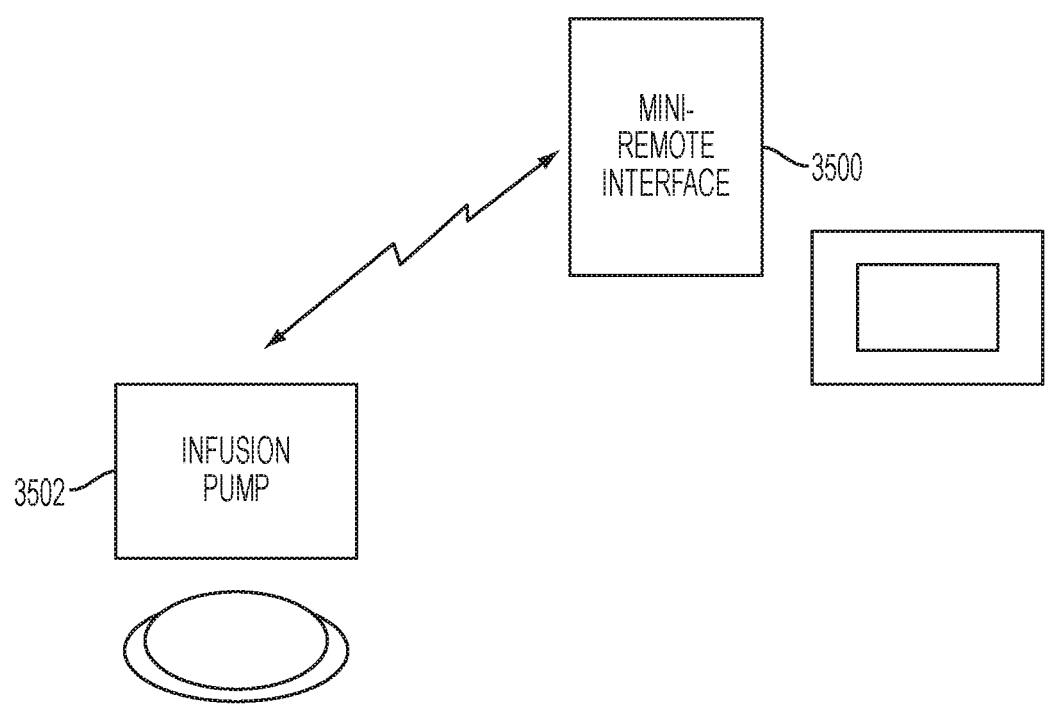
FIG. 35A is an illustration of one embodiment of the system.

Referring now also to FIG. 35A, in some embodiments, the remote interface 3500 is in communication with an infusion pump 3502. In some embodiments, the remote interface 3500 may be any device, including, but not limited to, a SMARTWATCH, for example, as manufactured to SONY Corporation, Tokyo, Japan, or other similar type devices, which may be referred to as a "mini-remote interface". In some embodiments, the mini-remote interface may include one or more user inputs which includes any mechanism by which a user and/or other operator/caregiver of the device and/or remote interface may control a function of the device and/or remote interface. User inputs may include one or more mechanical arrangements (e.g., switches, pushbuttons, jogwheel(s)), electrical arrangements (e.g., a slider, touch screen), wireless interfaces for communication with a remote interface (e.g., radio frequency ("RF"), infrared ("IR"), BLUETOOTH, BLUETOOTH LOW ENERGY, WiFi, ZIGBEE, XB, WiFi ad hoc, White Space, Ultra wide band, Ant, and/or wireless USB), acoustic interfaces (e.g., with speech recognition), computer network interfaces (e.g., USB port), light/light wave image including, but not limited to, camera input and/or images captured using a camera), sound wave and/or other types of interfaces.

In some embodiments, the mini-remote interface may include all or a portion of the functionality described above with respect to the remote interface. In some embodiments, therefore, the mini-remote interface may provide all of the same functionality (and additional in some embodiments) as described above with respect to the remote interface and may pair, etc., with the infusion pump in some embodiments, as described above.

Figure 35B:
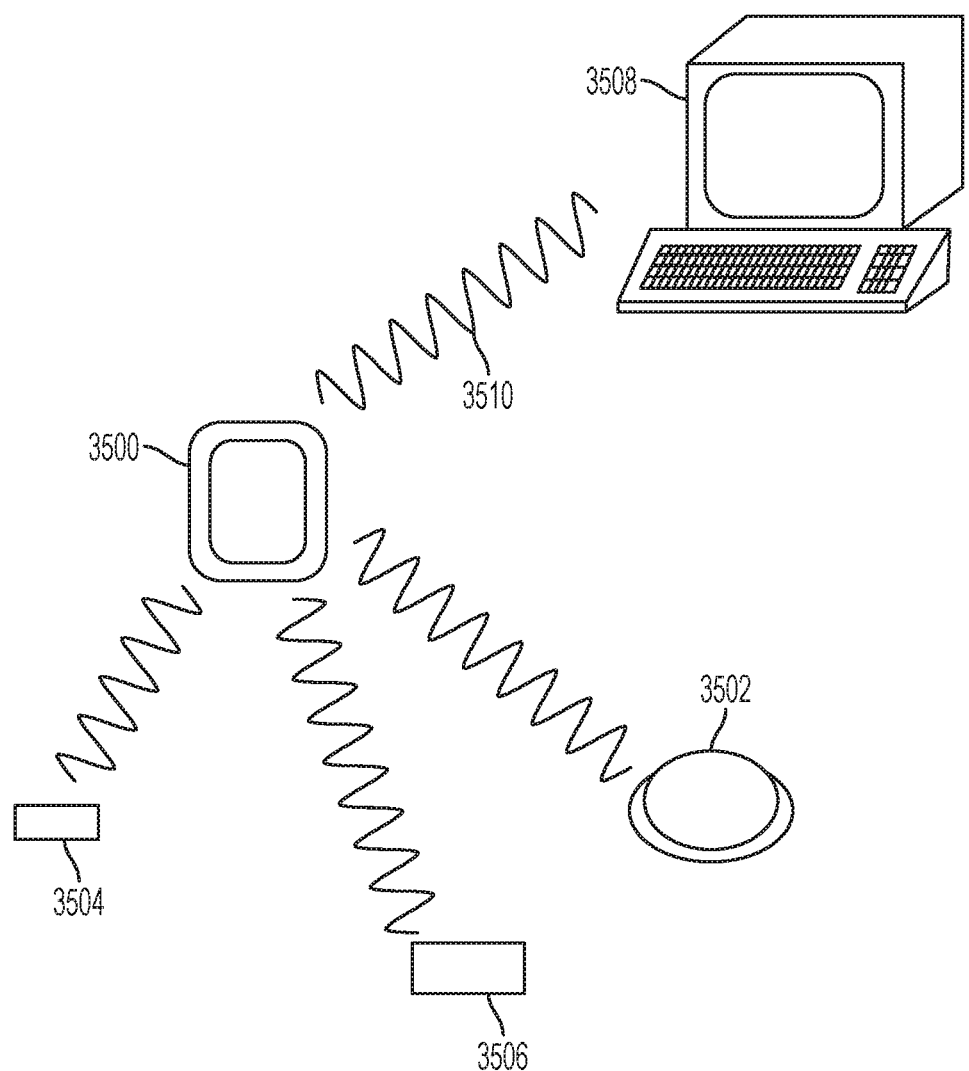
FIG. 35B is an illustration of one embodiment of the system.

Referring now also to FIG. 35B, in some embodiments, the mini-remote interface 3500 is in communication with an infusion pump 3502, and in some embodiments, may also be in communication with additional devices, including but not limited to, medical devices, which, in some embodiments, may include one or more devices, which, in some embodiments, may include at least one blood glucose meter 3506 and/or at least one continuous glucose monitor sensor/transmitter 3504. In various other embodiments, other devices may also be in communication with the mini-remote interface 3500. In some embodiments, the communication is wireless communication and may be using an RF communication protocol, for example, RF communication protocols as described above and/or may use BLUETOOTH/BLU- ETOOTH Low Energy or other non-proprietary protocols. In some embodiments, the communication may be the same between each device, and in some embodiments, the communications may differ between each device. In some embodiments, in addition to the communication protocols listed above, one or more of, but not limited to, the following communications protocols may be used: WiFi, ZIGBEE, XB, WiFi ad hoc, White Space, Ultra wide band, Ant, and/or wireless USB. In some embodiments, the communication may be the same between each device, and in some embodiments, the communications may differ between each device. In some embodiments, the mini-remote interface 3500 is in wireless communication with a personal computer 3508, however, in some embodiments, the remote interface 3500 may be connected to the personal computer 3508 by way of a USB connection and/or other wired connection. In some embodiments, the mini-remote interface 3500 and personal computer 3508 may be in communication by way of a web/internet connection 3510 and or by way of the mini-remote interface 3500 uploading information to the internet and the personal computer 3508 downloading the information from the internet. In some embodiments, the remote interface 3500 and personal computer 3508 may be in communication by way of a wired and/or infrared ("IR") connection 3510 i.e., by way of the mini-remote interface 3500 uploading information to the personal computer 3508. In some embodiments, the communication between the mini-remote interface 3500 and the infusion pump 3502 is two-way communication. In some embodiments, the communication between the mini-remote interface 3500 and the personal computer 3508 is one-way, i.e., the mini-remote interface 3500 may communicate to the personal computer 3508 (and/or internet), however, the personal computer 3508 (and/or internet) may not communicate to the mini-remote interface. This may be beneficial for many reasons, including, but not limited to, controlling the information that is uploaded to the mini-remote interface 3500 which may protect the mini-remote interface 3500 from viruses and/or undesirable and/or incorrect information being uploaded onto the mini-remote interface 3500. However, in various embodiments, the communication between one or more of the various devices 3500, 3504, 3506, 3602, 3510, 3508 may be either one way or two way, and in some embodiments, the communications may be one way for some communication of predefined types or categories of information and may be two way for other types or categories of information. This may be desirable for many reasons, including but not limited to, limiting the communication of, e.g., therapy critical information to one way communication between a proprietary and/or secure device and another device.

Figure 35C:
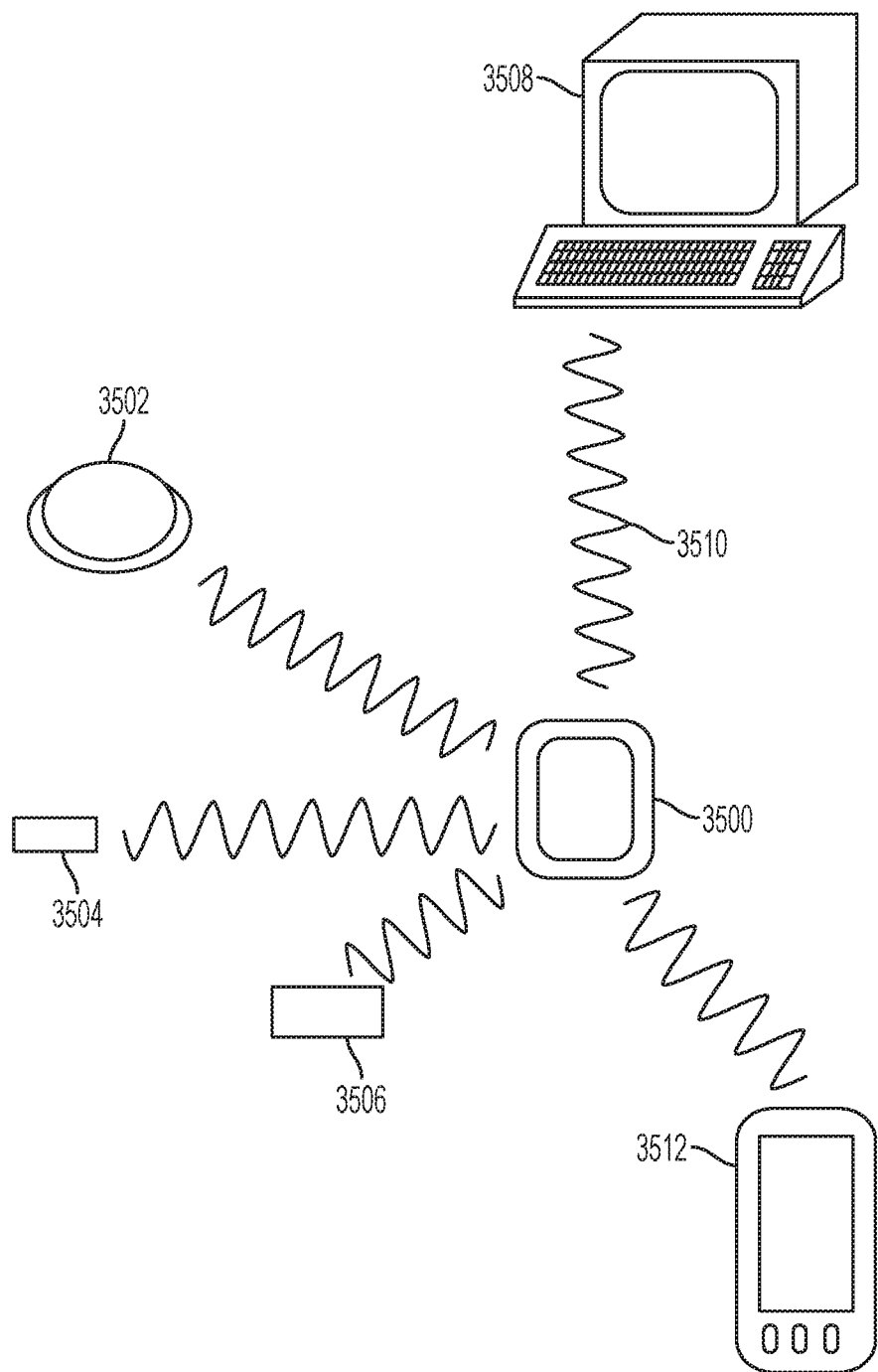
FIG. 35C is an illustration of one embodiment of the system.

Referring now also to FIG. 35C, in some embodiments, the mini-remote interface 3500 is in communication with an infusion pump 3502, and in some embodiments, may also be in communication with additional devices, including but not limited to, medical devices, which, in some embodiments, may include one or more devices, which, in some embodiments, may include at least one blood glucose meter 3506 and/or at least one continuous glucose monitor sensor/transmitter 3504. In some embodiments, the mini-remote interface 3500 may also be in communication with a remote interface 3512, which may be any remote interface, including, but not limited to, a Smartphone, for example, an ADROID® Smartphone. In some embodiments of this embodiment, the remote interface 3512 may include one-way communication between the mini-remote interface 3500 and the remote interface 3512. Thus, in these embodiments, the remote interface 3512 may receive and display information related to the one or more devices/medical devices 3502, 3504, 3506 in which are in communication with the mini-remote interface 3500, however, the remote interface 3512 may not control the one more devices 3502, 3504, 3506, nor control the mini-remote interface 3500, nor send information to the mini-remote interface 3500. In some embodiments, therefore, the remote interface 3512 may be used as an adjunct user interface, including the ability to display information, for example, graphs and logbook information, in a larger format for easier viewing by the user. In some embodiments, the remote interface 3512 may be a Smartphone that may be used as a phone, however, may also include an application that allows for the mini-remote interface 3500 to send information to the remote interface 3512 to present the information to the user in a graphic rich format. Thus, in this embodiment, the mini-remote interface 3500 controls the infusion pump 3502, and also receives information from the other devices 3504, 3506, and is the only device in the system that may send commands and/or control the infusion pump 3502, wherein said control includes, but is not limited to, one or more of the following: programming/commanding the delivery of a bolus and/or programming and delivering basal and/or programming/commanding any therapy related command, including, but not limited to, changing therapy or commanding the delivery of therapy. In some embodiments of this embodiment of the system, the mini-remote interface 3500 may also communicate with and send information to a personal computer 3508 and/or the internet. In some embodiments of this embodiment of the system, the remote interface 3512 may also display alarms, alerts, etc., and show the status of the infusion pump 3502 and/or other devices 3504, 3506. In some embodiments, the mini-remote interface 3500 may send data to the remote interface 3512 at regular/programmable intervals, for example, every 2 minutes, however, the intervals may be any interval desired. In some embodiments, the mini-remote interface 3500 may send data to the remote interface 3512 when commanded by the user. In some embodiments, information that is programmed by the user/caregiver into the mini-remote interface 3500 may be shared by the mini-remote interface 3500 to other devices 3512, 3504, 3506 in the system. This information may include, but is not limited to, a blood glucose reading, e.g., a reading from the blood glucose meter that is not otherwise in wireless communication with the mini-remote interface 3500.

In various embodiments, the mini-remote interface 3500 may pair, for example, with the infusion pump 3502, and or the various devices 3504, 3506 and/or the remote interface 3512, using any one or more of the protocols described above. However, in various embodiments, one or more devices 3504, 3506, 3512 may pair with the mini-remote interface 3500 using standard BLUETOOTH pairing protocols, including BLUETOOTH Low Energy protocols. In some embodiments, one or more devices 3504, 3506, 3512 may pair with the mini-remote interface 3500 using Near Field Communication ("NFC") protocol, for example, the devices would share a private key and, use NFC to receive a real time key. In some embodiments, the network range may be limited during pairing. In some embodiments, the network range may be limited during pairing and one or more other types of transmissions (which may be preprogrammed in some embodiments and may include, but is not limited to, changes in therapy and/or commands for therapy and/or delivery commands and/or changes in delivery commands), otherwise, may resume regular transmissions. In some embodiments, the network range may be limited during all transmissions, including, but not limited to, pairing. Various other embodiments of pairing that may be used between any two or more of the devices in various embodiments of the system are described above and below.

In some embodiments, the communication is wireless communication and may be using RF communication, for example, RF communication protocols as described above and/or may use BLUETOOTH/BLUETOOTH Low Energy or other non-proprietary protocols and/or may include, but is not limited to, one or more of the following protocols: WiFi, ZIGBEE, XB, WiFi ad hoc, White Space, Ultra wide band, Ant, and/or wireless USB. In some embodiments, the communication may be the same between each device, and in some embodiments, the communications may differ between each device. In some embodiments, the mini-remote interface 3500 is in wireless communication with a personal computer 3508, however, in some embodiments, the remote interface 3500 may be connected to the personal computer 3508 by way of a USB connection and/or other wired connection. In some embodiments, the mini-remote interface 3500 and personal computer 3508 may be in communication by way of a web/internet connection 3510 and or by way of the mini-remote interface 3500 uploading information to the internet and the personal computer 3508 downloading the information from the internet. In some embodiments, the remote interface 3500 and personal computer 3508 may be in communication by way of a wired and/or infrared ("IR") connection 3510 i.e., by way of the mini-remote interface 3500 uploading information to the personal computer 3508. In some embodiments, the communication between the mini-remote interface 3500 and the infusion pump 3502 is two-way communication. In some embodiments, the communication between the mini-remote interface 3500 and the personal computer 3508 is one-way, i.e., the mini-remote interface 3500 may communicate to the personal computer 3508 (and/or internet), however, the personal computer 3508 (and/or internet) may not communicate to the mini-remote interface. This may be beneficial for many reasons, including, but not limited to, controlling the information that is uploaded to the mini-remote interface 3500 which may protect the mini-remote interface 3500 from viruses and/or undesirable and/or incorrect information being uploaded onto the mini-remote interface 3500. In any one or more of the embodiments described above, in some embodiments, the mini-remote interface 3500 may include two or more radios with the ability to communicate by way of BLUETOOTH Low Energy and/or BLUETOOTH High Energy and/or by way of a low energy protocol and a high energy protocol. For example, in some embodiments, the mini-remote interface 3500 may communicate using a low power protocol radio with the infusion pump 3502 and a high energy BLUETOOTH radio or high power protocol radio with the remote interface 3512. Various other embodiments of pairing that may be used between any two or more of the devices in various embodiments of the system are described above and below.

Figure 35D:
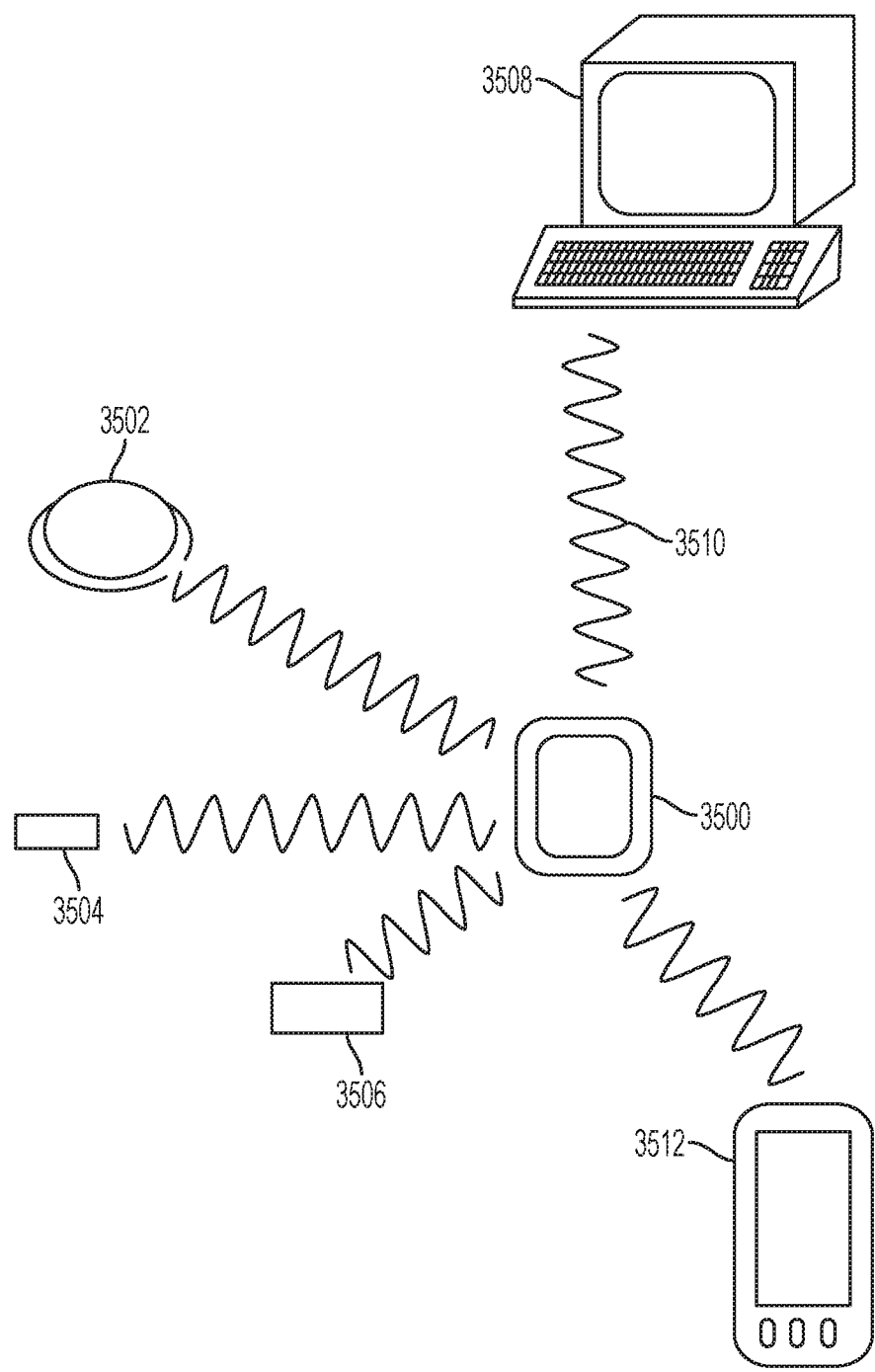
FIG. 35D is an illustration of one embodiment of the system.

Still referring to FIG. 35D, in some embodiments, the remote interface 3512 may be used to control one or more devices/medical devices 3502, 3504, 3506, however, in some embodiments, the remote interface 3512 must communication via the mini-remote interface 3500. Thus, the mini-remote interface 3500 serves as a security "firewall", i.e., a security barrier, thus only the mini-remote interface 3500 may communicate directly with the infusion pump 3502 and/or other devices/medical devices 3504, 3506. Also, the infusion pump 3502 and/or other devices/medical devices 3504, 3506, in some embodiments, only communicate directly with the mini-remote interface 3500. In some embodiments of this embodiment, the mini-remote interface 3500 may communicate the information received from the infusion pump 3502 and/or other devices/medical devices 3504, 3506 to the internet and/or personal computer 3508 using the connection 3510.

Figure 35E:
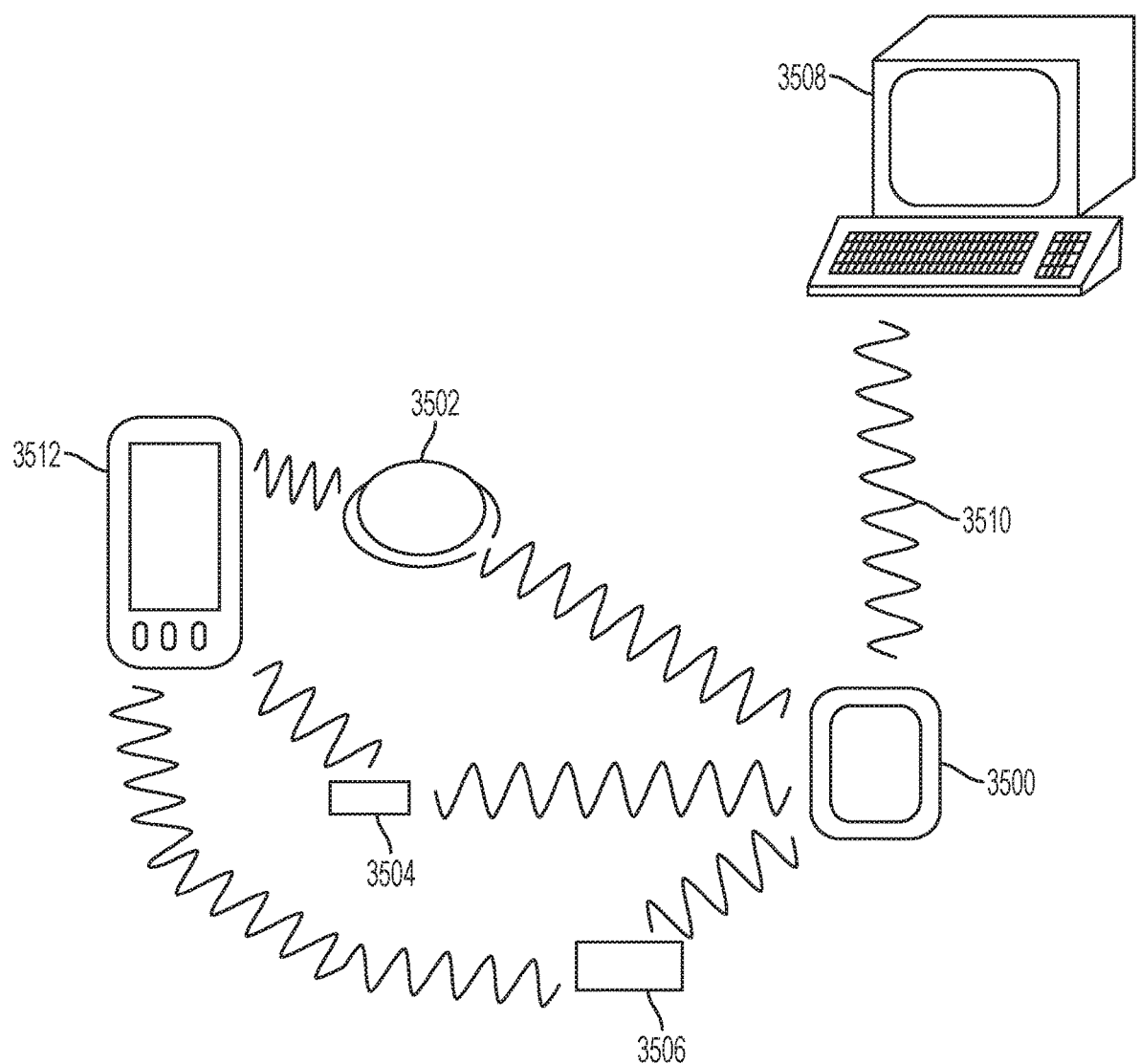
FIG. 35E is an illustration of one embodiment of the system.

Referring now also to FIG. 35E, in some embodiments, the mini-remote interface 3500 and a remote interface 3512 may each be used to control an infusion pump 3502 and/or one or more additional device/medical devices 3504, 3506. In some embodiments of this embodiment of the system, the mini-remote interface 3500 may "trump" and therefore, if the remote interface 3512 and the mini-remote interface 3500 were simultaneously both within communication distance with the infusion pump 3502 and/or the one or more devices/medical devices 3504, 3506, then the mini-remote interface 3500 would be the device that may communicate with the infusion pump 3502 and/or the one or more devices/medical devices 3504, 3506. In some embodiments, the mini-remote interface 3500 and the remote interface 3512 may communicate and synchronize information at pre-programmed intervals and/or when within a pre-programmed communication distance, for example, when the mini-remote interface 3500 and the remote interface 3512 recognize that they are within communication distance and/or an interval of time has passed since the last synchronization, the mini-remote interface 3500 and the remote interface 3512 may synchronize using a synchronization protocol which may be any synchronization protocol. The mini-remote interface 3500 and the remote interface 3512 may also pair using the various protocols described and discussed herein.

In some embodiments, the communication is wireless communication and may be using RF communication, for example, RF communication protocols as described above and/or may use BLUETOOTH/BLUETOOTH Low Energy or other non-proprietary protocols and/or may include, but is not limited to, one or more of the following protocols: WiFi, ZIGBEE, XB, WiFi ad hoc, White Space, Ultra wide band, Ant, and/or wireless USB. In some embodiments, the communication may be the same between each device, and in some embodiments, the communications may differ between each device. In some embodiments, the mini-remote interface 3500 is in wireless communication with a personal computer 3508, however, in some embodiments, the remote interface 3500 may be connected to the personal computer 3508 by way of a USB connection and/or other wired connection. In some embodiments, the mini-remote interface 3500 and personal computer 3508 may be in communication by way of a web/internet connection 3510 and or by way of the mini-remote interface 3500 uploading information to the internet and the personal computer 3508 downloading the information from the internet. In some embodiments, the remote interface 3500 and personal computer 3508 may be in communication by way of a wired and/or infrared ("IR") connection 3510 i.e., by way of the mini-remote interface 3500 uploading information to the personal computer 3508. In some embodiments, the communication between the mini-remote interface 3500 and the infusion pump 3502 is two-way communication. In some embodiments, the communication between the mini-remote interface 3500 and the personal computer 3508 is one-way, i.e., the mini-remote interface 3500 may communicate to the personal computer 3508 (and/or internet), however, the personal computer 3508 (and/or internet) may not communicate to the mini-remote interface. This may be beneficial for many reasons, including, but not limited to, controlling the information that is uploaded to the mini-remote interface 3500 which may protect the mini-remote interface 3500 from viruses and/or undesirable and/or incorrect information being uploaded onto the mini-remote interface 3500. In any one or more of the embodiments described above, in some embodiments, the mini-remote interface 3500 may include two or more radios with the ability to communicate by way of BLUETOOTH Low Energy and/or BLUETOOTH High Energy and/or by way of a low energy protocol and a high energy protocol. For example, in some embodiments, the mini-remote interface 3500 may communicate using a low power protocol radio with the infusion pump 3502 and a high energy BLUETOOTH radio or high power protocol radio with the remote interface 3512. Various other embodiments of pairing that may be used between any two or more of the devices in various embodiments of the system are described above and below.

Figure 36:
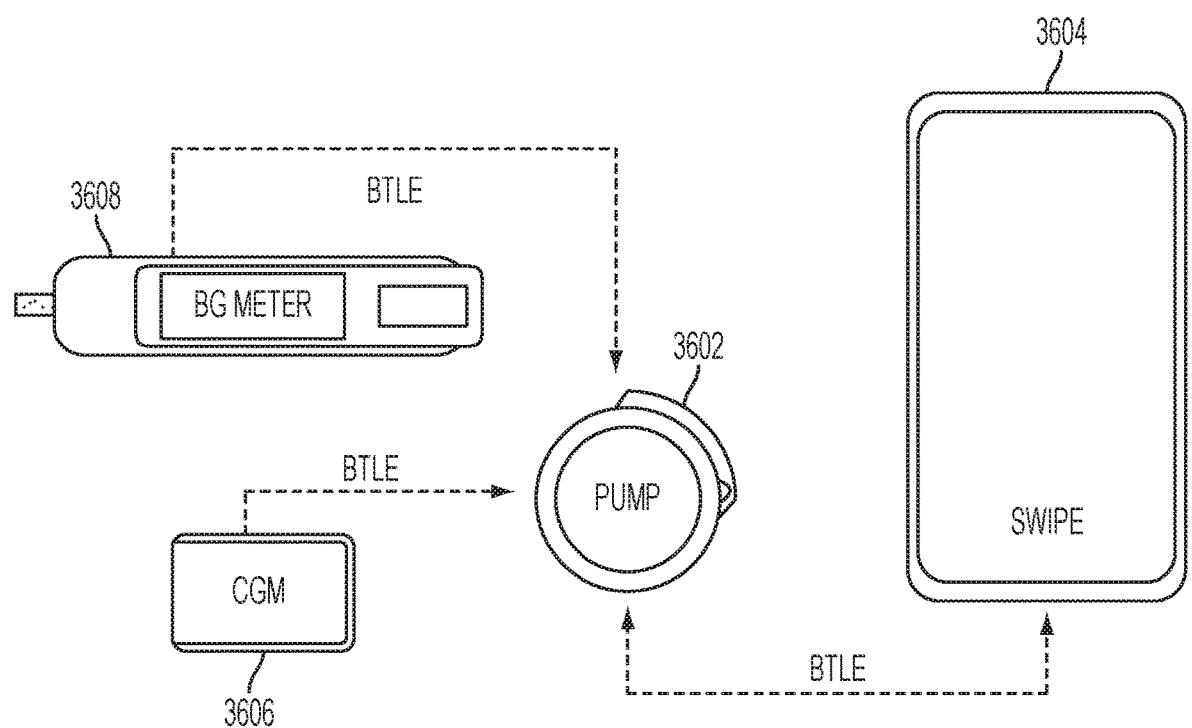
FIG. 36 is an illustration of one embodiment of the system.

Referring now to FIG. 36, one embodiment of the various embodiments of the system is shown. In this embodiment, the system 3600 includes an infusion pump 3602 a remote interface 3604, a continuous glucose monitor/transmitter 3606 and a blood glucose meter 3608. In this embodiment, the various devices communicate using a BLUETOOTH Low Energy (BTLE) protocol. Also, in this embodiment, the infusion pump 3602 and the remote interface 3604 communicate using two way communications. In this embodiment, the remote interface 3604 may command the infusion pump 3602 including, but not limited to, commands related to: changes in therapy and various therapy commands including: setting related to therapy which may include but are not limited to, insulin sensitivity factor, carbohydrate to insulin rations, blood glucose correction factors, blood glucose targets; delivery commands including bolus commands including normal and dual wave or extended bolus or combination bolus; and setting basal rates as well as changing basal rates and commanding temporary basal rates; alarms & alerts; log/history; initiation commands; setup/system edit; alarm and alert troubleshooting; reminders; reservoir changes and cannula changes etc., may all be entered by a user or caregiver through the remote interface 3604, and these commands may be communicated to the infusion pump 3602. Although this embodiment is shown to use a BTLE protocol, in various other embodiments, any one or more wireless communication protocols may be used, including, but not limited to: BLUETOOTH/BLUETOOTH Low Energy or other non-proprietary protocols and/or may include, but is not limited to, one or more of the following protocols: WiFi, ZIGBEE, XB, WiFi ad hoc, White Space, Ultra wide band, Ant, and/or wireless USB. In some embodiments, the communication may be the same between each device, and in some embodiments, the communications may differ between each device. Additionally, the devices, in some embodiments, may communicate via wired and/or USB connection. In any one or more of the embodiments described above, in some embodiments, the one or more devices may include two or more radios with the ability to communicate by way of BLUETOOTH Low Energy and/or BLUETOOTH High Energy and/or by way of a low energy protocol and a high energy protocol. For example, in some embodiments, the remote interface 3604 may communicate using a low power protocol radio with the infusion pump 3602 and a high energy BLUETOOTH radio or high power protocol radio with the blood glucose meter 3608.

Figure 37:
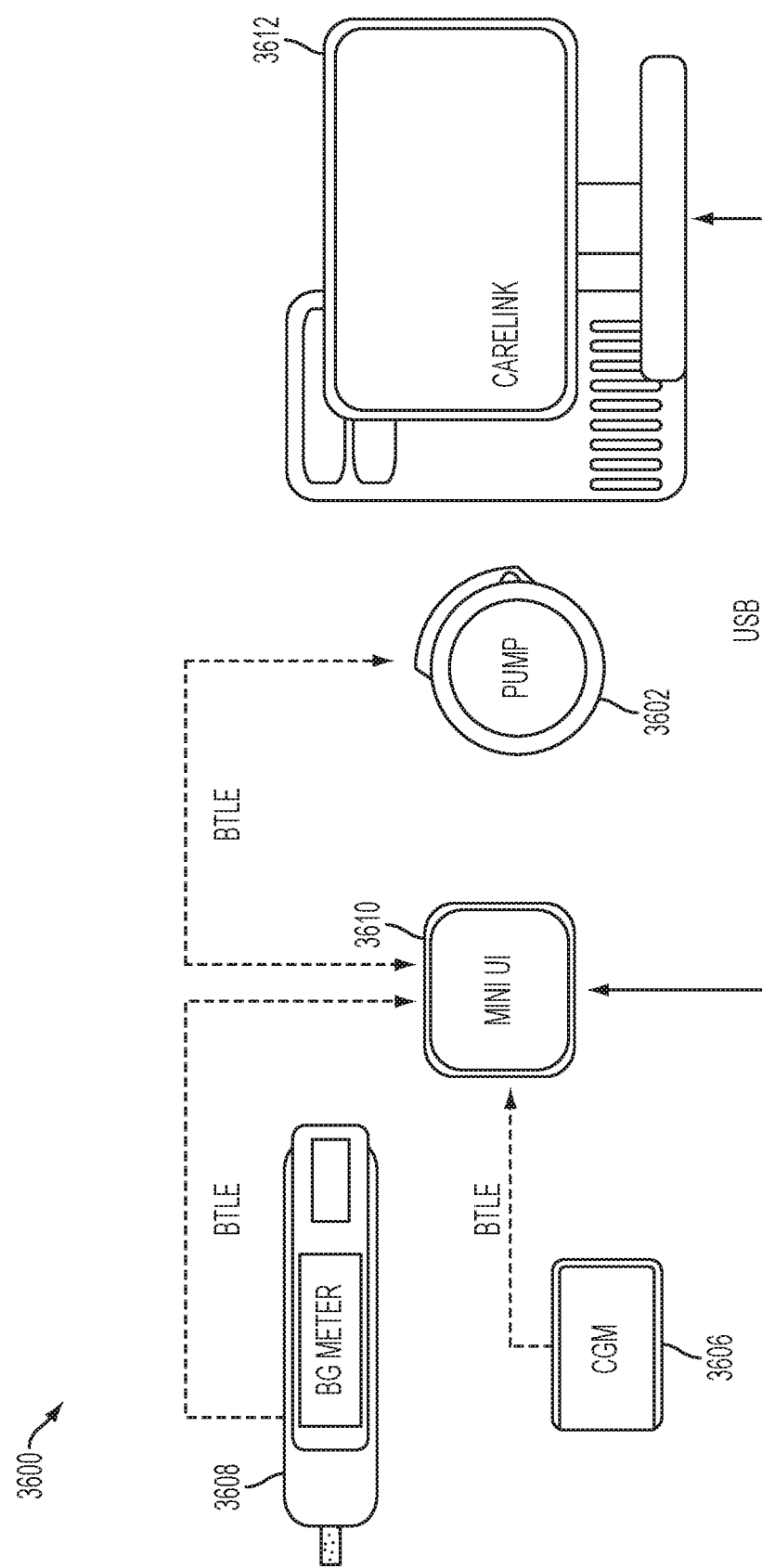
FIG. 37 is an illustration of one embodiment of the system.

Referring now also to FIG. 37 one embodiment of the various embodiments of the system is shown. In this embodiment, the system 3600 includes an infusion pump 3602 a mini-remote interface 3610, a continuous glucose monitor/transmitter 3606 and a blood glucose meter 3608. In this embodiment, the various devices 3602, 3606, 3608, 3610 may communicate using a BLUETOOTH Low Energy (BTLE) protocol. However, this embodiment of the system 3600 additionally includes a personal computer 3612 that may be connected to the mini-remote interface 3610, when desired, via a USB/wired connection. Also, in this embodiment, the infusion pump 3602 and the mini-remote interface 3610 communicate using two way communications. In this embodiment, the mini-remote interface 3604 may command the infusion pump 3602 including all of the various commands any embodiment of the remote interface 3604 (described above) may include which may include, but are not limited to, commands related to: changes in therapy and various therapy commands including: setting related to therapy which may include but are not limited to, insulin sensitivity factor, carbohydrate to insulin rations, blood glucose correction factors, blood glucose targets; delivery commands including bolus commands including normal and dual wave or extended bolus or combination bolus; and setting basal rates as well as changing basal rates and commanding temporary basal rates; alarms & alerts; log/history; initiation commands; setup/system edit; alarm and alert troubleshooting; reminders; reservoir changes and cannula changes etc., may all be entered by a user or caregiver through the mini-remote interface 3610, and these commands may be communicated to the infusion pump 3602. Additionally, the personal computer 3612 may communicate via USB with the mini-remote interface 3610 and in some embodiments, this communication may be limited to various predefined/preselected functions. For example, in some embodiments, the personal computer 3612 may be used to modify or establish a basal profile and/or view log/history. This may be desirable for many reasons, including but not limited to, the ability to attach the mini-remote interface 3610 to any personal computer desired 3612 and log into, for example, a web site, which in some embodiments may be secure/password protected, and modify one or more of the basal profile and/or view log/history, which may be desirable for many reasons, including, but not limited to, a physician or medical provider viewing logs/history as well as basal profiles and modifying same. In some embodiments, additional functions may be viewed and/or modified using the personal computer 3612. In some embodiments, the functions that may be viewed and/or modified may vary and/or be preset and/or predefined and/or hardwired into the system. In some embodiments, the personal computer 3612 may be used to view/modify more or less functions including, but not limited to, any one or more of the following: settings and/or setup, as well as food libraries and preferences for alerts including but not limited to reminders.

Although this embodiment is shown to use a BTLE protocol and a USB connection, in various other embodiments, any one or more wireless communication protocols may be used, including, but not limited to: BLUETOOTH/BLUETOOTH Low Energy or other non-proprietary protocols and/or may include, but is not limited to, one or more of the following protocols: WiFi, ZIGBEE, XB, WiFi ad hoc, White Space, Ultra wide band, Ant, and/or wireless USB. In some embodiments, the communication may be the same between each device, and in some embodiments, the communications may differ between each device. Additionally, two or more of the devices, in some embodiments, may communicate via wired and/or USB connection and/or may communicate with a particular device via wired and/or USB connection but may communicate with other devices via wireless communication. In any one or more of the embodiments described above, in some embodiments, the one or more devices may include two or more radios with the ability to communicate by way of BLUETOOTH Low Energy and/or BLUETOOTH High Energy and/or by way of a low energy protocol and a high energy protocol. For example, in some embodiments, the remote interface 3604 may communicate using a low power protocol radio with the infusion pump 3602 and a high energy BLUETOOTH radio or high power protocol radio with the blood glucose meter 3608.

Figure 38:
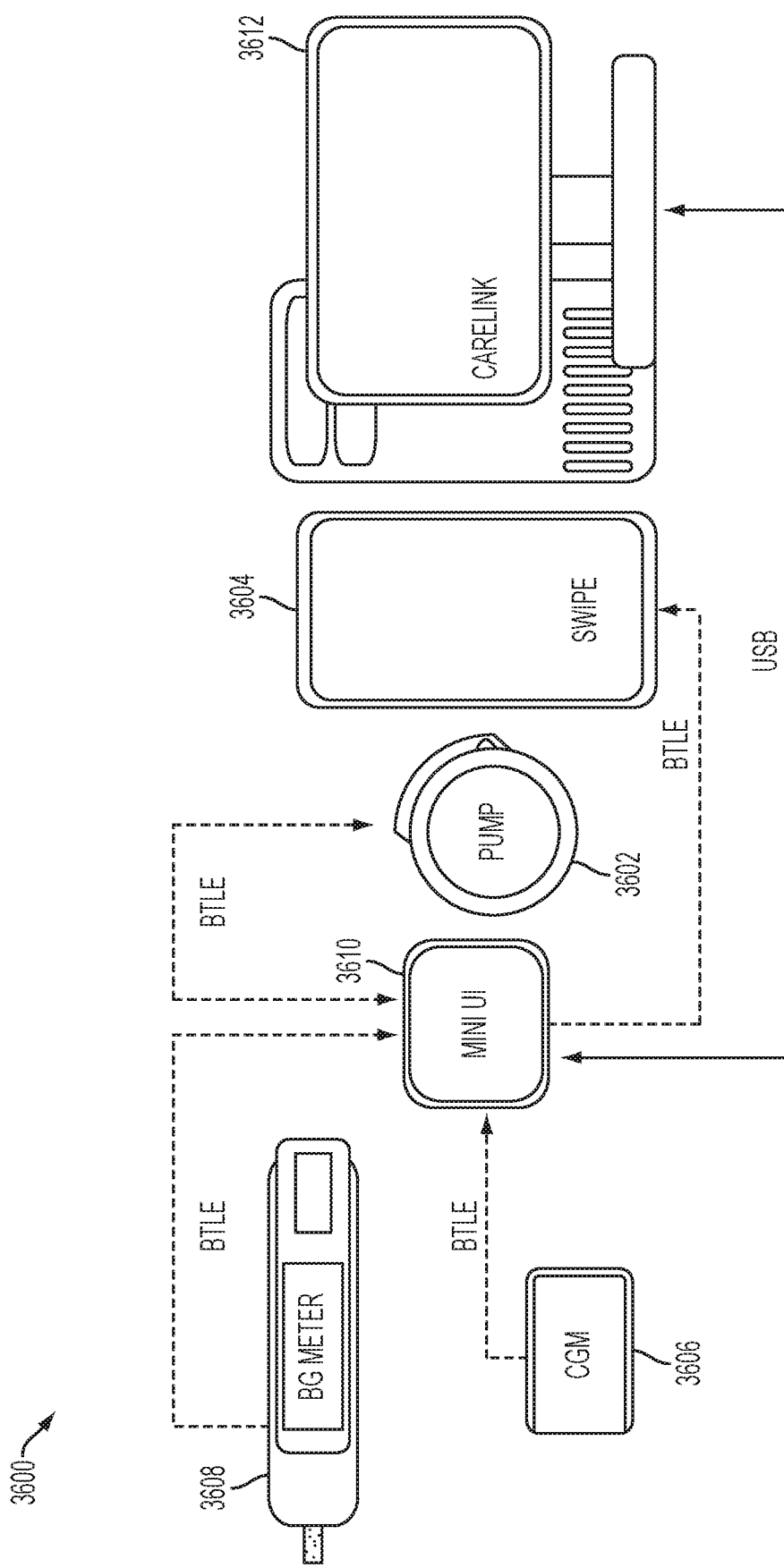
FIG. 38 is an illustration of one embodiment of the system.

Referring now also to FIG. 38 one embodiment of the various embodiments of the system is shown. In this embodiment, the system 3600 includes an infusion pump 3602, a remote interface 3604, a mini-remote interface 3610, a continuous glucose monitor/transmitter 3606 and a blood glucose meter 3608. In this embodiment, the various devices 3602, 3604, 3606, 3608, 3610 may communicate using a BLUETOOTH Low Energy (BTLE) protocol. However, this embodiment of the system 3600 additionally includes a personal computer 3612 that may be connected to the mini-remote interface 3610, when desired, via a USB/wired connection. Also, in this embodiment, the infusion pump 3602 and the mini-remote interface 3610 communicate using two way communications. In this embodiment, the mini-remote interface 3604 may command the infusion pump 3602 including all of the various commands any embodiment of the remote interface 3604 and/or the mini-remote interface 3610 (described above) may include which may include, but are not limited to, commands related to: changes in therapy and various therapy commands including: setting related to therapy which may include but are not limited to, insulin sensitivity factor, carbohydrate to insulin rations, blood glucose correction factors, blood glucose targets; delivery commands including bolus commands including normal and dual wave or extended bolus or combination bolus; and setting basal rates as well as changing basal rates and commanding temporary basal rates; alarms & alerts; log/history; initiation commands; setup/system edit; alarm and alert troubleshooting; reminders; reservoir changes and cannula changes etc., may all be entered by a user or caregiver through the mini-remote interface 3610, and these commands may be communicated to the infusion pump 3602. Additionally, the personal computer 3612 may communicate via USB with the mini-remote interface 3610 and in some embodiments, this communication may be limited to various predefined/preselected functions. For example, in some embodiments, the personal computer 3612 may be used to modify or establish a basal profile and/or view log/history. This may be desirable for many reasons, including but not limited to, the ability to attach the mini-remote interface 3610 to any personal computer desired 3612 and log into, for example, a web site, which in some embodiments may be secure/password protected, and modify one or more of the basal profile and/or view log/history, which may be desirable for many reasons, including, but not limited to, a physician or medical provider viewing logs/history as well as basal profiles and modifying same. In some embodiments, additional functions may be viewed and/or modified using the personal computer 3612. In some embodiments, the functions that may be viewed and/or modified may vary and/or be preset and/or predefined and/or hardwired into the system. In some embodiments, the personal computer 3612 may be used to view/modify more or less functions including, but not limited to, any one or more of the following: settings and/or setup, as well as food libraries and preferences for alerts including but not limited to reminders.

In some embodiments of this embodiment of the system 3600, the remote interface 3604 may serve as a larger display for the mini-remote interface 3610, however, may not be used to command the infusion pump 3602 or command the mini-user interface 3610. For example, in some embodiments, the remote interface 3604 may be used to display data including logs and/or history and/or CGM and/or BG meter trending and/or graphs and/history. Thus, in some embodiments, the remote interface 3604 may be desirable as a larger display (and portable larger display) to display data and other information larger and/or more clearly for the user/caregiver. In various embodiments of this embodiment, the remote interface 3604 may be any type of interface including, but not limited to, a smart phone and may include a downloadable application. Thus, in some embodiments the remote interface 3604 may be an MDDS or Medical Device Data Systems and the mini-remote interface 3610 may be a proprietary device including secure protocols.

Although this embodiment is shown to use a BTLE protocol and a USB connection, in various other embodiments, any one or more wireless communication protocols may be used, including, but not limited to: BLUETOOTH/BLUETOOTH Low Energy or other non-proprietary protocols and/or may include, but is not limited to, one or more of the following protocols: WiFi, ZIGBEE, XB, WiFi ad hoc, White Space, Ultra wide band, Ant, and/or wireless USB. In some embodiments, the communication may be the same between each device, and in some embodiments, the communications may differ between each device. Additionally, two or more of the devices, in some embodiments, may communicate via wired and/or USB connection and/or may communicate with a particular device via wired and/or USB connection but may communicate with other devices via wireless communication. In any one or more of the embodiments described above, in some embodiments, the one or more devices may include two or more radios with the ability to communicate by way of BLUETOOTH Low Energy and/or BLUETOOTH High Energy and/or by way of a low energy protocol and a high energy protocol. For example, in some embodiments, the remote interface 3604 may communicate using a low power protocol radio with the infusion pump 3602 and a high energy BLUETOOTH radio or high power protocol radio with the blood glucose meter 3608.

Figure 39:
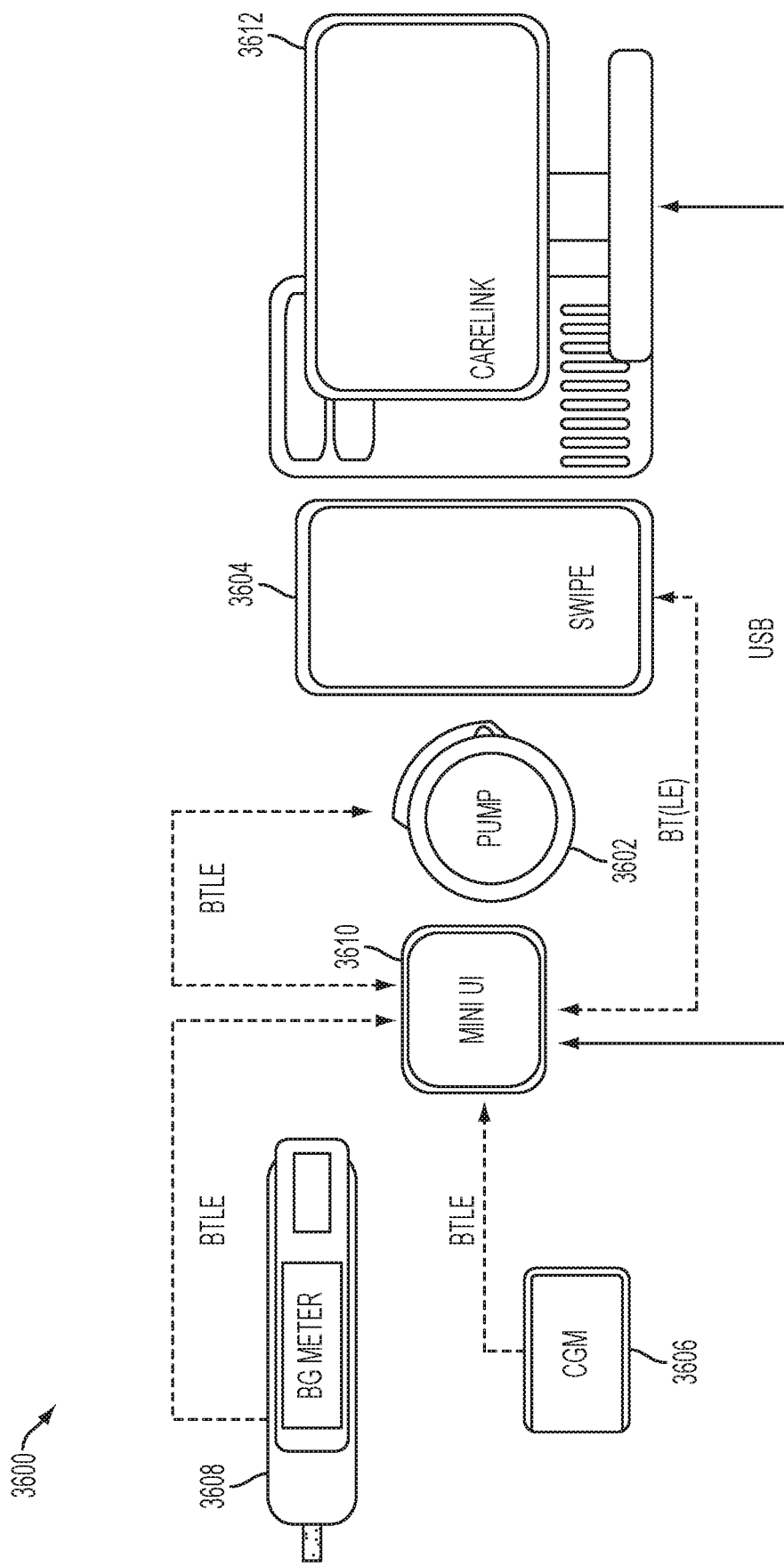
FIG. 39 is an illustration of one embodiment of the system.

Referring now also to FIG. 39 one embodiment of the various embodiments of the system 3600 is shown. In this embodiment, the system 3600 includes an infusion pump 3602, a remote interface 3604, a mini-remote interface 3610, a continuous glucose monitor/transmitter 3606 and a blood glucose meter 3608. In this embodiment, the various devices 3602, 3604, 3606, 3608, 3610 may communicate using a BLUETOOTH Low Energy (BTLE) protocol. However, this embodiment of the system 3600 additionally includes a personal computer 3612 that may be connected to the mini-remote interface 3610, when desired, via a USB/wired connection. Also, in this embodiment, the infusion pump 3602 and the mini-remote interface 3610 communicate using two way communications and the mini-remote interface 3610 and the remote interface 3604 may communicate using two way communications.

In one embodiment of this embodiment, either the mini-remote interface 3610 or the remote interface 3604 may command the infusion pump 3602 including all of the various commands any embodiment of the remote interface 3604 or mini-remote interface 3610 (described above) may include which may include, but are not limited to, commands related to: changes in therapy and various therapy commands including: settings related to therapy which may include but are not limited to, insulin sensitivity factor, carbohydrate to insulin rations, blood glucose correction factors, blood glucose targets; delivery commands including bolus commands including normal and dual wave or extended bolus or combination bolus; and setting basal rates as well as changing basal rates and commanding temporary basal rates; alarms & alerts; log/history; initiation commands; setup/system edit; alarm and alert troubleshooting; reminders; reservoir changes and cannula changes etc., may all be entered by a user or caregiver through the mini-remote interface 3610, and these commands may be communicated to the infusion pump 3602. Additionally, the personal computer 3612 may communicate via USB with the mini-remote interface 3610 and in some embodiments, this communication may be limited to various predefined/preselected functions. For example, in some embodiments, the personal computer 3612 may be used to modify or establish a basal profile and/or view log/history. This may be desirable for many reasons, including but not limited to, the ability to attach the mini-remote interface 3610 to any personal computer desired 3612 and log into, for example, a web site, which in some embodiments may be secure/password protected, and modify one or more of the basal profile and/or view log/history, which may be desirable for many reasons, including, but not limited to, a physician or medical provider viewing logs/history as well as basal profiles and modifying same. In some embodiments, additional functions may be viewed and/or modified using the personal computer 3612. In some embodiments, the functions that may be viewed and/or modified may vary and/or be preset and/or predefined and/or hardwired into the system. In some embodiments, the personal computer 3612 may be used to view/modify more or less functions including, but not limited to, any one or more of the following: settings and/or setup, as well as food libraries and preferences for alerts including but not limited to reminders.

In some embodiments of this embodiment the remote interface 3604 may serve as a larger display version of the mini-remote interface 3610, and may not be used to command the infusion pump 3602 or command the mini-user interface 3610. Thus, in some embodiments, the remote interface 3604 may be desirable as a larger display (and portable larger display) to display data and other information larger and/or more clearly for the user/caregiver. In various embodiments of this embodiment, the remote interface 3604 and the mini-remote interface 3610 may each be any type a proprietary device including secure protocols.

Although this embodiment is shown to use a BTLE protocol and a USB connection, in various other embodiments, any one or more wireless communication protocols may be used, including, but not limited to: BLUETOOTH/ BLUETOOTH Low Energy or other non-proprietary protocols and/or may include, but is not limited to, one or more of the following protocols: WiFi, ZIGBEE, XB, WiFi ad hoc, White Space, Ultra wide band, Ant, and/or wireless USB. In some embodiments, the communication may be the same between each device, and in some embodiments, the communications may differ between each device. Additionally, two or more of the devices, in some embodiments, may communicate via wired and/or USB connection and/or may communicate with a particular device via wired and/or USB connection but may communicate with other devices via wireless communication. In any one or more of the embodiments described above, in some embodiments, the one or more devices may include two or more radios with the ability to communicate by way of BLUETOOTH Low Energy and/or BLUETOOTH High Energy and/or by way of a low energy protocol and a high energy protocol. For example, in some embodiments, the remote interface 3604 may communicate using a low power protocol radio with the infusion pump 3602 and a high energy BLUETOOTH radio or high power protocol radio with the blood glucose meter 3608.

Still referring to FIG. 39, in this embodiment, the system 3600 includes an infusion pump 3602, a remote interface 3604, a mini-remote interface 3610, a continuous glucose monitor/transmitter 3606 and a blood glucose meter 3608. In this embodiment, the various devices 3602, 3604, 3606, 3608, 3610 may communicate using a BLUETOOTH Low Energy (BTLE) protocol. However, this embodiment of the system 3600 additionally includes a personal computer 3612 that may be connected to the mini-remote interface 3610, when desired, via a USB/wired connection. Also, in this embodiment, the infusion pump 3602 and the mini-remote interface 3610 communicate using two way communications and the mini-remote interface 3610 and the remote interface 3604 may communicate using two way communications.

In another embodiment of the embodiment shown in FIG. 39, the mini-remote interface 3610 and the remote interface 3604 together function collectively as a single remote interface or mini-remote user interface as described above. In some embodiments, the remote interface 3604 may perform non safety critical steps/functions and may be any device, including a smart phone, and may include a downloadable application. Thus, in some embodiments the remote interface 3604 may be an MDDS or Medical Device Data System. In these embodiments, the mini-remote interface 3610 may be a proprietary device including secure protocols and may perform safety critical steps/functions.

Figure 40:
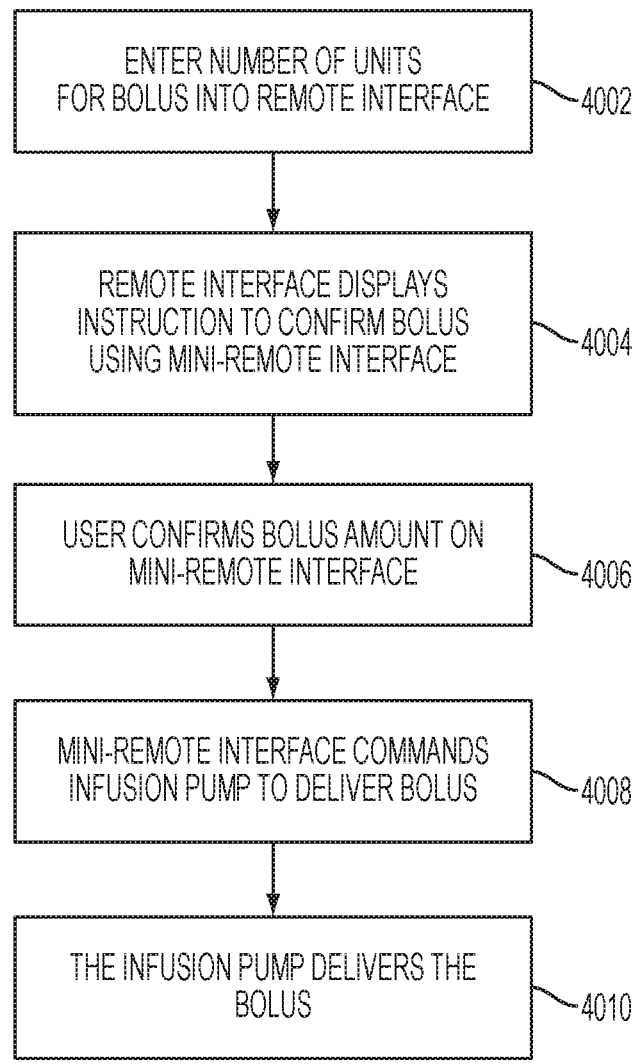
FIG. 40 is a flow chart of one method of the system according to one embodiment.

Thus, in these embodiments, the mini-remote interface 3610 may command the infusion pump 3602 and the remote interface 3604 and the mini-remote interface 3610 may communicate with each other. However, in some embodiments, the critical steps/commands/confirmations are only input through the mini-remote interface 3610. Referring now also to FIG. 40, an example of a method for commanding the delivery of a bolus 4000 is shown. This method is one embodiment and shows the steps of commanding a normal bolus, however, similar steps may be used to command any type of bolus. The user/caregiver first enters the number of units requested for the bolus using the remote interface (3604) 4002 (and in some embodiments, the blood glucose and the carbohydrates may also be entered into the remote interface 3604 using the bolus calculator). The remote interface 3604 displays an instruction to the user/ caregiver to confirm the bolus amount using the mini-remote interface (3610) 4004 (thus, the remote interface 3604 in various embodiments either displays the number of units entered by the user/caregiver or, in a bolus calculator function, shows the number of units recommended based on the input blood glucose value and carbohydrates). The user/ caregiver then must confirm the bolus amount displayed using the mini-remote interface (3610) 4006. In various embodiments, the mini-remote interface may include a message that shows the user the number of units the bolus will deliver, e.g., 4.0 units, and may include a go, start or confirm icon and also a cancel icon, which, in some embodiments, the cancel icon may be highlighted as a default. In some embodiments, using the remote interface 3604, the user may modify the number of units either in the normal bolus or the number resulting from the calculation in a bolus calculator function. However, the user/caregiver then confirms the amount on the mini-remote interface (3610) 4006 and the mini-remote interface (3610) commands the infusion pump to deliver the bolus 4008. The infusion pump 3602 then delivers the bolus 4010. In various embodiments, the user may select to cancel the bolus using the mini-remote interface rather than confirm the amount in step 4006. Also, in various embodiments, the delivery of the bolus in step 4010 may be cancelled by a user/caregiver cancelling the bolus delivery using the mini-remote interface 3610. Thus, in these embodiments, safety critical commands are only sent from the mini-user interface 3610. The remote interface 3604 is used to input information and view information, thus presenting to the user/caregiver a larger and in some embodiments, clearer display, which may be beneficial for many reasons, including but not limited to, the ability to present large amounts of information on the display at any given time, the ability to present information in a larger format, the ability to navigate to various menu items easily and quickly. Whereas the mini-remote interface 3610 in some embodiments includes a limited screen and thus may be more difficult for a user/caregiver to view large amounts of information on a single screen. Thus, the embodiments described above present an MDDS to display non safety critical information and a proprietary secure, smaller device, to present safety critical information and to command safety critical information. In various embodiments of this embodiment, all safety critical inputs must be confirmed on the mini-remote interface 3610 before the commands are sent to the infusion pump 3602. For example, and referring now also to FIG. 41, where the user/caregiver uses the remote interface 3604 to enter or change safety critical settings and or enter a command 4100, the remote interface displays an instruction for the user/caregiver to confirm the entry/change to the safety critical settings and/or command on the mini-remote interface 4102. A confirmation screen on the mini-remote interface 3610 then requests that the user confirm or cancel the setting or command 4104. If the user confirms the setting or command on the mini-remote interface (3610) 4106, then the setting/command is communicated to the infusion pump 3602 and/or implemented into the system 4108.

In various embodiments, safety critical commands and/or settings may include, but are not limited to, one or more of the following: any setting or command that effects either the computation of the amount of infusible fluid (e.g., insulin) to deliver to the user, the amount of infusible fluid (e.g., insulin) to deliver to the user, the time of delivery of the infusible fluid to the user, and/or commands the delivery of infusible fluid to the user; and/or the cancelling of delivery of infusible fluid. In some embodiments, therefore, the remote interface 3604 may be used for non safety critical inputs and viewing, for example, initiate commands (but not confirming them), entering information for the bolus calculator/wizard and viewing the calculations and recommended volume of infusible fluid to be delivered using the remote interface 3604, but not confirming the information/volume or instructing the infusion pump 3602 to deliver. Also, the remote interface 3604 may be used to view alarms and alerts, to troubleshoot alarms and alerts, to view logbook/ logs and history, to set up and edit basal profiles. However, in some embodiments, while setting up and editing basal profiles may be completed using the remote interface 3604 (or the person computer 3612), they must be confirmed using the mini-remote interface 3610. In some embodiments, setting up and editing basal profiles may be completed and confirmed using the remote interface 3604 (or the person computer 3612). In addition, in various embodiments, reminders may be entered using the remote interface 3604 and in some embodiments, the reminders do not require a confirmation from the mini-remote interface 3610, however, in some embodiments, the reminders do require a confirmation from the mini-remote interface 3610. In some embodiments, settings such as time of day may require confirmation using the mini-remote interface 3610, however, in other embodiments, changes to the time of day may be done through the remote interface 3604.

In various embodiments, various changes and/or commands may be classified as safety critical and require confirmation using the mini-remote interface 3610, however, in some embodiments, various changes and/or command may be classified as non safety critical and may be implemented through the remote interface 3604, and/or the personal computer 3612, depending on the embodiment. However, whichever changes/commands are classified as safety critical in any given embodiment, these must be confirmed using the mini-remote interface 3610 or may not be implemented/commanded to the infusion pump 3602. Thus, in these embodiments, information that is sent from the remote interface 3604 to the mini-remote interface 3610 is treated as data and is not treated as a command and none of this data is communicated to the infusion pump 3602 until and unless the user/caregiver confirms the information on the mini-remote interface 3610. Thus, in these embodiments, the remote interface 3604 cannot command the infusion pump 3610 directly.

Figure 41:
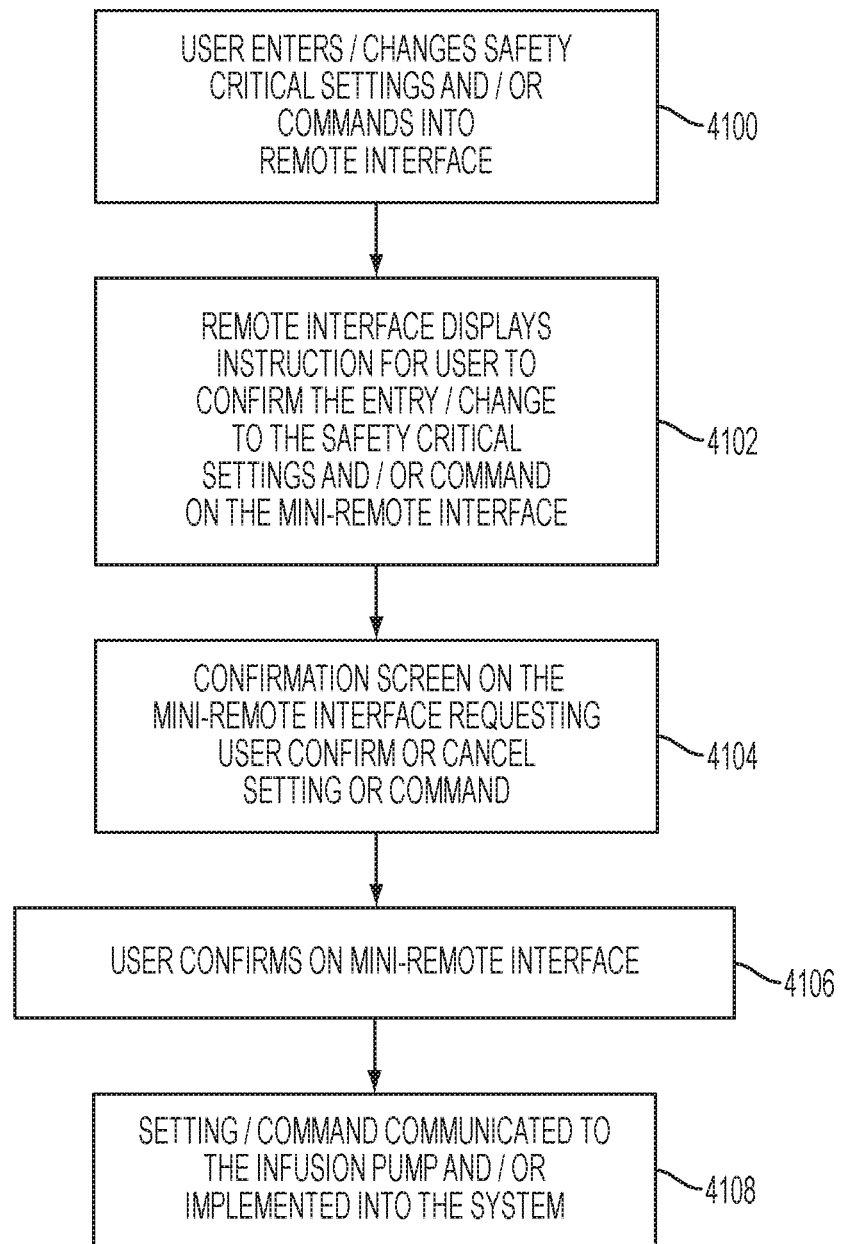
FIG. 41 is a flow chart of one method of the system according to one embodiment.

Still referring to FIGS. 39-41, in various embodiments, commands/settings that may be considered safety critical may include, but are not limited to, one or more of the following: commands related to: changes in therapy and various therapy commands including: settings related to therapy which may include but are not limited to, insulin sensitivity factor, carbohydrate to insulin rations, blood glucose correction factors, blood glucose targets; delivery commands including bolus commands including normal and dual wave or extended bolus or combination bolus; and setting basal rates as well as changing basal rates and commanding temporary basal rates; confirming and/or silencing one or more alarms & alerts; initiation commands; setup/system edit; alarm and alert troubleshooting, may all be entered by a user or caregiver through the remote interface 3604, but the final confirmation must be completed on the mini-remote interface 3610 or the changed/commands will not be communicated to the infusion pump 3602. Additionally, in some embodiments, the personal computer 3612 may communicate via USB with the mini-remote interface 3610 and in some embodiments, this communication may be limited to various predefined/preselected functions. For example, in some embodiments, the personal computer 3612 may be used to modify or establish a basal profile and/or view log/history. This may be desirable for many reasons, including but not limited to, the ability to attach the mini-remote interface 3610 to any personal computer desired 3612 and log into, for example, a web site, which in some embodiments may be secure/password protected, and modify one or more of the basal profile and/or view log/history, which may be desirable for many reasons, including, but not limited to, a physician or medical provider viewing logs/history as well as basal profiles and modifying same. In some embodiments, additional functions may be viewed and/or modified using the personal computer 3612. However, in some embodiments, although the various functions may be viewed and modified using the personal computer 3612, where the function is safety critical, the user/caregiver must confirm any changes using the mini-remote interface 3610. In some embodiments, the functions that may be viewed and/or modified using the personal computer 3612 may vary and/or be preset and/or predefined and/or hardwired into the system. In some embodiments, the personal computer 3612 may be used to view/modify more or less functions including, but not limited to, any one or more of the following: settings and/or setup, as well as food libraries and preferences for alerts including but not limited to reminders.

In various embodiments, viewing and or changing log/history, alarms and alert troubleshooting, reminders including reservoir changes and cannula changes etc., may not all be classified as non safety critical. In some embodiments, one or more of these may be classified as safety critical.

In some embodiments of this embodiment the remote interface 3604 may serve as a larger display for the mini-remote interface 3610, however, may not be used to command the infusion pump 3602 or command the mini-user interface 3610. For example, in some embodiments, the remote interface 3604 may be used to display data including logs and/or history and/or CGM and/or BG meter trending and/or graphs and/history. Thus, in some embodiments, the remote interface 3604 may be desirable as a larger display (and portable larger display) to display data and other information larger and/or more clearly for the user/caregiver. In various embodiments of this embodiment, the remote interface 3604 may be any type of interface including, but not limited to, a smart phone and may include a downloadable application. Thus, in some embodiments the remote interface 3604 may be an MDDS or Medical Device Data Systems and the mini-remote interface 3610 may be a proprietary device including secure protocols.

Although this embodiment is shown to use a BTLE protocol and a USB connection, in various other embodiments, any one or more wireless communication protocols may be used, including, but not limited to: BLUETOOTH/BLUETOOTH Low Energy or other non-proprietary protocols and/or may include, but is not limited to, one or more of the following protocols: WiFi, ZIGBEE, XB, WiFi ad hoc, White Space, Ultra wide band, Ant, and/or wireless USB. In some embodiments, the communication may be the same between each device, and in some embodiments, the communications may differ between each device. Additionally, two or more of the devices, in some embodiments, may communicate via wired and/or USB connection and/or may communicate with a particular device via wired and/or USB connection but may communicate with other devices via wireless communication. In any one or more of the embodiments described above, in some embodiments, the one or more devices may include two or more radios with the ability to communicate by way of BLUETOOTH Low Energy and/or BLUETOOTH High Energy and/or by way of a low energy protocol and a high energy protocol. For example, in some embodiments, the remote interface 3604 may communicate using a low power protocol radio with the infusion pump 3602 and a high energy BLUETOOTH radio or high power protocol radio with the blood glucose meter 3608.

In some embodiments, to confirm a command on the mini-remote interface, the user may be required to swipe the screen either left to right, right to left, top to bottom, bottom to top and/or diagonally. In some embodiments, one or more buttons will be required to be depressed for a predetermined, e.g. 3 second, period of time. However, in various embodiments, the amount of time may be different. In some embodiments, the user may be required to place the mini-remote interface in close proximity to the remote interface to confirm. In some embodiments, confirmation may be accomplished by depressing the switch assembly on the infusion pump.

In some embodiments where the mini-remote interface is required for confirming a command, if the user/caregiver loses access to the mini-remote interface, the user may use a predetermined encrypted signal, e.g., dial tones, voice recognition, played/spoken to the mini-the infusion pump to confirm the command. In some embodiments, there may be a secure call-center and the user/caregiver may call and after identifying themselves using either a pass code, patient confidential information, etc., receive a confirmation tone that may be received by the infusion pump to complete the command from the remote interface.

Pairing the various devices may be accomplished using any of the methods described above or those known in the art such as BLUETOOTH pairing. However, in some embodiments, the various devices may be paired using Near Field Communication. In some embodiments, the devices may be paired using a wired connection including, but not limited to, a USB connection. In some embodiments, the methods for pairing the infusion pump with the mini-remote interface and/or the remote interface and or any one or more of the various devices of the system with any one or more device may include maintaining the devices to be paired in close proximity to one another and performing the pairing in an area where additional devices are unlikely to interfere, e.g., the user/caregiver's home/office.

Figure 42:
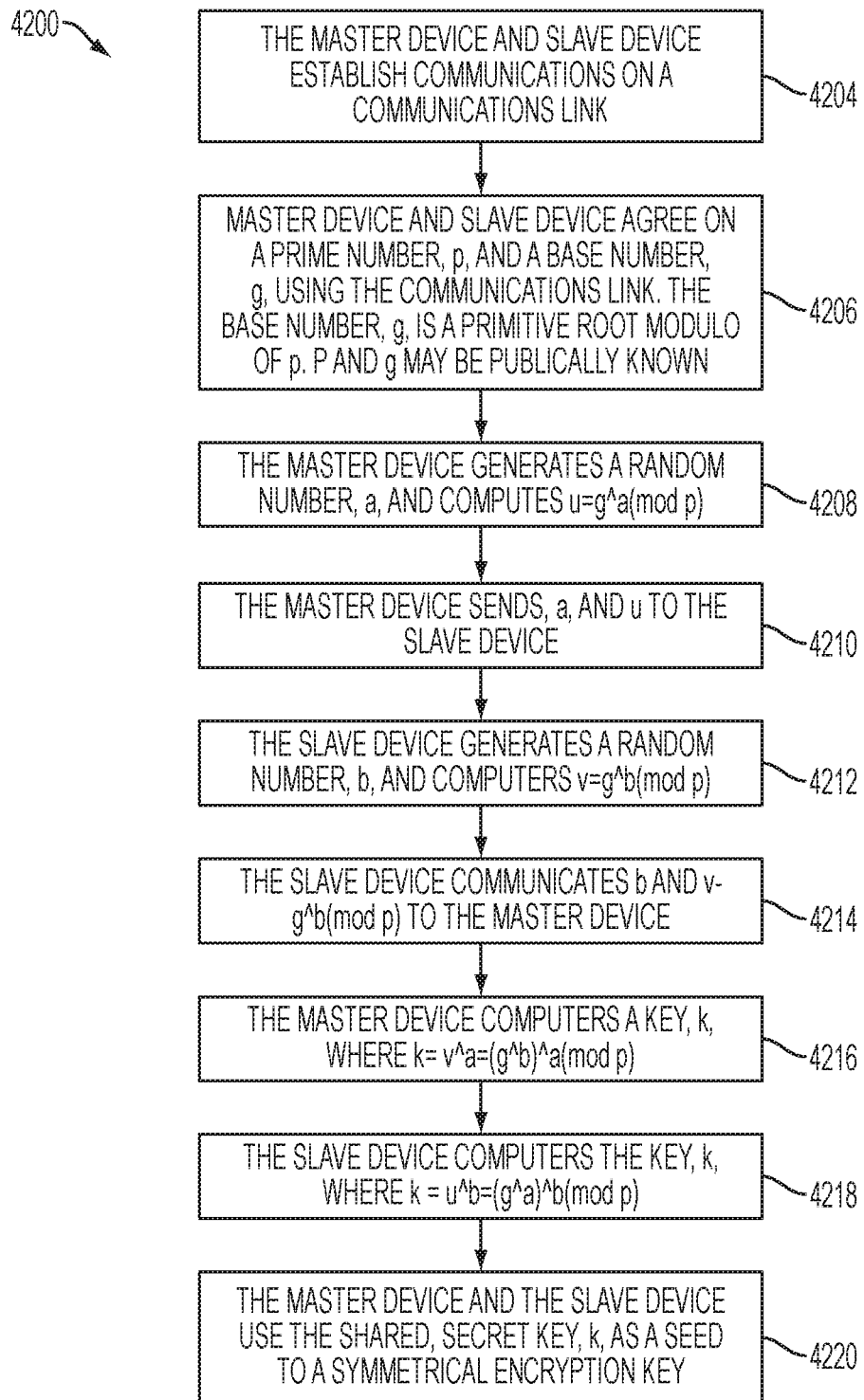
FIG. 42 is a flow chart of one method of the system according to one embodiment.

Referring now also to FIG. 42, a flow chart diagram that illustrates a methodology 4200 for securely communicating between one or more devices, such as between a medical device and a user interface/remote interface/mini-user interface device in accordance with an embodiment of the present disclosure is shown. The method 4200 includes acts 4204-4220. In Act 4204, the master device and slave device establish communications on a communications link. The communications link may be unsecure. In some embodiments, the communications link may use public-private key cryptography. In Act 4206, The master device (e.g., a medical UI/remote interface/mini-remote interface device) and slave device (e.g., a blood glucose meter, continuous glucose monitor transmitter, etc) agree on a prime number, p, and a base number, g, using the communications link. The agreement may occur using an encrypted communications link, over a wired link, or using public-private key-pair cryptography. The base number, g, is a primitive root modulo of p. P and g may be publically known. In Act 4208, the master device generates a random number, a, and computes u=g^a(mod p). In Act 4210, the master device sends, a, and u to the slave device. In Act 4212, the slave device generates a random number, b, and computers v=g^b(mod p) and communicates b and v-g^b(mod p) to the master device.

In Act 4216, The master device computers a key, k, where k=v^a=(g^b)^a(mod p). In Act 4218, the slave device computers the key, k, where k=u^b=(g^a)^b(mod p). The symmetric keys were never communicated; they were internally generated by a respective device. In Act 4220, the master device and the slave device use the shared, secret key, k, as a seed to a symmetrical encryption key. The secret key may be used as an index to a pseudorandom number index, in which case, the pseudorandom number index is the key for the symmetrical keys.

Figure 43A:
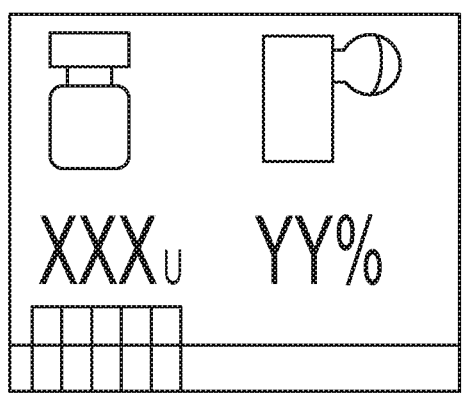
FIGS. 43A-43O are embodiments of various screen shots of a mini-remote interface according to one embodiment of the system.
Figure 43A:
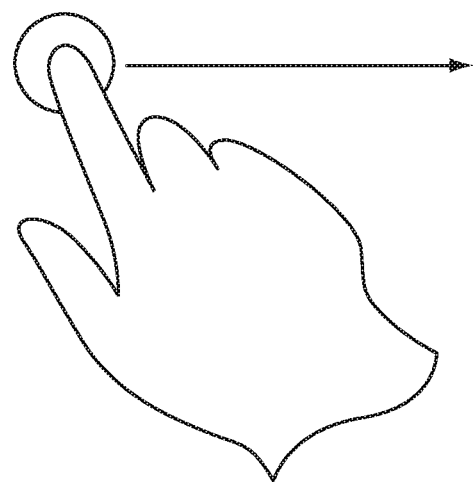
Figure 43B:
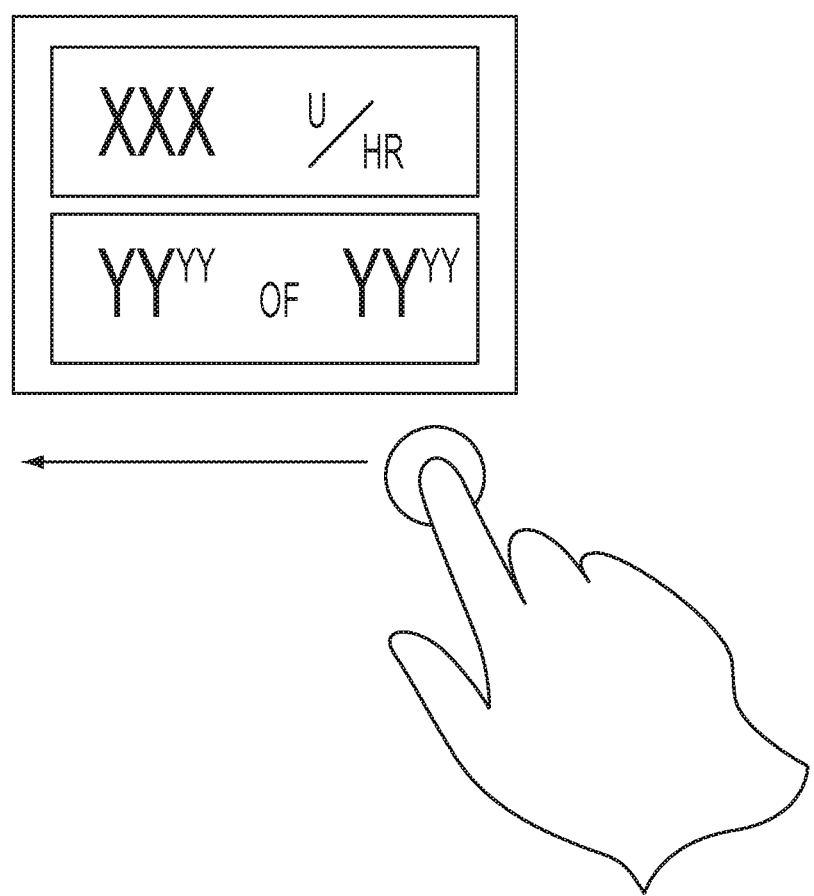
Figure 43C:
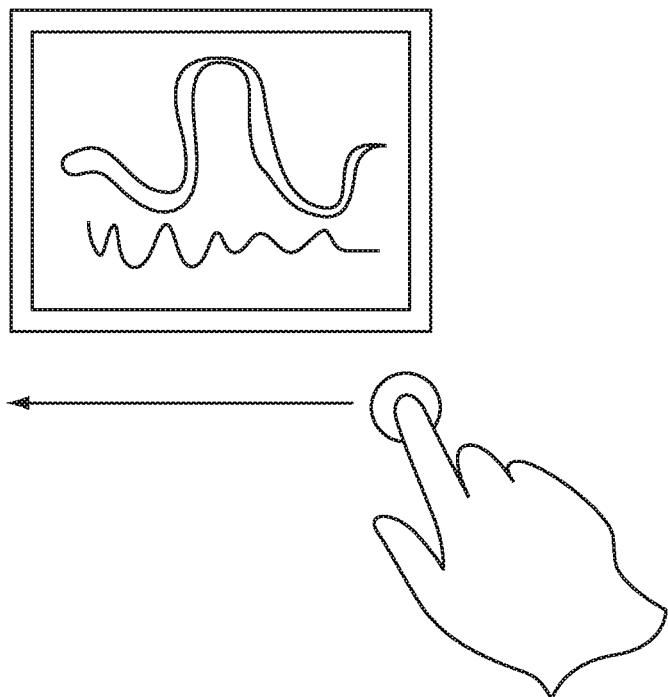
Figure 43D:
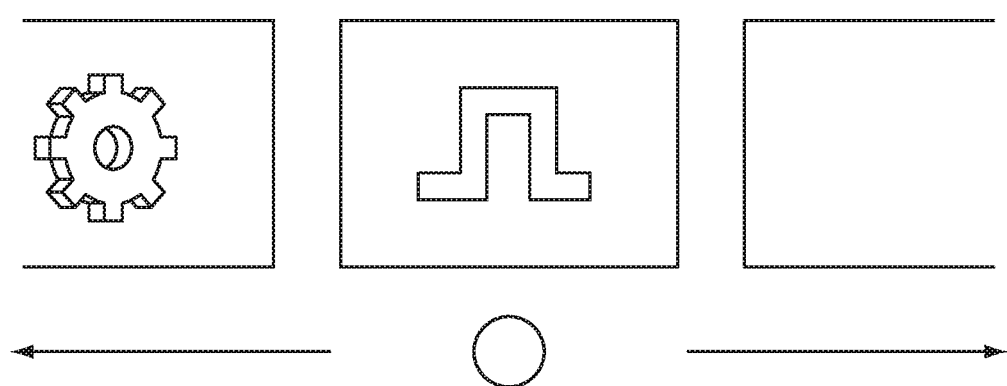
Figure 43E:
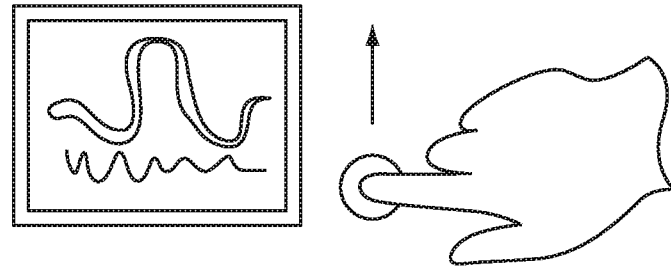
Figure 43F:
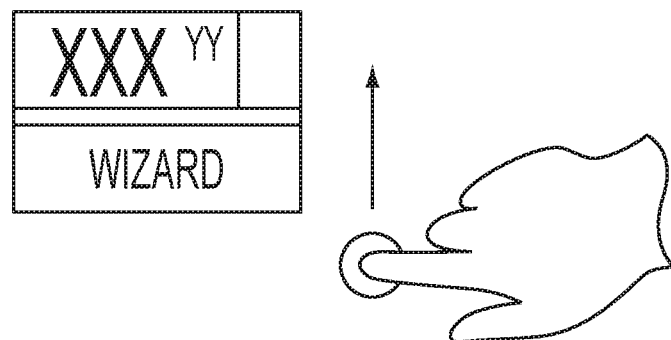
Figure 43G:
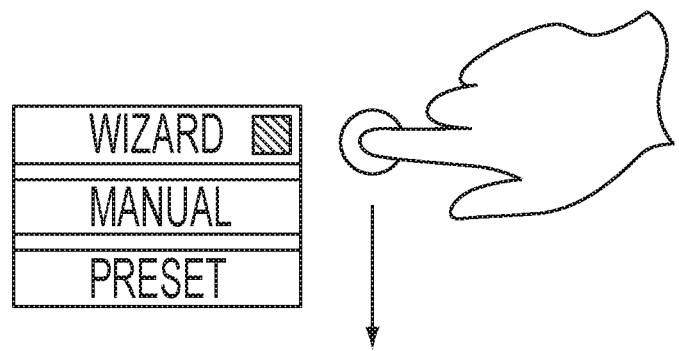

Referring now also to FIGS. 43A-43J, some embodiments of screen shots on the mini-remote interface 3610 are shown. In various embodiments, the mini-remote interface 3610 may include one or more user inputs which may include, but are not limited to, one or more of the following: one or more buttons, scroll wheel, touch screen. In some embodiments, the display may include a touch screen where the user/caregiver confirms or selects a particular command by first scrolling to select that particular command (which may be done using any of the user inputs) and then touching the screen at another particular location and swiping the screen either left to right or right to left. In some embodiments, to unlock the screen, for example, as shown in FIG. 43A, the user/caregiver may be required to swipe the screen from left to right, whereas in some embodiments, for example, as shown in FIG. 43J, to select or confirm, the user/caregiver may be required to swipe the screen from right to left. This may be desirable/beneficial for many reasons, including but not limited to, preventing unintentional confirmation by requiring the user to confirm by swiping in a different direction than the direction of unlocking. In various embodiments, the direction for each action may be different. In some embodiments, the direction for unlocking may be right to left and the direction for confirming/selecting may be left to right. In some embodiments, swiping the confirmation direction on a screen which does not have any selections will advance the screen to another screen, which may be the next screen in the user interface. Referring now also to FIGS. 43C-43D, in some embodiments, the mini-remote interface 3610 may include a display that includes a menu selection. The menu selection may be scrolled through by swiping the screen or by another user input. The menu selection may then be selected by the user/caregiver. Referring now also to FIGS. 43E-43G, in various embodiments, one the user/caregiver has navigated to the bolus home screen, the user/caregiver may elect the type of bolus to deliver, for example, using the wizard/calculator, manual or another type (represented by preset). In some embodiments, scrolling through the menu items may be accomplished by using the touch screen, touching at a particular position and then swiping up or down from that position as the various options are highlighted. Once the option desired is highlighted, the user/caregiver may select that option by swiping right to left, for example, or by using another user input, for example, one or more buttons and/or a scrollwheel. Referring now also to FIG. 43G, once the desired option is selected, e.g., Wizard, the user may swipe the screen. In some embodiments, the user may touch the screen to select.

Referring now also to FIGS. 43K-43N, in various embodiments, once the bolus type, e.g., Wizard, is selected, the next screens request the user to enter the blood glucose value and the carbohydrate value. In various embodiments, there may be a screen/scroll function for entering these values and movement of the screen scroll may be effected by touch screen swiping the screen up or down to effect the scroll. In some embodiments, other user inputs may be used. In some embodiments, once the desired values have been entered, the user may swipe the screen, e.g., right to left, to select the values and move on to the next screen.

Referring also to FIGS. 43M and 43N, in various embodiments, the mini-remote interface may include a timeout feature which may include the display turning off or becoming locked after a predetermined amount of time, e.g., 3 seconds. In some embodiments, the mini-remote interface may give a warming to the user/caregiver of the timeout being close in time, for example, graying out part of the screen or fading out parts of the screen as shown in FIGS. 43M-43N. Other methods for warning of the timeout may also be used.

Figure 43O:
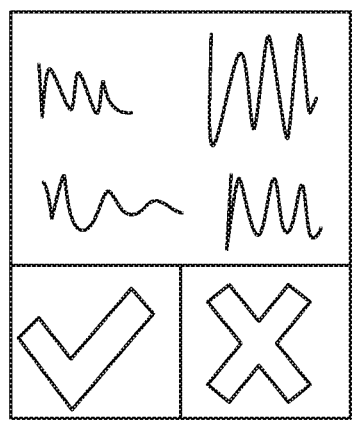

Referring now also to FIG. 43O, in various embodiments, information may be displayed to the user/caregiver on the display of the mini-remote interface and there may be displayed a symbol or word indicating either accept or cancel. In various embodiments the user/caregiver may scroll to either the accept or cancel icon and select by either swiping in the appropriate direction or selecting using any one or more of the various user inputs.

In some embodiments, confirmation/selecting may be completed by pressing, for example, one or more or a combination of button user inputs simultaneously.

Various embodiments of screen shots and methods that may be used by the remote interface are discussed above. However, additional screen shots and methods for the user interface, of which one or more may be used by the mini-remote interface and/or the remote interface, in the various embodiments of the systems described herein, are shown in FIGS. 44A-58T.

Figure 44A:
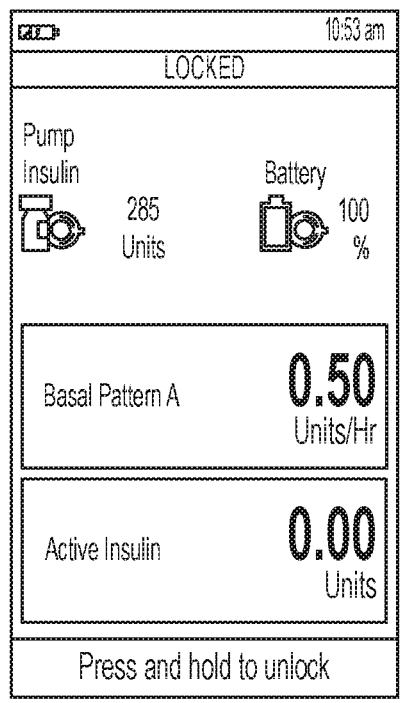
Figure 44B:
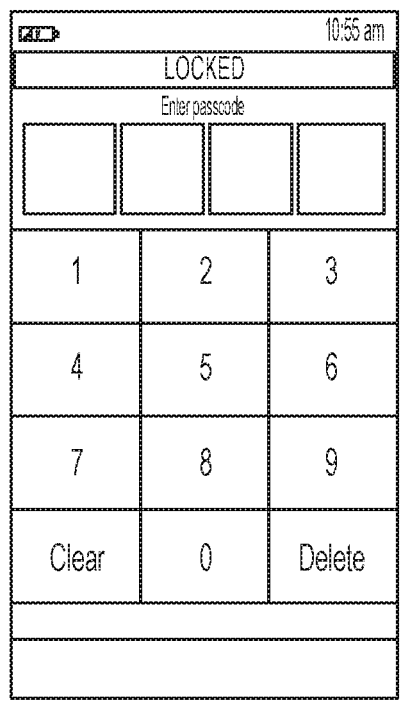

Referring now also to FIGS. 44A-44B, in various embodiments, the screen may be locked which may be beneficial for many reasons, including, but not limited to, prevention of unintentional changes in settings and/or commands being sent to the infusion pump. In some embodiments, the locked screen may require a passcode to unlock the screen. In various embodiments, unless or until the passcode unlocks the screen, the screen remains locked and no settings may be changed nor commands sent.

Figure 45A:
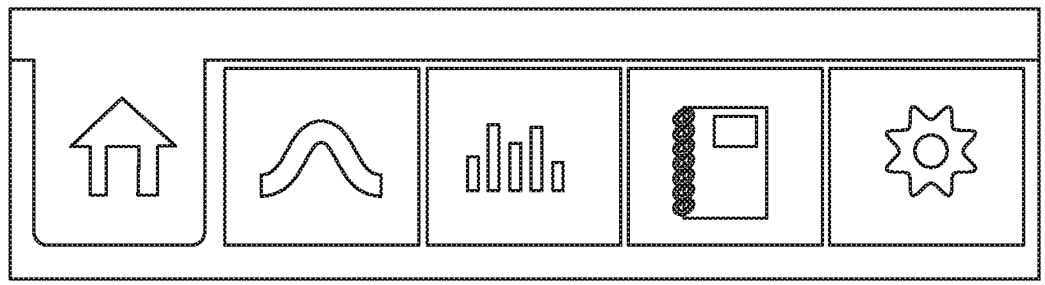
Figure 45B:
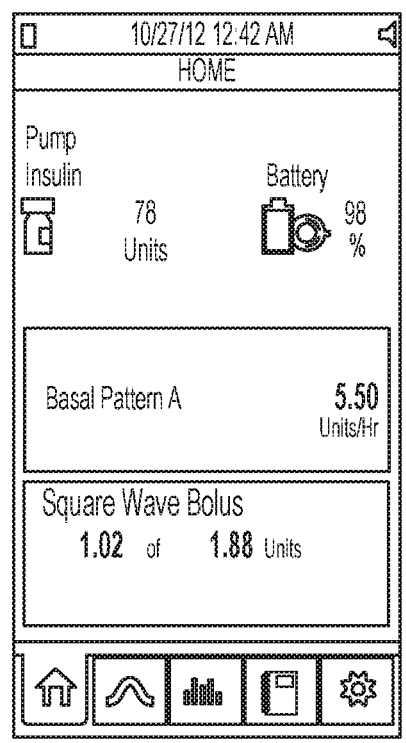

Referring now to FIG. 45A, in various embodiments, the home screen may include icons for selecting to navigate to a specific function menu. Referring now also to FIG. 45B, the icons may be seen located at the bottom of the home screen. In various embodiments, the home screen may include information indicated the amount of insulin (or other infusible fluid) remaining in the reservoir, the percentage of battery life remaining and the current deliver rate(s) for basal and, where applicable, bolus. For example, in FIG. 45B, the home screen indicates that basal pattern A is currently delivering and the rate, e.g. 5.50 Units/Hr, is also indicated. The home screen additionally indicates a square wave bolus is saved and has delivered 1.02 of 1.88 units and that there are 6 minutes remaining in the square wave bolus.

Figure 45C:
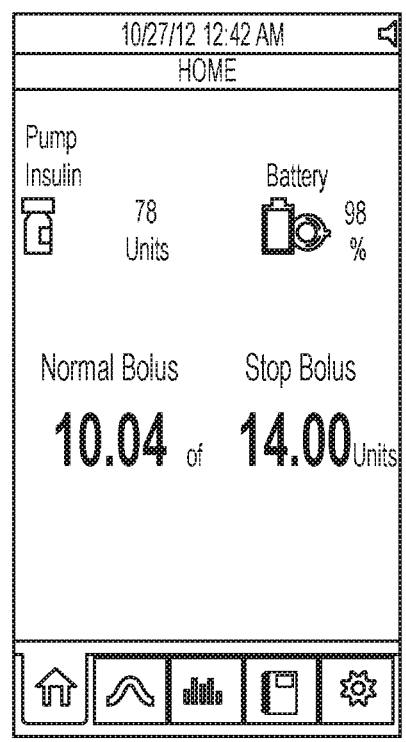
Figure 45D:
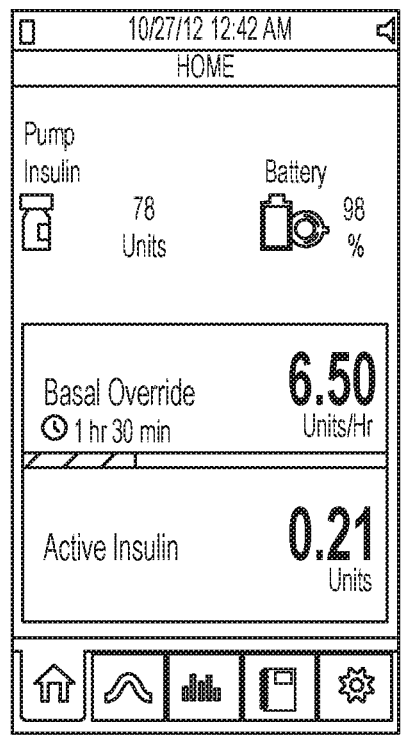
Figure 45E:
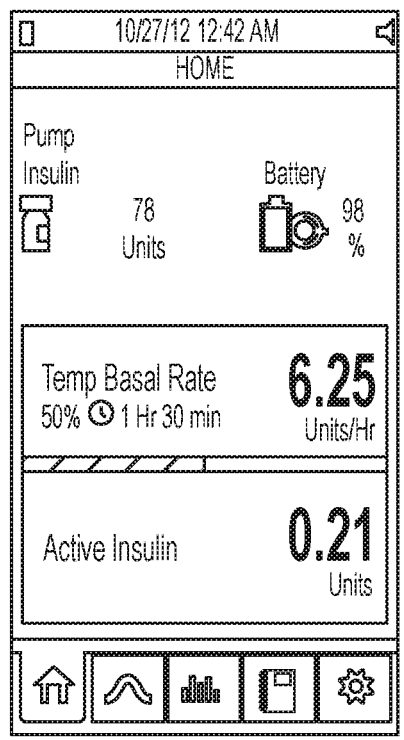

Referring now also to FIG. 45C, the home screen shown includes an indication that a normal bolus is being delivered and that 10.04 of 14.00 units has been delivered. During the bolus event, the user/caregiver may stop the bolus by pressing the "stop bolus" button on the home screen. Referring now also to FIGS. 45D and 45E, another embodiment of the home screen is shown. In FIG. 45D, a "basal override" event lasting 1 hour and 50 minutes is also indicated. In this example, the rate is indicated as 6.50 Units/Hr. Referring now also to FIG. 45E, in this embodiment of the home screen, a "Temp Basal Rate" event that includes a 50% increase of basal rate for 1 hour and 30 minutes is indicated. The rate is 6.25 Units/Hr. In both FIGS. 45D-45E, the active insulin is indicated, e.g. 0.21 Units. Thus, in all of the embodiments shown, the home screen presents the current delivery status and the active insulin/infusible fluid.

Figure 46A:
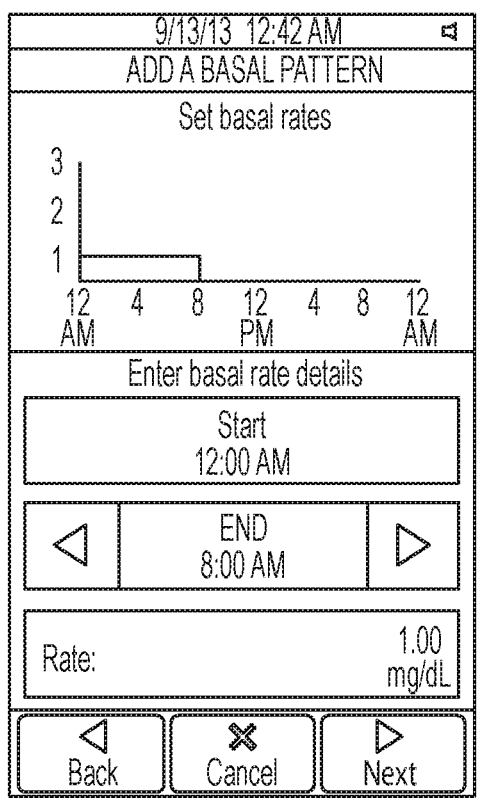
Figure 46B:
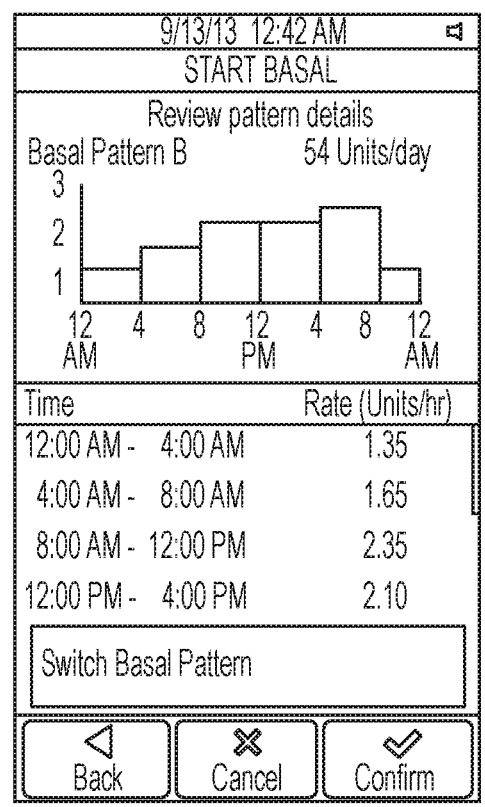

Referring now also to FIGS. 46A-46B, in various embodiments, a basal pattern may be programmed by entering the start and end times as well as the rate for that time frame. In various embodiments, the basal pattern may be displayed as a graph representing the basal pattern delivery rates throughout a twenty-four hour period. In various embodiments, as shown in FIG. 46B, once the basal pattern is programmed, the user/caregiver may review the entire pattern, including the graphical representation, and the time frames on a single screen. In addition, the basal pattern may be switched by selecting "switch basal patter" and then selecting another basal pattern. The graphical representation may be beneficial/desirable for many reasons, including, but not limited to, presenting the basal pattern/profile in a style which represents to the user/caregiver easily and clearly when the rate is higher or lower and presents a picture for the entire day.

Figure 47A:
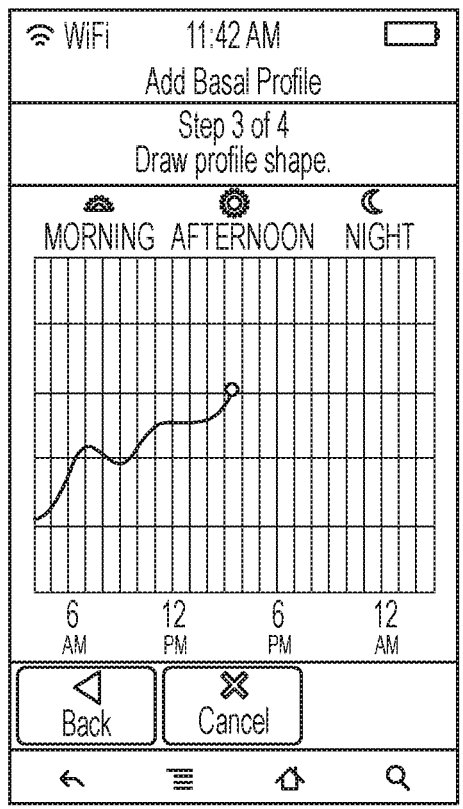
Figure 47B:
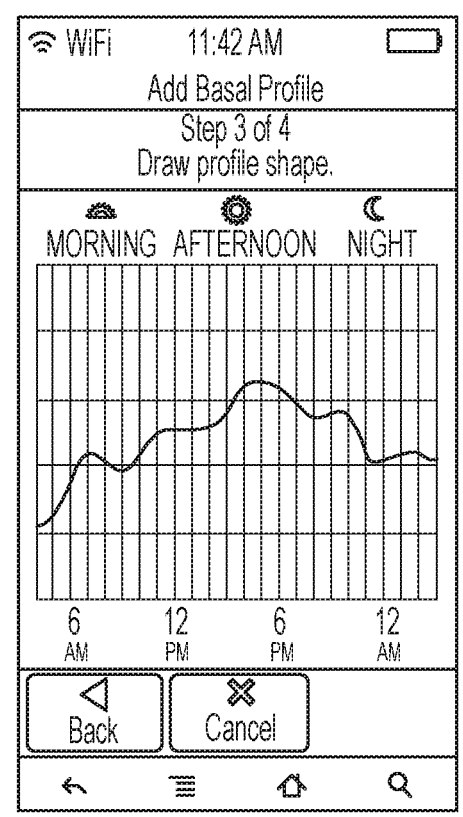
Figure 47C:
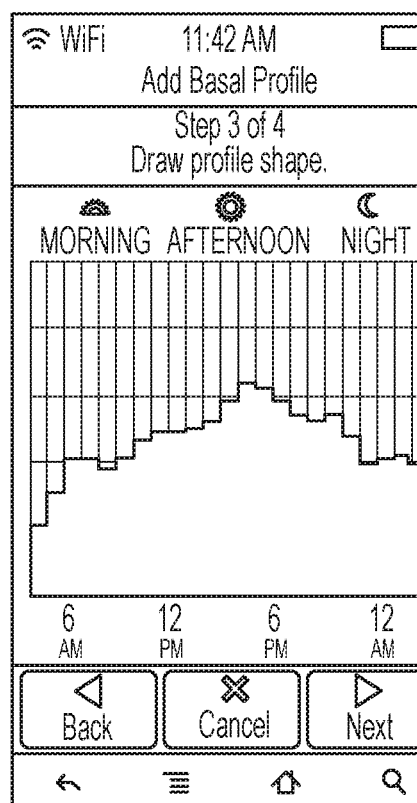
Figure 48A:
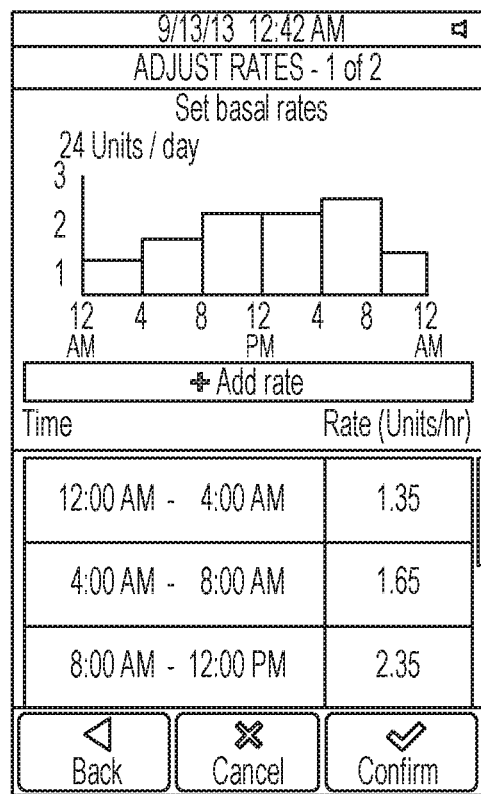
Figure 48B:
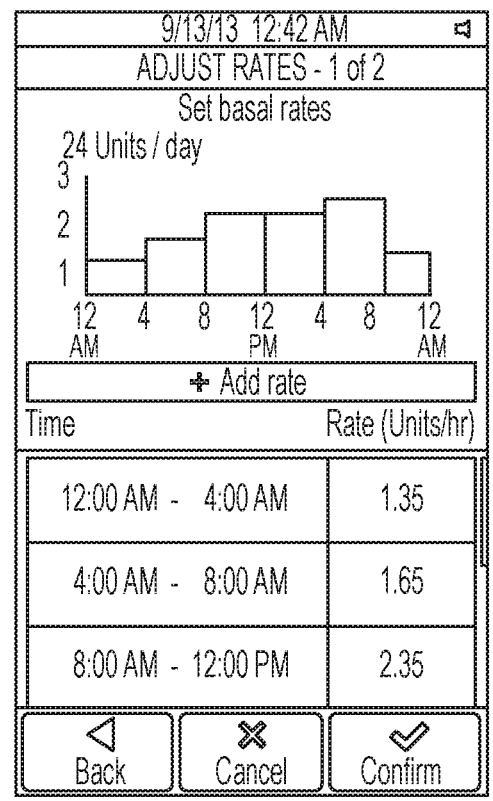
Figure 48C:
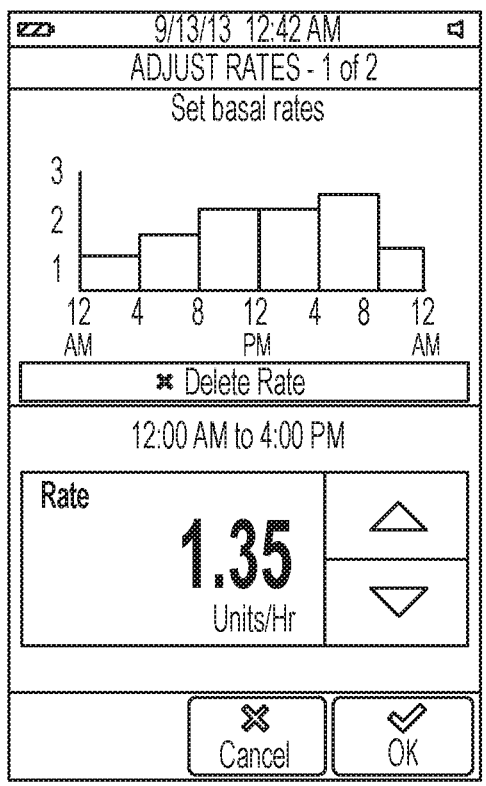
Figure 48D:
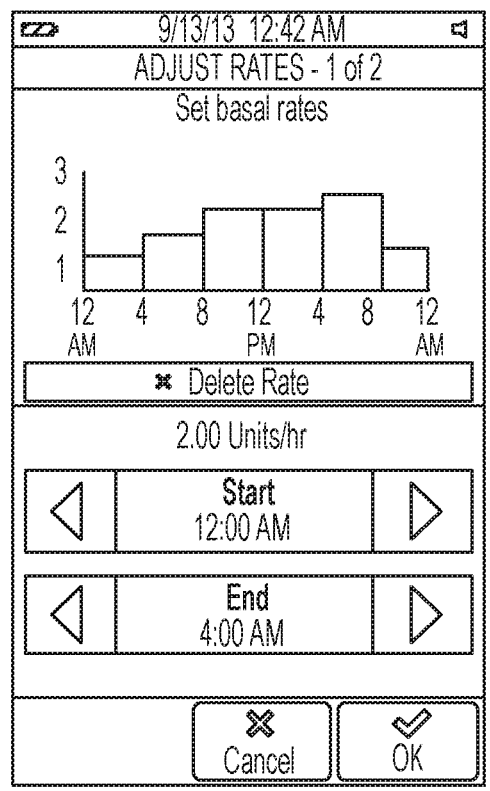

Referring now also to FIGS. 47A-47C, in some embodiments, a basal pattern/profile may be programmed by the user/caregiver tracing the rate, using the touch screen functionality of the interface and their finger or a stylus, etc. Once the basal pattern/profile is drawn, the system renders a graphical depiction and the user may view and/or edit the pattern/profile.

Referring now also to FIGS. 48A-48D, in various embodiments, to adjust any rate in a basal pattern, the user/caregiver may navigate to adjust the basal pattern, then select the rate in which they wish to adjust. Once selected, an indication of the current rate, with scroll when function, is presented to the user/caregiver. The user/caregiver may then adjust the rate by using the arrows of the scroll wheel and then select "OK" to save the new rate.

Figures 49A, 49B:
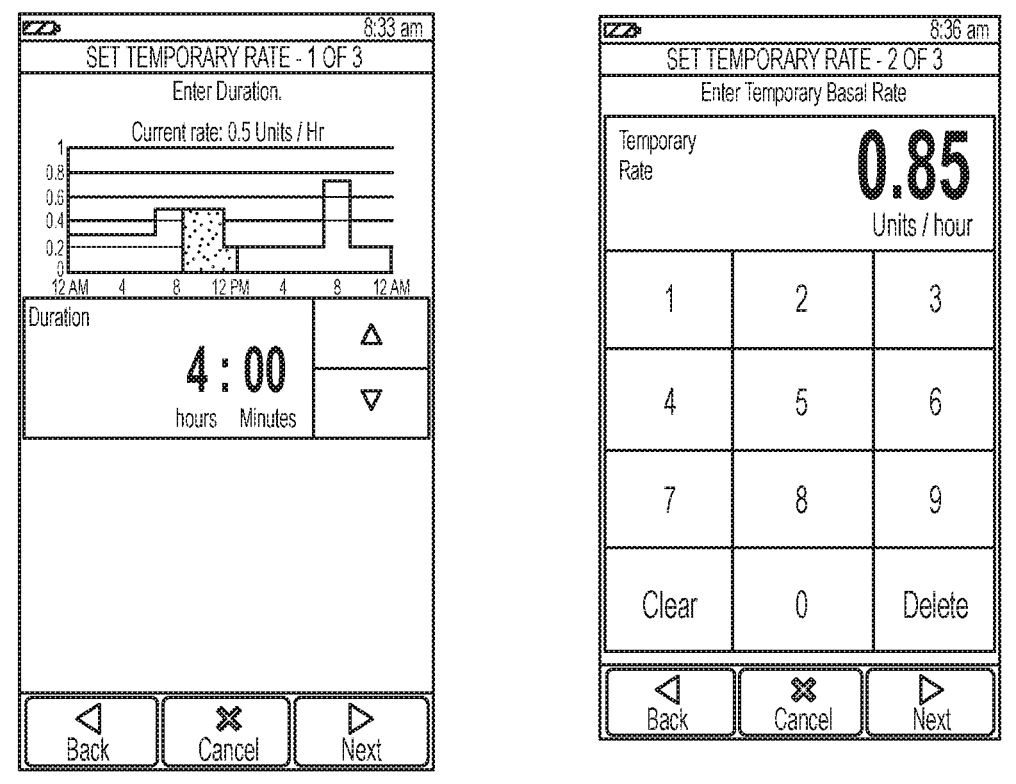

Referring now also to FIGS. 49A-49B, in various embodiments, a temporary basal rate may be set. In some embodiments this may be done by navigating to the "set temporary rate" screen where the new rate may be entered (see FIG. 49B) using, in some embodiments, a keypad, and the duration of the new rate may be entered using, in some embodiments, a scroll wheel function (see FIG. 49A). The graphical depiction of the basal pattern may also aid the user/caregiver in programming temporary rates for they may visualize the difference between the rate before and after the temporary rate which may aid in programming a sufficient rate.

Figure 50A:
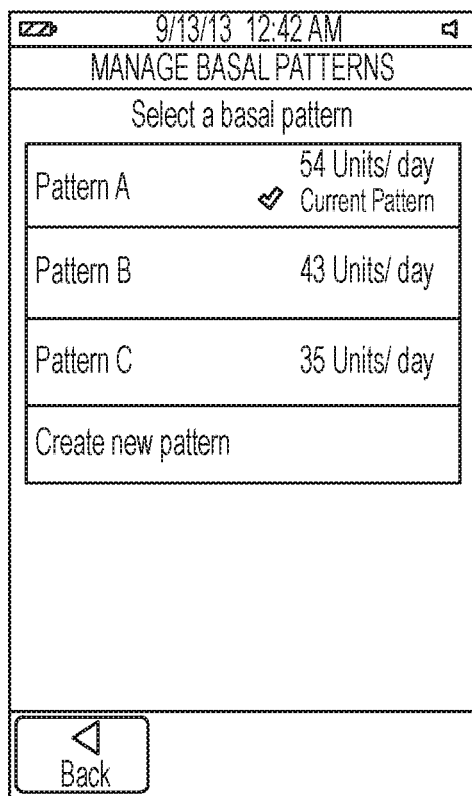
Figure 50B:
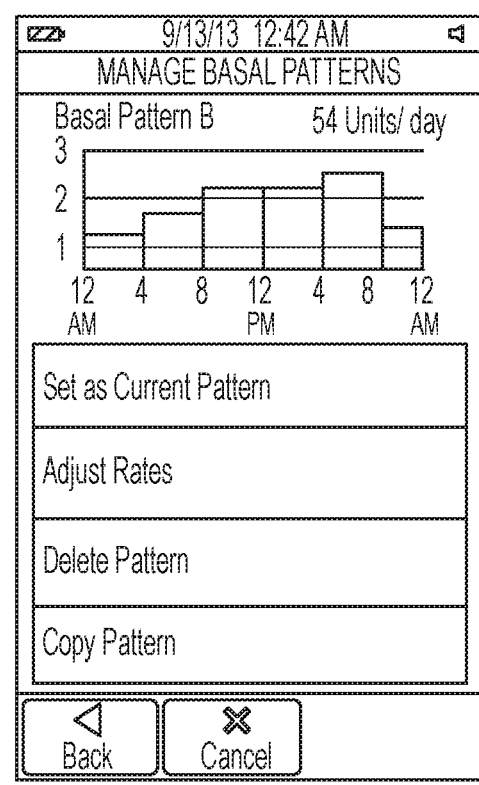

Referring now also to FIGS. 50A-50B, in various embodiments, the basal patterns/profiles may be managed using basal profile manager screens. For example, and as shown in FIG. 50A, in some embodiments, the basal patterns may be viewed, collectively, on a single screen, which indicated the number of units per day. This screen also includes that current pattern. This screen may also include a button to create a new pattern. In some embodiments, once a pattern is selected from the manage basal patterns screen, the graphical depiction of that pattern may be shown (see FIG. 50B) and options to adjust the rates, set as current pattern, delete the pattern or copy the pattern (to create another pattern with a new name but having the same pattern).

Figure 51A:
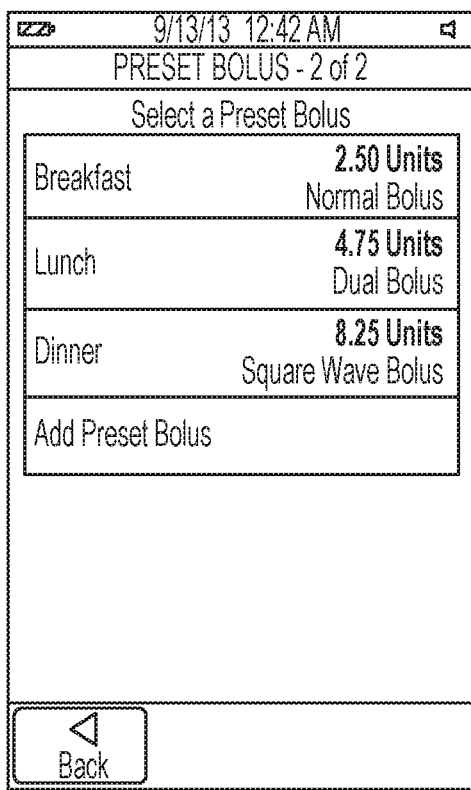
Figure 51B:
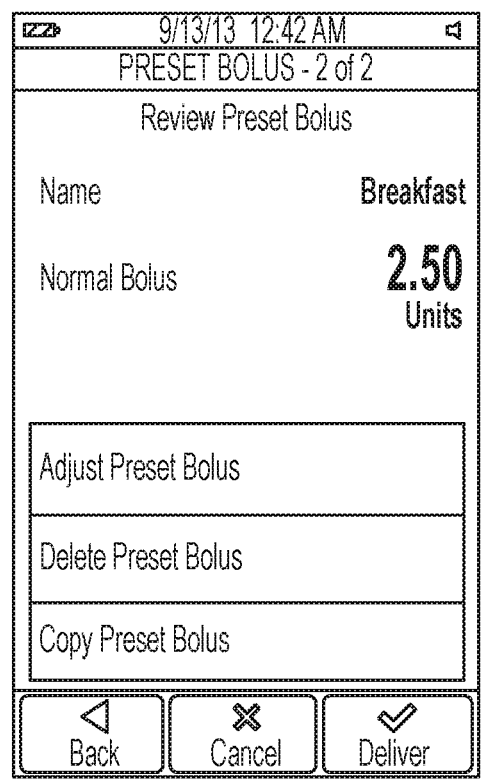

Referring now to FIGS. 51A-51B, in various embodiments, the user interface may include "preset bolus" options wherein the user/caregiver may preset bolus amounts and/or types of boluses for, e.g. breakfast, lunch and dinner. To request the delivery of the preset bolus, in some embodiments, the user selects a preset bolus, e.g. breakfast. Then the user interface navigates to another screen (see FIG. 51B) that shows the bolus type and amount, e.g., normal bolus and 2.50 units. The user/caregiver may they select "deliver" and the preset bolus may be delivered. In various embodiments, preset boluses may be added using the screen shown on FIG. 51A, and/or adjusted, deleted or copied (see FIG. 51B).

Figures 52A, 52B:
Figure 52C:
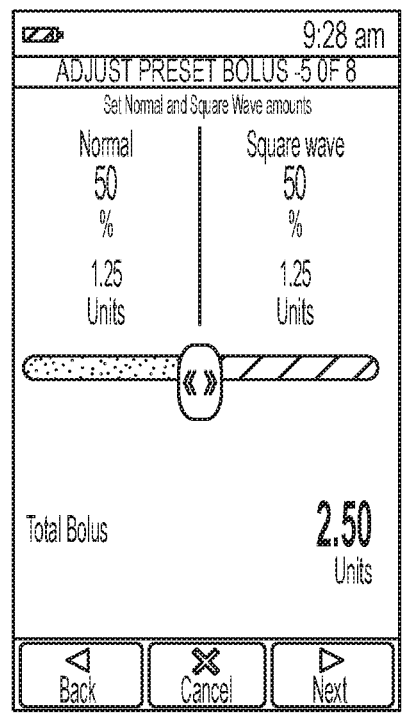

Referring now to FIGS. 52A-52D, in various embodiments, the user interface may include a "bolus wizard" or bolus calculator. In various embodiments, the bolus wizard or bolus calculator may request the user enter, using a keypad, the amount of carbohydrates and blood glucose using a keypad (the carbohydrate screen shot is shown in FIG. 52A. The blood glucose keypad, in various embodiments, is similar). In some embodiments, however, the last blood glucose reading may be used if the user elects to use it, or the user may elect to calculate the bolus without using a blood glucose reading. The next screen, an embodiments of which is shown in FIG. 52B, shows the user the calculations of the correction bolus, based on the blood glucose (which, in this example, is 125 mg/dl), the insulin correction (based on the active insulin, which, in this example, is 2.45 units) and the meal bolus (based on the carbohydrates). The total bolus amount is also shown (which, in this example, is 7.50). The user may then elect to adjust the calculated "total bolus" amount and/or deliver part or all of the total bolus as an extended bolus or "square wave" or "dual wave" bolus. Referring now to FIG. 52C, in various embodiments, to deliver a portion of the bolus as a normal bolus and a portion of the bolus as a square wave bolus (or extended bolus), the user interface presents to the user/caregiver a sliding scale where the amount, represented in both units and percentage of the total, to be delivered as normal is represented on one side of a line and the amount, represented in both units and percentage of the total, to be delivered as a square wave on the other. The user/caregiver may adjust the percentage of the amount to be delivered as normal and square wave by moving the rectangular icon towards the square wave side or normal size. While moving the rectangular icon, the totals on both sides is adjusted such that the user/caregiver may watch the percentages and total units change in real time.

Figure 52D:
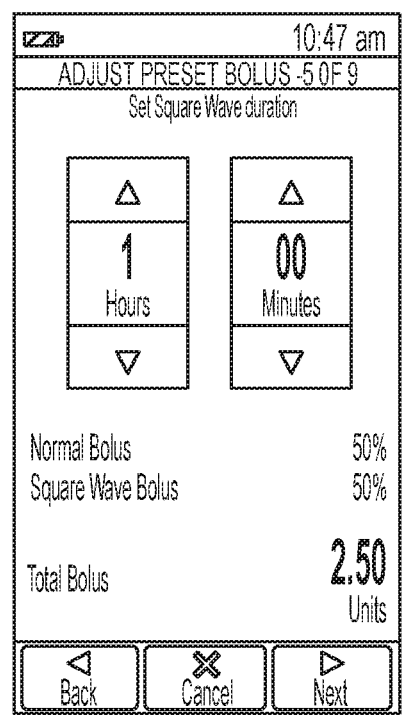

Once the total amounts to be delivered as normal and square wave are selected, then the user/caregiver may program the duration of the square wave using scroll wheels on the screen, see FIG. 52D.

Figure 53:
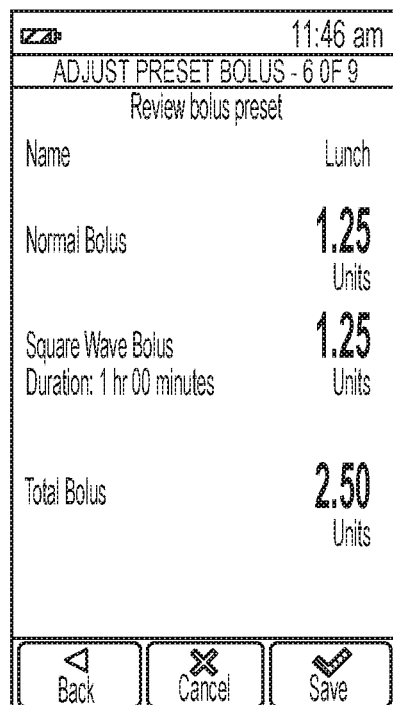

Referring now also to FIG. 53, in various embodiments, the preset boluses may also be adjusted to include normal and square wave portions. In various embodiments, the normal and square wave percentages are pre-programmed into the preset bolus. For example, in FIG. 53, the "Lunch" preset bolus includes 1.25 units delivered as a normal bolus and 1.25 units delivered as a square wave bolus over 1 hour, for a total of 2.50 units.

In various embodiments, the user may enter a normal bolus amount and then elect to deliver part or all of the total bolus as an extended bolus or "square wave" or "dual wave" bolus. Referring now to FIG. 52C, in various embodiments, to deliver a portion of the bolus as a normal bolus and a portion of the bolus as a square wave bolus (or extended bolus), the user interface presents to the user/caregiver a sliding scale where the amount, represented in both units and percentage of the total, to be delivered as normal is represented on one side of a line and the amount, represented in both units and percentage of the total, to be delivered as a square wave on the other. The user/caregiver may adjust the percentage of the amount to be delivered as normal and square wave by moving the rectangular icon towards the square wave side or normal size. While moving the rectangular icon, the totals on both sides is adjusted such that the user/caregiver may watch the percentages and total units change in real time.

Figure 54A:
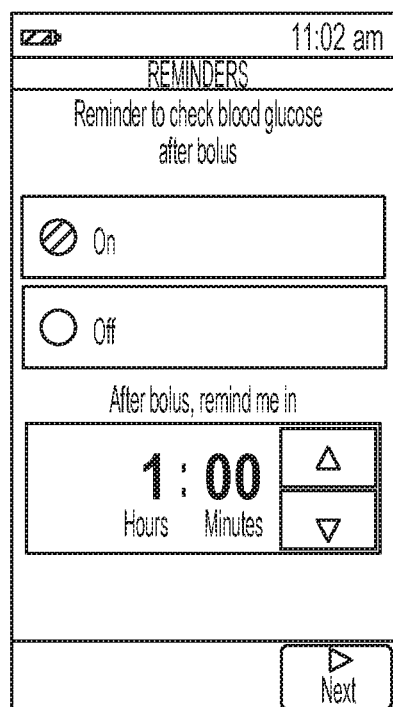
Figure 54B:
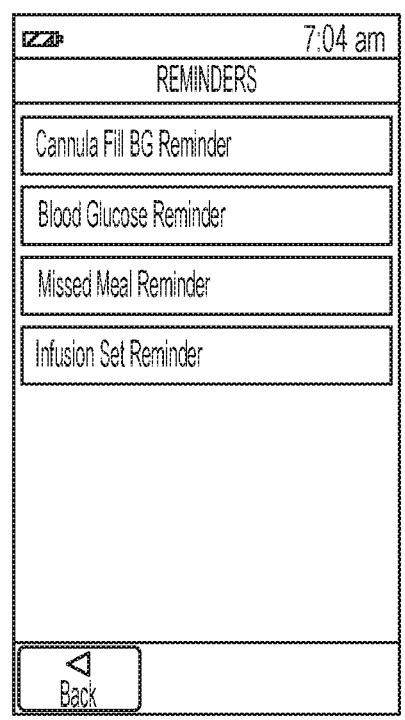
Figure 54C:
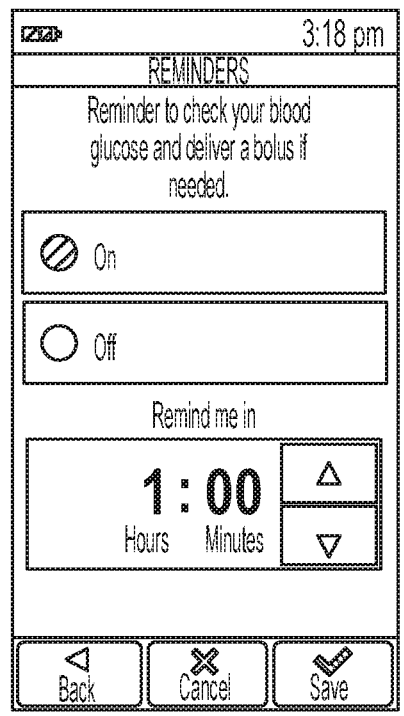
Figure 54D:
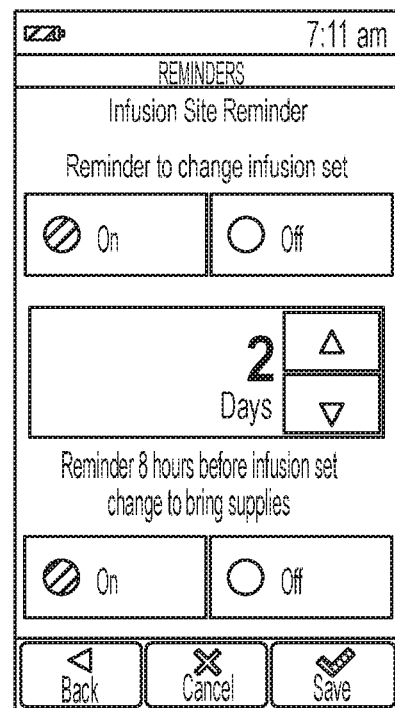
Figure 55:
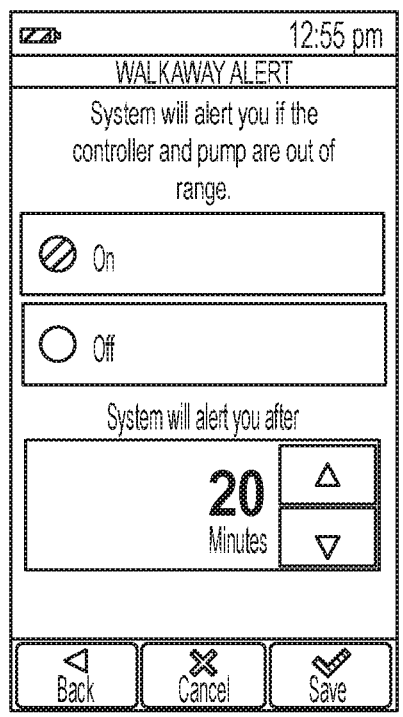

Referring now also to FIGS. 54A-54D, in various embodiments, various reminders may be entered/programmed by the user/caregiver. These include, but are not limited to, a reminder for the user/caregiver to check blood glucose after bolus (see FIG. 54A). With respect to the check blood glucose reminder, the user/caregiver may program the duration between the bolus and the reminder by using a scroll wheel to program the hours and minutes until the reminder. Additionally, the user/caregiver may turn the reminder on and off. Additional reminder may include, but are not limited to, cannula fill blood glucose reminder which may be programmed to remind the user/caregiver to check their blood glucose after a certain (programmed) duration after filling a cannula. Also, an infusion site reminder may be programmed. As shown in FIG. 54D, in some embodiments, once the infusion site is changed, a reminder may be set to remind the user/caregiver to change the infusion set again after a programmed number of days. The programmed number of days may be selected by the user/caregiver using a screen scroll wheel. In some embodiments, the system may include a default number of days, e.g. 2 days, which may be altered by the user/caregiver to any number of days desired, e.g., 3. As with other reminders, in this embodiments, this reminder may be turned on or off by the user/caregiver preference. In some embodiments, a reminder to check blood glucose may be set by the user/caregiver and this may be set for any number of hours/minutes from the reminder creation time. In some embodiments, this type of reminder is triggered by the user/caregiver's desire, for example, in some embodiments; a user/caregiver may have recently treated a low blood glucose with sugar and may desire a reminder to remind them to re-check their blood glucose after a certain duration of time, e.g., 15 minutes. However, any duration of time may be programmed by the user using, in some embodiments, and as shown in FIG. 54C, a screen scroll wheel.

Other reminders may be programmed by the user and include, but are not limited to, a missed meal reminder. In some embodiments, the user/caregiver may program a reminder for the times of day when a meal is expected. In some embodiments, if a bolus is not requested during a preprogrammed/user programmed duration before or after that time, a reminder may alert the user that they may have either missed a meal or failed to deliver a bolus for the meal. In various embodiments, these reminders may be programmed to alert the user daily, as a recurrent reminder, or may be a single reminder.

Referring now also to FIG. 55A, in some embodiments, a walkaway alert may be included in the remote interface/infusion pump/and/or mini-remote interface system. The user may turn the walkaway alert either on or off and may program the alert for a duration of time after the system determines the controller and pump are out of range. In some embodiments, the duration may be preprogrammed and may be adjustable by the user. In some embodiments, the user may adjust the duration using a screen scroll wheel.

Figure 56A:
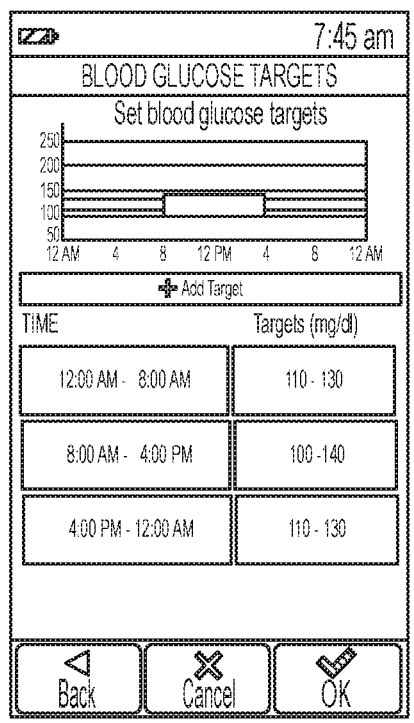
Figure 56B:
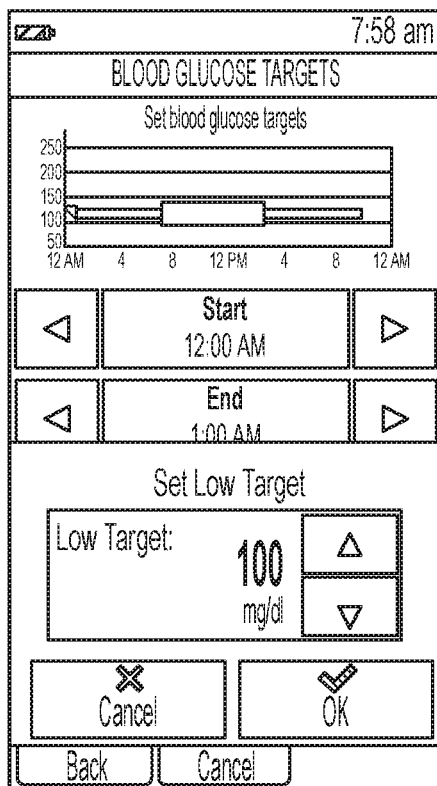
Figure 56C:
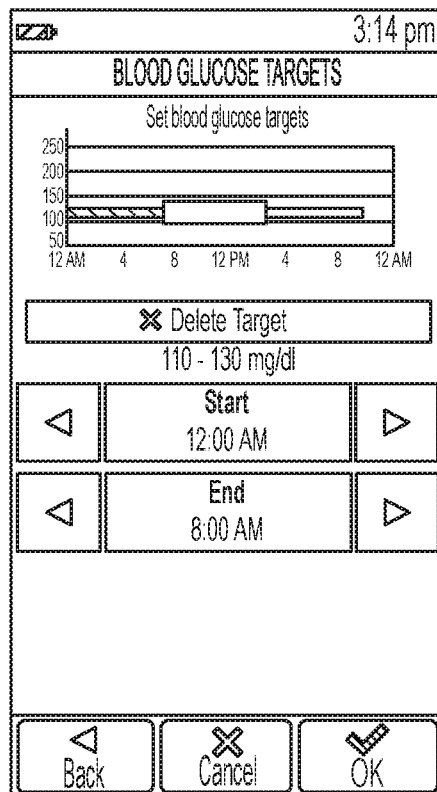

Referring now also to FIGS. 56A-56C, in some embodiments, the user interface may include blood glucose targets which may be programmed by the user/caregiver and which may be used in various calculations by the system, including, but not limited to, a blood glucose correction bolus calculation. In various embodiments, the user interface includes the ability to set various blood glucose targets for various time frames/intervals throughout a twenty-four hour period. In various embodiments, the blood glucose targets may be represented to the user/caregiver in a graphic form. The blood glucose targets, in various embodiments, may include a low target and a high target for each timeframe/interval. This may be desirable for many reasons, including, but not limited to, the ability of the user/caregiver to visualize the various timeframes/intervals and the targets for that time frame/interval in a single graphical representation. This may be beneficial/desirable for many reasons, including but not limited to, selecting the correct targets when programming and in some embodiments, this may prevent errors in programming. In addition to the graphical representation, each timeframe/interval is written and includes the high and low targets (see FIG. 56A). To change a particular interval, the user may, using the touchscreen, tap on the particular interval, and in some embodiments, may either tap on the written interval section or the graphical representation of that interval. A new screen appears and includes screen scroll wheels to change the intervals and/or change the targets (low and/or high), see FIG. 56B. In some embodiments, by selecting the interval, the user may "delete target" by selecting the option on the screen, see FIG. 56C.

Figure 57A:
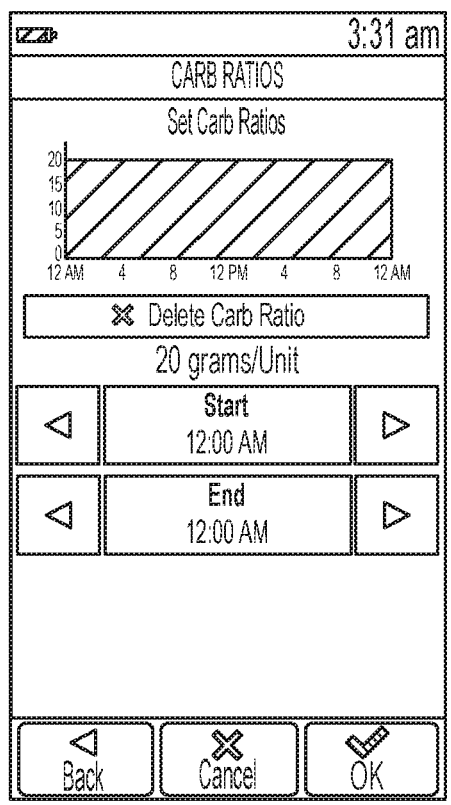
Figure 57B:
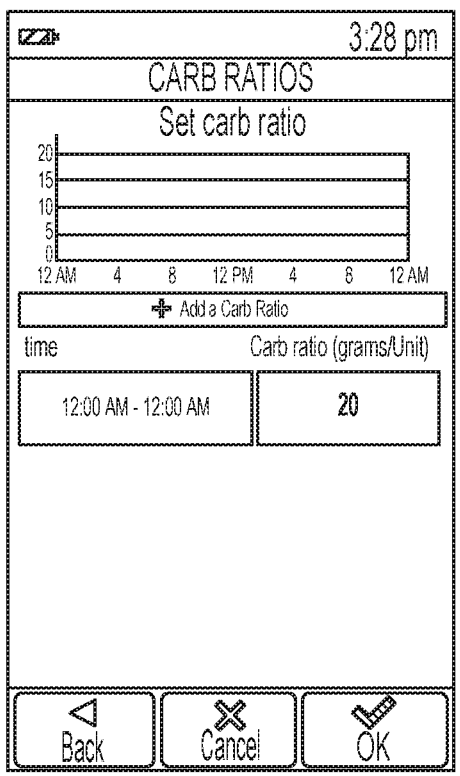
Figure 57C:
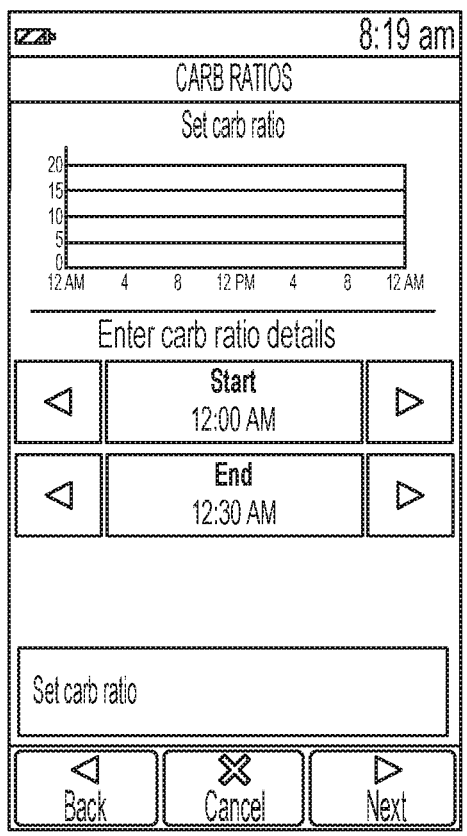

Referring now to FIGS. 57A-57C in some embodiments, the user interface may include carbohydrate ratios which may be programmed by the user/caregiver and which may be used in various calculations by the system, including, but not limited to, a meal bolus calculation and/or a meal and correction bolus calculation. In various embodiments, the user interface includes the ability to set carbohydrate ratios for various time frames/intervals throughout a twenty-four hour period. In various embodiments, the carbohydrate ratios may be represented to the user/caregiver in a graphic form. The carbohydrate ratios, in various embodiments, include value which represents the grams of carbohydrates per one unit of infusible fluid, e.g. insulin. This may be desirable for many reasons, including, but not limited to, the ability of the user/caregiver to visualize the various timeframes/intervals and the ratios for that time frame/interval in a single graphical representation. This may be beneficial/desirable for many reasons, including but not limited to, selecting the correct ratios when programming and in some embodiments, this may prevent errors in programming. In addition to the graphical representation, each timeframe/interval is written and includes the carbohydrate ratio for that timeframe/interval (see FIG. 57B). To change a particular interval, the user may, using the touchscreen, tap on the particular interval, and in some embodiments, may either tap on the written interval section or the graphical representation of that interval. A new screen appears and includes screen scroll wheels to change the intervals and/or change the ratio, see FIG. 57C. In some embodiments, by selecting the interval, the user may "delete target" by selecting the option on the screen, see FIG. 57A.

Figure 58A:
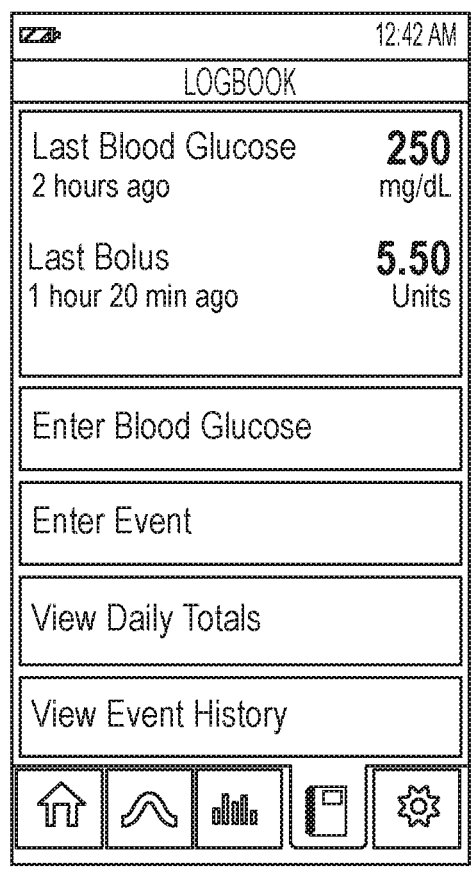
Figure 58B:
Figure 58C:
Figures 58D, 58E:
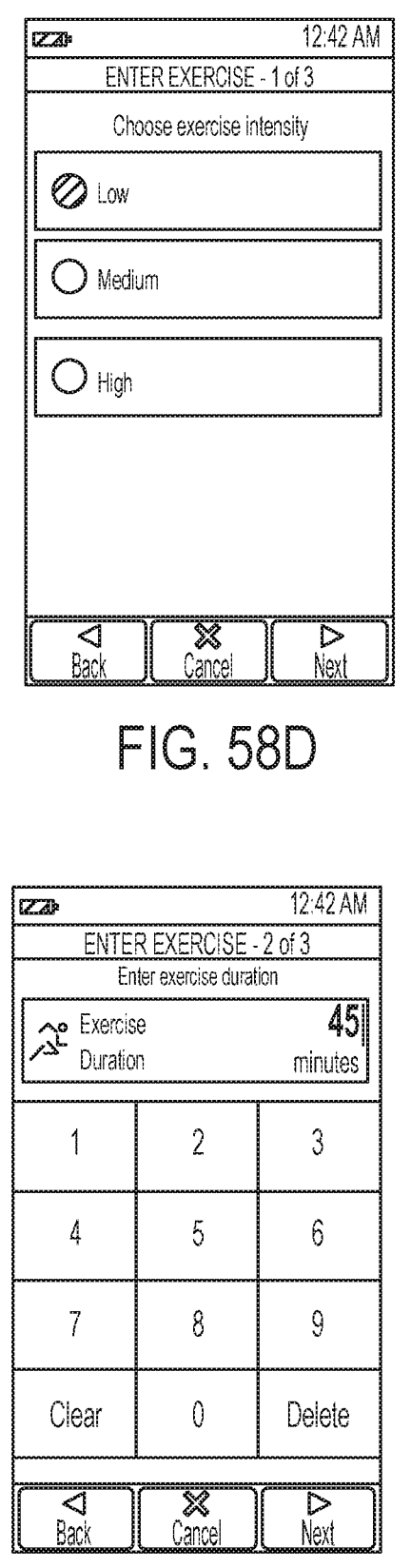
Figure 58F:
Figure 58G:
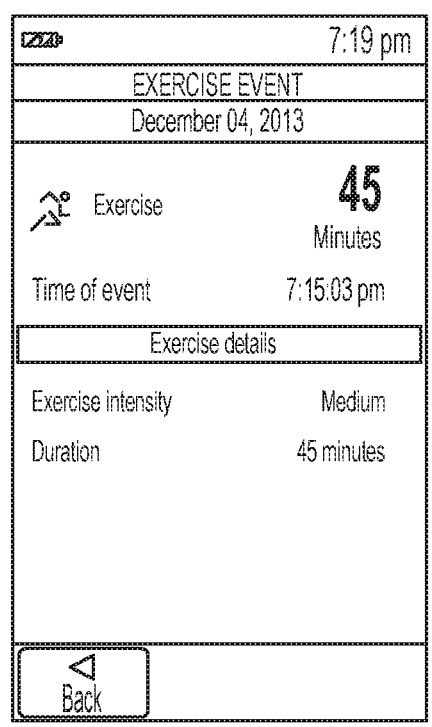
Figure 58H:
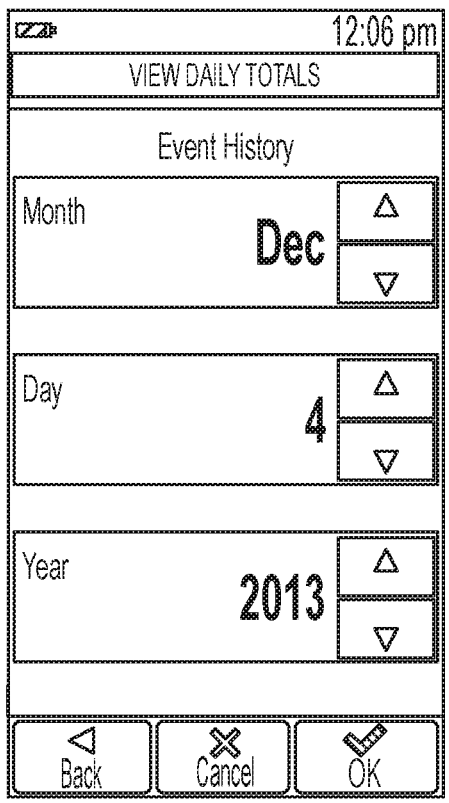
Figure 58I:
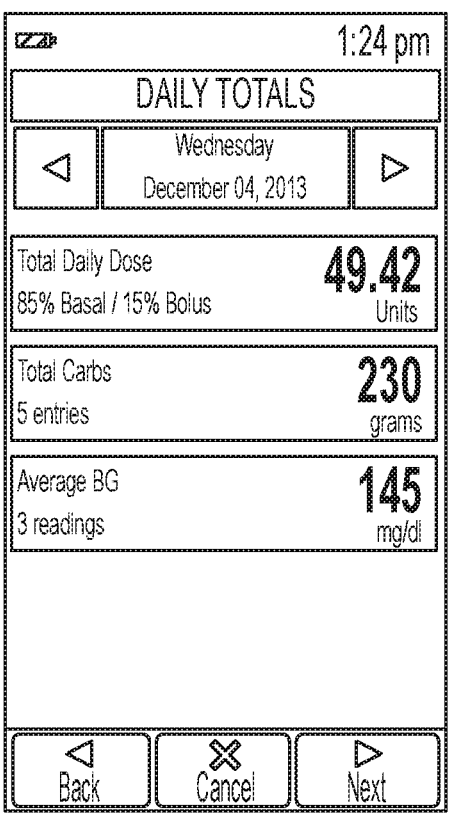
Figure 58J:
Figure 58K:
Figures 58L, 58M:
Figure 58N:
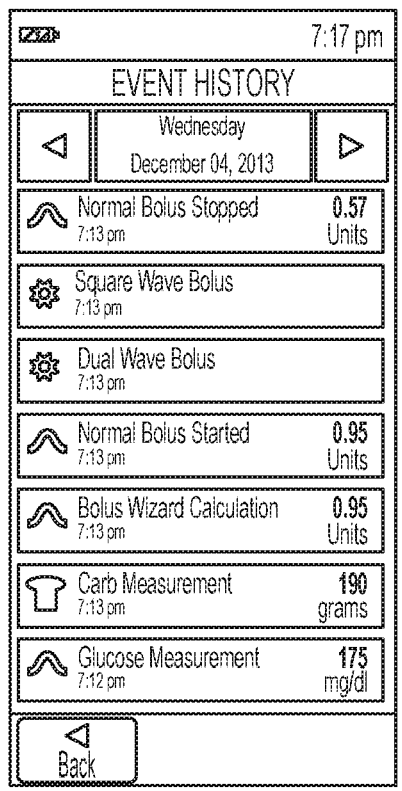
Figure 58O:
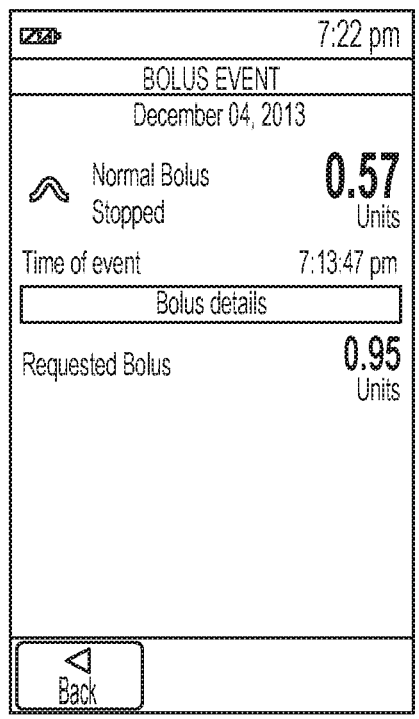
Figure 58P:
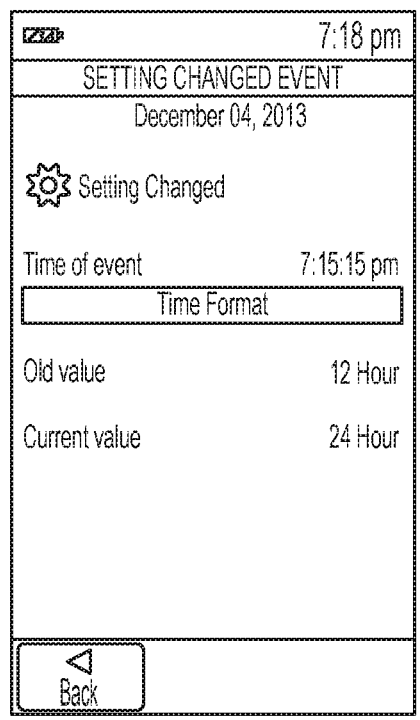
Figure 58Q:
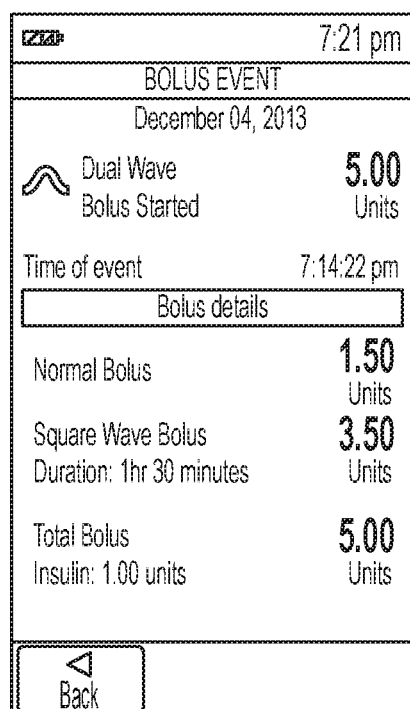
Figure 58R:
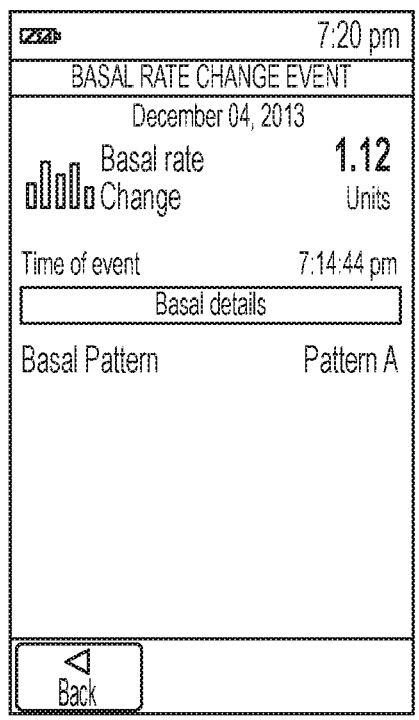
Figure 58S:
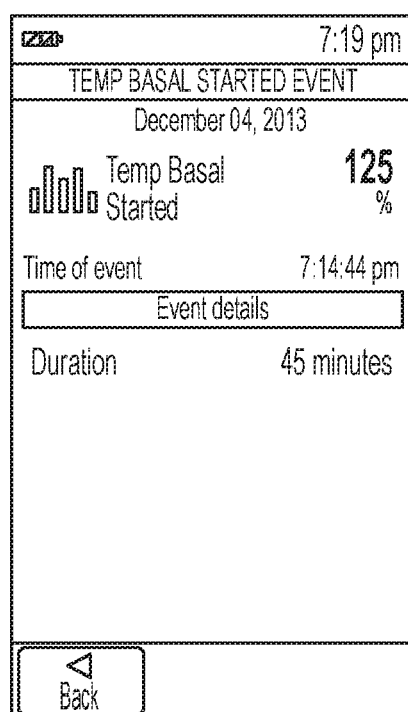
Figure 58T:
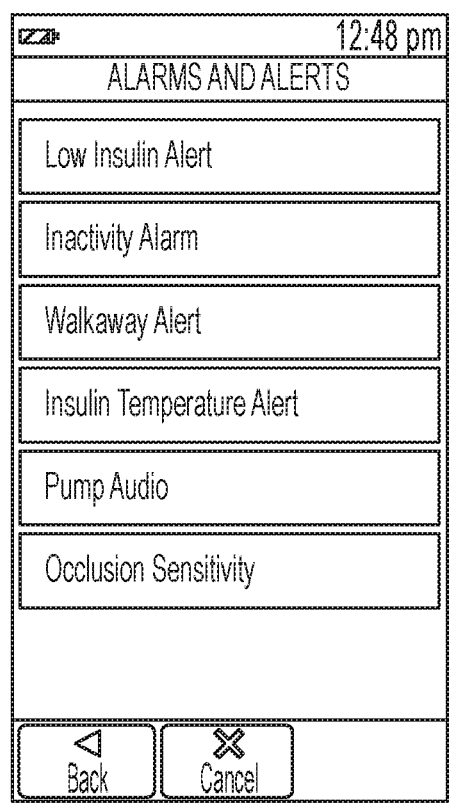

Referring now to FIGS. 58A-58T, in various embodiments, the user interface includes a logbook. In various embodiments, the logbook includes both the functionality to receive information from a user/caregiver and process that information (termed "events") as well as the functionality to display the historical data of the system. Referring now to FIG. 58A, in some embodiments, the logbook home page may include the last blood glucose entered into the system (or, in some embodiments, collected directly by the system), the duration since the last blood glucose, the volume of the last bolus delivery, as well as the duration since the last bolus. The logbook home page, in some embodiments, also includes menu options for the user/caregiver to navigate to various sections of the logbook. In some embodiments the various sections include, but are not limited to, "enter last glucose", "enter event", "view daily totals", and "view event history". In various embodiments, the logbook home page additional includes menu icons to navigate to another section of the user interface.

Referring now also to FIGS. 58B-58G, in some embodiments, the logbook includes the ability for a user/caregiver to input an "event" which may include the grams of carbohydrates ingested by the user, an exercise event, and/or an insulin injection/medicine event. The user/caregiver may then navigate to enter the appropriate event. In some embodiments, the user/caregiver may enter a "carb event" by navigating to the appropriate screen and entering the grams of carbohydrates consumed (see FIG. 58B). In some embodiments, the user interface may also include the type of carbohydrate/food consumed, for example, pizza, cupcake, sushi, lasagna, brown rice, mom's chicken soup, etc. Once the user/caregiver presses "next", the review screen appears (see FIG. 58C) which shows the grams of carbohydrates as well as the time and date of the event. In some embodiments, the user/caregiver may enter an "exercise event" by navigating to the appropriate screen and entering the intensity of the exercise; whether low, medium, or high (see FIG. 58D). In some embodiments, the user interface may also include the type of exercise, whether skiing, hiking, walking, weight lifting, mountain biking, swimming, paddle boarding, kayaking, etc. Once the user/caregiver presses "next", the user/caregiver enters the duration of the exercise (see FIG. 58E). Finally, the details of the exercise event may be reviewed by the user/caregiver (see FIG. 58F). Once the user/caregiver confirms the information is correct, the event is saved in the logbook for future reference by the user/caregiver (see FIG. 58G). A similar event entry method may be followed for entering an insulin injection or other medicine event. The type of medicine and the dosage may be entered which will then be saved in the logbook and indicate the time as well as the type and dosage for later review.

The ability to enter specific events may be beneficial/desirable for many reasons, including, but not limited to, the ability of the user/caregiver to review previous events and track either the results of that event, for example, review blood glucose readings following the exercise, medicine or carb event, in order to make decisions with respect to future dosages of insulin or other medicines, and/or make decisions to change eating patterns based on results from exercise or from ingesting specific foods. The ease of entering these events may encourage those with diabetes and other conditions to enter the events which may lead to improved health.

Referring now also to FIGS. 58H-58L, in various embodiments, the logbook additionally includes historical data which is presented to the user/caregiver on request by navigating the user interface to the daily totals (FIG. 58I), daily doses (FIG. 58J), total carbohydrates (FIG. 58K) and average blood glucose (FIG. 58L) sections of the logbook. Referring also to FIG. 58H, the user/caregiver may select to view the "daily totals" from a specific date, e.g., Dec. 4, 2013. However, in various embodiments, another date may be selected. The total daily dose, total carbs and average BG are then displayed for that particular date (FIG. 58I). The user/caregiver may then select to view in detail any one of those menu items. Where the user/caregiver selects the "total daily dose" menu item, a daily dose screen appears (FIG. 58J) which in some embodiments includes the total insulin given, the percentages of basal and bolus with respect to the total, as well as the different types of boluses delivers, e.g. carb (meal) bolus, BG (correction) bolus, manual (normal) bolus, etc. Where the user/caregiver selects the "total carbs" menu item, a total carbs screen appears (FIG. 58K) which in some embodiments includes the total carbohydrates (entered into the system, for example, in some embodiments, through carb/meal boluses, carbohydrate events and/or through bolus calculator with carbs entered), bolus wizard carbs (which includes carbs entered only through the bolus wizard/bolus calculator with carbs entered), the time the carbs were entered through the bolus wizard/bolus calculator, and the total logbook carbs (carbs entered as an event) as well as the time of the carb event. In various embodiments, the types of information displayed on the various screens may vary.

Referring now also to FIG. 58L, in various embodiments, the logbook includes an "average book glucose" screen which present information regarding the blood glucose readings for a particular day (which is selected by the user/caregiver, and in this example, is Dec. 3, 2013). The average glucose screen includes the average blood glucose for all the blood glucose readings that day and lists the number of readings by time and any other comments/indications that the system or, in some embodiments, the user/caregiver, attributed to that reading (i.e., through comments or preprogrammed target values). In some embodiments, the system may attribute the description of "LOW" to any blood glucose reading under the low blood glucose target for that timeframe/interval and may attribute the description "HIGH" to any blood glucose reading above the low blood glucose target for that timeframe/interval.

Referring now also to FIGS. 58M-58T, in various embodiments, a user/caregiver may view the events in the logbook, for example, by specifying the date, e.g., Dec. 5, 2013 (see FIG. 58M). The event history screen will present the various events from the specified date (FIG. 58N) which, in FIG. 58N is Dec. 4, 2013. For each event, a user/caregiver may select the event, for example, by tapping on the section using the touchscreen, and the event itself will be shown. For example, if the first event shown in FIG. 58N, the "normal bolus stopped" event is selected, the screen shown in FIG. 58O will be shown which includes the specific information about the event. Likewise, if a setting changed event is listed in the event history, a user/caregiver may select the event, for example, by tapping on the section using the touchscreen, and the event itself will be shown (see FIG. 58P). Thus, the user/caregiver may review exactly which settings were changes and when. If a dual wave bolus event is listed in the event history, a user/caregiver may select the event, for example, by tapping on the section using the touchscreen, and the event itself will be shown (see FIG. 58Q). The bolus event includes the type of bolus (dual wave) the time of the event (7:14:22 pm) and the details, for example, the units delivered as normal bolus and the units delivered as square wave bolus. If a basal rate change event is listed in the event history, a user/caregiver may select the event, for example, by tapping on the section using the touchscreen, and the event itself will be shown (see FIG. 58R). The basal rate change event includes the pattern changed and the units of the pattern. If a temp basal event is listed in the event history, a user/caregiver may select the event, for example, by tapping on the section using the touchscreen, and the event itself will be shown (see FIG. 58S). The temp basal event includes the percentage change of the basal, the time of the event and the duration. Referring now also to FIG. 58T, the logbook additionally includes a listing of all alarms and alerts. A user/caregiver may select the event, for example, by tapping on the section using the touchscreen, and the event itself will be shown. The various alarms and alerts include, but are not limited to: low insulin alert, inactivity alarm, walkaway alert, insulin temperature alert, pump audio, and occlusion sensitivity. However, more or less alarms and alerts may be included in various embodiments. When viewing the alarm and alert, the screen displays the type of alarm or alert, the time and in some embodiments, whether it was silenced.

As discussed above, in various embodiments of the infusion pump embodiment, the system may include two or more reusable portions. In these cases, in some embodiments, while one reusable portion is in use, the other may be on a recharger. While the first reusable portion is in use, as described above, therapy may be administered by the supervisor processor and the command processor. Actions by the reusable portion are communicated to the remote interface. To "switch" the reusable portions (such that the reusable portion on the charger becomes the reusable portion in use and vice versa), the controller, which has uploaded information during use from the first reusable portion, downloads the various logs onto the second reusable portion such that the memory on the second reusable portion includes all of the same memory as the first reusable portion. This is done during the pairing process. In one step of the process, following pump activation (done, in some embodiments, by the user holding down the switch assembly on the reusable portion while the remote interface is in connection mode). During this step, profiles and user therapy configurations are transferred to the second reusable pump and/or synchronized with the reusable portions nonvolatile memory.

One this step is completed, in some embodiments, the second reusable portion, after internalizing, sends the basal profile back to the remote interface, such that the remote interface verifies that the basal profile is correct. This step may confirm that the second reusable portion receives that correct information. In some embodiments, the display may show the user the basal profile and the user may confirm.

Thus, as described above with respect to administering therapy, the infusion pump completes all decision making and controls the delivery of infusible fluid. The remote interface is an interface to the infusion pump and in some embodiments provides for an enhanced user interface (e.g. a display screen) with diverse opportunities to interact with the device (e.g., the infusion pump) and/or the user.

Information related to therapy is therefore stored on both the controller and in the reusable portion/infusion pumps nonvolatile memory. Thus during the connection process between the reusable portion and the remote interface, the remote interface may confirm that the reusable portion contains the updated information. If the remote interface determines that the reusable portion does not contain the updated information, the remote interface updates the information and/or synchronizes the reusable portion's nonvolatile memory with the updates that information. Thus, in various embodiments, all therapy information and or profiles may be stored on both the reusable portions of the infusion pump and on the remote interface.

As discussed above, the device 800 (which, in some embodiments, is an infusion pump) may be configured to deliver an infusible fluid to a user. Further, the infusion pump 800 may deliver the infusible fluid by way of infusion events which may include sequential and/or multi-part, and/or discrete infusion events and/or one-time infusion events. Some of the infusion events may include, but not limited to, one or more of the following: bolus, extended bolus, basal, temporary basal, combination bolus. As is known in the art, a basal infusion event refers to the repeated infusion of small quantities of infusible fluid at a predefined interval (e.g. every three minutes) that may be repeated until stopped, e.g., by a user or by the system. Further, the basal infusion rates may be pre-programmed and may include specified rates for pre-programmed time-frames, e.g., a rate of 0.50 units per hour from 6:00 am-3:00 pm; a rate of 0.40 units per hour from 3:00 pm-10:00 pm; and a rate of 1.0 units per hour from 10:00 pm-6:00 am, and/or may include pre-programmed time frame, e.g., 0.50 units for 1 hour then 1.0 for 2 hours, then 0.05 units for 30 minutes. In some embodiments, the basal rate may pre-programmed to remain constant, for example, 1.0 units per hour, and may not change throughout a time-frame. The basal rates may be repeated regularly/daily and/or on particular days until otherwise changed. These pre-programmed basal rates may be referred to as a basal profile.

A temporary basal rate refers to the modification of an existing basal profile/basal rate for a pre-defined time-frame. For example, where an existing basal profile includes a rate of 2.0 units from 6 am-10 am, a temporary basal rate may be requested that modifies the 2.0 units rate by a percentage, by either increasing or decreasing the 2.0 units rate by that percentage, for example, decreasing the rate by 20%, over a pre-defined period of time, for example, 30 minutes. In some instances, a temporary basal may include of modification of 100%, either higher or lower, than the basal profile rate and therefore, in some instances, the temporary basal rate may be 0.00 units per hour for a pre-defined time period.

As is known in the art, a bolus is a pre-determined volume of fluid which, when delivered as a normal bolus, is typically delivered as fast as the device can deliver the fluid. In some embodiments, bolus volumes of a pre-determined volume, e.g., 20 units, or larger may be delivered at a slower than "normal bolus" rate, which may be desired by a user, for purposes of, for example, absorption into the tissue. However, in any case, typically bolus events are delivered over a short period of time, for example, in some embodiments, in ten minutes or less.

Further and as is known in the art, an extended-bolus infusion event may refer to a pre-defined volume of fluid delivered in repeated injections of small quantities of infusible fluid at a predefined interval (e.g. every three minutes) over a pre-defined period of time (e.g., three hours). Some extended-bolus infusion events may include a pre-defined volume of infusible fluid delivered as a normal bolus (i.e., a percentage of the total extended-bolus volume delivered as a normal bolus) followed by the remaining volume of the pre-defined volume delivered as an extended-bolus infusion event (i.e., over a pre-defined period of time).

An extended-bolus infusion event may occur simultaneously with a basal infusion event. In various embodiments, the control of the delivery of various types of infusion events simultaneously may be as described in U.S. patent application Ser. No. 12/837,193, filed Jul. 15, 2010 and entitled Apparatus, Systems and Methods for An Infusion Pump Assembly, now U.S. Publication No. US-2011-0144574, published Jun. 16, 2011, which is hereby incorporated herein by reference in its entirety.

Various embodiments of the infusion pump shown and described herein and also various embodiments of infusion pumps, may include those apparatus, methods, devices and systems similar to or described in, but not limited to, one or more of the following, including: U.S. Pat. No. 7,498,563, issued Mar. 3, 2009 and entitled Optical Displacement Sensor for Infusion Devices; U.S. Pat. No. 7,306,578, issued Dec. 11, 2007 and entitled Loading Mechanism for Infusion Pump; PCT Application Serial No. PCT/US2009/060158, filed Oct. 9, 2009 and entitled Infusion Pump Assembly, now Publication No. WO 2010/042814, published Apr. 15, 2010; U.S. patent application Ser. No. 13/076,067, filed Mar. 30, 2011 and entitled Infusion Pump Methods, Systems and Apparatus, now U.S. Publication No. US-2011-0230837, published Sep. 22, 2011; U.S. patent application Ser. No. 13/121,822, filed Mar. 30, 2011 and entitled Infusion Pump Assembly, now U.S. Publication No. US-2011-0208123, published Aug. 25, 2011; U.S. patent application Ser. No. 11/704,899, filed Feb. 9, 2007 and entitled Fluid Delivery Systems and Methods, now U.S. Publication No. US-2007-0228071-A1 published Oct. 4, 2007; U.S. patent application Ser. No. 12/347,985, filed Dec. 31, 2008 and entitled Infusion Pump Assembly, now U.S. Publication No. US-2009-0299277-A1 published Dec. 3, 2009; U.S. patent application Ser. No. 12/560,106 filed Sep. 15, 2009 and entitled Systems and Methods for Fluid Delivery, now U.S. Publication No. US-2010-0185142-A1, published Jul. 22, 2010; U.S. patent application Ser. No. 12/837,193, filed Jul. 15, 2010 and entitled Apparatus, Systems and Methods for An Infusion Pump Assembly, now U.S. Publication No. US-2011-0144574, published Jun. 16, 2011; and U.S. patent application Ser. No. 13/011,384, filed Jan. 21, 2011 and entitled Method and System for Shape-Memory Alloy Wire Control, now U.S. Publication No. US-2011-0300001, published Dec. 8, 2011, all in which are hereby incorporated herein by reference in their entireties, as well as in various embodiments of various devices, a remote interface may be used. In some embodiments, the remote interface may be a proprietary device or a non-proprietary device and may include those described above with respect to FIGS. 6-8. However, in some embodiments, the remote interface may be a multifunctional web connected/web enabled device, for example, a GOOGLE ANDROID type device or any other device which may run using an open source operating system, for example, the ANDROID Operating System, which may include, but is not limited to a DROID RAZER, by Motorola, Inc., Schaumburg, Ill., U.S.A.; an HTC GOOGLE Nexus one by HTC, Taoyuan 330, Taiwan; a SAMSUNG Nexus S by SAMSUNG Corporation; and a CASIO G'zOne Commando by CASIO COMPUTER CO., LTD., Tokyo, Japan. In some embodiments, the remote interface may be a tablet or other personal computing device and/or in some embodiments, the remote interface may be any so-called "smart-phone" type device. Thus, in various embodiments, the remote interface may include peripherals including but not limited to: GPS, accelerometer, phone, web connection, camera, email, etc.

Referring now also to FIG. 18 and FIG. 19, in some embodiments, the remote interface 1800, 1900 may be, or have the ability of, a web connected remote interface which may include, but is not limited to, capability to download applications, download software updates, upload information and/or send information to various machines, including, but not limited to, through a web based secure portal and/or through electronic mail and/or by way of a wireless communications protocol. Thus, in various embodiments, the remote interface application may run on any capable device and is not limited to a so-called proprietary device. Further, in some embodiments, the remote interface may be BLUETOOTH® enabled, or otherwise enabled, to communicate, for example, using radio frequency ("RF") communication, with one or more devices which may include, but are not limited to, one or more of the following: an infusion pump 1802, 1902 and/or a continuous glucose monitor transmitter/sensor 1804, 1904 ("CGM") and/or a BLUETOOTH® or other communication protocol enabled blood glucose meter 1806, 1906 and/or any other medical device and/or patient care device or any other device.

Although FIGS. 18-19 illustrates the remote interface 1800, 1900 being in communication with a personal computer 1808, 1908, infusion pump 1802, 1902, blood glucose meter 1806, 1906 and/or CGM 1804, 1904, in various embodiments, the remote interface 1800, 1900 may be in communication with one or more of any one of a personal computer 1808, 1908 (which, in some embodiments, may be a web portal), infusion pump 1802, 1902, blood glucose meter 1806, 1906 and/or CGM 1804, 1904, and/or any one or more of any other device including, but not limited to, medical device. Further, in some embodiments, one or more of the personal computer 1808, 1908 (which, in some embodiments, may be a web portal), infusion pump 1802, 1902, blood glucose meter 1806, 1906 and/or CGM 1804, 1904, may in addition to being in communication with the remote interface 1800, 1900, may also be in communication with one or more of the following: a personal computer 1808, 1908 (which, in some embodiments, may be a web portal), an infusion pump 1802, 1902, a blood glucose meter 1806, 1906 and/or a CGM 1804, 1904. In some embodiments, the remote interface 1800, 1900 may be in communication with one or more devices not described herein, however, it should be appreciated that the remote interface 1800, 1900 may be in communication with any device. Further, communication may be defined as one-way and/or two-way communication. In some embodiments, the web portal may be a secure web portal.

In some embodiments, the remote interface device 1800, 1900 may share data to a secure web page/web portal/personal computer 1808, 1909. This shared data may, in some embodiments, be automatically transferred 1810, 1910 at predetermined and/or preprogrammed intervals (i.e., synchronized). In some embodiments, data from the remote interface 1800, 1900 is uploaded to the secure web page/web portal/personal computer 1808, 1908 by a password protected application which, in some embodiments, ensures the information is not shared. In some embodiments, the information from the remote interface 1800, 1900 may be stored on a secured web page and thus, the information may be downloaded to a replacement remote interface and/or a second remote interface and/or other devices upon request. Thus, in some embodiments, this system allows for a remote interface 1808, 1908 to be easily replaced upon malfunction and/or loss. As discussed above, in some embodiments, the secure web page and/or the transfer of data is secured by a password or other type of security.

Further, a secure web portal/personal computer 1808, 1908 may be utilized by a user to review infusion pump therapy, CGM data and/or glucose meter data (as well as, in some embodiments, additional devices connected either to the remote interface 1800, 1900 and/or to the secure web page/personal computer 1808, 1908 in the same location. Further, the secure web page/personal computer 1808, 1908 may include a food library and/or user customizable therapy recommendations that may be customized by the user on, for example, a personal computer and then, in some embodiments, automatically synchronized with the remote interface 1800, 1900. In some embodiments, the user may edit and/or "tag" the CGM and/or infusion pump and/or other data with an event. These edits may be entered in real time, i.e., while the event is occurring, or at a later time. These events, in some embodiments, may then be "named" by the user, and, in some embodiments, therapy regimes may be preprogrammed by the user for each of these events. For example, if a user is eating pizza, the user may associate the therapy given with the food being consumed, which may include, but is not limited to, indication of number of slices and the origin of the slices, e.g., "Sal's Pizza, cheese, 2 slices". Thus, the user may enter this into the remote interface 1800, 1900 and, in some embodiments, later, while reviewing the CGM and/or pump and/or glucose meter data, the user may design a therapy to be used when eating "Sals Pizza, cheese, 2 slices". The user may name this event and the therapy may be associated with this name. Thus, the user may select the "Sals Pizza, cheese, 2 slices" event at any time and authorize the remote interface 1800, 1900 to institute the saved therapy that is associated with the pizza. In some embodiments, events may be linked to the food library, thus, as a user includes an item from the food library, the remote interface 1800, 1900 may "link" the food item(s) with therapy and/or CGM and/or blood glucose meter data. As discussed above, changes to software and/or profiles may be made by the user using a personal computer (and/or a secure web page) 1808, 1908 and these changes may be uploaded onto the remote interface 1800, 1900. Once these changes are uploaded from the personal computer (and/or a secure web page) 1808, 1908 to the remote interface 1800, 1900, they may then be downloaded onto other devices connected to the remote interface 1800, 1900, including, but not limited to, the infusion pump 1802, 1902.

In some embodiments, rather than a web page, there may be a dedicated application on the remote interface 1800, 1900 including similar functionality as discussed above with respect to, for example, the food library and/or user customizable therapy recommendations, which may be performed directly on the remote interface device. In some of these embodiments, the dedicated application may be updated to the remote interface 1800, 1900 by downloading information from, e.g., web database which, in some embodiments, may be a secure web database.

Thus, the user may perform post event analysis and design and/or make changes to therapies based on analysis. In some embodiments, the user may use this information and examine the trends and modify basal and/or bolus profiles. In some embodiments, the analysis may be completed with or by a physician and/or caregiver through the secure web page 1808, 1908. In some embodiments, the user may "filter" the database for specific events and/or foods consumed and analyze them with their care giver or alone, to determine basal and/or bolus profiles to link with specific events and/or food items. Thus, in some embodiments, the user may, using the remote interface 1800, 1900 (or the secure web page 1808, 1908) filter out all, e.g., "Sals Pizza, cheese, 2 slices", events and analyze both the therapy, the time of the event and the CGM profile and/or blood meter readings for that event.

In some embodiments, the remote interface 1800, 1900 may learn user habits both from the collected CGM and/or pump and/or glucose meter data together with information entered by the user. Applications and/or software may recommend therapy changes and those recommendations may be accepted or denied by the user.

In some embodiments, the CGM and/or infusion pump and/or blood glucose meter data and/or event data may be delivered to a secure web portal 1808, 1908 set up between the user and the user's doctor and/or medical provider. In some embodiments, the secure web portal used by the user's physician and/or medical provider may be separate from the user's secure web portal. Thus, in some embodiments, the portal may require the user to either accept, or deny, recommended changes, etc., prior to any changes being downloaded and/or synchronized with the remote interface 1800, 1900 from the secure web portal 1808, 1908 accessed by the user's physician and/or medical provider.

In some embodiments, the CGM sensor 1804, 1904 may communicate directly with the infusion pump 1802, 1902 and/or the remote interface 1800, 1900 (see FIGS. 18 and 19). In some embodiments, the CGM sensor 1804, 1904 may communicate with one or the other and in some embodiments, the CGM sensor 1804, 1904 may communication with both the infusion pump 1802, 1902 and the remote interface 1800, 1900. In some embodiments, safety critical information, e.g., alarms, may be communicated directly to the infusion pump 1802, 1902 and the remote interface 1800, 1900 may be used merely as a display.

Referring now also to FIG. 7, in some embodiments, the remote interface 1800, 1900 may include at least one accelerometer as well as at least one screen containing multiple buttons 706, 710, which in some embodiments, may be customizable by the user. The buttons 706, 710, in some embodiments, may be used to directly navigate to a particular screen, for example, but not limited to, in order to enter information concerning events and/or to simply indicate to the remote interface 524 the event is occurring. In some embodiments, this information may be stored and sent to a secure web page and/or other which may include the ability to synchronize with therapy/infusion pump information and/or CGM and/or blood glucose meter information.

In some embodiments, information may be sent to a remote interface 1800, 1900 for a security monitoring service. The service may monitor and call and/or text (e.g., "are you OK?") the remote interface 1800, 1900 when data indicates there may be a problem, for example, a low blood glucose is indicated and/or an infusion pump alert/alarm and/or a CGM alert/alarm has not been confirmed, e.g., an alarm/alert has not been acknowledged/verified by the user which may include, but is not limited to, a button press and/or screen touch to acknowledge receipt of the alarm/alert. For example, in some embodiments, where the user fails to respond to a service call and/or text, the service may then call an emergency service and/or a parent or guardian and/or emergency contact. In some embodiments, a GPS in the remote interface 1800, 1900 may locate the user and thus, emergency personal may be contracted and called to the user. In some embodiments, where the service has contacted a parent or emergency personal or emergency contact, the service may also send the current CGM and/or pump data for review.

As discussed above, in some embodiments, the remote interface 1800, 1900 may be web enabled (and/or have access to a database which may be either downloaded onto the remote interface 1800, 1900 or accessed by the remote interface 1800, 1900), and in some embodiments, the user may access menus and/or nutritional information easily using the remote interface 1800, 1900. In some embodiments, this information may be "auto filled" into a bolus calculator and/or other to assist in calculating carbohydrates, fat content, etc. and determining the proper therapy. In some embodiments, the actual calculations may be performed on the device (which, in some embodiments, may be an infusion pump 1802, 1902) but the remote interface 1800, 1900 may be the user interface the user uses to input information.

In some embodiments, the remote interface 1800, 1900, secure web page 1808, 1908 and infusion pump 1802, 1902 may be encrypted with, in some embodiments, 128 bit encryption. However, in other embodiments, the encryption may vary.

In some embodiments, the remote interface 1800, 1900 may pair with the devices, which may include an infusion pump 1802, 1902 and/or a CGM sensor 1802, 1902 532 and/or a blood glucose meter 1806, 1906, through a series of audio indications, i.e., sounds. The sounds may be personalized and/or unique to each remote interface 1800, 1900 which may increase safety in pairing the remote interface 1800, 1900 to the user's device(s). In some embodiments, pairing may be accomplished using NFC (near field communication), i.e., holding the device and remote interface 1800, 1900 close enough to be within the near field and the two may communicate and pair, i.e., communication enable.

In some embodiments, the remote interface display/screen may indicate to the user the scheduled delivery trajectory together with the actual volume delivered. This may increase the user's awareness of the amount of fluid being delivered by the infusion pump and therefore enable the user to make more educated therapy decisions. Further, the actual volume delivered may be helpful for health care providers in tweaking or perfecting basal levels, insulin to carbohydrate ratios, etc.

In some embodiments, as the remote interface may appear to be an ordinary device rather than a medical device, the remote interface may include password protections required for changing therapy. For example, to open the "therapy screens", which term may be used to refer to any screen capable of making any changes to therapy, including, but not limited to, insulin/drug sensitivity, carbohydrate to drug ratios, duration of drug, basal profiles, bolus requests, food library information, blood glucose screens, etc., the user may, in some embodiments, be required to enter a password. In some embodiments, a finger print or other may be used. In some embodiments a "tap code", i.e., force being applied to the remote interface at an interval, may be used (e.g., in embodiments where the remote interface 1800, 1900 may include at least one accelerometer, tapping on the device in specific codes may convey information. In some embodiments, in addition or rather than the remote interface 1800, 1900 having the at least one accelerometer, the infusion pump 1802, 19002 may include at least one accelerometer.).

In some embodiments, where the remote interface is web enabled and/or BLUETOOTH® enabled, where one or more devices (e.g., the CGM sensor/transmitter 1804, 1904, the infusion pump 1802, 1902, the blood glucose meter 1806, 1906) experiences a problem, the user may send the engineering logs for that particular device directly to the manufacture. This may be desirable as it may save the user from having to mail the device experiencing a problem to the manufacturer. The manufacture, upon receipt, may recommend a code or other to the user to clear the alarm or other once the manufacture has determined the cause of the problem. In some embodiments, the remote interface may include a preprogrammed protocol to only send the engineering logs to the manufacture and not the medical information. This may ensure the user does not unintentionally send their secure medical information to the manufacturer. Thus, the remote interface 1800, 1900, in some embodiments, includes the logs and/or information for all of the devices connected to the remote interface 1800, 1900. Thus, replacing a device may be accomplished by downloading, from the remote interface 1800, 1900, the logs, user profiles, user preferences, etc., such that the device may be used with minimum "set-up" time by the user and the replacement device may function/be configured exactly as the old device that was replaced.

In some embodiments, it may be desirable to send the screen, e.g., "screen shot", from the remote interface 1800, 1900 to a service person and or manufacturer, i.e., the service person may be able to see the screen while discussing any problems with the device e.g., either over a web chat and/or on the phone.

In some embodiments, the manufacture may send the remote interface 1800, 1900 a "video" or a link to a web site for instruction on correcting the device. In some embodiments, the "video" or other animations may be available on the remote interface 1800, 1900 itself which may include, but is not limited to, video or animation to show/describe and/or "walk" the user and/or caregiver through, attending to an alarm and/or other action with regards to a device 1802, 1902, 1804, 1904, 1806, 1906 and/or a remote interface 1800, 1900 of the device (see FIGS. 29A-29F for examples of some embodiments).

Further, in some embodiments, the remote interface 1800, 1900 may include the capability to compile a list of approved addresses for sending secure information, which may include, but is not limited to, medical information. Thus, where the user unintentionally enters an incorrect email address or web address, etc., the remote interface 1800, 1900 may prevent the user from being able to send the secure information without further steps, which may include, for example, entering the new address onto the approved address list. In some embodiments, alterations to the list may be password or other (tap, fingerprint, etc.) protected.

In some embodiments, the status of one or more of the devices (i.e., CGM sensor/transmitter 1804, 1904 and/or infusion pump 1802, 1902 and/or blood glucose meter 1806, 1906) may be indicated through audio sounds through an ear phone connected to the remote interface 1800, 1900 and/or a speaker on the remote interface 1800, 1900, which may include, but is not limited to, current glucose reading.

In some embodiments, a device 1802, 1902, 1804, 1904, 1806, 1906 may communicate with the remote interface 1800, 1900 using an acoustic signal coupled with a radio signal to indicate the proximity of one or more of the devices, so called "thunder and lightning". In some embodiments, a message may be sent by a first device to a second device using a radio signal. This radio signal may be coupled together with an ultrasonic "churp" at the same time. This may be used to determine and/or calculate the distance between the devices. This method may be used to ensure the message being sent and/or request made by for example, a remote interface 1800, 1900, is within an appropriate distance from the device which may be indicative of whether the user of the devices's remote interface 1800, 1900 is sending the message or indicate whether another (i.e., non-user) remote interface and/or device is sending a message. This may be used to ensure safety in communications and control of one or more of the devices by the remote interface 1800, 1900. For example, where a user is sending a signal/communication from their remote interface 1800, 1900 to their infusion pump 1802, 1902, this may ensure that the user is wearing the infusion pump 1802, 1902, as it is unlikely the remote interface 1800, 1900 would be more than a particular distance from the infusion pump 1802, 1902, e.g., 4 feet. Thus, where the system determines and/or calculates, using the above described method, that the remote interface 1800, 1900 is greater than a threshold (which may be, in some embodiments, pre-determined and/or pre-set either by the manufacturer and/or by the user, which threshold may be, in some embodiments, based on, e.g., the user's own measurements and/or the length of the tubing) distance from the infusion pump 1802, 1902, the remote interface 1800, 1900 may alert/alarm and/or notify the user. In some embodiments, the alarm/alert may also include a message stating that an unidentified device is attempting communication with the infusion pump 1802, 1902. Thus, this may be one method of the remote interface 1800, 1900 determining whether a communication being received and/or being transmitted to a device within the system is an "approved device", i.e., a device in which the user has incorporated into the system, i.e., paired to the remote interface 1800, 1900 and/or paired to another device that may be paired with the remote interface 1800, 1900.

In some embodiments, a method to manage communication between non approved and approved devices may be as follows. When the remote interface 1800, 1900 sends out a message there is a known delay of the radio and response between the device and the remote interface 1800, 1900. The delay between the time the device 1802, 1902, 1804, 1904, 1806, 1906, for example, received the message to when it sends a message may be measured to determine the round trip time. This may be used to determine the distance between the remote interface 1800, 1900 and the device 1802, 1902, 1804, 1904, 1806, 1906. Where the measured distance indicates that the distance exceeds a pre-programmed threshold, then the remote interface 1800, 1900 may, in some embodiments, for example, alert and/or alarm the user.

In some embodiments, the information uploaded from the remote interface 1800, 1900 to a web portal/personal computer 1808, 1909 may also be synchronized with an electronic calendar, for example, but not limited to, an OUTLOOK calendar or other. Thus, events in the user's life may be linked to the data of the devices 1802, 1902, 1804, 1904, 1806, 1906 connected to the system. This may be desired to indicate events that occurred and bring relevance and breadth to the data for analysis. Also, where the user may not have entered an event into the remote interface 1800, 1900, but the event is on an electronic calendar, the events may automatically be entered with the data for review and analysis. For example, where the user's calendar may indicate "soccer practice", but during soccer practice, the user did not indicate an event on the remote interface 1800, 1900, upon uploading the data from the remote interface 1800, 1900 to the web portal/personal computer 1808, 1908, the data from the remote interface 1800, 1900 may incorporate, into, for example, a software program designed to readily view information and data from the devices, the event, "soccer practice", for example, above the area of a graph representing the amount of fluid delivered (which may be the basal rate) and the blood glucose data, for example, data from the CGM sensor/transmitter 1804, 1904 and/or data from the blood glucose meter 1806, 1906. Thus, the user may, in one representative graph, for example, view drug delivery data, CGM and blood glucose data, together with an indication of what the user was doing at the time.

Thus, the user may connect the remote interface 1800, 1900 to a personal computer 1808, 1908 and/or, in some embodiments, upload data from the remote interface 1800, 1900 to a web portal or other. In some embodiments, this may be accomplished during "recharging" of the remote interface 1800, 1900, which, in some embodiments, may be done using a USB connection to the personal computer 1808, 1908, which, in additional to charging/recharging the remote interface 1800, 1900 may synchronize and/or upload/download data from the personal computer 1808, 1908 and/or web portal. At this time, the system may determine software updates for one or more of the devices and or for the remote interface 1800, 1900 are available. The user may select "download updates" and these may be downloaded to the remote interface 1800, 1900, again, at the time of charging and/or at any time the remote interface 1800, 1900 is either connected, directly or indirectly, to the personal computer 1808, 1908 and/or to a web portal designed specifically for the system. As discussed above, the remote interface 1800, 1900 is capable of communication with the various devices. Thus, software updates may be communicated to any one or more device by the remote interface 1800, 1900. This has many advantages, including, but not limited to, only having to connect the remote interface 1800, 1900 to the personal computer/web portal 1808, 1908 to both upload data/information from all of the devices and/or download updates and/or applications from the personal computer and/or from the internet/web portal to any of the devices. This may be desirable for many reasons, including but not limited to, the ability to efficiently and easily update all devices from one connection and/or the ability to view all of the data from all the devices on one location and/or the ability to download information and/or settings from the personal computer/web portal to any of the devices through the remote interface.

Thus, in some embodiments, as the personal computer/web portal contains all the information from all the devices, including, but not limited to, the remote interface, at any time, a new "remote interface" may be introduced to the system. This may be accomplished by connecting the new remote interface to the personal computer/web portal and downloading all the information regarding the system to the remote interface. In some embodiments, this may first require that the old remote interface be removed from "approved devices", however, in other embodiments; the system may "allow" additional remote interfaces by permission from the user. Thus, the system includes the ability to download all the information and applications to any internet connected and/or remote interface capable of communicating to the devices and/or capable of connecting the personal computer and/or web portal.

This also allows the remote interface to download any application from the internet to any device in the system. Thus, in various embodiments of the system, a user can turn any apparatus (including some parameters such as ability to wirelessly communicate and connect to the personal computer and/or web portal) into a device that could control the various device, for example, the infusion pump and/or receive data from and/or control a CGM sensor/transmitter, and/or other analyte sensors, and/or other devices. In some embodiments, the remote interface and/or the one or more applications on the remote interface may be password or other protected and is paired with the one or more devices, for example, paired with an infusion pump and/or CGM sensor and or one or more other devices.

In some embodiments, the information on the remote interface may be uploaded and/or synchronized with another device and/or a computer and/or machine, including, but not limited to, uploading the data to an internet site that may be password protected (web portal). Thus, a user may access the information from any device and or may download the information to any device including any device specific applications and therefore the user information may be downloaded to any device including, but not limited to, history, preferred settings, etc., information.

In some embodiments of the system, a blood glucose meter 1806, 1906 may be included which may not include a user interface, but rather, only a strip reader and the minimum components to function. In some embodiments, the blood glucose meter 1806, 1906 communicates with the remote interface 1800, 1900 and the remote interface 1800, 1900 display indicates the readings and/or in some embodiments, the remote interface 1800, 1900 includes broader functions than the blood glucose meter 1806, 1906, which may include, but are not limited to, graphical representations of the blood glucose meter 1806, 1906 readings and/or historical data as well as user preferences, etc.

Although the system as discussed above takes examples from an infusion pump system, in various embodiments, the device(s) may be any device(s), including any medical device, and/or there may be more than or less than the number of devices represented on the FIGS. shown.

As discussed above, in various embodiments, the remote interface 1800, 1900 may include a tablet computer or a multifunctional web connected/web enabled device, for example, in some embodiments, the remote interface may be a DROID RAZER. In some embodiments, one or more peripherals may be turned off and/or may "sleep" while the remote interface is communicating with one or more of the devices in the system, for example, with a medical device. In some embodiments, the antenna and or the wireless communications software may be modified to a proprietary version, for example, as described above or in any of the information incorporated by reference. In some embodiments, the wireless communications may be that in the remote interface device itself, for example, BLUETOOTH low energy wireless communication protocol. In some embodiments, together with this communications protocol, a translator may be included to translate to a proprietary protocol on one or more of the devices in the system. In some embodiments, the messaging may be accomplished through the protocols discussed herein, or through similar protocols and/or using protocols from the remote interface device.

The remote interface therefore, in various embodiments, includes a display assembly which may include a color touch screen. In some embodiments, the remote interface additionally includes at least one switch assembly. In some embodiments, the remote interface includes animated "set-up" instructions for the one or more devices. Additionally, in some embodiments, the remote interface includes alarm recovery and or alarm animations, which may include, but are not limited to, instructions to the user for checking and/or confirming and/or recovering from the alarm condition. These animations may include, but are not limited to, written/word instructions and/or audio instructions. In some embodiments, the graphical user interface may present different color backgrounds to represent different conditions, for example, "red" for alarm, "blue" for idol, "green" for delivering/action, etc. In some embodiments, one or more of the above functions may additionally include sound/audio which may include, but is not limited to, audio instructions, beeps, etc.

Referring now to FIGS. 20A-30 various "screen shots" are depicted which serve as some embodiments of the graphical user interface for a remote interface for an infusion pump for example, for one of the embodiments of the infusion pump described herein. In some embodiments, screen shots are shown for the remote interface for a blood glucose meter. In some embodiments, the screens may be used as instructional interfaces.

Referring now to FIGS. 20A-22H, in some embodiments, the remote interface may include animations and/or pictorial/graphical instructions to demonstrate to a user how to perform certain actions with respect to the device. In some embodiments, these animations and/or pictorial/graphical instructions may include voice over and/or audio and/or may include text and written instructions. FIGS. 20A-22H include some embodiments and/or examples of embodiments of a graphical user interface (GUI) for setting up an infusion pump. These examples are shown as illustrative screen shots and various embodiments are not limited to the words and/or pictures shown. Also, the order of the screen shots may vary throughout the embodiments. Additionally, in some embodiments, the various screen shots may include one or more of the following buttons: a "back", "cancel" and/or "next" button. In these embodiments, on any screen, the user may choose to go back, cancel the screen and/or proceed to the next screen. In some embodiments where an animation is included, the animation may replay indefinitely until and unless the user selects a button, for example, back, cancel and/or next. In some embodiments, a button may be highlighted and or de-highlighted (which may be represented as a dotted line in the Figures).

Figure 20B:
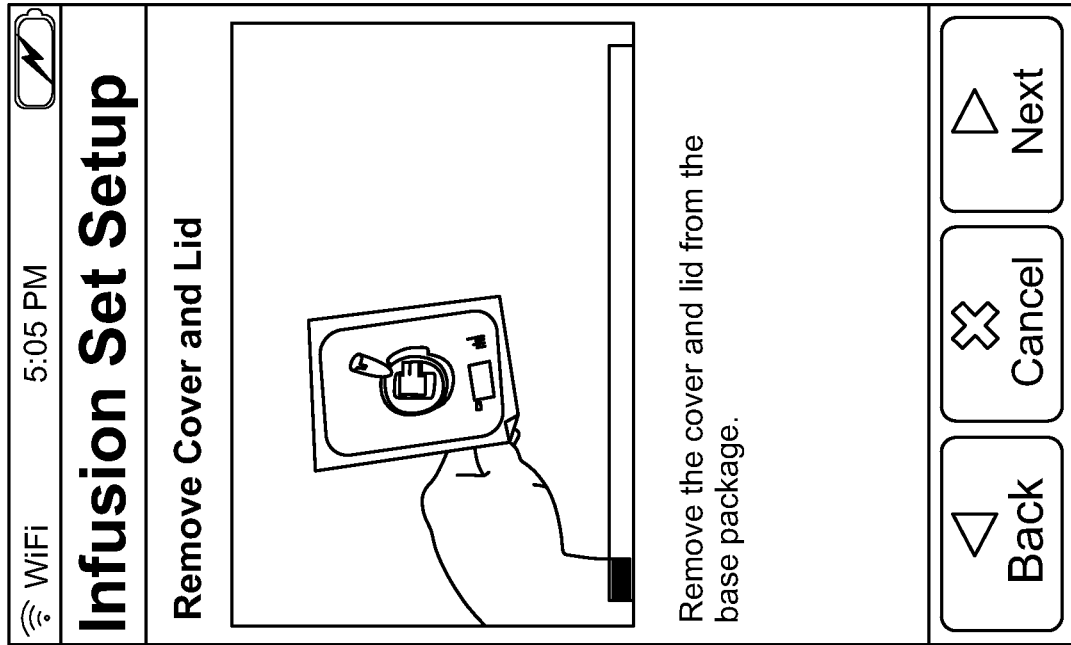
Figure 20A:
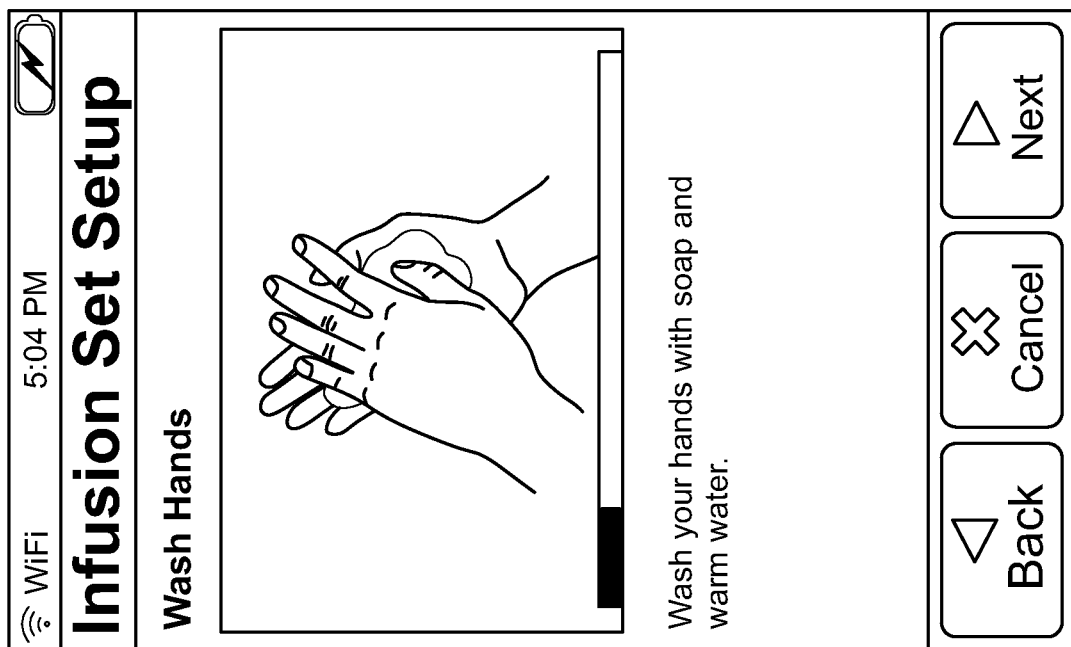

Referring now to FIGS. 20A-20M, graphical instructions for filling a disposable portion (which may also be referred to as a reservoir) and priming the disposable portion are shown. Referring to FIG. 20A, some embodiments include at least one screen instructing the user to wash their hands.

Figure 20D:
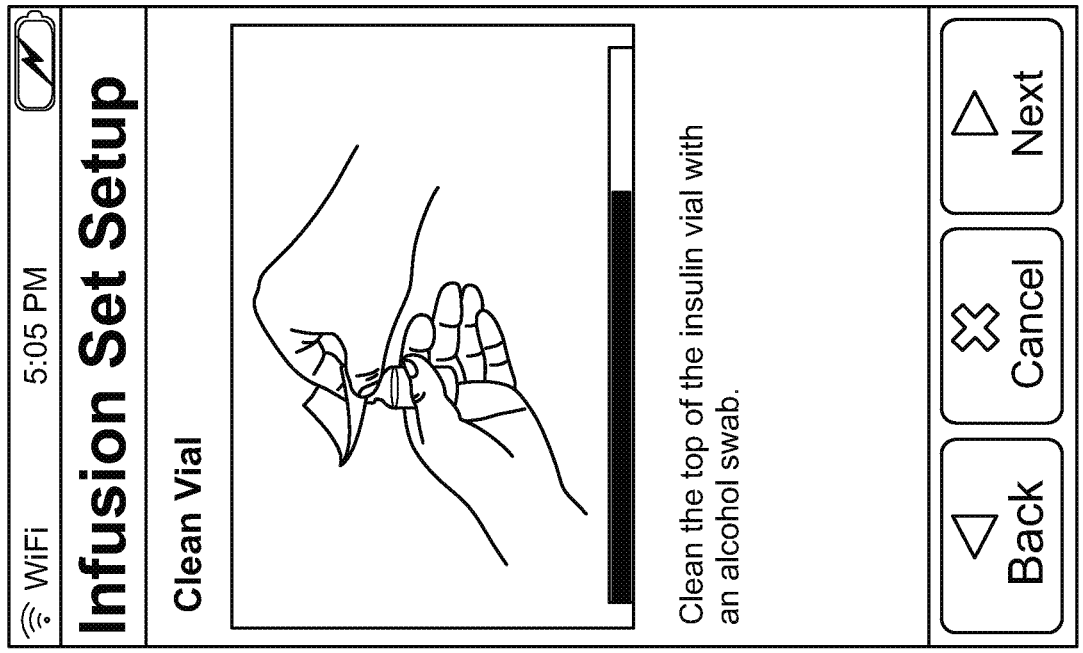
Figure 20C:
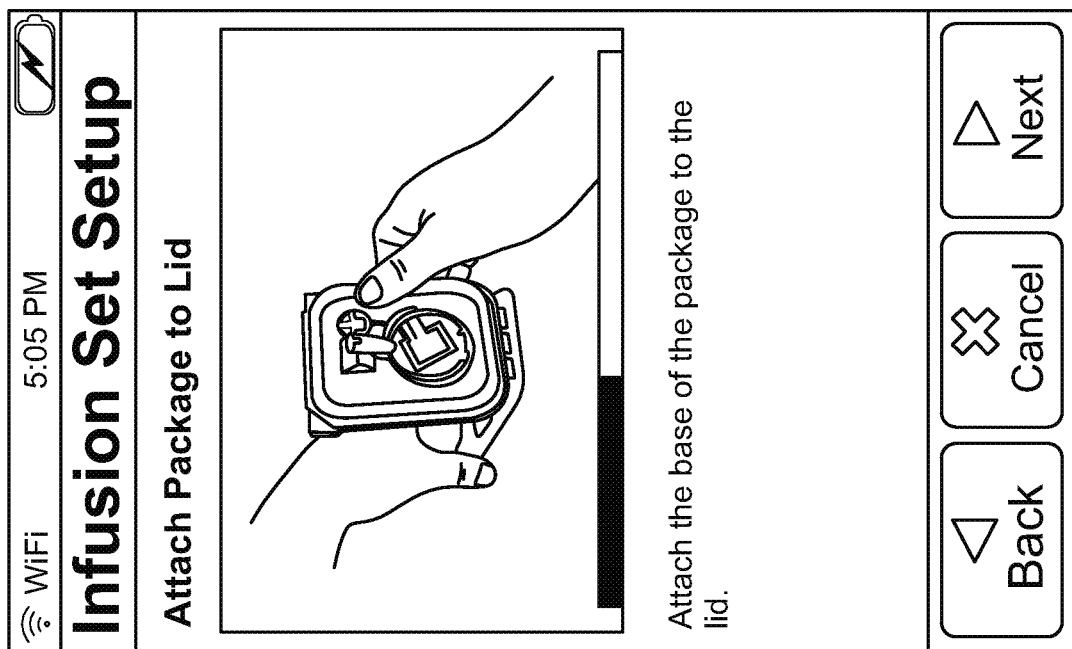
Figure 20F:
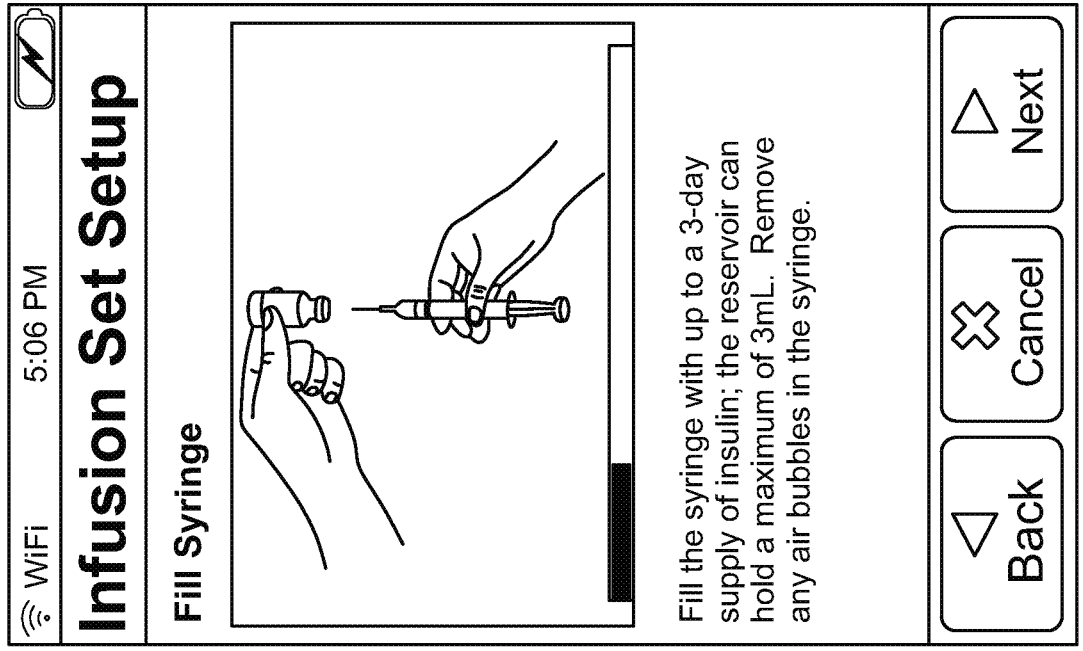
Figure 20E:
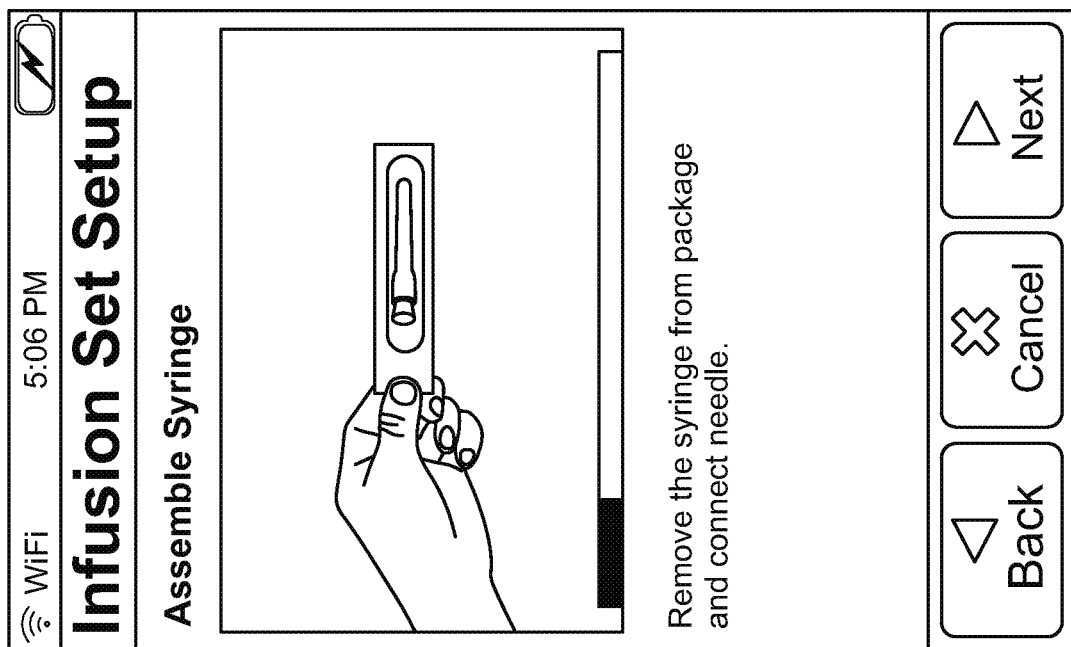

In some embodiments, at least one screen is included showing a user washing their hands and may instruct the user to wash their hands with soap and warm water. In some embodiments, a screen may include an animation showing the user washing their hands with soap and water. Referring to FIG. 20B, some embodiments include at least one screen instructing the user to remove the cover and lid of the disposable portion. In some embodiments, the screen may show the disposable portion. In this embodiment, the screen shows an embodiment of a disposable portion in a packaging and instructs the user to remove the cover and lid from the package. In some embodiments, this embodiment is an animation and in some embodiments, the graphical animation shows the cover and lid being removed from the package. Referring now to FIG. 20C, some embodiments include at least one screen shot showing that the base of the package is attached to the lid. In some embodiments, this embodiment is an animation, and in some embodiments, the graphical animation shows the base of the package being attached to the lid. Referring now to FIG. 20D, some embodiments include at least one screen showing the vial (of infusible fluid) being cleaned. In this embodiment, the screen shows an embodiment of a vial and an alcohol swab and instructs the user to clean the top of the insulin vial with an alcohol swab. In some embodiments, this embodiment is an animation of the vial being cleaned with an alcohol swab. Referring now to FIG. 20E, some embodiments include at least one screen showing a syringe in a package. In this embodiment, the screen shows an embodiment of a syringe in a package and instructs the user to remove the syringe from the package and connect needle. In some embodiments, this embodiment is an animation of the syringe being removed from the package and the needle being connected. Referring now to FIG. 20F, some embodiments include at least one screen showing the syringe and the vial. In this embodiment, the screen shows an embodiment of a vial and a syringe and instructs the user to fill the syringe with up to a 3-day supply of insulin; the reservoir can hold a maximum of 3 mL. Remove any air bubbles in the syringe. In some embodiments, this embodiment is an animation of the syringe being filled with insulin from the vial.

Figure 30:
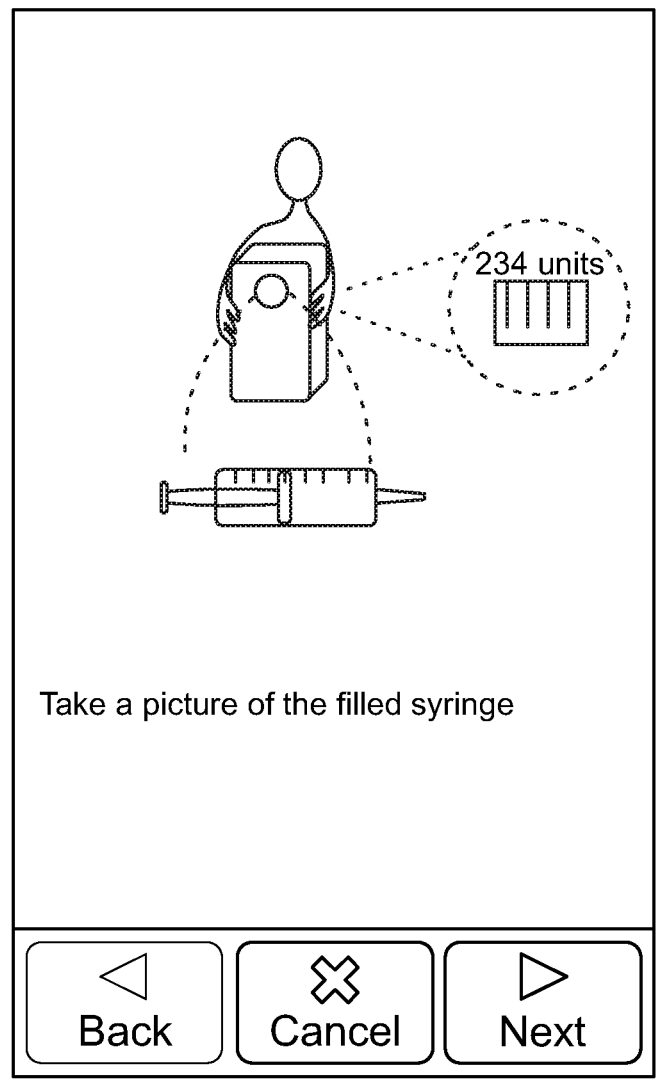

Referring now to FIG. 30 in some embodiments, at least one screen may be included that may show an embodiment of a syringe, filled with fluid ("filled" does not necessary mean to capacity, filled may be used to refer to any volume of fluid having been loaded into the syringe and/or reservoir) and a remote interface placed near the syringe, held by a user, and taking a picture of the syringe. In some embodiments, this embodiment is an animation of the remote interface and a syringe, the remote interface taking a picture of the syringe. In some embodiments, at least one screen may instruct the user to take a picture of the syringe. In some embodiments, when the user reaches this screen, the remote interface may automatically enter a camera mode such that the user then sees the view finder in the display assembly and may take a picture of the filled syringe. In some embodiments, the remote interface may confirm whether the picture is acceptable. In some embodiments, when the remote enters camera mode from the "take a picture of the filled syringe" screen, the camera mode may be an "auto-focus" mode and/or may be a proprietary camera mode that is designed to take the picture at such a resolution such that pattern recognition software, and in some embodiments, designed specifically for this task, may determine the fluid level in the syringe. In some embodiments, this recognition software may be similar to software used to read 2D bar codes. In some embodiments, the camera on the remote interface may be used for other purposes, for example, for scanning 2D barcodes, for example, on the disposable portions and or on reusable portions (for example, in some embodiments, this may be used for pairing the device with the remote interface) and/or for scanning 2D barcodes on insulin and/or infusible fluid vials and or other peripherals that may be used in various embodiments of the system, whether the system includes an infusion pump.

Figure 32:
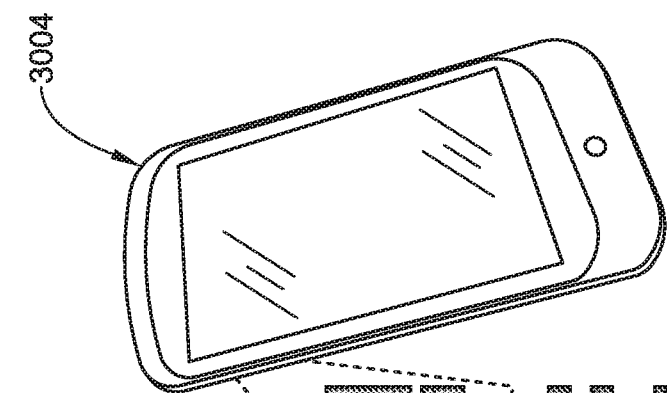
FIG. 32 is an embodiment of a system for programming a basal profile using the remote interface and a 2D bar code.
Figure 31:
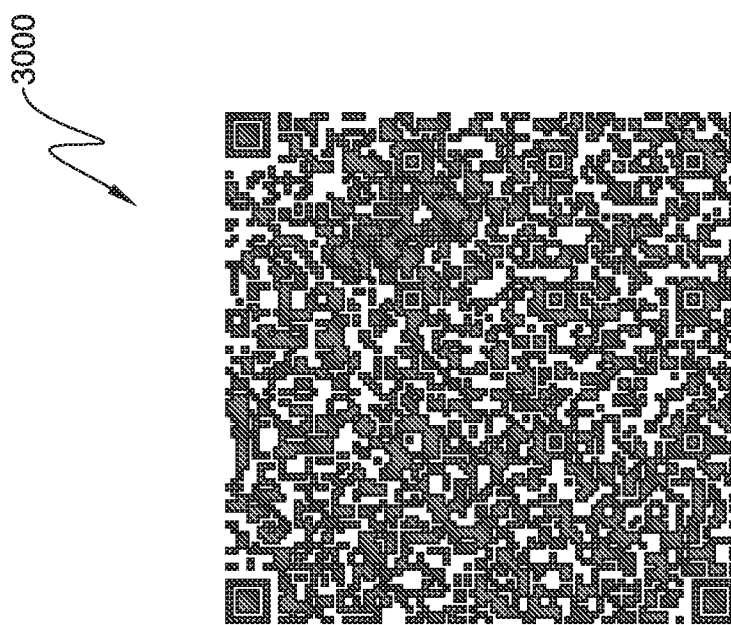
FIG. 31 is an embodiment of a 2D bar code.
Figure 33:
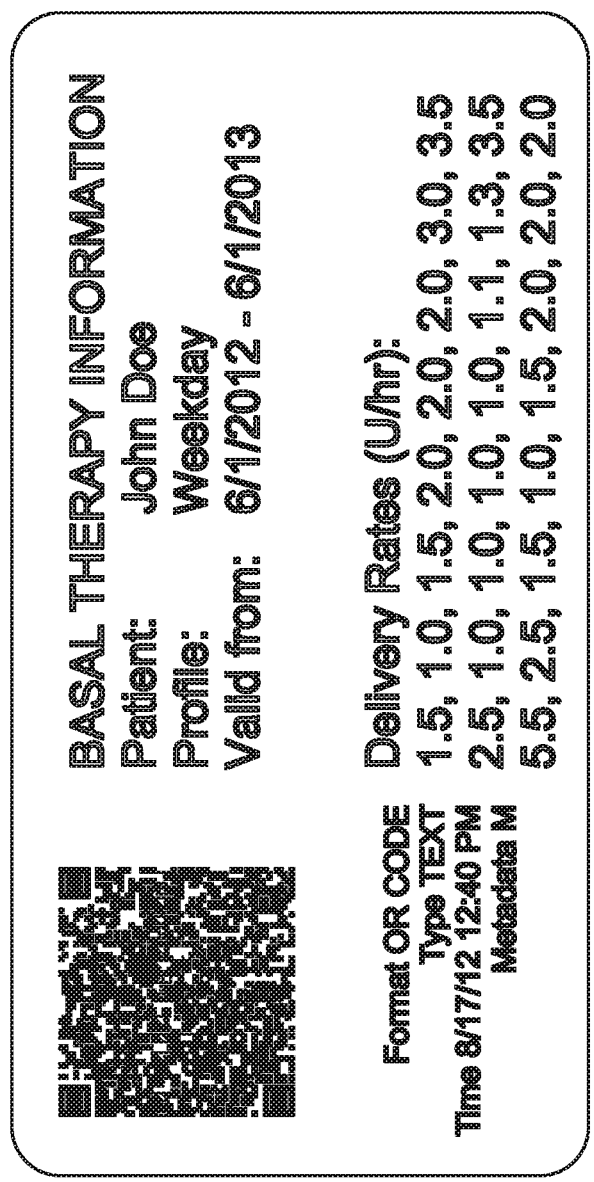
FIG. 33 is an embodiment of information that may be embedded in a 2D bar code.

Referring now also to FIGS. 31-34, in some embodiments, a basal profile may be entered into the remote interface using the camera in the remote interface 3004 and a bar code 3000, including, but not limited to, a 2D bar code, examples of which are given for illustration purposes only, see item 3000 in FIG. 31 and item 3002 in FIG. 32. In various embodiments, the 2D bar code may be generated by prescription by a user's physician. In some embodiments, the 2D bar code may be communicated to the user, mechanisms of communications which may include, but are not limited to, providing a hard copy of the 2D bar code and/or providing the 2D bar code in an email and/or on a secure web portal, for example. In various embodiments, the camera in the remote interface 3004 reads the 2D bar code 3000, 3002. The 2D bar code includes an embedded prescription basal profile embedded into the 2D bar code which, when read by bar code reading software, provides the information needed by the remote interface to program the basal profile. An example of the information included in the 2D bar code may include is shown in FIG. 33 as 3006. The information may include, but is not limited to, one or more of the following: user's name, date of birth, profile type, dates of validity of the profile, and the rates per hour given by time frame. In some embodiments, where the 2D bar code includes dates of validity, the remote interface may alert/alarm the user when the dates of validity are coming to a close so that the user may prompt their physician to prescribe an updated basal profile 2D bar code to be entered as discussed above. In various embodiments, once the validity of the profile expires the remote interface may stop pumping until and unless an updated profile prescription is entered. In various embodiments, a user may receive multiple 2D bar codes, each including a different basal profile, which may include, for example, but are not limited to, weekday, weekend, exercise, sick day, etc. In some embodiments, a single 2D bar code may encode more than one basal profile. In various embodiments, the system described above may use a 3D bar code and in other embodiments, the system may use QR CODE or "quick response code". This system may be beneficial for many reasons, including but not limited to, preventing or diminishing the instances of manual programming errors, for example, where the user is entering the prescription manually, there may be a transcribing error. However, using the 2D bar code, programming errors are eliminated and therefore, the system may be safer than manual entry. Additionally, the system may be beneficial for the prescription may be emailed and/or available electronically to the user, for example, in a secure web portal. In some embodiments, the system may request the user enter a passcode/password before the system will read the 2D bar code. This may be beneficial to prevent the prescription bar code from being read and programmed into the wrong remote interface. In some embodiments, once the remote interface 3004 reads the 2D bar code 3000, 3002, the remote interface 3004 may display the basal profile in graphical form for the user to review.

Figure 34:
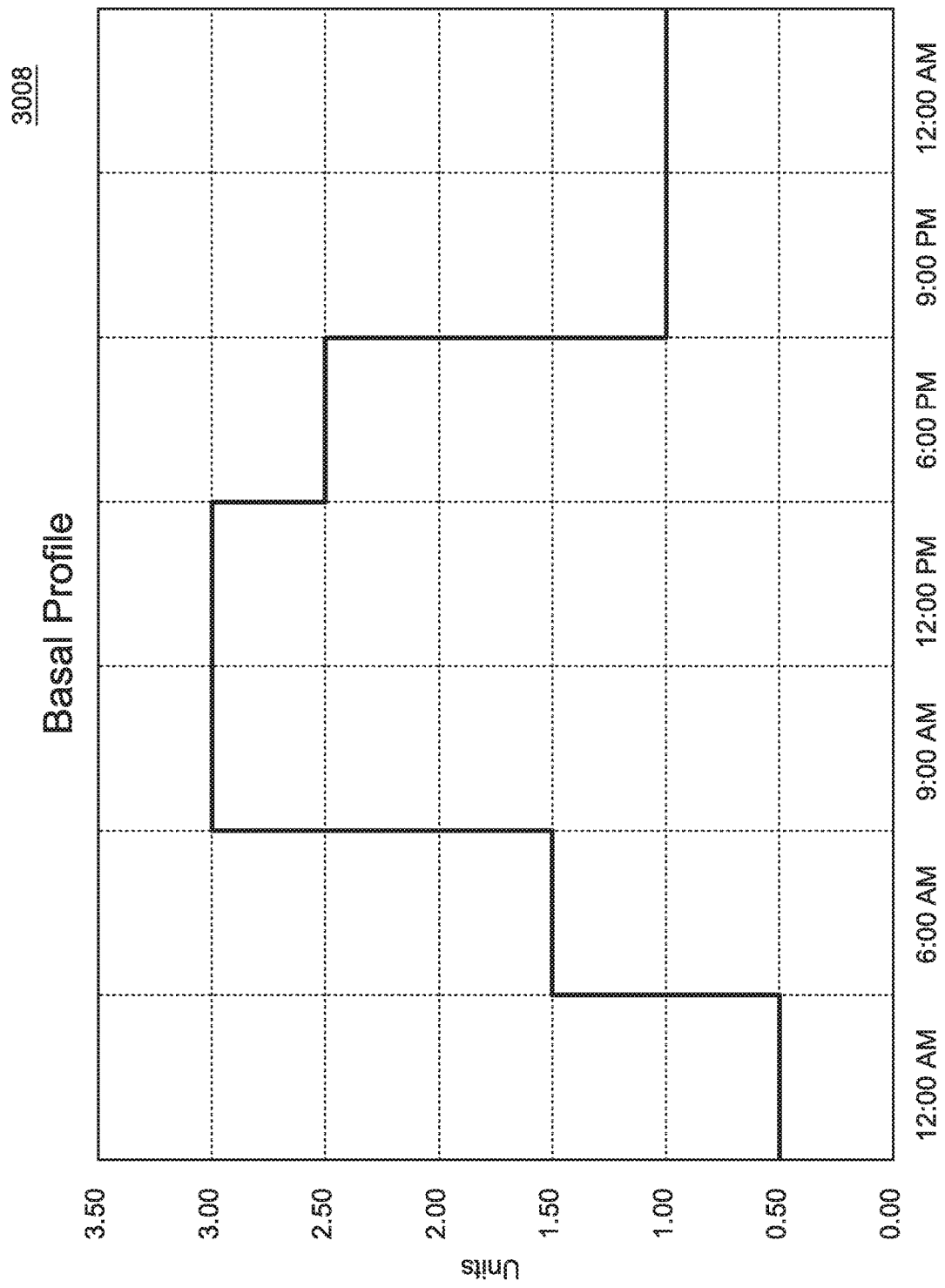
FIG. 34 is an example of a basal profile that may be programmed into a remote interface using a camera.

Referring now also to FIG. 34, in some embodiments, the remote interface 3004 may, using the camera, take a picture of a basal profile 3008 in graphical form, whether on paper or presented in an electronic format, for example. The remote interface 3004, in some embodiments, may include recognition software that may recognize the parameters of the basal profile 3008 and may program the basal profile 3008 into the remote interface 3004 such that the intended basal profile 3008 is automatically entered into the remote interface 3004. This system may be beneficial for many reasons, including but not limited to, preventing or diminishing the instances of manual programming errors, for example, where the user is entering the prescription manually, there may be a transcribing error. However, using the basal profile 3008 read by the remote interface 3004, programming errors are eliminated and therefore, the system may be safer than manual entry. In some embodiments, once the remote interface 3004 reads the basal profile 3004, the remote interface 3004 may display the basal profile 3008 in graphical form for the user to review. In some embodiments, the system may request the user enter a passcode/password before the system will read the basal profile 3008. This may be beneficial to prevent the prescription basal profile from being read and programmed into the remote interface without the user's consent.

Figure 20H:
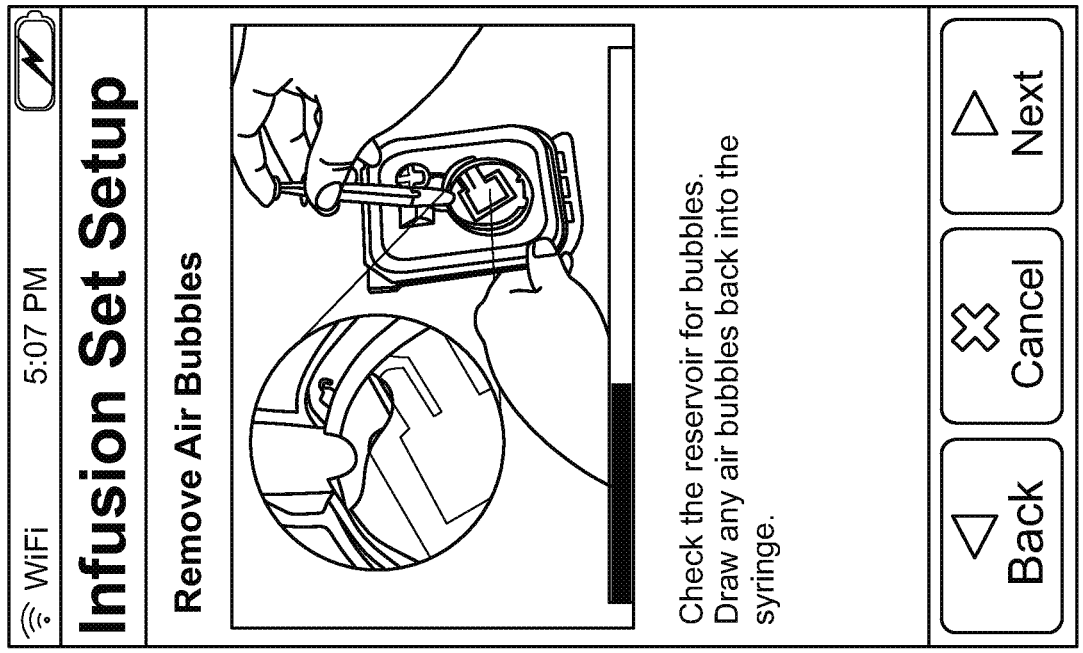
Figure 20G:
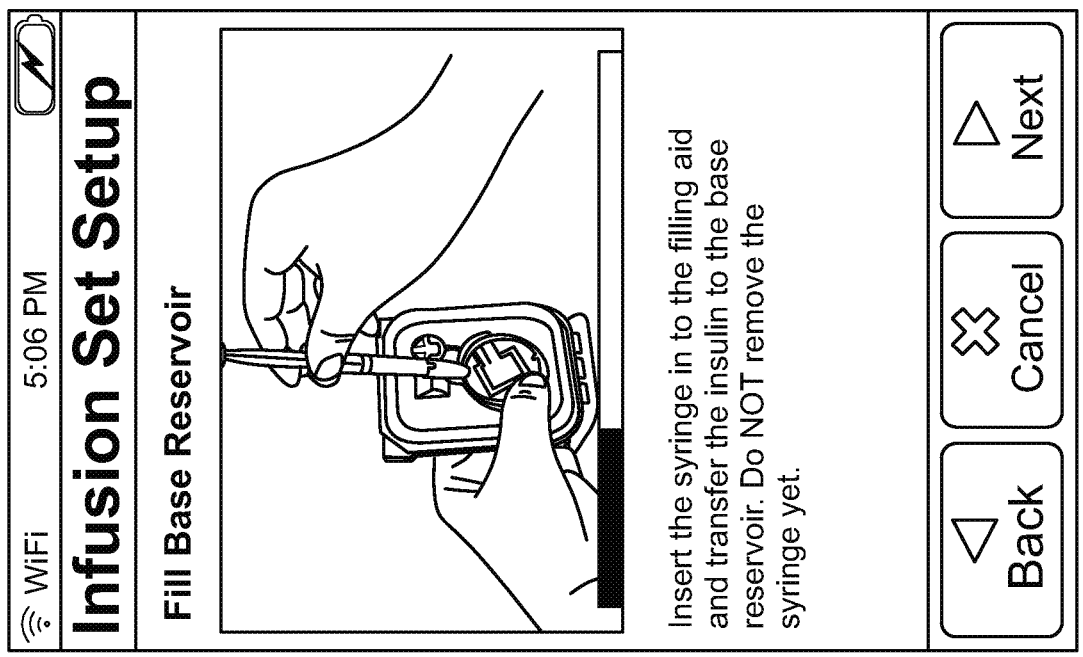

Referring now to FIG. 20G, some embodiments include at least one screen instructing the user to fill the base reservoir. In some embodiments, the screen may show an embodiment of a syringe in the filling aid in the reservoir package and instructs the user to insert the syringe in the filling aid and transfer the insulin to the base reservoir, do not remove the syringe yet. In some embodiments, this embodiment is an animation of the syringe being inserted into the filling aid and the plunger moving towards the base to transfer the insulin the base reservoir.

Referring now to FIG. 20H, some embodiments include at least one screen showing a syringe removing bubbles from a filled reservoir. In this embodiment, the screen shows an embodiment of a syringe in the filling aid in the reservoir package and instructs the user to check the reservoir for bubbles, draw any air bubbles back into the syringe. In some embodiments, this embodiment is an animation of the user checking for reservoir bubbles and drawing the air bubbles back into the syringe.

Figures 20I, 20J:
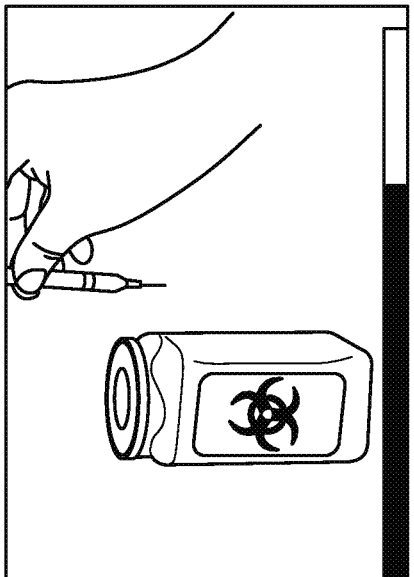

Referring now to FIG. 20I, some embodiments include at least one screen showing a syringe and a "sharps" container. In this embodiment, the screen shows an embodiment of a user holding a syringe next to a sharps container and instructs the user to remove the syringe and dispose of the needle in a sharps container. In some embodiments, this embodiment is an animation of the user removing the syringe and disposing of the needle in a sharps container.

Referring to FIG. 20J, in some embodiments, a screen requesting the user enter the reservoir volume may be included. In some embodiments, as shown in FIG. 20J, a key pad may be included and the user may touch the appropriate number buttons so that the display, in units in some embodiments, reflects the volume of fluid that was transferred to the reservoir. In some embodiments, the system may compare the volume entered to the volume determined from the image of the filled syringe. In some embodiments, if the two volumes are within a threshold of error, for example, + or −0.5 units, the system may rely on either one or the other, and in some embodiments, may rely on the user inpu (for example, the units input on the keypad in FIG. 20J). In some embodiments, the remote interface may ask the user to re-enter or "are you sure?" if the difference between the two number exceeds a threshold. This may be desirable a confirmation of the volume of fluid transferred to the reservoir.

Figure 20L:
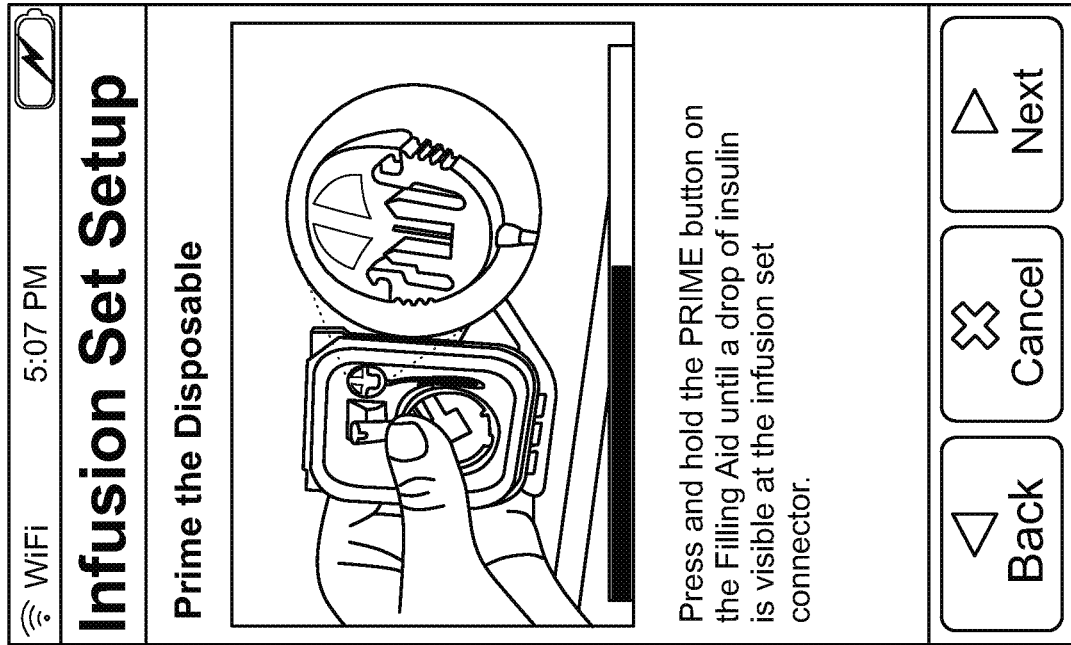
Figure 20K:
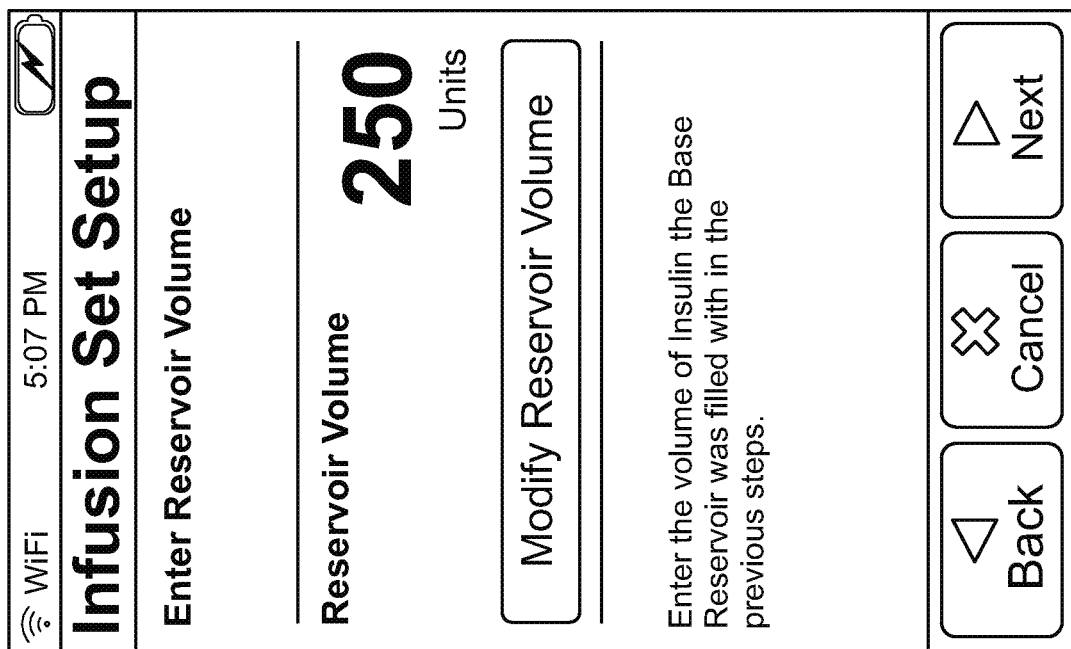

Referring now to FIG. 20K, in some embodiments, the user interface may include at least one confirmation screen with the reservoir volume and in some embodiments, may include a button to "modify reservoir volume", which may, in some embodiments, take the user to a screen to input a different volume value, for example, the screen shown in FIG. 20J.

Referring now to FIG. 20L, some embodiments include at least one screen instructing the user priming the disposable. In this embodiment, the screen shows a thumb/hand pressing on the filling aid on the disposable portion/reservoir and a caption of an infusion set connector and instructs the user to press and hold the prime button on the filling aid until a drop of insulin is visible at the infusion set connector. In some embodiments, this embodiment is an animation of a thumb/hand pressing and holding the prime button on the filling aid until a drop of insulin is visible at the infusion set connector.

Figure 20N:
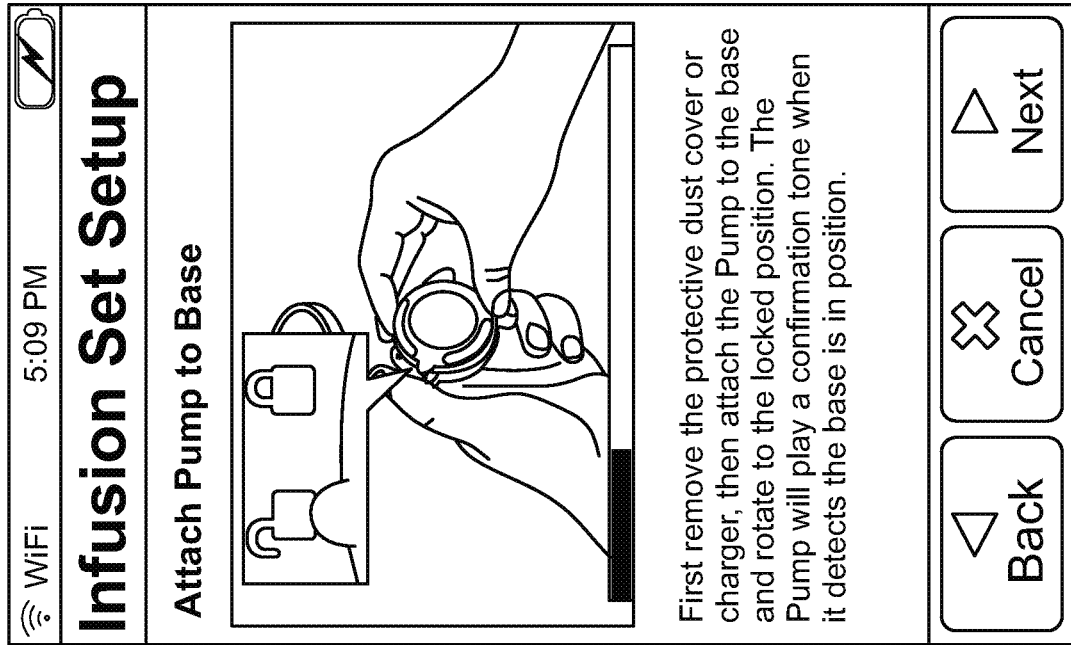
Figure 20M:
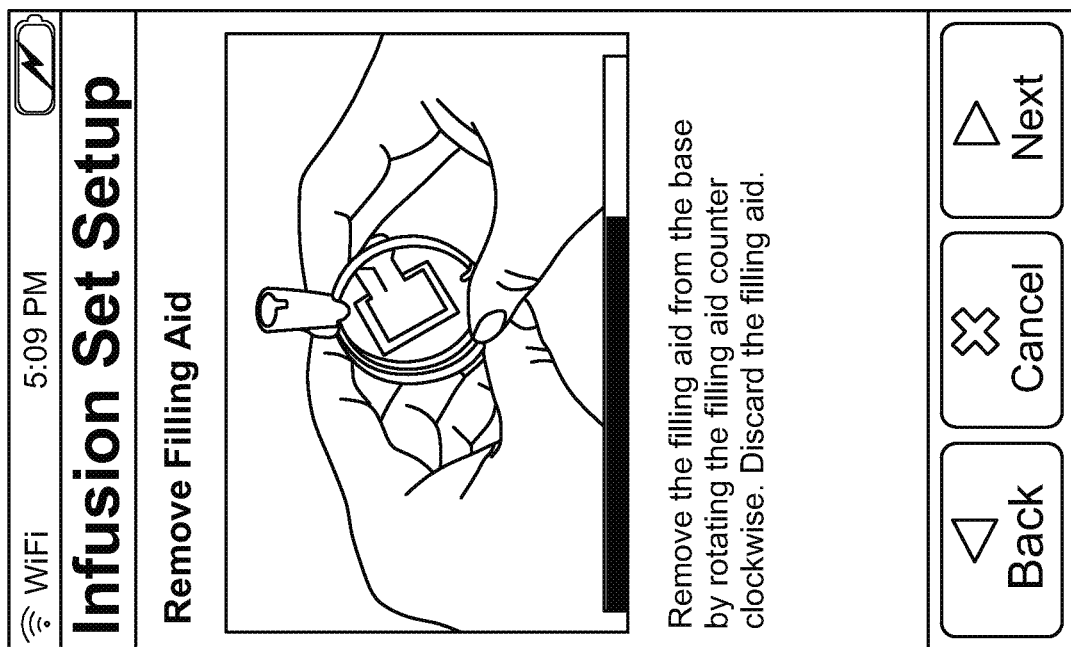

Referring now to FIG. 20M, some embodiments include at least one screen instructing the user to remove the filling aid. In this embodiment, the screen shows a hands rotating the filling aid on the disposable portion/reservoir and instructs the user to remove the filling aid from the base by rotating the filling aid counter clockwise, discard the filling aid. In some embodiments, this embodiment is an animation of hands removing the filling aid from the base by rotating the filling aid counter clockwise and discarding the filling aid.

Referring now to FIG. 20N, some embodiments include at least one screen instructing the user to attach the pump to the base. In this embodiment, the screen shows a user attaching the pump to the base and includes an insert/caption that may be an enlargement of a "lock" and "unlock" position icons and instructs the user to first remove the protective dust cover or charger, then attach the pump to the base and rotate to the locked position; the pump will play a confirmation tone when it detects the base in position. In some embodiments, this embodiment is an animation of hands first removing the protective dust cover or charger, then attaching the pump to the base and rotating to the locked position.

Figure 20P:
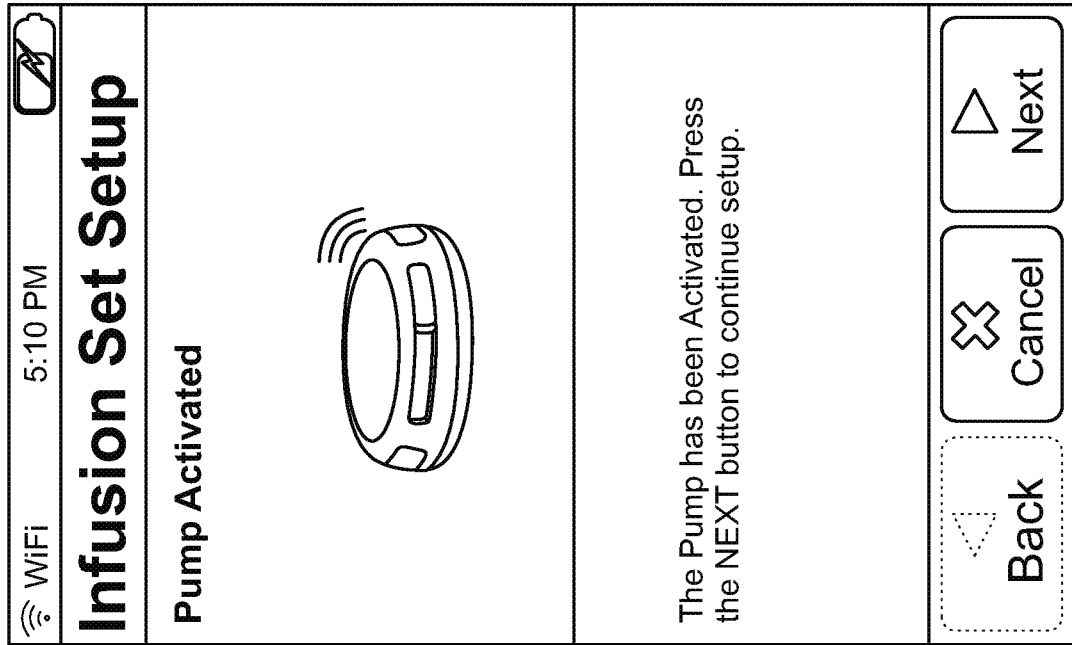
Figure 20O:
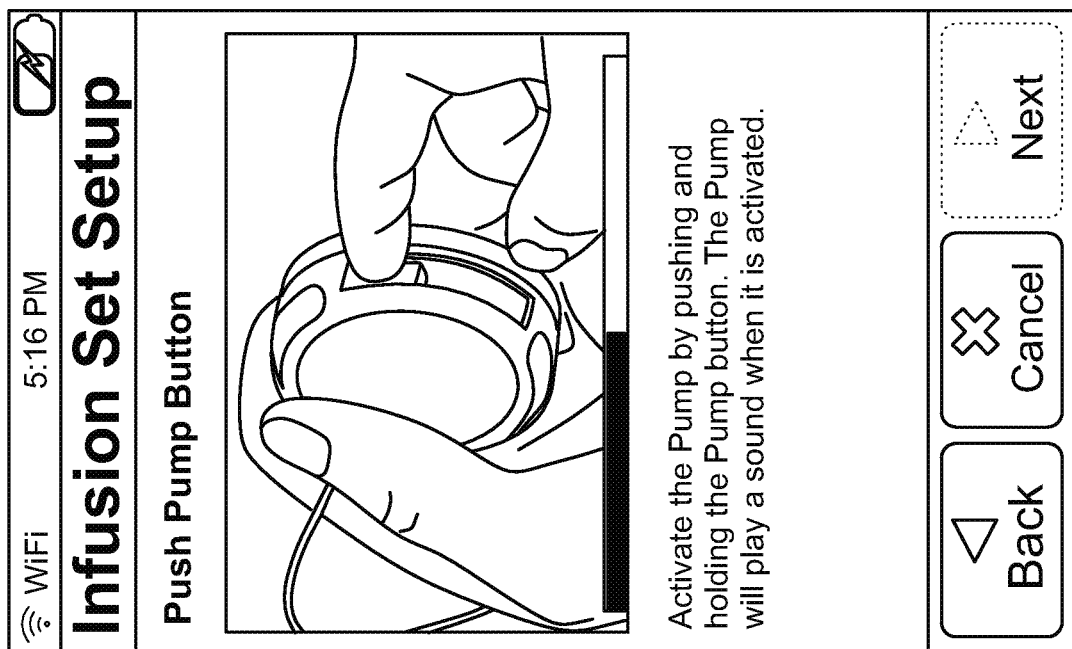

Referring now to FIG. 20O, some embodiments include at least one screen instructing the user to push the pump button. In this embodiment, the screen shows a user pushing a pump button on the reusable portion and instructs the user to activate the pump by pushing and holding the pump button; the pump button will play a sound when it is activated. In some embodiments, this embodiment is an animation of hands activating the pump by pushing and holding the pump button.

Referring now to FIG. 20P, some embodiments include at least one screen instructing the user that the pump is activated. In this embodiment, the screen shows a pump vibrating or playing a sound and instructs the user that the pump has been activated and to press the next button to continue setup.

Figure 20R:
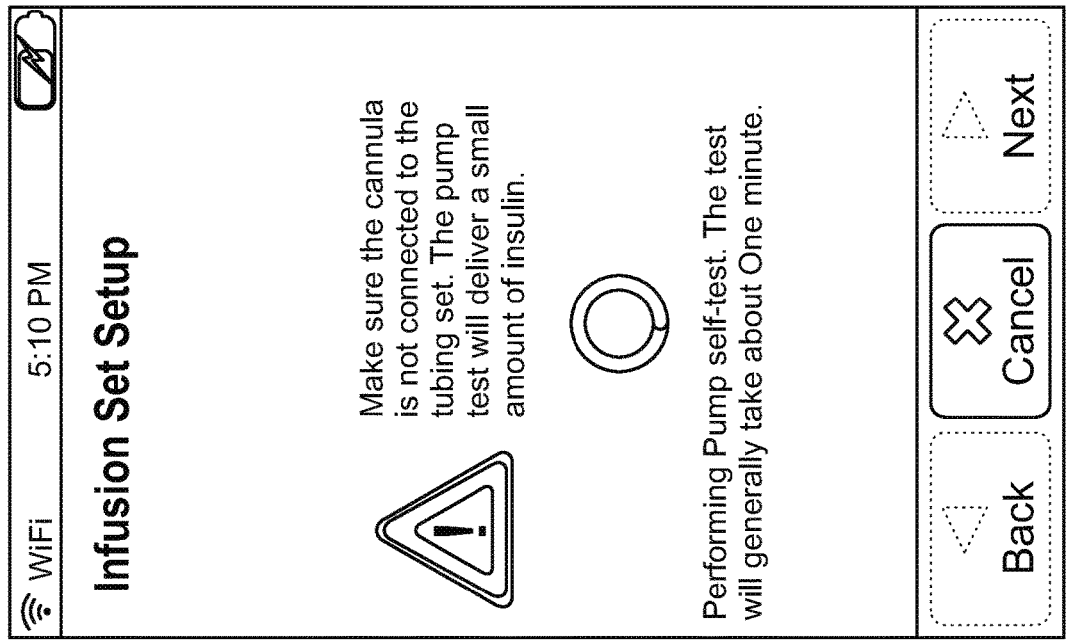
Figure 20Q:
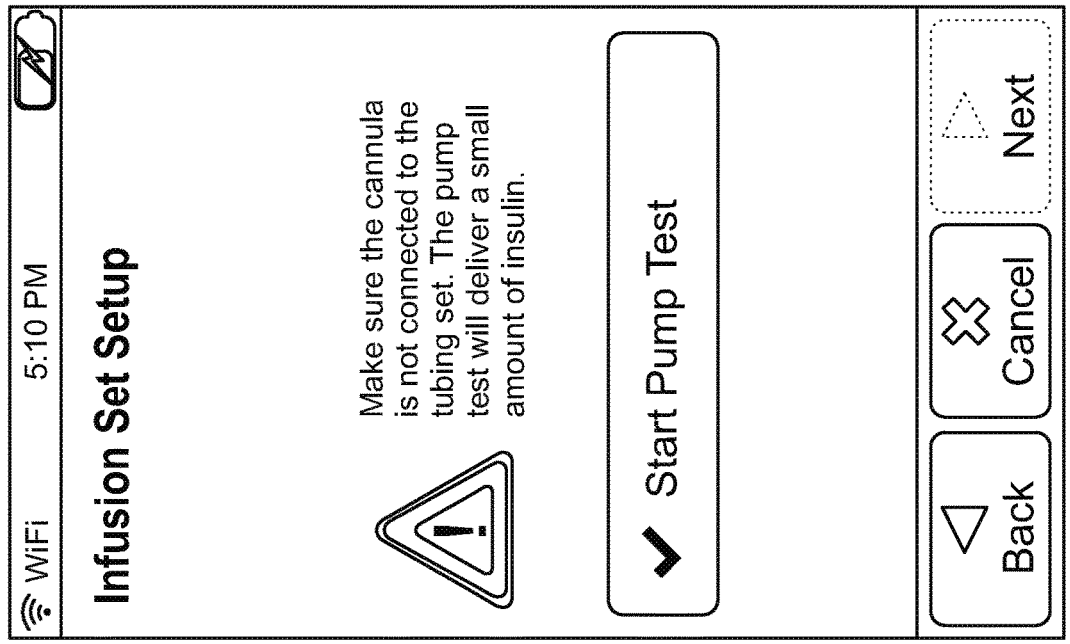

Referring now to FIG. 20Q, some embodiments include at least one screen requesting the user start a pump test. In this embodiment, the screen shows a caution sign instructs the user to make sure the cannula is not connected to the tubing set; the pump test will deliver a small amount of insulin. A button on the screen indicates the user should press to start the pump test after they have yielded to the caution.

Referring now to FIG. 20R, some embodiments include at least one screen stating that the pump is performing the pump self-test. In this embodiment, the screen shows a caution sign instructs the user to make sure the cannula is not connected to the tubing set; the pump test will deliver a small amount of insulin and also states that the pump is performing the pump self test; the test will generally take about one minute.

Figure 20T:
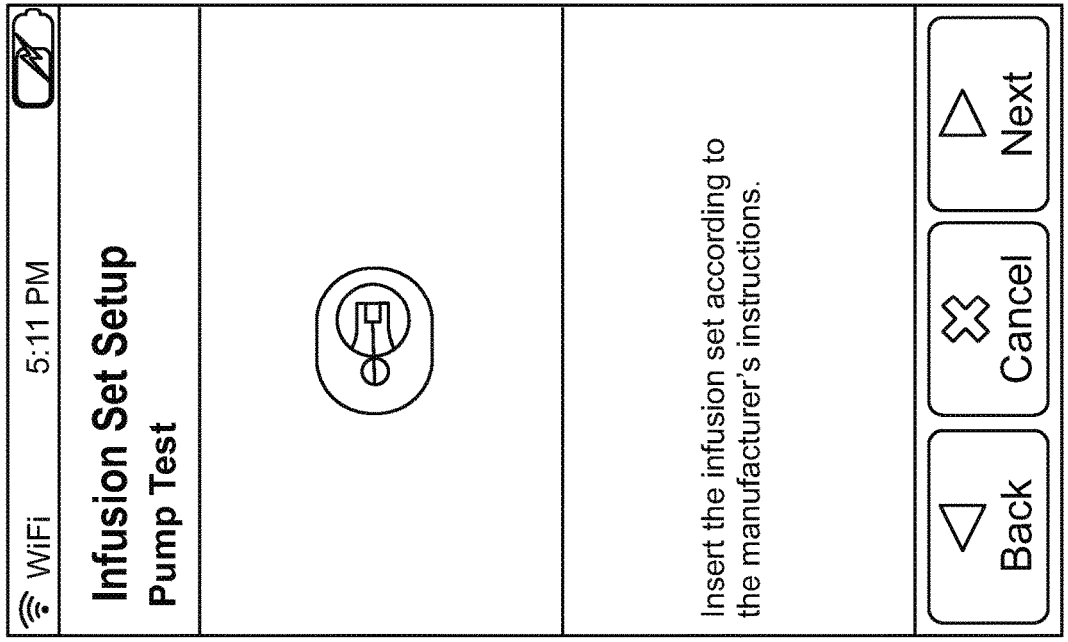
Figure 20S:
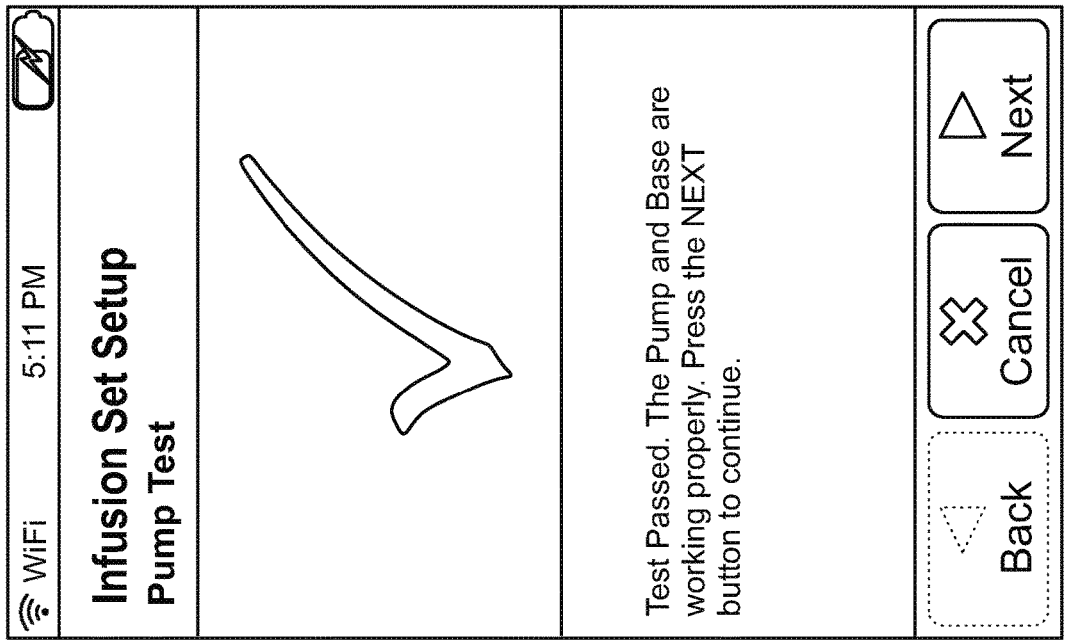

Referring now to FIG. 20S, some embodiments include at least one screen stating that the pump test is complete. In this embodiment, the screen shows a "check mark" and instructs the user that the test passed; the pump and base are working properly; press the next button to continue. In some embodiments, the "back" button may become de-highlighted, indicating that the system suggest to continue to next or cancel, in some embodiments. Referring to FIG. 20T, some embodiments include at least one screen instructed the user to insert the infusion set according to the manufacturer's instructions.

Figure 21B:
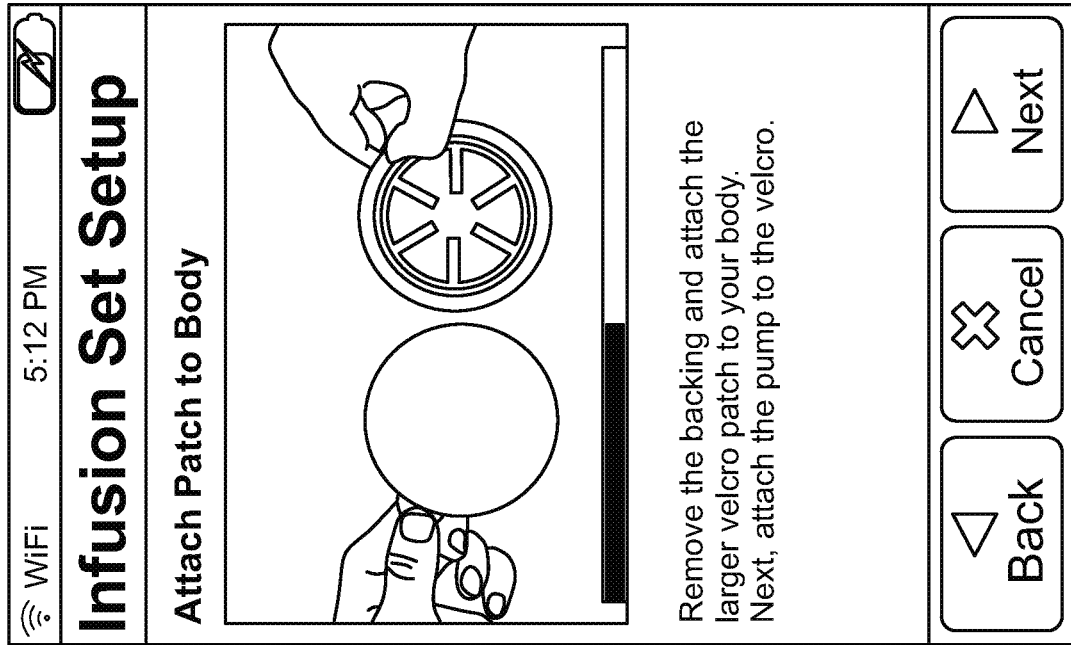
Figure 21A:
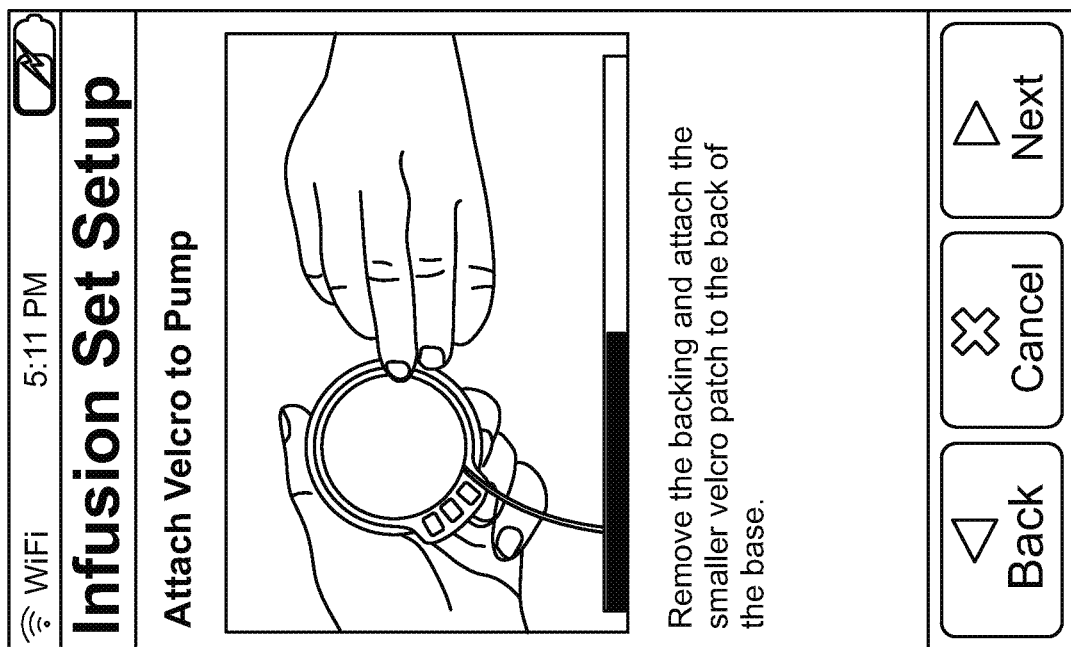

Referring now to FIG. 21A, some embodiments include at least one screen instructing the user to attach the VELCRO to the pump. As described above, in some embodiments (for example, as described and shown with respect to FIG. 3), the disposable portion may include an adhesive patch which in some embodiments may include a VELCRO fastener system. In this embodiment, the screen shows a user touching the backing of the patch on the back of the disposable and instructing the user to remove the backing and attach the smaller VELCRO patch to the back of the base. In some embodiments, this embodiment is an animation of hands removing the backing and attaching the smaller VELCRO patch to the back of the base.

Referring now to FIG. 21A, some embodiments include at least one screen instructing the user to attach the VELCRO to the pump. As described above, in some embodiments (for example, as described and shown with respect to FIG. 3), the disposable portion may include an adhesive patch which in some embodiments may include a VELCRO fastener system. In this embodiment, the screen shows a user touching the backing of the patch on the back of the disposable and instructing the user to remove the backing and attach the smaller VELCRO patch to the back of the base. In some embodiments, this embodiment includes an animation of hands removing the backing and attach the smaller VELCRO patch to the back of the base.

Referring now to FIG. 21B, some embodiments include at least one screen instructing the user to attach the patch to the user's body. As described above, in some embodiments (for example, as described and shown with respect to FIG. 3), the disposable portion may include an adhesive patch which in some embodiments may include a VELCRO fastener system that attaches to the body. In this embodiment, the screen shows a user touching the backing of the large patch and the large patch and instructing the user to remove the backing and attach the larger VELCRO patch to their body; next, attach the pump to the VELCRO. In some embodiments, this embodiment is an animation of hands removing the backing and attaching the larger VELCRO patch to the body and attaching the pump to the patch.

Figure 21D:
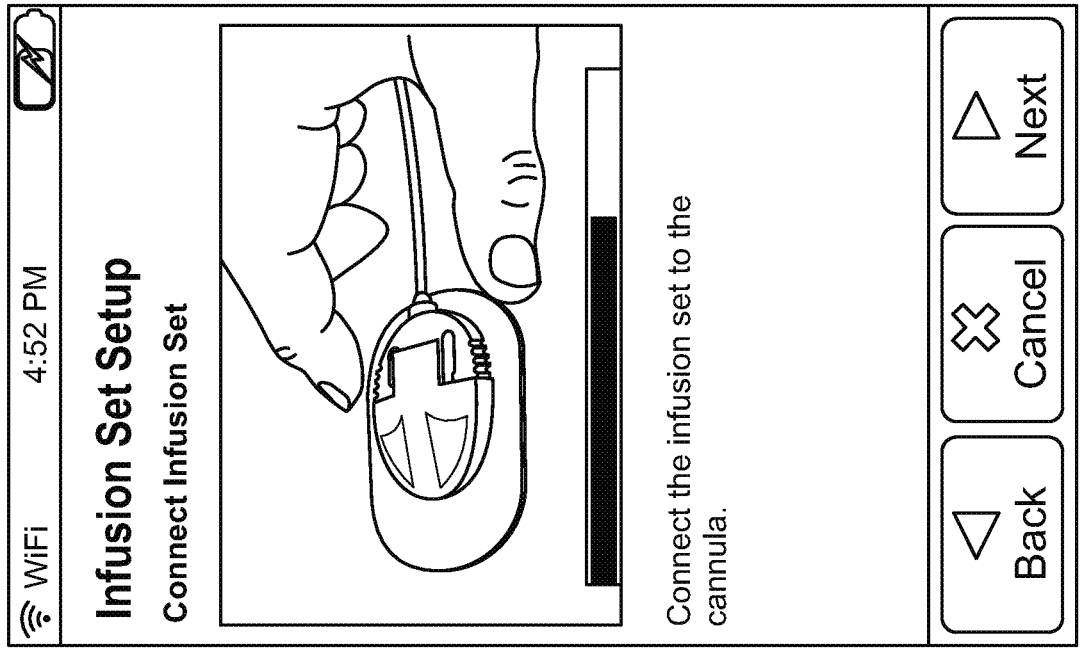
Figure 21C:
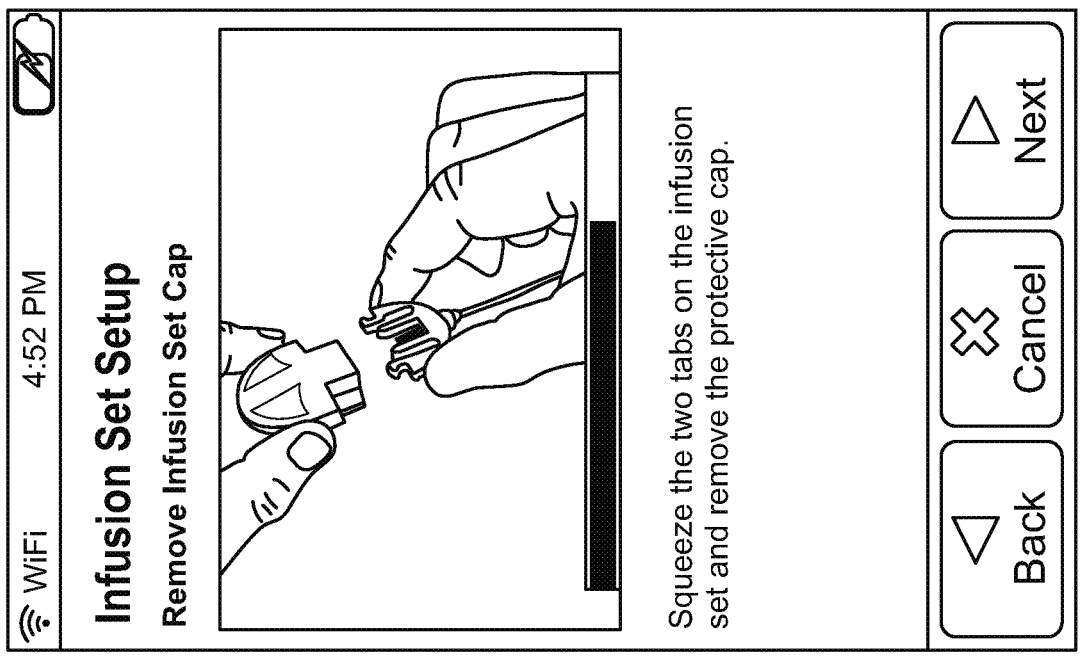

Referring now to FIG. 21C, some embodiments include at least one screen instructing the user to remove the infusion set cap. In this embodiment, the screen shows a user removing the infusion set cap and instructing the user to squeeze the two tabs on the infusion set and removing the protective cap. In some embodiments, this embodiment is an animation of hands squeezing the two tabs on the infusion set and removing the protective cap.

Referring now to FIG. 21D, some embodiments include at least one screen instructing the user to connect the infusion set. In this embodiment, the screen shows a user connecting the infusion set to the cannula and instructing the user to connect the infusion set to the cannula. In some embodiments, this embodiment is an animation of a hand connecting the infusion set to the cannula.

Figure 22B:
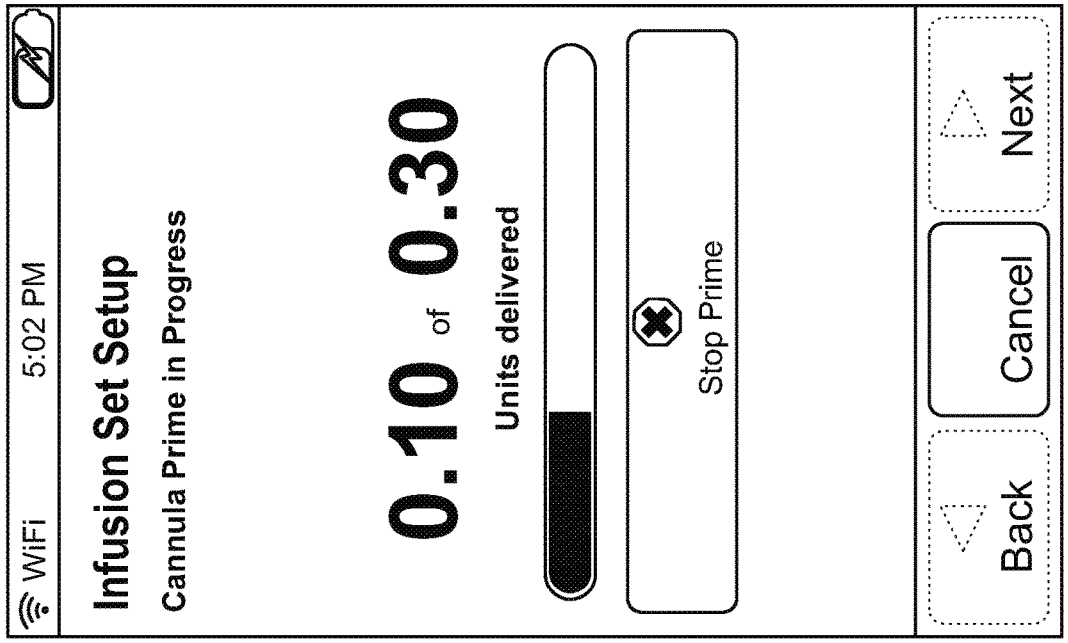
Figure 22A:
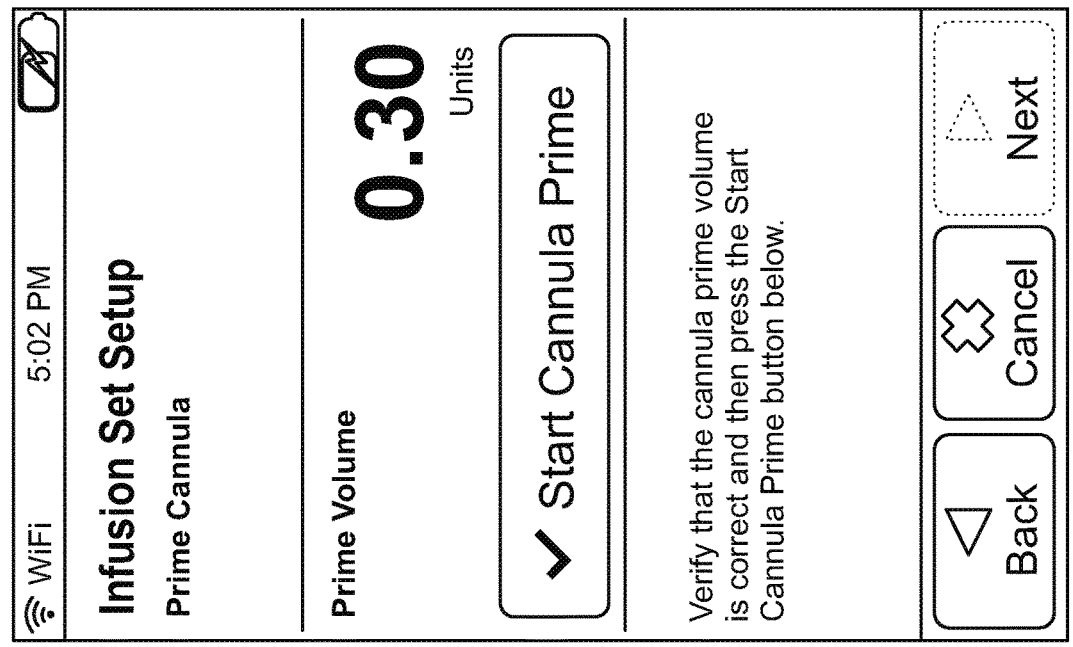

Referring now to FIG. 22A, some embodiments include at least one screen for priming the cannula. In this embodiment, the screen shows a prime volume and includes a button to start cannula prime and includes instruct to verify that the cannula prime volume is correct and then press the start cannula prime button. A button on the screen indicates the user should press to start the cannula prime.

Referring now to FIG. 22A, some embodiments include at least one screen for showing the cannula prime in progress. In this embodiment, the screen shows the volume of prime delivered and a total prime volume and includes a button to stop prime. The screen also includes a status bar that represents the volume delivered out of the total prime volume requested.

Figure 22D:
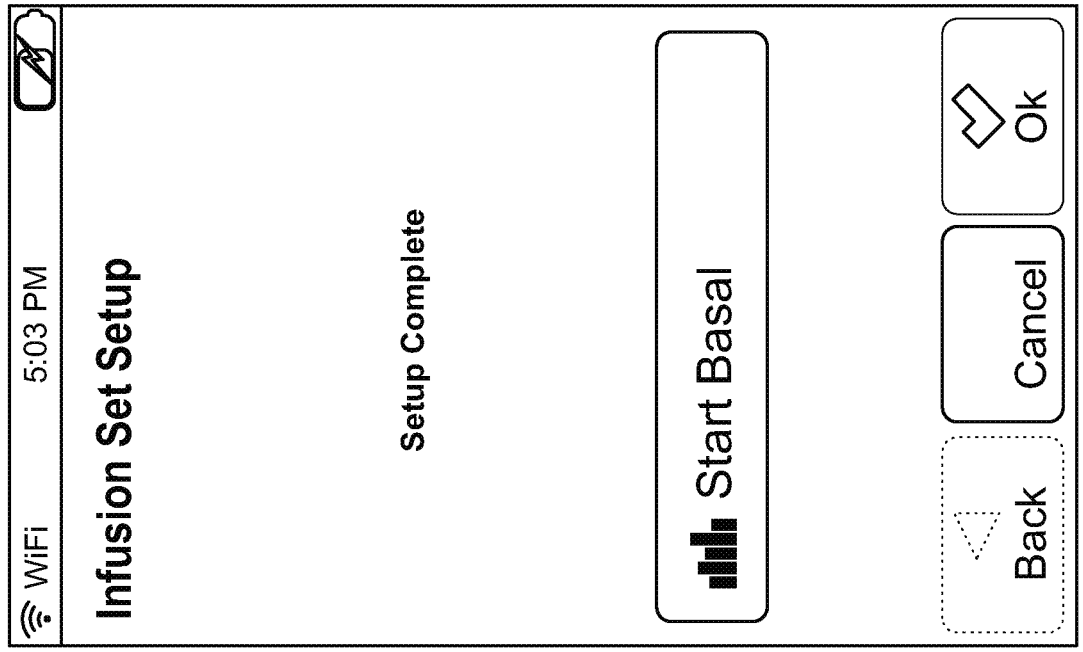
Figure 22C:
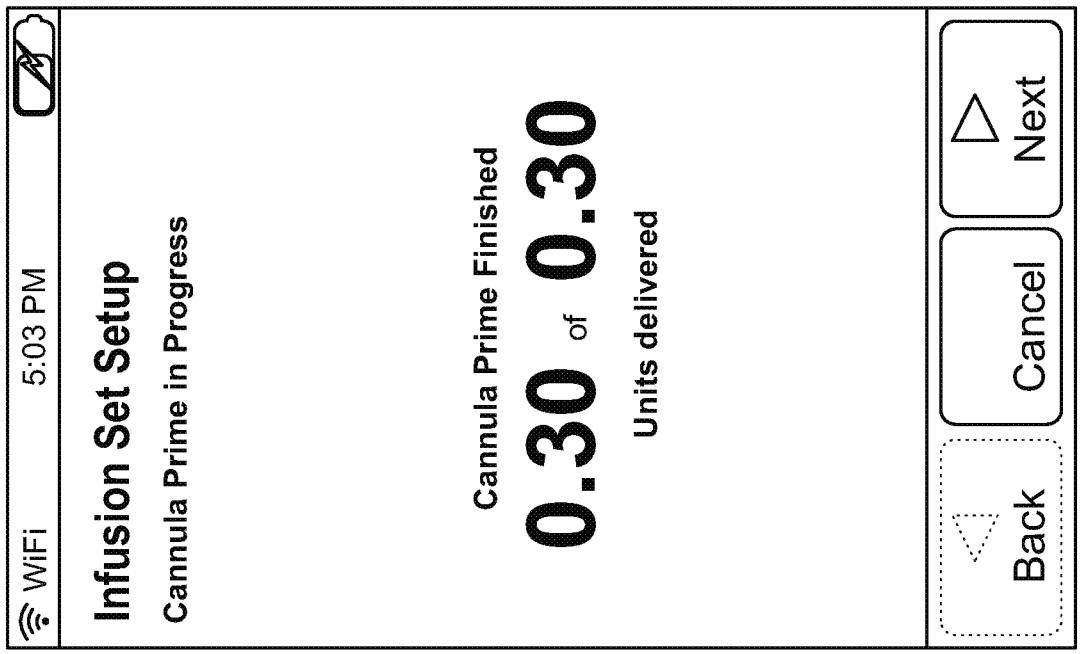

Referring now to FIG. 22B, some embodiments include at least one screen for confirming the cannula prime is finished. Referring to FIG. 22D, some embodiments include at least one screen for confirming the setup is complete and including a button to start basal. In some embodiments, this screen automatically appears after the setup is complete which may be beneficial for many reasons, including, but not limited to, reminding the user to start the basal on the infusion pump.

Figures 23A, 23B:
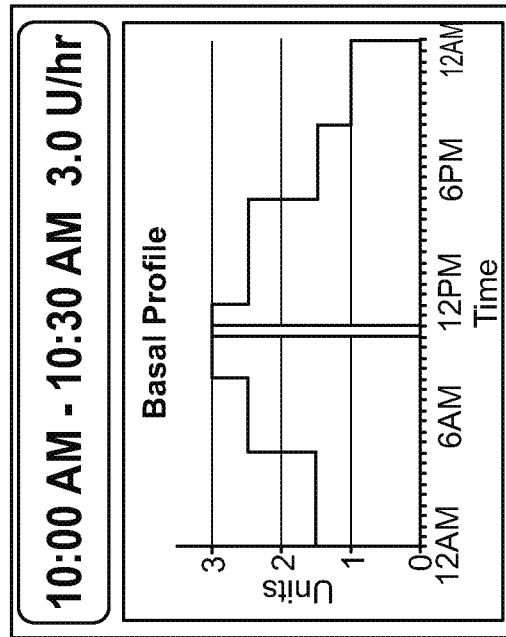

Referring now to FIG. 23A, some embodiments include at least one screen for programming basal profiles. In the embodiment shown, to program the basal profile, the user enters the rate, which, in some embodiments may be the volume, in units, per hour, and the start and end time. In various embodiments, a user may create basal profiles for various days (for example, a Monday profile, etc), and/or for weekdays and/or for weekends and/or may create custom profiles for events (for example, skiing).

Referring now to FIG. 23B, some embodiments include at least one screen for visually reviewing the basal profile for the day which may include both a graphical representation of a twenty-four hour period and also, an indication of the current rate for the time of viewing.

Figure 23D:
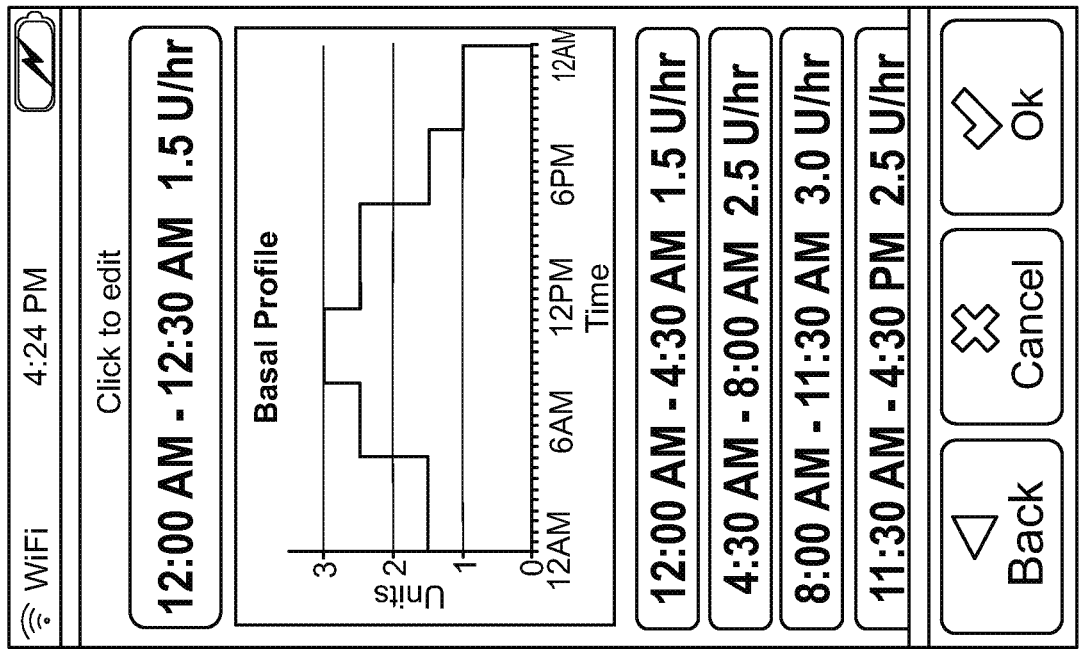
Figure 23C:
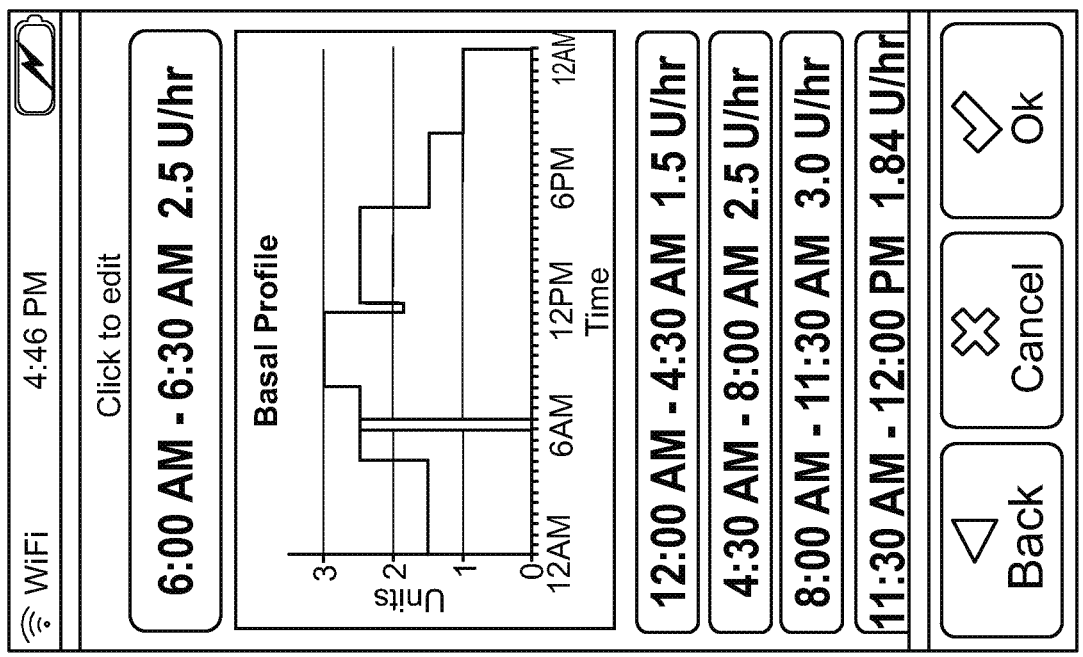

Referring now to FIGS. 23C and 23D, some embodiments include at least one basal profile screen that includes buttons including each rate during a range of time, for example, a twenty-four hour period. In some embodiments, a user may select a button representing one of the ranges of time and that will bring the user to a screen to edit that particular time-frame. In some embodiments, the screen may additionally include both a graphical representation of the current basal profile and the current time-frame on top.

Referring now to FIGS. 24A and 24B, in some embodiments, the remote interface may either be wirelessly connected to a blood glucose meter and/or may include a blood glucose meter. When the user takes a blood glucose reading, in some embodiments, the screen shown in FIG. 24A automatically is visible. In some embodiments, the screen may include a button that automatically presents a likely "tag", for example, as shown in FIG. 24A, based on the time of day, the screen button indicates "lunch". However, the user may edit this tag. For example, the user may select the button "add/edit" and the user may be brought to a screen that is similar to the one shown in FIG. 24B. The edit note and tag screen may include an area for custom editing (i.e. edit box), the user may type comments into the edit box. The tag list may include custom tags that the user may have pre-programmed into user settings either by using the personal computer/web portal or by using the remote interface. In some embodiments, the settings for the GUI may include default listings that may be edited.

Figures 25A, 25B:
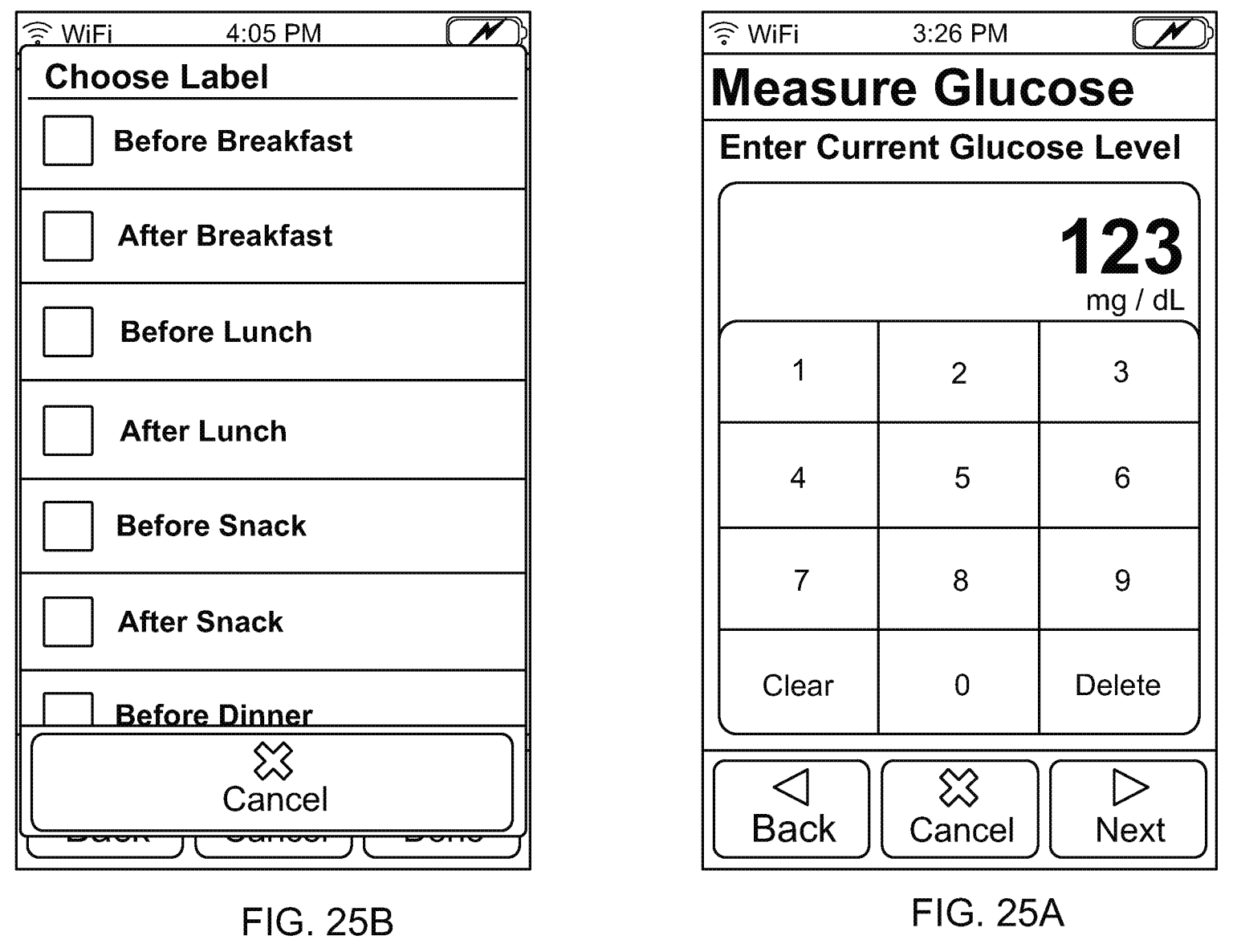

Referring now to FIGS. 25A and 25B, some embodiments may include a screen, as shown in FIG. 25A, where the user manually enters a blood glucose reading. In some embodiments, after entering and selecting "next", a label screen, for example, as shown in FIG. 25B, may allow the user to select a label. The label list may include custom tags that the user may have pre-programmed into user settings either by using the personal computer/web portal or by using the remote interface. In some embodiments, the settings for the GUI may include default labels that may be edited.

In some embodiments, upon manually entering a blood glucose value, for example, using a screen such as one shown in FIG. 25A, the user interface may indicate the amount of carbohydrates the user should consume. For example, if the user enters "40 mg/dL", the system may, by using the correction information that is entered with respect to a user profile (i.e., the amount of carbohydrates used treat low blood glucose levels/hypoglycemia, which may be determined by a user together with their health care provider), may computer the amount of carbohydrates to treat hypoglycemia. In some embodiments, the remote interface may be preprogrammed with specific instructions to treat hypoglycemia, for example, with fifteen skittles (for example, or any other candy or glucose item) and four ounces of apple juice (in some embodiments, however, these may vary) (all of which may be entered by the user into the user profile either through the remote interface or the personal computer/web portal) and, the user interface may show a picture of the food, for example, the 15 skittles and/or four ounces of apples juice, to the user upon entering a hypoglycemic glucose number (which number may be pre-programmed into the system). In some embodiments, the user may request additional suggestions which may also be presented to the user on the GUI in the form of words and or pictures. This may be desirable for many reasons, including but not limited to, quick and easy treatment of hypoglycemic events, where a user will quickly decipher the food they should eat to treat the hypoglycemic event and/or the user may show a friend or another person the picture and request they provide that food. In some embodiments, this may be beneficial especially in countries where the user may not speak the local language.

Figure 25C:
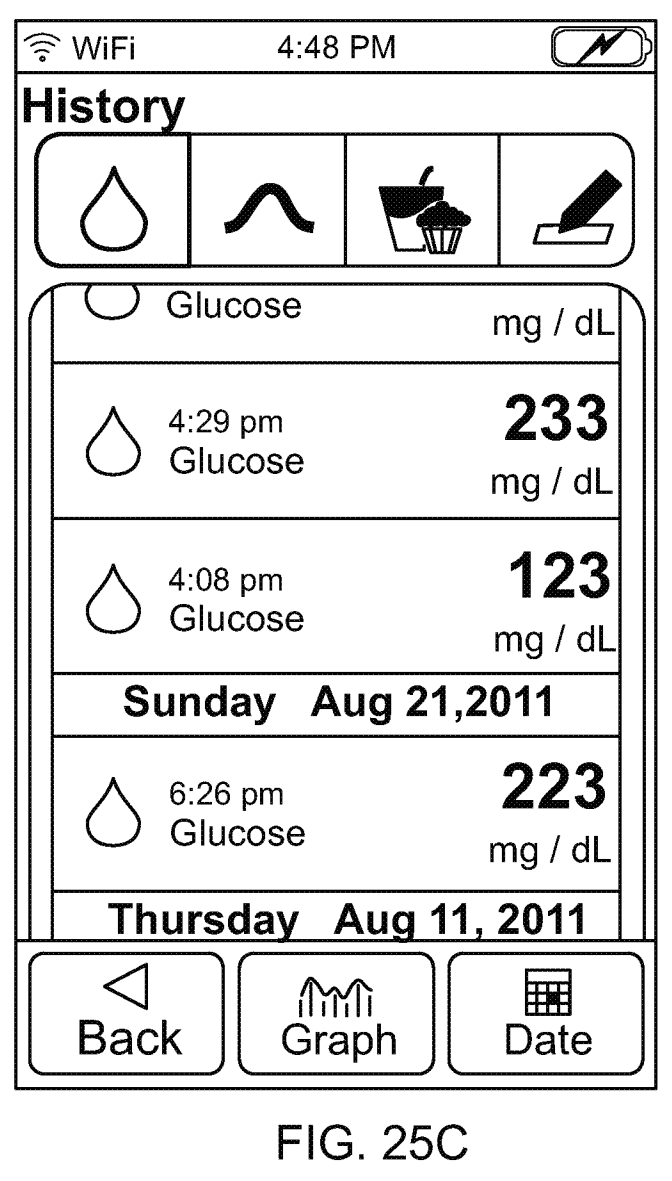

Referring now to FIG. 25C, some embodiments may include at least one glucose history screen, which may, in some embodiments, include a listing of the times and the glucose readings. In some embodiments, additional information may be readily available either on a screen such as this, or if the user selects a reading, another screen with more detail may be included, for example, the food eaten and/or the activity and/or the label and/or the tag, or any other indication that the user has tagged or labeled to the reading. In some embodiments, a "graph" tab may be accessible from the glucose screens to view a graph of blood glucose values. In some embodiments, the graph may be interactive and the user may touch points or locations on the graph that will take the user to a screen including more detail for that entry and or period of time, etc. In some embodiments, the GUI may show continuous glucose monitor (CGM), blood glucose meter (BGM) and infusion pump volumes on the same graph.

In some embodiments, the graphical user interface may include one or more screens for programming a bolus. Referring now to FIGS. 26A-26D, in some embodiments, a user may enter select a good from a food library, which, as discussed above, may include custom entries by the user (either using the remote interface and/or downloading food library from the web and/or completing custom entries on the personal computer and/or web portal and downloading/synchronizing with the remote interface) and/or may include default entries. In some embodiments, the user may navigate to the food library screen(s), for example, in some embodiments the screens may be similar to the screens shown in FIGS. 26K And 26L, select the food and/or select "keypad" and type the food into the search screen, and then another screen, for example, in some embodiments, the one shown or similar to the one shown in FIG. 26A, may request the user enter the quantity of the food. In some embodiments, the screen may also include indications of the nutritional value of the food, for example, which may include, but is not limited to, one or more of the following: carbohydrates, fat and/or calories. In some embodiments, where a food is not selected from the food library, a confirmation screen will indicate same to the user, which, in some embodiments, may be similar to the embodiment of the screen shown in FIG. 26M.

Figure 26B:
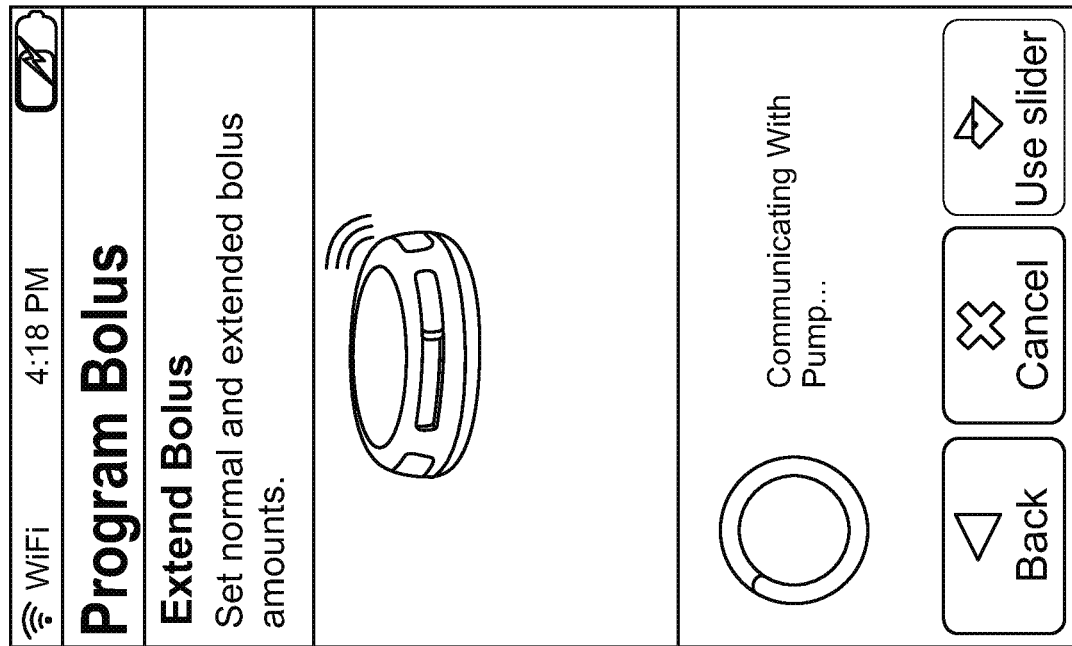
Figure 26A:
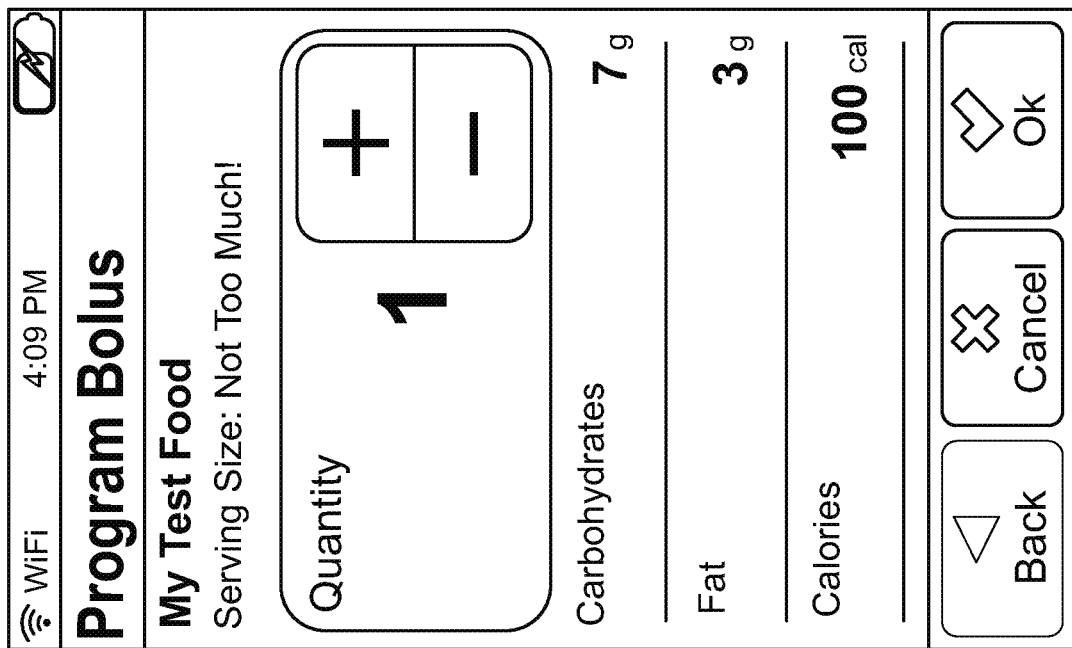

In some embodiments, the user may enter the carbohydrate amount using a keypad, which, in some embodiments, may be similar to one shown in FIG. 26D. In some embodiments, once the user has entered a food items, the user may return to add additional items, for example, by using a button similar to that shown in the screen shown in FIG. 26J, where the user may select the "add food/carbs" button. Once the user has added all the carbohydrates, including food items, for the bolus, the user may select "ok" and a screen, which may be similar to the one shown in FIG. 26B, may indicate to the user that the remote interface is establishing wireless communication with the infusion pump.

In some embodiments, the user may select to enter the units of insulin requested for a bolus, rather than enter the carbohydrates or the food items and quantity. In some embodiments, this may be accomplished using a keypad screen, for example, which may be similar to the screen shown in FIG. 26N. Once the user has entered the volume requested, the user may select "ok" and a screen, which may be similar to the one shown in FIG. 26B, may indicate to the user that the remote interface is establishing wireless communication with the infusion pump.

In some embodiments, during the bolus process, the remote interface may show a screen that includes the most recent blood glucose meter result, which may, in some embodiments, indicate to the user the time the test was taken and also, the time elapsed since the test. In some embodiments, the screen may be similar to the screen in FIG. 26H. In some embodiments, the screen may instruct to user to confirm whether they want a bolus calculator to use this recent glucose test for the correction portion of the bolus. The user may, in some embodiments, select "no, retest", in which case the user interface may open the blood glucose meter screens. In some embodiments, the user may select "no, skip correction bolus", in which case the bolus calculator will not use the value and will not bring the user to the blood glucose meter screens automatically. In some embodiments, the user may select "OK" and the bolus process may continue.

In any case, once the user has entered all of the information they wish to enter regarding the bolus, which may include, but is not limited to, one or more of the following: carbohydrate values, food items, blood glucose values and/or units of insulin volume requested, the user interface presents a summary screen, for example, which may be similar to the embodiment shown in FIG. 26I, that indicates, in some embodiments, the recommendation for each of the bolus categories, for example, meal bolus (for food), correction bolus (for glucose) and indicates to the user the bolus on board (which in some embodiments, may be termed the insulin on board or JOB), and indicates a total bolus recommended. The user may navigate from this window and adjust the total bolus to be delivered, for example, by touching the "total bolus" area of the screen and adjusting the value in units. In some embodiments, this may be done using a keypad. In some embodiments, this may be done using a slide adjust GUI, which, I some embodiment, may be similar to the one shown in FIG. 26G. In this embodiments, the total amount recommended, e.g., 3.51 units, is shown in the "modify bolus amount" box 2600. The user may, by moving the slider 2602, adjust the total volume. As, for example, the user slides the slider 2602 towards the left, both the total amount in the modify bolus amount box 2600 decreases and the percentage decreased is represented in the modify bolus amount box 2600. As, for example, the user slides the slider 2602 towards the right, both the total amount in the modify bolus amount box 2600 increases and the percentage increased is represented in the modify bolus amount box 2600. This may be desirable for many reasons, including, but not limited to, if a user desired to reduce or increase the recommended bolus amount by a given percentage, for example, reduce by 20% for pre-exercise and/or increase by 40% for illness, the modify bolus amount box 2600 makes this calculation easy for the user.

Figure 26F:
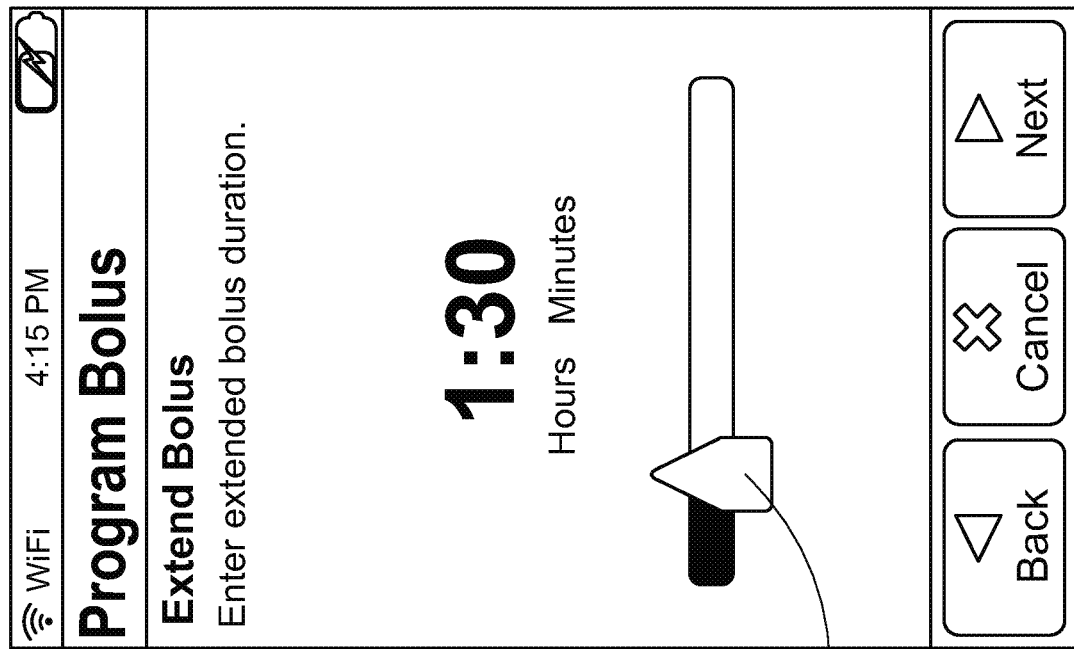
Figure 26E:
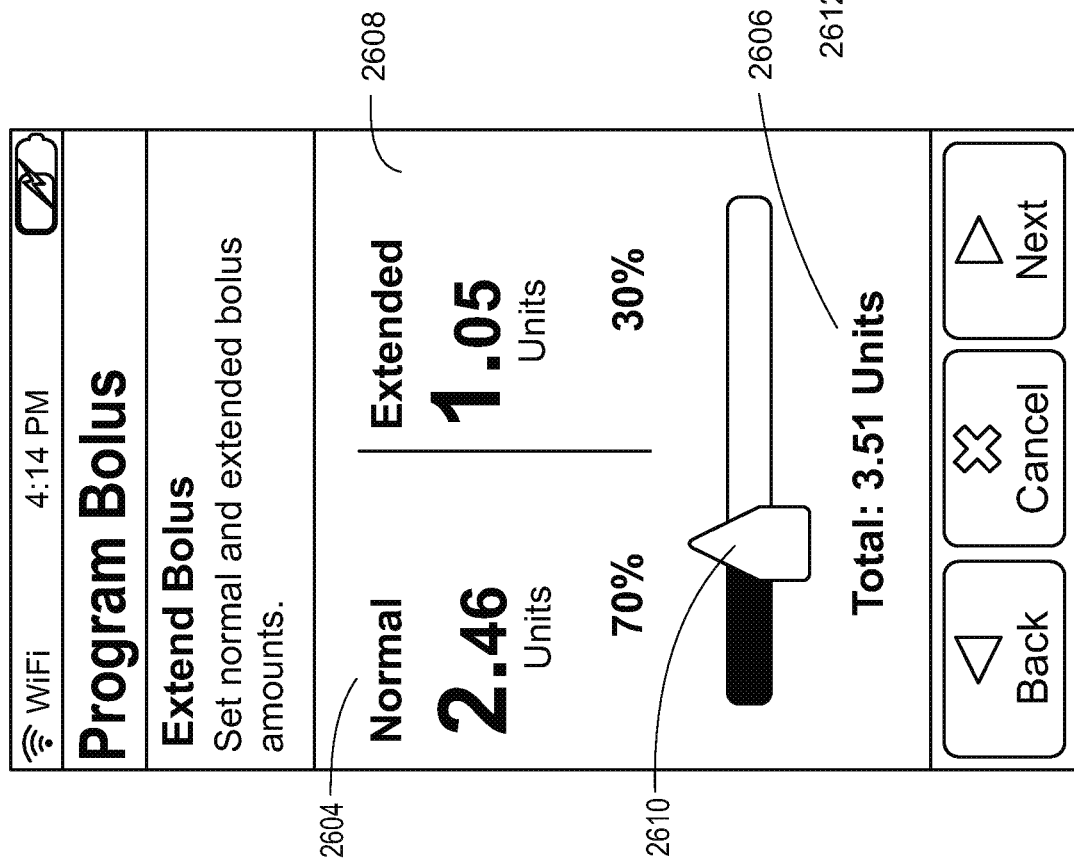
Figures 26I, 26J:
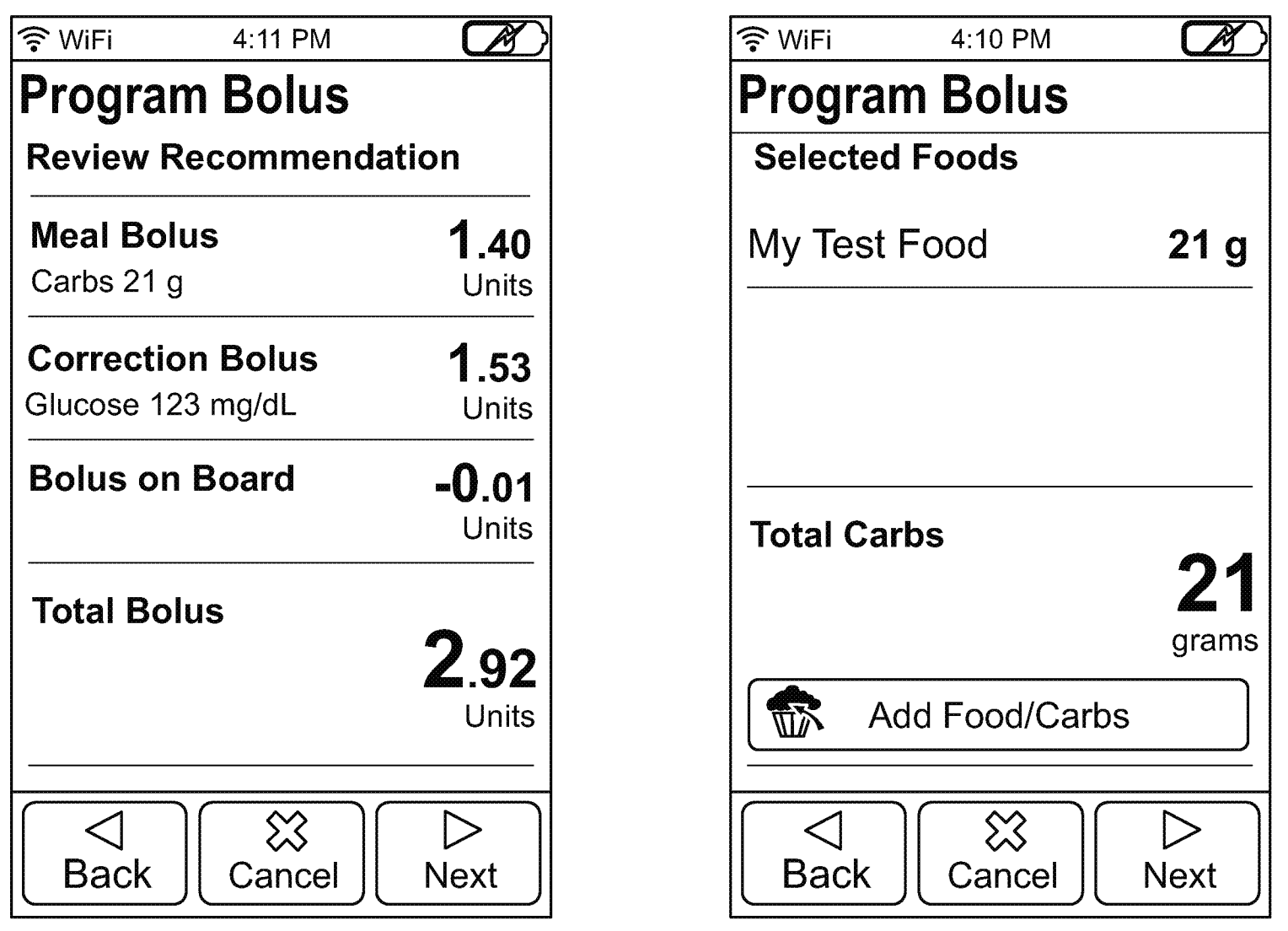
Figure 26L:
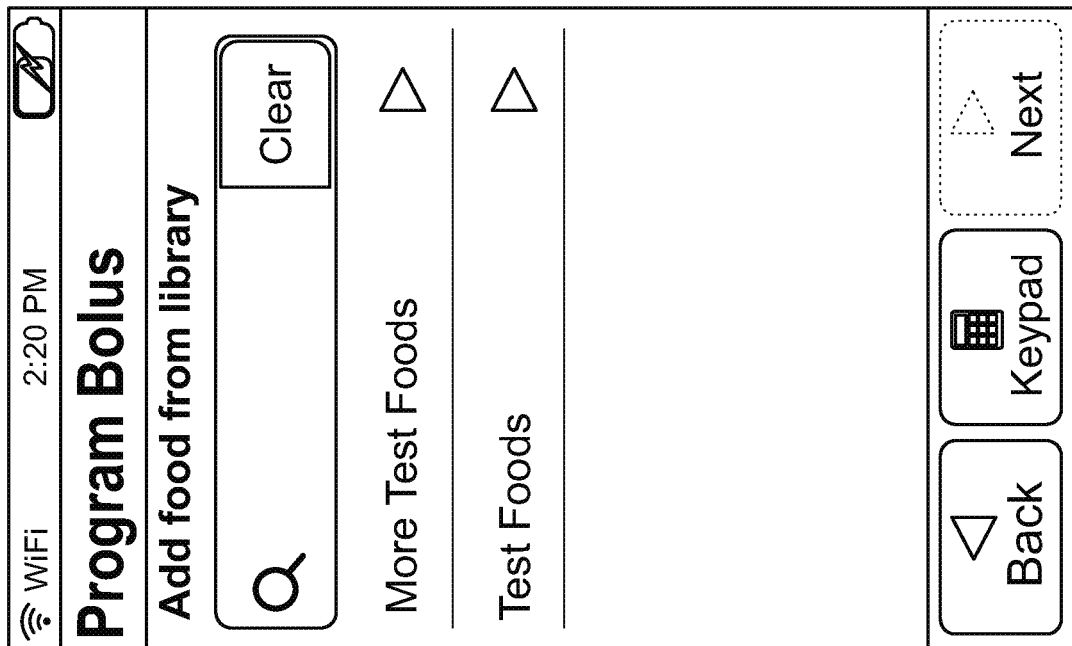
Figure 26K:
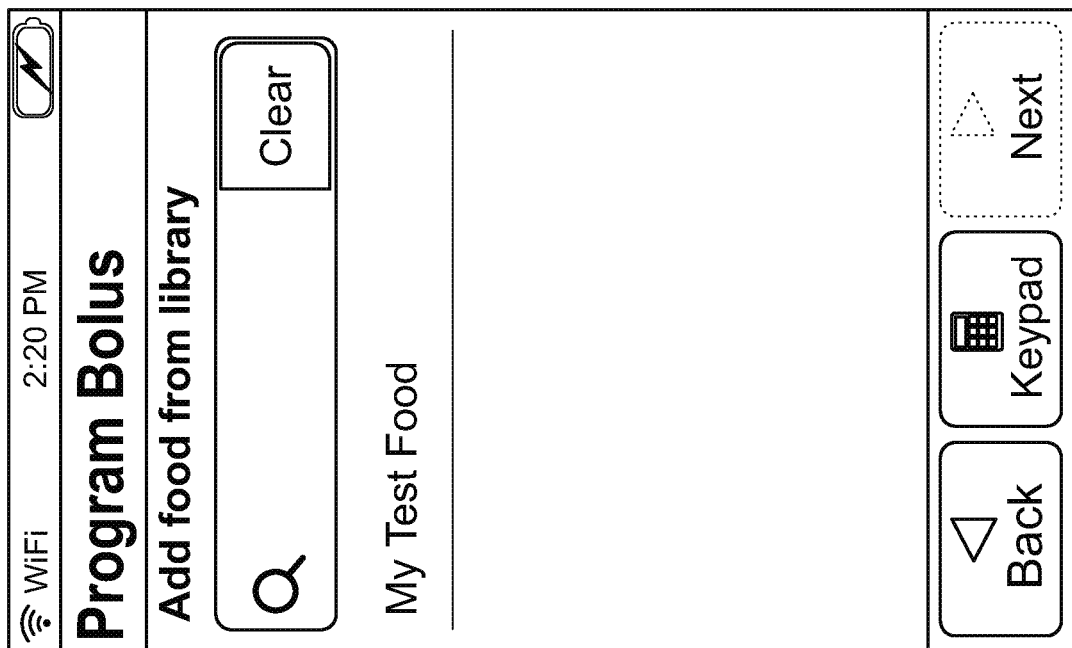
Figures 26M, 26N:
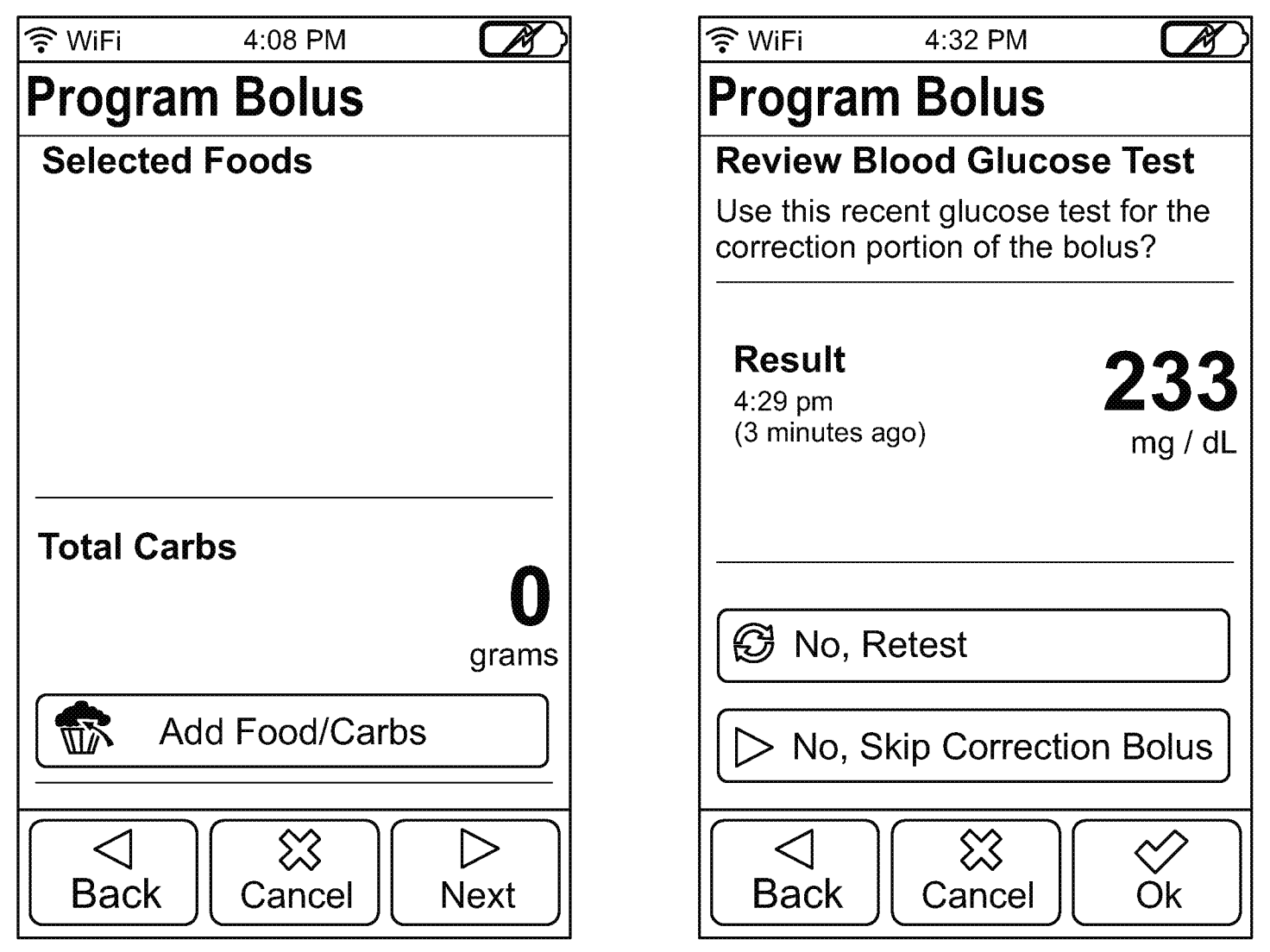

Once the volume to be delivered is determined, in some embodiments, the user interface presents a screen that allows the user to determine the However, if the user wishes to proceed from the review recommendation screen, the user may navigate, in some embodiments, using the "next" button. If the user is navigating from the modify bolus amount screen, the user may, in some embodiments, use the "OK" button. In some embodiments, the user will be brought to a screen allowing the user to determine how the bolus is to be delivered, i.e., as a normal, extended or as a combination. Referring now to FIGS. 26E and 26F, the total volume of insulin to be delivered, in some embodiments, may be, as a default, delivered as a normal bolus, unless the user modifies to add at least a percentage to be delivered as an extended bolus. In some embodiments, upon entering the screen shown in FIG. 26E, the normal 2604 may include the total amount recommended and the extended 2608 may include 0.00 units. The total units 2606 to be delivered may be shown under the slider 2610. The normal 2604 and the extended 2608 may also include percentages, which in some embodiments, represents the percentage of the total that will be delivered in that fashion, i.e., either normal or extended.

The user may, by moving the slider 2610, adjust total volume that may be delivered as normal 2604 and extended 2608. As, for example, the user slides the slider 2610 towards the left, both the total amount and the percentage of the total in the normal 2604 increases. The total amount and the percentage of the total amount in the extended 2608 decreases. However, as, for example, the user slides the slider 2610 towards the right, both the total amount and the percentage of the total in the extended 2608 increases. The total amount and the percentage of the total in the normal 2604 decreases. This may be desirable for many reasons, including, but not limited to, if a user desired to deliver a particular percentage as an extended, for example, if the user desired to deliver 80% as extended, the user may slide the slider 2610 to the right until the percentage in extended 2608 shows "80%". Also, if a user desires to deliver a particular volume, for example, 1.0 units, as normal, which may be desired in many situations, including, but not limited to, where the user desires to deliver the volume in the total that is attributed to correction bolus as normal, the user may slide the slider 2610 towards the right until the volume in the normal 2604 is 1.00 units. In some embodiments, the direction of the slider 2610 with respect to the increase or decreasing amounts under the normal 2604 and or the extended 2608 may vary.

Referring now to FIG. 26F, if any percentage or volume of the bolus is selected to be delivered as an extended, in some embodiments, a screen similar to the one shown in FIG. 26F, may be presented to the user after selecting "next" from the normal and extended bolus amount screen. The user may enter the amount of time they wish the extended volume (from FIG. 26E) to be delivered over as an extended bolus. In some embodiments, as the user slides the slider 2612 to the right, the time for the extended bolus increases and as the user slides the slider 2612 to the left, the time for the extended bolus decreases. In some embodiments, the direction of the slider 2612 with respect to the increase or decreasing of the time may vary. In some embodiments, the duration screen, such as the one shown in FIG. 26F, may open with a default time, for example, 1 hour, and allow the user to modify. In some embodiments, the default may be the most recently programmed extended bolus.

Once the user has programmed the method for delivery of the bolus volume, the user may select "OK" in some embodiments, and a review bolus setting screen may be viewable, for example, in some embodiments, one similar to the one illustrated in FIG. 26C. In some embodiments, the review bolus setting screen provides the total bolus amount to be delivered, the method of delivery, the volume of the total that is to be delivered as normal and the volume of the total that is to be delivered as extended, and if there is a volume to be delivered as extended, the duration of the extended bolus may be indicated. The user therefore has an opportunity to clearly review the bolus volume and the method of delivery. In some embodiments, to start the bolus delivery, the user must "slide" the "confirm" button. This may be desirable for many reasons, including but not limited to, a potentially decreased incidence of accidental or unintentional tapping of the "confirm" button. Thus, the action, i.e., tapping, to "cancel" using the cancel button is a completely different action from "confirm", i.e., sliding. Also, the location of the "confirm" button and slide being in a very different location from the "cancel" button may prevent unintentional cancellation. Thus, this method may decrease unintentional cancellation and also, unintentional delivery when cancellation was desired. Also, in some embodiments, the location of the "next" or "ok" button is in a similar location on many screens. Therefore, to prevent unintentional confirmation when a therapy change is being made, in some embodiments, the system requires a different action, for example, a slide rather than a touch/tap and in addition, in some embodiments, the start of the slide is in a opposite side from the "next" or "ok" buttons.

There are many advantages to this method of programming a bolus volume, including, but not limited to, the following. The user may first determine the volume of bolus and then, following, determine the method of delivery. Thus, a user does not have to decide that the bolus is "extended" before, for example, entering the carbohydrates/food and/or blood glucose value, for, as mentioned above, in some circumstances, a user may wish to deliver the food bolus portion of the total bolus as an extended bolus and the correction portion of the total bolus as a normal bolus. Also, the slider embodiments shown in FIGS. 26G, 26E and 26F allow for the user to view the percentage change as well as the total volume at any given time. This method therefore may prevent miscalculations and allow for closer tweaking and customization of insulin therapy. Also, with respect to the user programming the duration of the extended bolus after entering the portion of the bolus volume to be delivered as an extended bolus, the user may be less likely to "confirm" a delivery before modifying the duration.

Referring now to FIGS. 27A, 27B, 27C and 27E, in various embodiments, the user interface includes various opportunities for the user to cancel an action. In some embodiments, when the button "cancel" is pressed, another screen pops up that confirms that the user wishes to cancel. This may be desirable, for example, in the case where a user unintentionally taps the cancel button, the user has an opportunity to continue, rather than cancel.

Figure 27A:
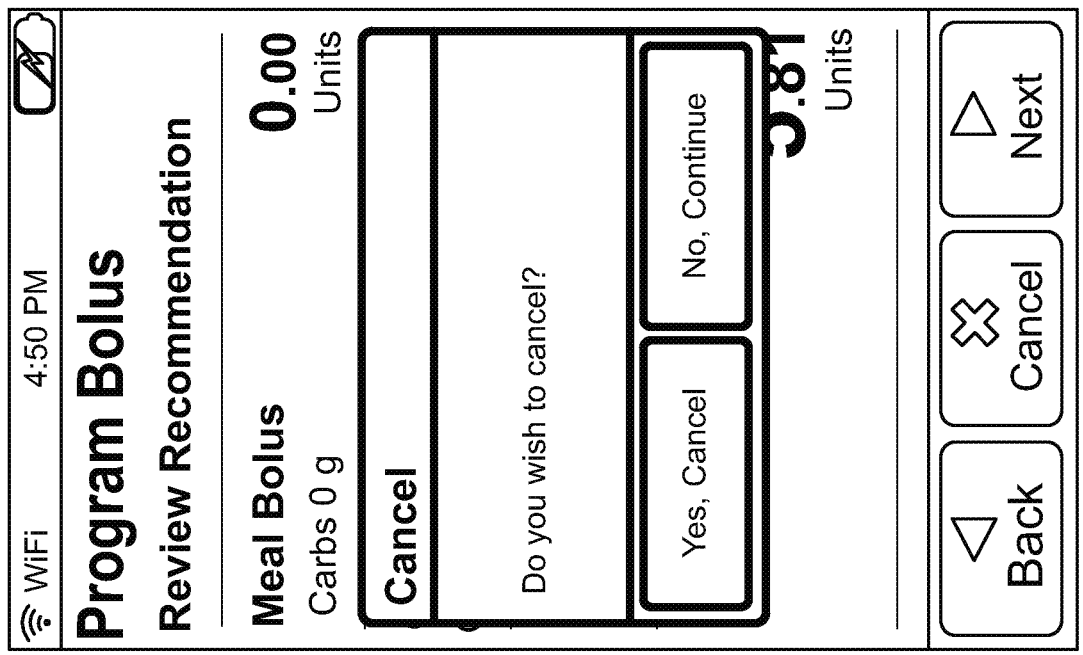
Figure 27B:
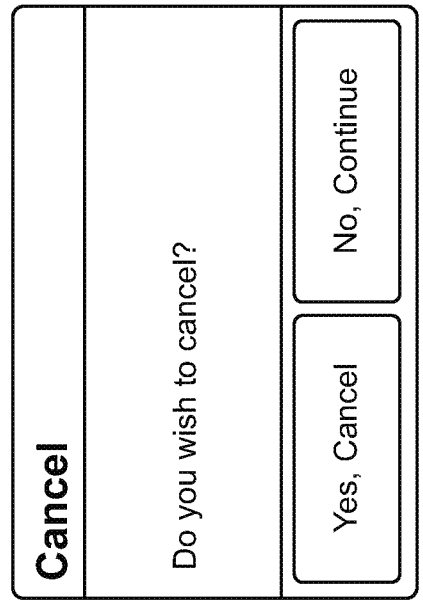
Figure 27G:
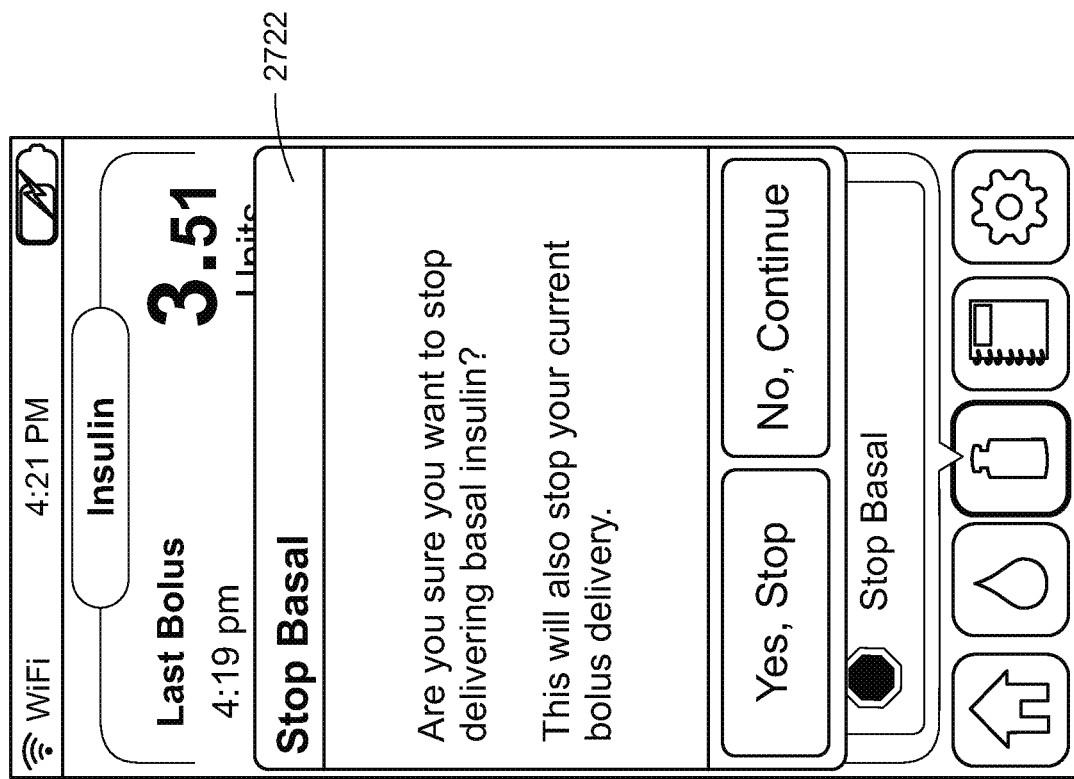
Figure 27F:
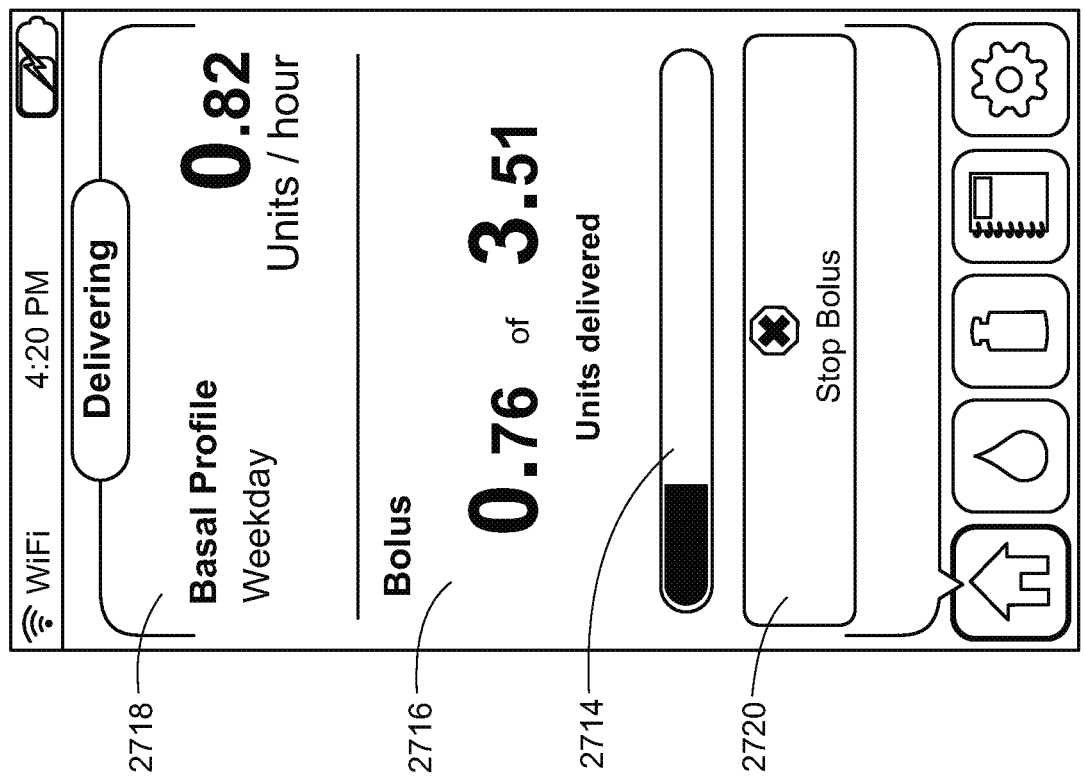

Referring now to FIGS. 27F and 27G, in some embodiments, while a bolus is active, for example, in the above example, a portion of the bolus may be delivered as normal and a portion may be delivered as extended, the user interface may include a "delivering" screen indicating the status of the active delivery. For example, in some embodiments, as shown in FIG. 27F, the volume delivered and the total volume to be delivered 2716 may be indicated, as well as a status bar 2714 representing the volume delivered as a function of the total volume to be delivered. In addition, in some embodiments, the delivering screen may also include the current basal profile 2718, which may indicate both the name of the profile, e.g., "weekday", and the pre-programmed basal rate, e.g., 0.82 units/hour.

In some embodiments, while a bolus is active, the home screen for the user interface may change to a bolus delivery status screen or delivering screen, for example, in some embodiments, may be similar to the delivering screen shown in FIG. 27F. In some embodiments, whenever an active bolus is being delivered, the home screen (which, in some embodiments, as described above, may be similar to a delivering screen) freezes and does not time out.

In some embodiments, while the infusion pump is delivering, the delivering screen and/or the various screens of the user interface, may include a different splash screen and/or background screen to indicate, visually, to the user that the delivering is occurring. In some embodiments, the background may be "green" to indicate delivering. However, this is just one embodiment, and other embodiments to indicate and/or differentiate the infusion pump status may be used.

Still referring to FIG. 27F, in some embodiments, while the infusion pump is delivering a bolus, a "stop bolus" button 2720 may be included on the delivery screen. In some embodiments, the stop bolus button 2720 may be a different color from the rest of the screen, for example, in some embodiments; the stop bolus button 2720 may be red.

Referring now to FIG. 27G, in some embodiments, while an active bolus is being delivered, if the user elects to "stop basal", a stop basal pop up screen 2722 may appear that asks the user to confirm that they wish to stop delivering basal insulin and reminds the user that this will also stop the current bolus delivery. In some embodiments, the infusion pump may not allow the user to stop basal unless they also stop bolus, as this may be desirable for if a user wishes to stop delivering of the basal insulin, it may indicate that all insulin delivery should cease. The stop basal pop up screen 2722 reminds users that a bolus delivering is in progress in case they did not realize when the elected to start the process to "stop basal".

Figure 27I:
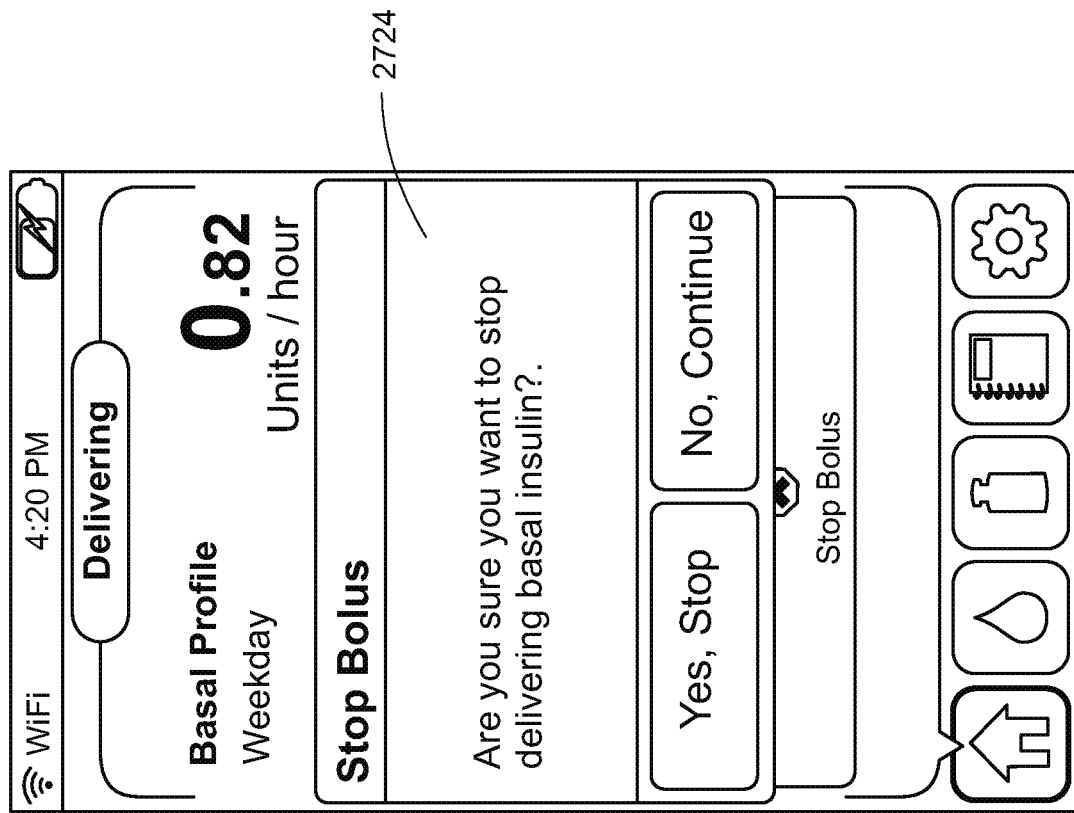
Figure 27H:
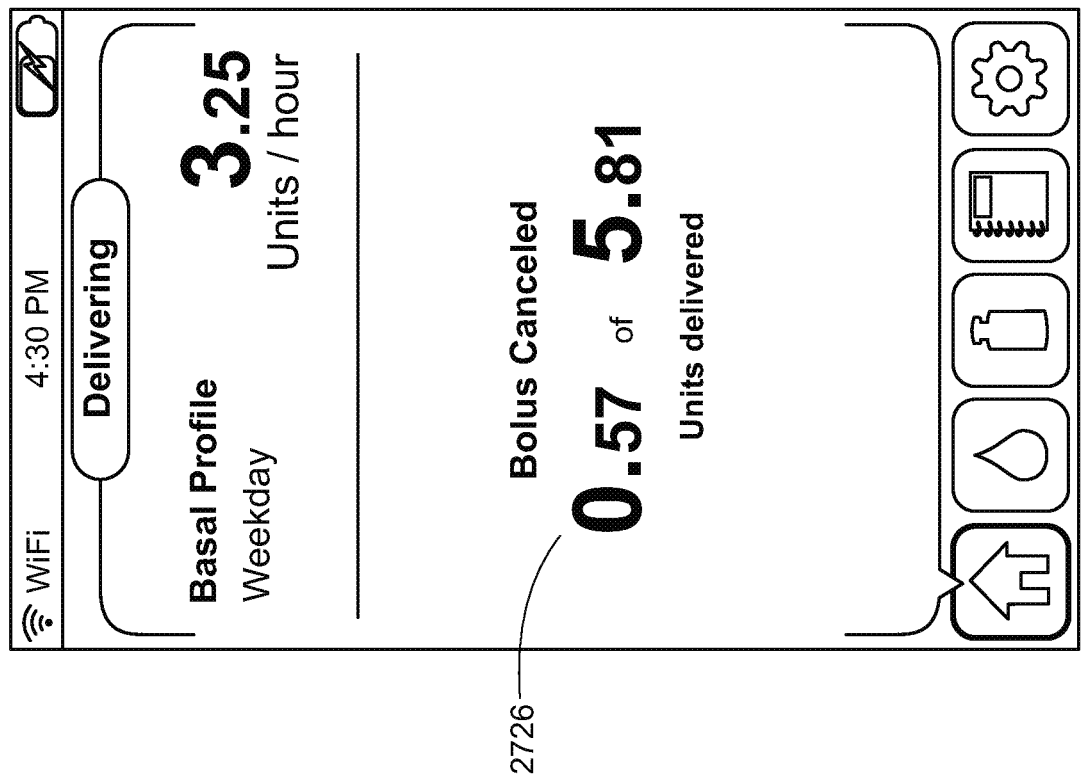

Referring now to FIGS. 27H and 27I, in some embodiments, while an active bolus is being delivered, if the user elects to "stop bolus", a stop basal pop up screen 2724 may appear that asks the user to confirm they wish to stop delivering basal insulin. In some embodiments, the infusion pump may not allow the user to stop bolus unless they also stop basal, as this may be desirable for if a user wishes to stop delivering of the bolus insulin, it may indicate that all insulin delivery should cease. Referring to FIG. 27H, in some embodiments, if the user chooses to cancel the bolus, a confirmation screen of the cancellation may appear and indicate the units delivered out of the total volume programmed 2726.

Figures 28A, 28B:
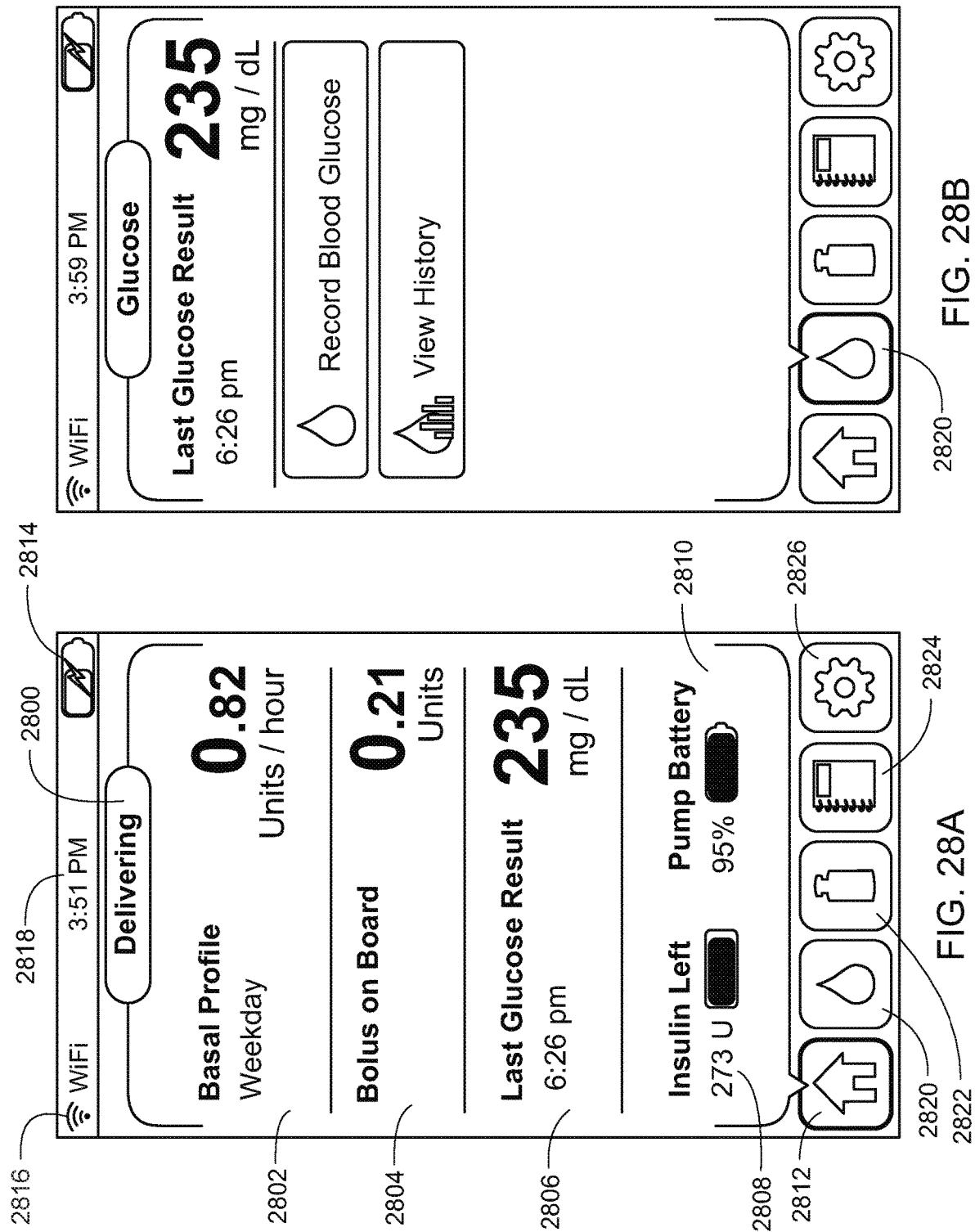
Figure 28D:
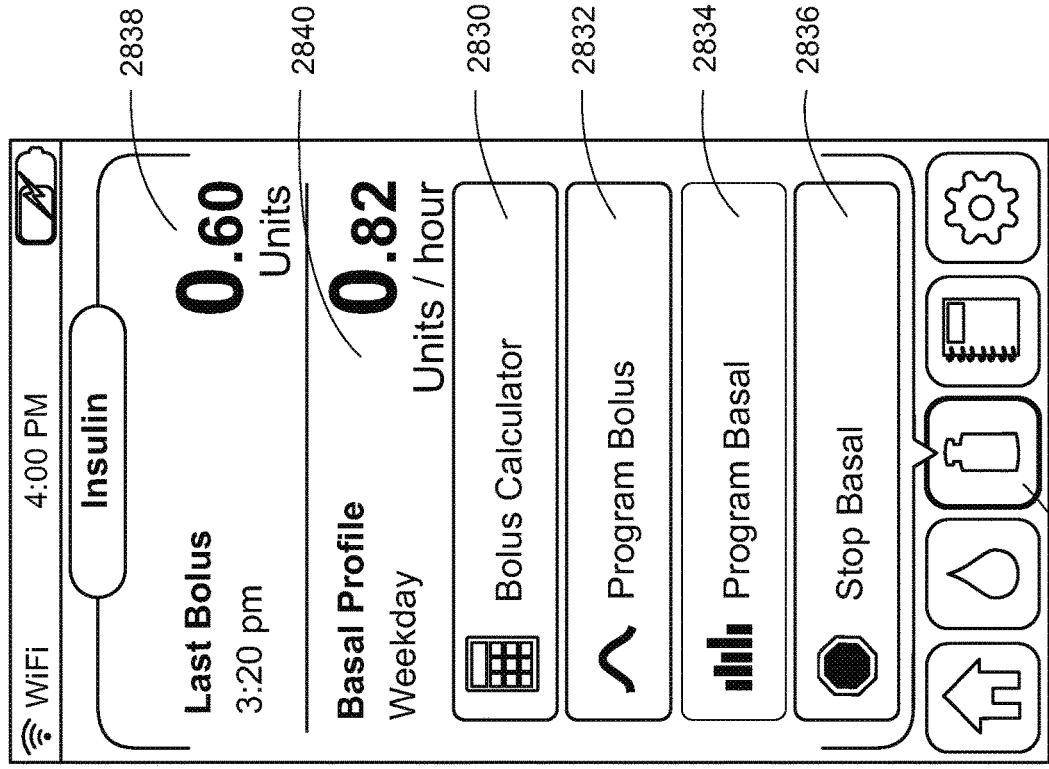
Figure 28C:
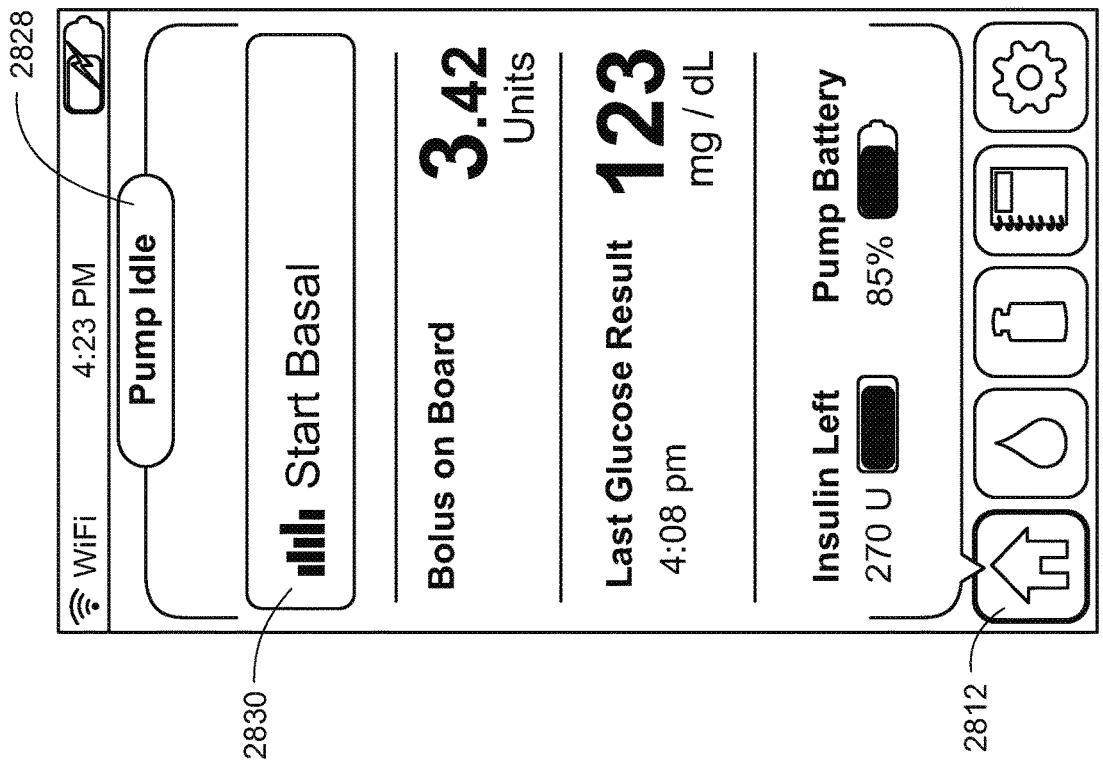
Figure 28E:
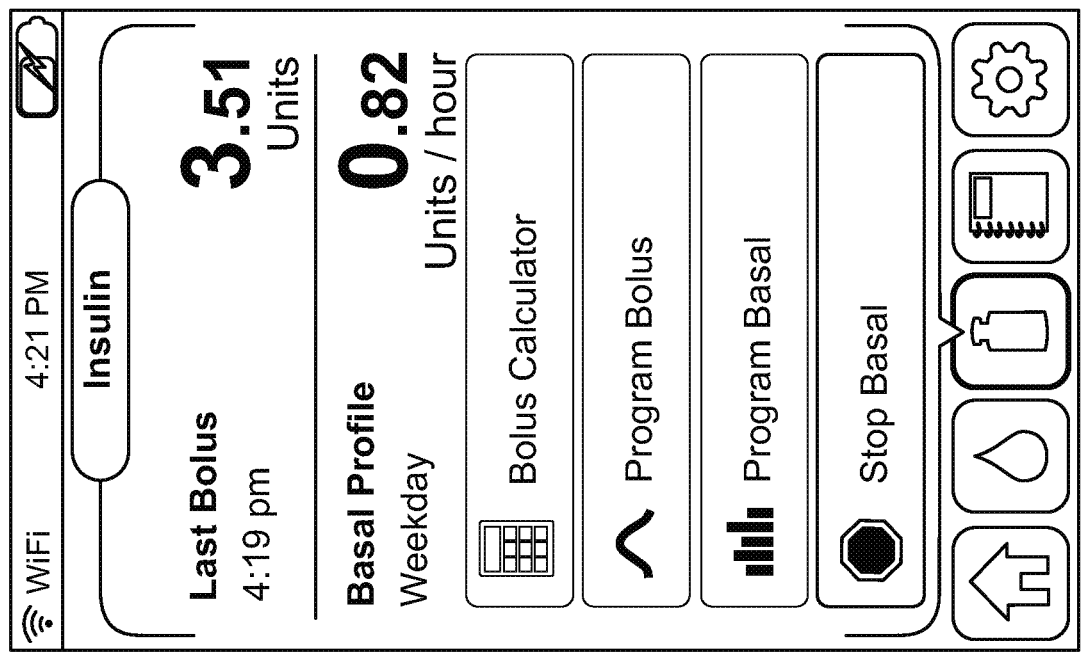
Figure 28F:
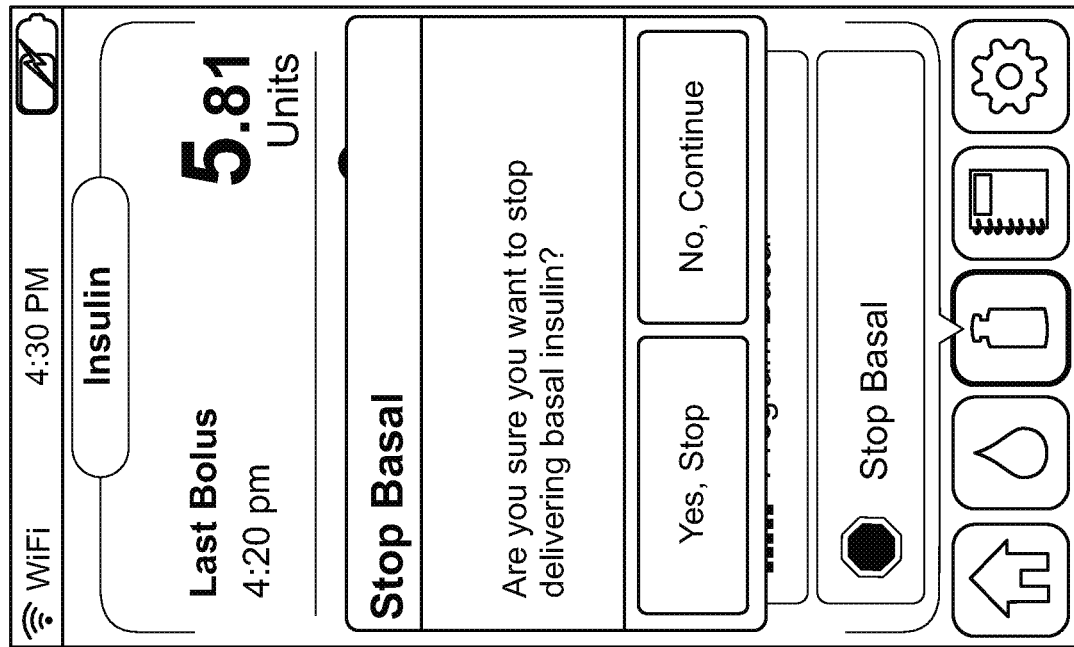
Figure 28H:
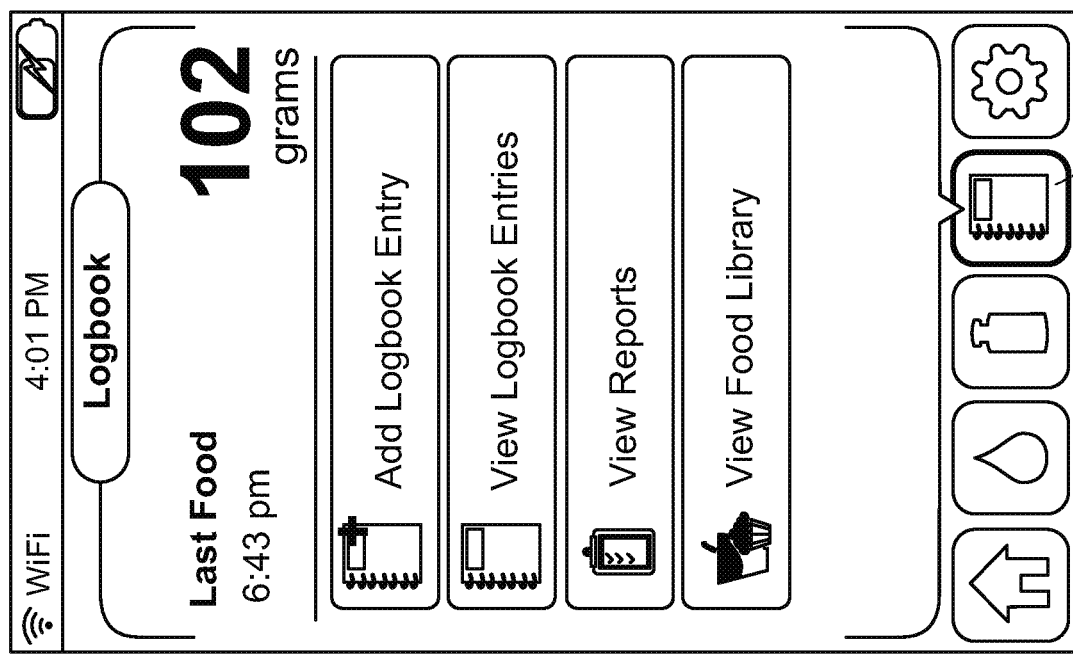
Figure 28G:
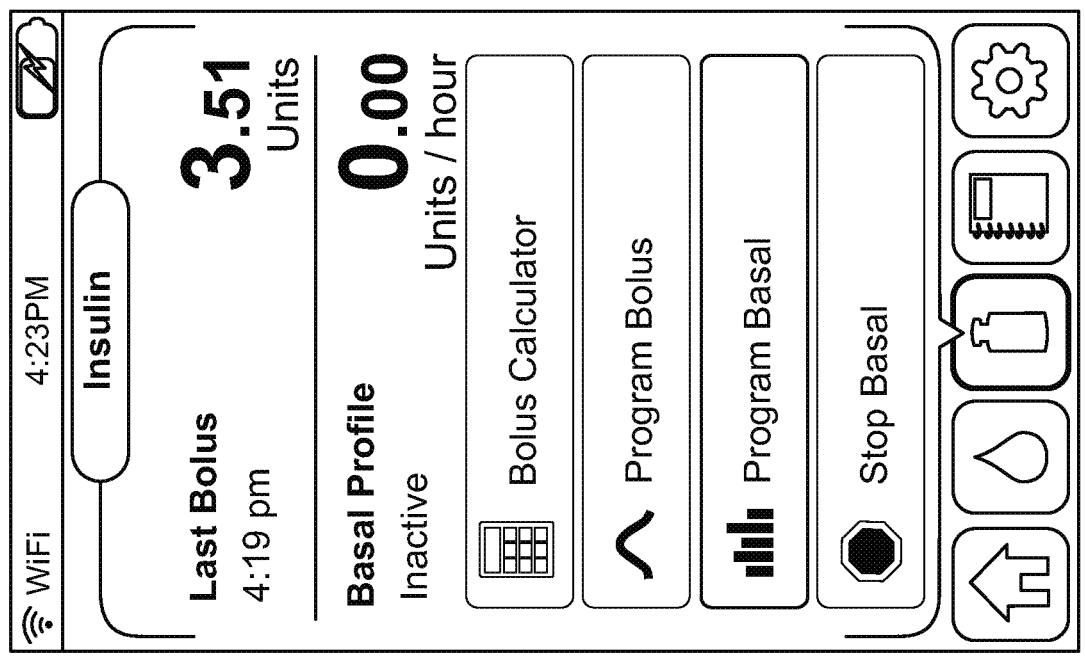
Figure 28I:
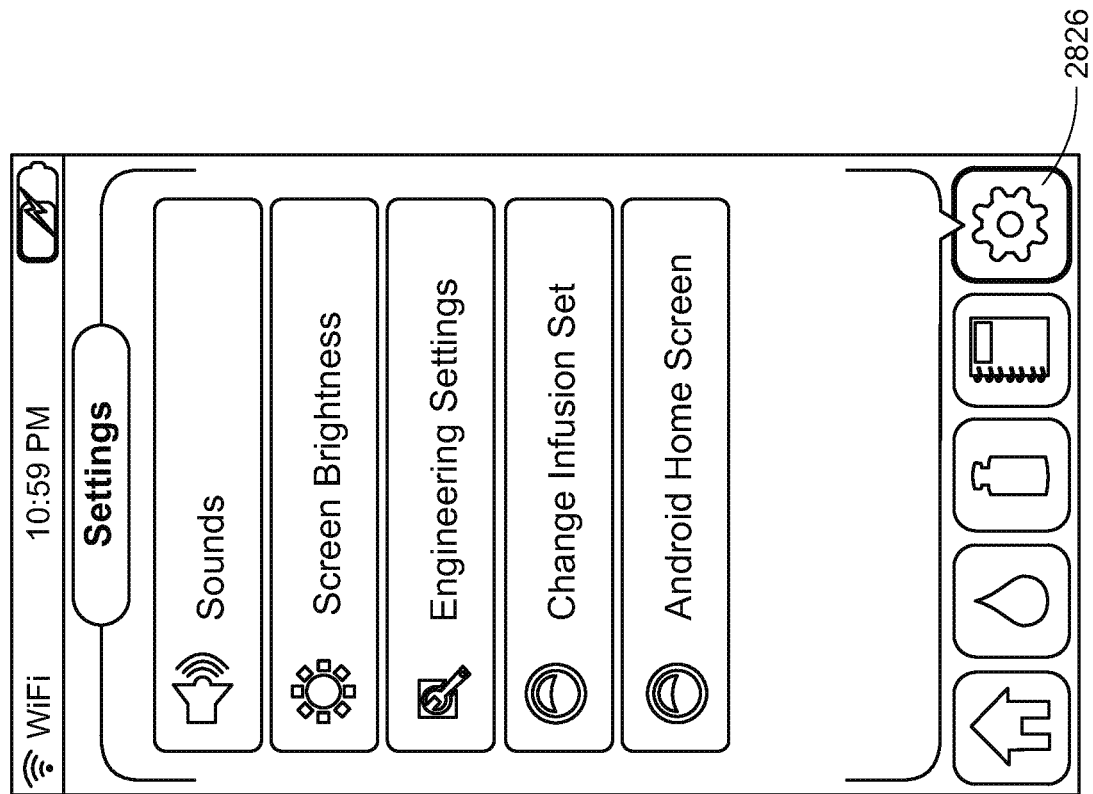

Referring now to FIG. 28A, an embodiment of a home screen is shown. In the embodiments shown, the home screen indicates a number of different information, and in some embodiments, the amount of information on the home screen may vary. However, in some embodiments, the following information may be included on the home screen, however, in various other embodiments, one or more, of the following information and/or additional information may be included: indication of the infusion pump status, e.g., the infusion pump is delivering 2800; indication of the active basal profile 2802; indication of the bolus on board 2804; indication of the last glucose result 2806 which, in some embodiments, includes the time of the last result; the volume of insulin remaining in the reservoir 2808; the percentage of pump battery life remaining 2810; the batter income 2814 (which may include a battery level indication); the current time 2818; the connectivity status 2816; and the section of the user interface in which the page resides 2812.

In some embodiments, as discussed above, while the infusion pump is delivering, the screen may include a backsplash, icon or other indication that readily indicates that status, for example, the backsplash of the page may be a different color depending on the status. In some embodiments, the delivering status may be green, the glucose status may be orange, the alarm status may be red and the idle status may be blue. In these embodiments, irrespective of the screen, the status of the infusion pump may be learned by the user. Embodiments of alarm status screens may be found in FIGS. 29A-29F, embodiments of an idle screen may be found in FIG. 28C. In some embodiments, when the infusion pump is idling, that indicates there is no delivery, which, in many circumstances, may not be desired for an extended period of time. Therefore, in some embodiments, when the infusion pump is in idle, the home screen indicates the idle status 2828 and the idle status home screen includes a large button for "start basal" 2830.

In some embodiments, one or more screens may include icon buttons for navigation to particular screens, for example, home 2812, glucose 2820, bolus or basal 2822, logbook 2824 and/or settings 2826. Examples of one embodiment of these screens are shown as follows: home, FIG. 29A, Glucose, FIG. 28B, Insulin (e.g. bolus or basal) FIG. 28D-28G, Logbook FIG. 28H and/or Settings FIG. 28I.

Referring now to the embodiments of the insulin screens, FIGS. 28D-28G, in some embodiments, the insulin screens include one or more, but not limited to, the following buttons: bolus calculator 2830, program bolus 2832, program basal 2834 and stop basal 2836. In some embodiments, the insulin screens may also include an indication of the last bolus 2838 which may include the volume and the time, as well as the currently active basal profile 2840 which may include the rate and the profile name.

Figure 29B:
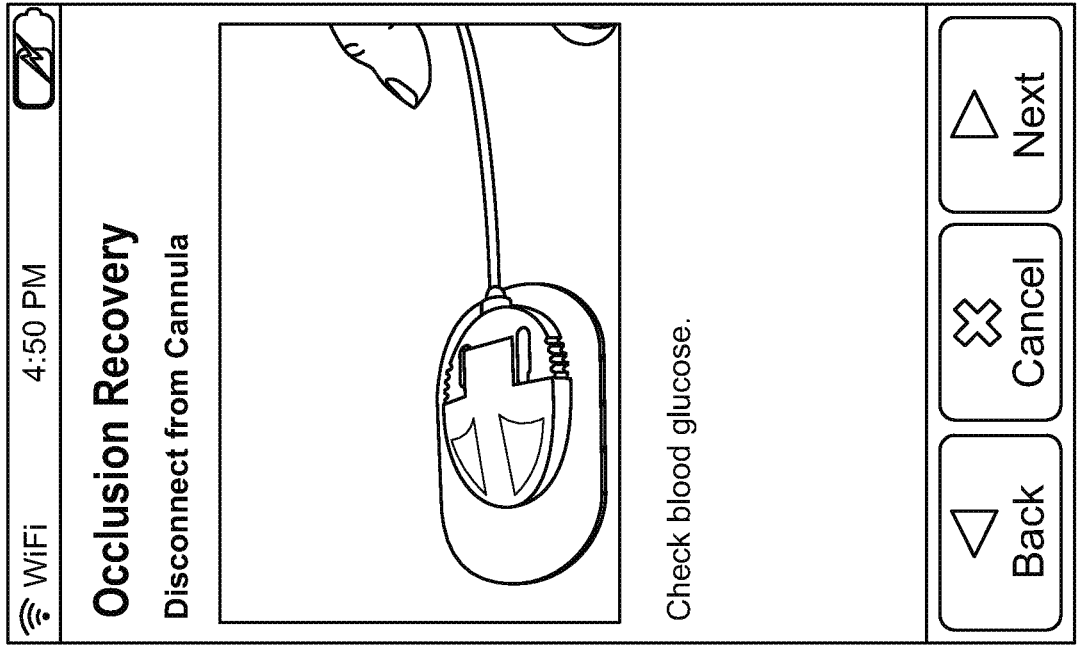
Figure 29A:
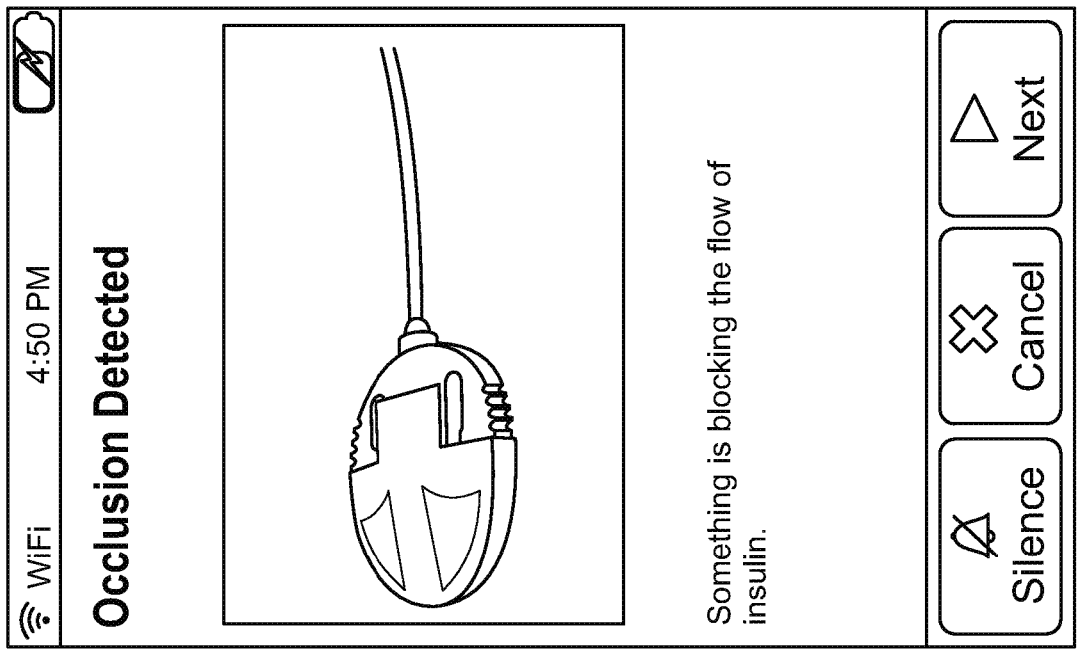
Figure 29C:
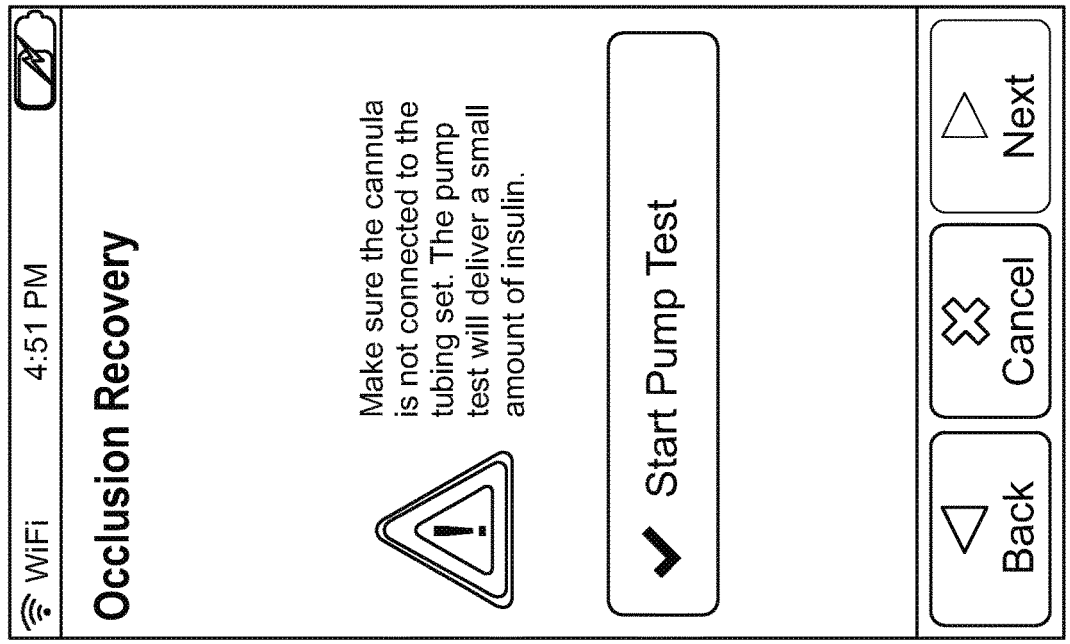
Figure 29D:
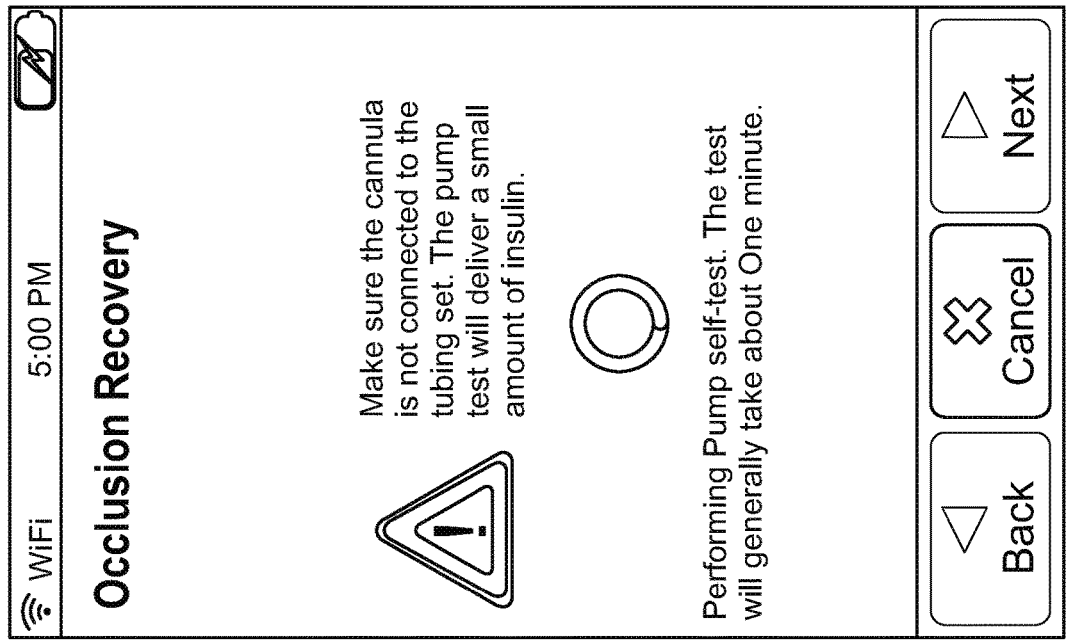
Figure 29F:
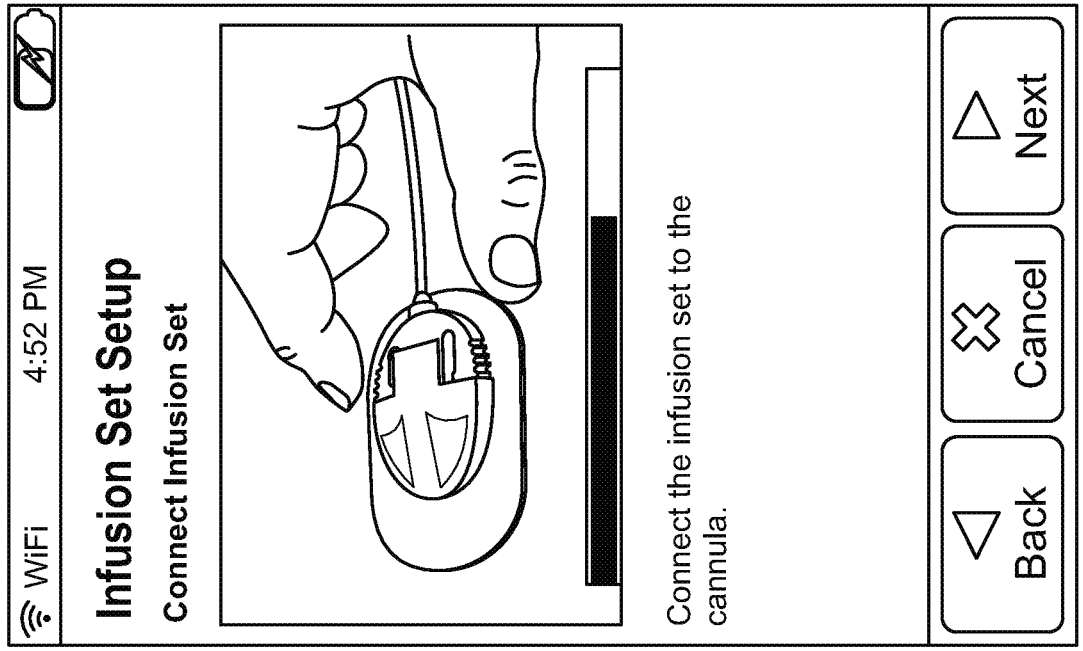
Figure 29E:
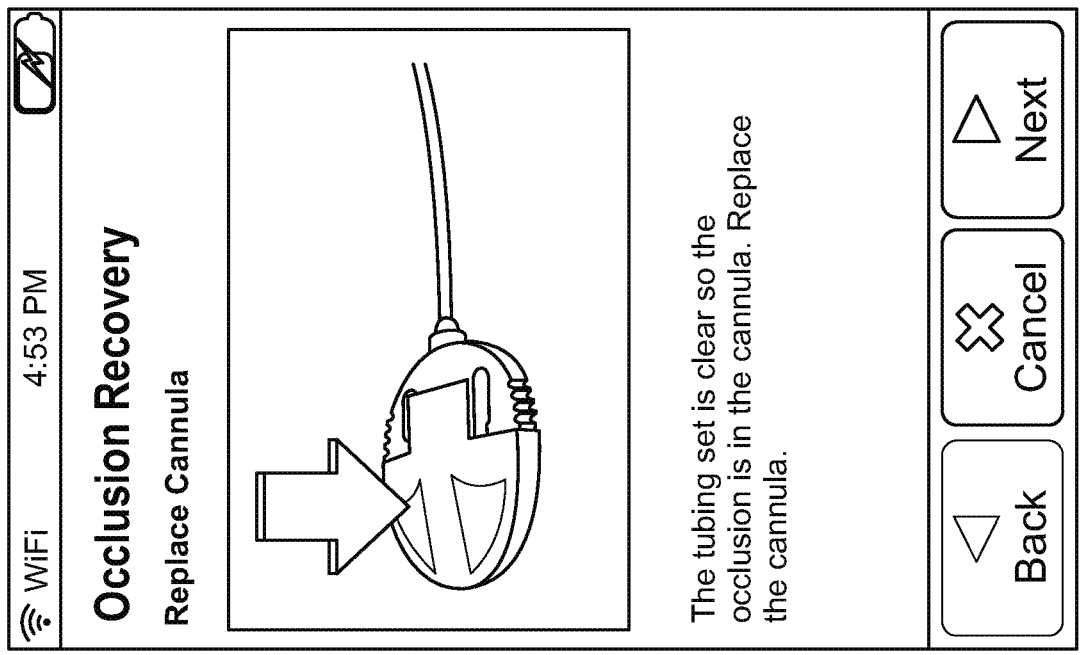

Referring now to FIGS. 29A-29F, embodiments of an occlusion detected alarm is shown. In some embodiments, as discussed above, an alarm condition may translate to a different backsplash/background or color, i.e., the backsplash of the screens may be red to indicate alarm condition. In some embodiments, when an alarm condition is sensed by the system, the system may provide a series of GUI screens that aid the user in recovering and or confirming the alarm condition. For example, in FIG. 29A, in some embodiments, the screen may indicate that the flow of insulin is blocked and therefore, an occlusion condition exists. In some embodiments, the user may select "next" and the GUI may walk the user through recommended actions. For example, in some embodiments, for example, in FIG. 29B, the screen may remind the use to check their blood glucose. Referring to FIGS. 29C and 29D, the screens may instruct the user to start the pump test (to determine if, for example, the occlusion is in the disposable portion or in the cannula). The pump test may determine, in some embodiments, if the disposable portion has an occlusion. Before starting the pump test, in some embodiments, the screen reminds the user to disconnect from the tubing set. Referring now to FIGS. 29E and 29F, in some embodiments, the system may determine that the occlusion is not within the disposable portion and may remind the user to replace the cannula. In some embodiments, the system may automatically start a series of screens, which, in some embodiments include those describe above, and in some embodiments, include animations, that remind the user to connect to the new cannula (and prime the new cannula, etc.). In some embodiments, where the system determines the occlusion is in the disposable, the system may instruct the user to replace the disposable portion.

Various embodiments of the system therefore include one or more devices and a remote interface. In some embodiments, the remote interface is configured to connect with and may communicate with a web portal and or a personal computer. In some embodiments, the remote interface may be a personal computer.

In some embodiments, the system includes a recharging apparatus and/or device for recharging the remote interface and/or for recharging the one or more device. In some embodiments, during recharge, the device and/or the remote interface may receive software updates/software downloads and/or synchronization with a database. In some embodiment, the recharging device and/or the charger includes a USB connection to a personal computer, the connection may be used as a data port and/or as a charging apparatus.

In some embodiments, the system includes at least two reusable portions of an infusion pump and/or other device, wherein, in some embodiments, both are configured to receive information and/or to communicate with the remote interface. In some embodiments, while one of the two reusable portions is being recharged, the second of the two reusable portions may be in use. Changing from one reusable portion to the second reusable portion may include the remote interface synchronizing data with the second reusable portion such that the second reusable portion includes updated information once in use. In some embodiments, each of the reusable portions includes nonvolatile memory and may include all the control and command capabilities with respect to one or more processors, which command the device. Thus, in some embodiments, the remote interface may be used as an user interface and commands, instructions and profiles may be input by the user using the remote interface, however, those commands are sent to the device, and in some embodiments, the device, after confirming, with the remote interface, that the device has received the information correctly, the device commands all action, for example, the infusion pump commands delivery of infusible fluid.

In some embodiments, for the user to change use from a first reusable portion to a second reusable portion, the user may indicate to the remote interface they wish to change reusable portions. The first reusable portion, in use, sends the current insulin on board and/or bolus on board (which may be referred to as JOB) information to the remote interface. The remote interface receives this information and starts counting time with respect to the IOB information. Once the second reusable portion is connected to the remote interface, the remote interface sends the IOB information to the second reusable portion, with the time stamp. The second reusable portion confirms the time on the IOB information. If the reusable portion finds that the time stamp does not match (which, in some embodiments, may be an indication that the first reusable portion's battery is not functioning properly and/or was 100% out of charge when placed on charger), a message is sent to the remote interface that appears to the user that the time does not match. The user may enter in the correct time and this time for both the remote interface and the reusable portions. However, where the time stamp matches, the second reusable portion may rely on the IOB information and therefore, the IOB calculations may be continuous, even while changing from a first reusable portion to a second reusable portion. In instances where the time stamps do not match, in some embodiments, the IOB information may be deleted, and the calculations begin at 0 from the new set time, and the user is informed of same using the remote interface.

The remote interface may be used to communicate with at least one device. In some embodiments, the remote interface may be used to communicate with a variety of devices. This may be desirable for many reasons, including, but not limited to, user familiarity. Using a single remote interface, the software platforms of which may be designed, and in many embodiments are designed, to be similar in nature, such that a single user may master a variety of software/applications for a variety of devices without significant learning time. Additionally, the remote interface may, while either connected by way of a USB to a personal computer and/or while connected to web portal, may download all software updates for all of the device in which it may be communicating with, and then, may transfer these updates to the devices themselves. This may be beneficial for many reasons, including, but not limited to, maintaining the devices in a streamline process and for updating the devices in an efficient manner.

Additionally, using various software applications which may, in some embodiments, be loaded onto the personal computer and/or accessed through a web portal, a user may configure the various profiles and or review various data regarding the devices in one location. Changes made to the information and or to the profiles may be downloaded onto the remote interface. Any relevant changes are then wirelessly communicated to the device(s). In some embodiments, the devices themselves may receive information by way of a USB connection to a personal computer.

In some embodiments, the remote interface may be used to capture images that aid in the control of the devices. For example, in some embodiments, the user may be instructed to take a picture, using the camera on the remote interface, of a filled syringe, such that the remote interface (and user interface) may either verify user entered information regarding the volume of fluid in the filled syringe and/or determine the volume of fluid in the filled syringe. This may be beneficial for many reasons, including, but not limited to, including approximately the correct volume of fluid that is loaded into a reservoir, in some embodiments, may lead to greater safety for the user. In some embodiments, the infusion pump determines the volume of fluid remaining in the reservoir and alarms the user when the volume is less than a particular, and in some embodiments, pre-programmed, volume. In these embodiments, the user may change the reservoir (i.e., replace with a filled reservoir) before the volume is completely depleted. Thus, this prevents the user from having an event where they have no medication. Thus, where an incorrect volume of fluid is entered, by the user, as having been transferred to the reservoir, the calculation of the volume of fluid in the reservoir may be inaccurate. This may not be desired for many reasons, including, but not limited to, where the volume of fluid transferred to the reservoir is miscalculated to a higher number, then the reservoir may be depleted faster than calculated and therefore, the user may have no medication in an unpredictable manner. However, where the volume of fluid transferred to the reservoir is miscalculated to a lower number, then the reservoir may be depleted slower than calculated and therefore, the user may replace the reservoir prematurely and thus, discard un-used fluid.

In some embodiments, a camera may be used as described above, but the camera may be part of a peripheral device to the remote interface. In some embodiments, the peripheral device may transfer the image to the remote interface and the remote interface may process the image in a similar manner as if it were provided by the remote interface's camera.

Referring now also to FIGS. 51A-51B and FIG. 53, in some embodiments, the user may pre-program "preset bolus" amounts for various times of day, events and/or meals. For example, in some embodiments, when entering a bolus, the user may select a preset bolus, which, for example, may include "Breakfast", "Lunch", or "Dinner", each having a pre-set amount as well as a pre-set delivery mode, which may include, but is not limited to, e.g., normal bolus, dual bolus, square wave bolus. In some embodiments, when a user has navigated to the bolus screen, the last bolus given is indicated, as well as the time elapsed since the last bolus. The menu may present to the user the option to navigate to the "Bolus Wizard", the "Manual Bolus" or the "Preset Bolus".

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A medical device system comprising:
a first medical device;
a first remote interface; and
a second remote interface, located separate from the first medical device and the first remote interface, in communication with the first remote interface and the first medical device,
wherein the first remote interface:
initiates a command related to the communication of safety critical information to the first medical device based on an input;
displays a message on the first remote interface that the communication of the safety critical information to the first medical device requires confirmation using the second remote interface;
sends the communication to the second remote interface; and once confirmation is received by the second remote interface, the second remote interface communicates the command to the first medical device.

2. The medical device system of claim 1, wherein the first medical device is an infusion pump.

3. The medical device system of claim 1, wherein the first remote interface is a medical device data system.

4. The medical device system of claim 1, wherein the first medical device sends a command to the first remote interface through the second remote interface.

5. The medical device system of claim 1, wherein the system further comprising a blood glucose meter in communication with the second remote interface.

6. The medical device system of claim 1, wherein the system further comprising a continuous glucose monitor transmitter in communication with the second remote interface.

7. The medical device system of claim 2, wherein the first remote interface:
receives an input of information related to the delivery by the infusion pump of a bolus volume of infusible fluid;
displays a message that the delivery of the bolus volume requires confirmation using the second remote interface; and
once confirmation is received by the second remote interface, the second remote interface communicates the information required for the delivery of the bolus volume of infusible fluid to the infusion pump.

8. A medical device system comprising:
an infusion pump;
a first remote interface comprising a medical device data system; and
a second remote interface, located separate from the infusion pump and the first remote interface, in communication with the first remote interface and the infusion pump,
wherein the first remote interface:
initiates a command related to the communication of safety critical information to the infusion pump based on an input;
displays a message on the first remote interface that the communication of the safety critical information to the infusion pump requires confirmation using the second remote interface;
sends the communication to the second remote interface; and
once confirmation is received by the second remote interface, the second remote interface communicates the command to the infusion pump.

9. The medical device system of claim 8, wherein the infusion pump sends a command to the first remote interface through the second remote interface.

10. The medical device system of claim 8, wherein the system further comprising a blood glucose meter in communication with the second remote interface.

11. The medical device system of claim 8, wherein the system further comprising a continuous glucose monitor transmitter in communication with the second remote interface.

12. The medical device system of claim 8, wherein the first remote interface:
receives an input of information related to the delivery by the infusion pump of a bolus volume of infusible fluid;
displays a message that the delivery of the bolus volume requires confirmation using the second remote interface; and
once confirmation is received by the second remote interface, the second remote interface communicates the information required for the delivery of the bolus volume of infusible fluid to the infusion pump.

* * * * *

UNITED STATES PATENT AND TRADEMARK OFFICE
CERTIFICATE OF CORRECTION

| | | |
|---|---|---|
| PATENT NO. | : 11,660,392 B2 | |
| APPLICATION NO. | : 16/266613 | |
| DATED | : May 30, 2023 | |
| INVENTOR(S) | : Dean Kamen, Gregory R. Lanier and Gregg W. Rivinius | |

It is certified that error appears in the above-identified patent and that said Letters Patent is hereby corrected as shown below:

On the Title Page

Page 2, Item (63) Please correct both instances of "13/322,896" to --13/332,896-- in the Related U.S. Application Data section.

Signed and Sealed this
Nineteenth Day of September, 2023

Katherine Kelly Vidal
*Director of the United States Patent and Trademark Office*